US011414439B2

(12) United States Patent
Abela et al.

(10) Patent No.: US 11,414,439 B2
(45) Date of Patent: Aug. 16, 2022

(54) MODULATORS OF CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATOR

(71) Applicant: Vertex Pharmaceuticals Incorporated, Boston, MA (US)

(72) Inventors: Alexander Russell Abela, Escondido, CA (US); Jeremy J. Clemens, San Diego, CA (US); Peter Diederik Jan Grootenhuis, Del Mar, CA (US); Sara Sabina Hadida Ruah, La Jolla, CA (US); Yoshihiro Ishihara, San Diego, CA (US); Haripada Khatuya, San Diego, CA (US); Jason McCartney, Cardiff by the Sea, CA (US); Mark Thomas Miller, Rancho Santa Fe, CA (US); Fabrice Jean Denis Pierre, La Jolla, CA (US); Joe Anh Tran, San Marcos, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 30 days.

(21) Appl. No.: 15/733,738

(22) PCT Filed: Apr. 12, 2019

(86) PCT No.: PCT/US2019/027202
§ 371 (c)(1),
(2) Date: Oct. 9, 2020

(87) PCT Pub. No.: WO2019/200246
PCT Pub. Date: Oct. 17, 2019

(65) Prior Publication Data
US 2021/0032272 A1    Feb. 4, 2021

Related U.S. Application Data

(60) Provisional application No. 62/657,513, filed on Apr. 13, 2018.

(51) Int. Cl.
| | | |
|---|---|---|
| *C07F 7/08* | (2006.01) | |
| *C07F 7/30* | (2006.01) | |
| *A61K 31/404* | (2006.01) | |
| *A61K 31/47* | (2006.01) | |

(52) U.S. Cl.
CPC .......... *C07F 7/0816* (2013.01); *C07F 7/0807* (2013.01); *C07F 7/0814* (2013.01); *C07F 7/0832* (2013.01); *C07F 7/30* (2013.01); *A61K 31/404* (2013.01); *A61K 31/47* (2013.01)

(58) Field of Classification Search
None
See application file for complete search history.

(56) References Cited

U.S. PATENT DOCUMENTS

| | | |
|---|---|---|
| 5,410,061 A | 4/1995 | Gilmore et al. |
| 6,441,004 B1 | 8/2002 | Faull et al. |
| 6,787,651 B2 | 9/2004 | Stolle et al. |
| 6,949,572 B2 | 9/2005 | Bertinato et al. |
| 6,979,692 B2 | 12/2005 | Bertinato et al. |
| 7,368,573 B2 | 5/2008 | Bertinato et al. |
| 8,058,299 B2 | 11/2011 | Bolin et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 10,570,115 B2 | 2/2020 | Alcacio et al. |
| 10,654,829 B2 | 5/2020 | Dhamankar et al. |
| 10,793,547 B2 | 10/2020 | Abela et al. |
| 2002/0055631 A1 | 5/2002 | Augeri et al. |
| 2002/0086887 A1 | 7/2002 | Augeri et al. |
| 2005/0171185 A1 | 8/2005 | Yamasaki et al. |
| 2005/0197376 A1 | 9/2005 | Kayakiri et al. |
| 2007/0105833 A1 | 5/2007 | Ruah et al. |
| 2010/0227888 A1 | 9/2010 | Hadida Ruah et al. |
| 2011/0165118 A1 | 7/2011 | Chan et al. |
| 2013/0072483 A1 | 3/2013 | Wenge et al. |
| 2013/0267493 A1 | 10/2013 | Bhattacharya et al. |
| 2013/0317000 A1 | 11/2013 | Chowdhury et al. |
| 2013/0317001 A1 | 11/2013 | Andrez et al. |
| 2014/0080825 A1 | 3/2014 | Hadida-Ruah et al. |
| 2014/0296200 A1 | 10/2014 | Brown et al. |
| 2015/0320736 A1 | 11/2015 | Phenix et al. |
| 2015/0322002 A1 | 11/2015 | Dehnhardt et al. |
| 2018/0099932 A1 | 4/2018 | Altenbach et al. |
| 2018/0141954 A1 | 5/2018 | Strohbach et al. |

(Continued)

FOREIGN PATENT DOCUMENTS

| | | |
|---|---|---|
| AU | 2013231151 A1 | 10/2013 |
| AU | 2013270464 A1 | 1/2014 |

(Continued)

OTHER PUBLICATIONS

Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.

(Continued)

*Primary Examiner* — Joseph R Kosack
(74) *Attorney, Agent, or Firm* — Finnegan, Henderson, Farabow, Garrett & Dunner LLP

(57) ABSTRACT

This disclosure provides modulators of Cystic Fibrosis Transmembrane Conductance Regulator (CFTR), pharmaceutical compositions containing at least one such modulator, methods of treatment of cystic fibrosis by administering such modulators and pharmaceutical compositions, and processes for making such modulators.

31 Claims, 7 Drawing Sheets

(56) References Cited

U.S. PATENT DOCUMENTS

| | | | |
|---|---|---|---|
| 2018/0170938 A1 | 6/2018 | Strohbach et al. |
| 2018/0244611 A1 | 8/2018 | Altenbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0153000 A1 | 5/2019 | Munoz et al. |
| 2019/0240197 A1 | 8/2019 | Chu et al. |
| 2019/0269683 A1 | 9/2019 | Miller et al. |
| 2020/0138798 A1 | 5/2020 | Chen et al. |
| 2020/0171015 A1 | 6/2020 | Haseltine et al. |
| 2020/0283405 A1 | 9/2020 | Alcacio et al. |
| 2020/0369608 A1 | 11/2020 | Angell et al. |

FOREIGN PATENT DOCUMENTS

| | | |
|---|---|---|
| CA | 2145473 A1 | 9/1995 |
| EP | 0 194 599 A2 | 9/1986 |
| EP | 0 673 930 A1 | 9/1995 |
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2004/111014 A1 | 12/2004 |
| WO | WO 2005/049018 A1 | 6/2005 |
| WO | WO 2005/054191 A1 | 6/2005 |
| WO | WO 2005/070006 A2 | 8/2005 |
| WO | WO 2005/075435 A1 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/002421 A2 | 1/2006 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/113327 A2 | 10/2007 |
| WO | WO 2007/117715 A2 | 10/2007 |
| WO | WO 2007/134279 A2 | 11/2007 |
| WO | WO 2008/005457 A2 | 1/2008 |
| WO | WO 2008/100867 A2 | 8/2008 |
| WO | WO 2008/127399 A2 | 10/2008 |
| WO | WO 2008/141385 A1 | 11/2008 |
| WO | WO 2009/006315 A1 | 1/2009 |
| WO | WO 2009/027730 A1 | 3/2009 |
| WO | WO 2009/032116 A1 | 3/2009 |
| WO | WO 2009/038683 A2 | 3/2009 |
| WO | WO 2009/064848 A1 | 5/2009 |
| WO | WO 2009/071947 A2 | 6/2009 |
| WO | WO 2009/073757 A1 | 6/2009 |
| WO | WO 2009/076142 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/019239 A2 | 2/2010 |
| WO | WO 2010/022307 A2 | 2/2010 |
| WO | WO 2010/025295 A2 | 3/2010 |
| WO | WO 2010/053471 A1 | 5/2010 |
| WO | WO 2010/054138 A2 | 5/2010 |
| WO | WO 2010/065824 A2 | 6/2010 |
| WO | WO 2010/083441 A2 | 7/2010 |
| WO | WO 2010/102758 A2 | 9/2010 |
| WO | WO 2010/108162 A1 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A1 | 2/2011 |
| WO | WO 2011/068560 A1 | 6/2011 |
| WO | WO 2011/072241 A1 | 6/2011 |
| WO | WO 2011/102514 A1 | 8/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/128251 A1 | 10/2011 |
| WO | WO 2011/133751 A2 | 10/2011 |
| WO | WO 2011/133951 A1 | 10/2011 |
| WO | WO 2011/150016 A1 | 12/2011 |
| WO | WO 2012/027247 A2 | 3/2012 |
| WO | WO 2012/027731 A2 | 3/2012 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A2 | 10/2012 |
| WO | WO 2012/166415 A1 | 12/2012 |
| WO | WO 2012/170061 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/070961 A1 | 5/2013 |
| WO | WO 2013/082102 A1 | 6/2013 |
| WO | WO 2013/112804 A1 | 8/2013 |
| WO | WO 2013/118805 A1 | 8/2013 |
| WO | WO 2013/130669 A1 | 9/2013 |
| WO | WO 2013/158121 A1 | 10/2013 |
| WO | WO 2013/177224 A1 | 11/2013 |
| WO | WO 2013/185112 A1 | 12/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |

(56) References Cited

FOREIGN PATENT DOCUMENTS

| | | |
|---|---|---|
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/105484 A1 | 6/2016 |
| WO | WO 2016/105485 A2 | 6/2016 |
| WO | WO 2016/128529 A1 | 8/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/026075 A1 | 10/2019 |
| WO | WO 2019/191620 A1 | 10/2019 |
| WO | WO 2019/200246 A1 | 10/2019 |

OTHER PUBLICATIONS

Atzrodt J, Derdau V, Fey T, Zimmermann J. "The Renaissance of H/D Exchange" Angew. Chem. Int. Ed. 2007: 46, 7744-7765.

Atzrodt J, Derdau V, Kerr W, Reid M. "C—H functionalization for hydrogen isotope exchange" Angew. Chem. Int. Ed. 2018: 57, 3022-3047.

Bhattacharya, S. et al. (1999) Polymorphism in Pharmaceutical Solids: Thermoanalytical and Crystallographic Methods (Brittain H. ed., 2d ed. Informa Healthcare USA, Inc. 2009) 318-335.

Belikov, V.G., (2007) *Farmatsevticheskaya khimiya (Pharmaceutical Chemistry)*, Moscow: MEDpress-inform, pp. 27-29.

Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.

Boyle, M. "A CFTR corrector (lumacaftor) and a CFTR potentiator (ivacaftor) for treatment of patients with cystic fibrosis who have a phe508del CFTR mutation: a phase 2 randomised controlled trial," The Lancet Respiratory Medicine (Jul. 1, 2014) Retrieved from the Internet: https://www-clinicalkeycom-ez03.infotrieve.com/#!/content/playContent/1-s2.0S2213260014701328?returnurl=null&referrer=null.

Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.

Byrn, S. et al. (1995) "Pharmaceutical solids: A strategic approach to regulatory considerations," (12): 945-954.

Caira, M. R. (1998) "Crystalline Polymorphism of Organic Compounds," *Topics in Current Chemistry*, 163-208.

Cargnin S, Serafini M, Pirali T. "A primer of deuterium in drug design" Future Med. Chem. 2019; 11(16): 2039-2042.

Chen, Y. (Jan. 26, 2016) "N-Monoacylation of Sulfonimidamides" *Synthesis*, 48(7):1019-1028.

Czeskis B, Elmore, CS, Haight A, Hesk D, Maxwell BD, Miller SA, Raglione T, Schildknegt K, Traverse JF, Wang P. "Deuterated active pharmaceutical ingredients: A science-based proposal for synthesis, analysis, and control. Part 1: Framing the problem" J. Label. Compd. Radiopharm. 2019, 62: 690-694. DOI: 10.1002/jlcr.3743.

Dao HT, Li C, Michaudel Q, Maxwell BD, Baran PS. J. Am. Chem. Soc. 2015; 137, 8046-8049.

Database Caplus, Accession No. 1965:51408. Abstract of French Patent No. FR M2868, filed Nov. 23, 1964, by Roussel-UCLAF [online]. Retrieved Jan. 6, 2017 (1 page).

Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).

Database Pubchem, CID: 20050716. Compound Summary, 1-[2-[[2-[(2-Amino-3-methylbutanoyl)amino]-3-methylpentanoyl]amino]-3-phenylpropanoyl]pyrrolidine-2-carboxylic acid. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).

Database Pubchem, CID: 20091118. Compound Summary, [4-(5-Hexylpyrimidin-2-yl)phenyl] 2-methoxypropanoate. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).

Database Pubchem, CID: 20120819. Compound Summary, 4-(Cyclopentyloxy)-3-fluorobenzene-1-sulfonyl chloride. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).

Database Pubchem, CID: 2545578. Compound Summary, *T5339296*. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).

Database Pubchem, CID: 44419393. Compound Summary, *CHEMBL374189*. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).

Database Pubchem, CID: 49774135. Compound Summary, *SCHEMBL13395127*. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).

Database Pubchem, CID: 58132855. Compound Summary, *SCHEMBL831192*. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).

Dorwald, F. A. (2006) "Side Reactions in Organic Synthesis" Wiley: VCH, Weinheim p. IX of Preface p. 1-15.

Gant TG. "Using Deuterium in Drug Discovery: Leaving the Label in the Drug" J Med. Chem. 2014; 57(9): 3595-3611.

Garg, V. et al. "Pharmacokinetic and Drug-Drug Interaction Profiles of the Combination of Tezacaftor/Ivacaftor", Clinical and Transla-

(56) References Cited

OTHER PUBLICATIONS tional Science—CTS, vol. 12, No. 3, Jan. 29, 2019 (Jan. 29, 2019), pp. 267-275, XP055719490, US ISSN: 1752-8054, DOI: 10.1111/cts.12610.
Halford B. "The deuterium switcheroo" Chemical & Engineering News 2016; 94(27), 32-36.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2015/54316: International Search Report and Written Opinion, dated Feb. 5, 2016 (11 pages).
International Patent Application No. PCT/US2017/025381: International Search Report and Written Opinion, dated Jun. 6, 2017 (11 pages).
International Patent Application No. PCT/US2017/054611: International Search Report and Written Opinion, dated Jan. 3, 2018 (10 pages).
International Patent Application No. PCT/US2017/065425: International Search Report and Written Opinion, dated Feb. 27, 2018 (10 pages).
International Patent Application No. PCT/US2018/036610: International Search Report and Written Opinion, dated Sep. 19, 2018 (9 pages).
International Patent Application No. PCT/US2018/040427: International Search Report and Written Opinion, dated Oct. 9, 2018 (15 pages).
International Patent Application No. PCT/US2018/042415: International Search Report and Written Opinion, dated Oct. 31, 2018 (12 pages).
International Patent Application No. PCT/US2018/042486: International Search Report and Written Opinion, dated Nov. 7, 2018 (13 pages).
International Patent Application No. PCT/US2018/044963: International Search Report and Written Opinion, dated Sep. 25, 2018 (15 pages).
International Patent Application No. PCT/US2018/056772: International Search Report and Written Opinion, dated Jan. 29, 2019 (13 pages).
International Patent Application No. PCT/US2018/063871: International Search Report and Written Opinion, dated Feb. 25, 2019 (16 pages).
International Patent Application No. PCT/US2019/016537: International Search Report and Written Opinion, dated Apr. 23, 2019 (13 pages).
International Patent Application No. PCT/US2018/064522: International Search Report and Written Opinion, dated Jun. 25, 2019 (21 pages).
International Patent Application No. PCT/US2019/018042: International Search Report and Written Opinion, dated Apr. 17, 2019 (10 pages).
International Patent Application No. PCT/US2019/024890: International Search Report and Written Opinion, dated Jun. 17, 2019 (13 pages).
International Patent Application No. PCT/US2019/026075: International Search Report and Written Opinion, dated Jun. 17, 2019 (13 pages).
International Patent Application No. PCT/US2019/027202: International Search Report and Written Opinion, dated Jun. 17, 2019 (10 pages).
International Patent Application No. PCT/US2020/028699: International Search Report and Written Opinion, dated Jul. 20, 2020 (9 pages).
International Patent Application No. PCT/US2020/034199: International Search Report and Written Opinion, dated Aug. 11, 2020 (15 pages).
Ivanisevic, I. (2011) "Uses of X-Ray Powder Diffraction in the Pharmaceutical Industry," Pharm. Form. Qual. 30-33.
Jain, B.C. et al. (1947) "Studies in Sulphanilamides. Part XIII. Reaction With Dicarboxylic Acids. Some New N1- and N4-Acyl and Heterocyclic Derivatives" Journal of the Indian Chemical Society, 24:173-176.
Kettle, J.G. et al. (2004) "N-Benzylindole-2-carboxylic acids: potent functional antagonists of the CCR2b chemokine receptor" Bioorganic & Medicinal Chemistry Letters, 14(2): 405-408.
Kieltsch, I. et al. Laureates: Awards and Honors SCS Fall Meeting 2007 260 Recent Advances in Electrophilic $CF_3$—Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.
Lai, J.T. et al. (1980) "Rearrangement of 2,2,6,6-tetramethyl-4-piperidone in phase-transfer catalyzed reactions," Journal of Organic Chemistry, 45(8):1513-1514.
Liu, J. F. et al. "CTP-354: A Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.
Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" Journal of Medicinal Chemistry, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].
NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.
Norman, P. (2014) "Novel picolinamide-based cystic fibrosis transmembrane regulator modulators: evaluation of WO2013038373, WO2013038376, WO2013038381, WO2013038386, and WO2013038390," Expert Opinion on Therapeutic Patents, 24(7):829-837.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.
Passarella, D. et al. (2001) "Cyclodimerization of indol-2-ylacetylenes. An example of intermolecular enyne-alkyne cycloaddition" Journal of the Chemical Society, Perkin Transactions 1, 127-129.
Pirali T, Serafini M, Cargnin S, Genazzani AA. "Applications of Deuterium in Medicinal Chemistry" J Med. Chem. 2019; 62(11): 5276-5297.
Qun, C. et al. "Synthesis of 3,3,3-trifluoro-2,2-dimethylpropionic acid", Huaxue Shiji—Chemical Reagents, Beijing : Huaxue Huaxue Shiji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.
Rosebraugh, C.J. (2015) "Highlights of Prescribing Information for Orkambi," [online] Retrieved from the Internet: https://www.accessdata.fda.gov/drugsatfda_docs/label/2015/206038Orig1s000lbl.pdf, on Aug. 24, 2017.
Schmidt C. "First deuterated drug approved" Nat. Biotechnol. 2017, 35, 493-494.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" Journal für Pracktische Chemie, 331(3):503-506.
Tsong-Long H. et al. "Synthesis and pharmacological characterization of 2-aminobenzaldehyde oxime analogs as dual inhibitors of

(56) References Cited

OTHER PUBLICATIONS neutrophil elastase and proteinase 3", Bioorganic & Medicinal Chemistry, vol. 23, No. 5, Jan. 16, 2015, pp. 1123-1134, XP029199003.

Tullis, E. et al. (2018) "Preliminary safety and efficacy of triple-combination CFTR modulator regimens," *Respirology*, 23(51):33.

U.S. Appl. No. 16/620,265, filed Dec. 6, 2019, by Chen et al.

U.S. Appl. No. 16/625,028, filed Dec. 20, 2019, by Chu et al.

U.S. Appl. No. 16/836,155, filed Mar. 31, 2020, by Miller et al.

U.S. Appl. No. 16/994,875, filed Aug. 17, 2020, by Abela et al.

Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.

Venkatesh, S. et al. (2000) "Role of the development scientist in compound lead selection and optimization" *J. Pharm. Sci.* 89(2), 145-154.

Verado, G. et al. (1999) "Reductive One Batch Synthesis of N-Substituted Pyrrolidines from Primary Amines and 2,5-Dimethoxytetrahydrofuran" *Synthesis*, (1):74-79.

Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.

Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].

Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.

"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.

Vodak, D. (2014) "Design and Development of HPMCAS-Based Spray-Dried Dispersions," 303-322.

Wainwright, C.E. et al. (2015) "Lumacaftor-Ivacaftor in Patients with Cystic Fibrosis Homozygous for Phe508del CFTR," *The New England Journal of Medicine*, 373(3):220-231.

Willson T. M. et al. (1996) "Bone targeted drugs 2. Synthesis of estrogens with hydroxyapatite affinity," Bioorg. & Med. Chem. Lett., (6):1047-1050.

Winn, M. et al. (1993) "2-(Alkylamino)nicotinic Acid and Analogs. Potent Angiotensin II Antagonists" *Journal of Medicinal Chemistry*, 36(18):2676-2688.

Yarnell AT. "Heavy-Hydrogen Drugs Turn Heads, Again" Chemical & Engineering News 2009; 87(25), 36-39.

| Mutation cDNA Name | Mutation Protein Name | Mutation Legacy Name |
|---|---|---|
| c.1A>G | | M1V |
| c.54-5940_273+10250de 121kb | p.Ser18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATins G | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |
| c.489+1G>T | No protein name | 621+1G->T |
| c.531delT | p.Ile177MetfsX12 | 663delT |
| c.532G>A | p.Gly178Glu | G178R |

(continued)

| Mutation cDNA Name | Mutation Protein Name | Mutation Legacy Name |
|---|---|---|
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| C.595OT | p.His199Tyr | H199Y |
| C.613CM | p.Pro205Ser | P205S |
| c.617T>G | p.Leu206Trp | L206W |
| C.658OT | p.Gln220X | Q220X |
| c.580T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 1079C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |
| c.1202G>A or c.1203G>A | p.Trp401X | W401X |
| c.1209+1G>A | No protein name | 1341+1G->A |
| c.1210-12[5] | No protein name | 5T |

(continued)

| Mutation cDNA Name | Mutation Protein Name | Mutation Legacy Name |
|---|---|---|
| c.1210-12(7) | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1G47T>G | p.Ser549Arg | S549R |
|  |  |  |
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |

(continued)

| Mutation cDNA Name | Mutation Protein Name | Mutation Legacy Name |
|---|---|---|
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985del13insAGAAA | p.Arg658 LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G+ |
| c.2051_2052delAAinsG | p.Lys684SerfsX38 | 2183delAA->G# |
| c.2052_2053insA | p.Gln685ThrfsX4 | 2184insA |
| c.2052delA | p.Lys684AsnfsX38 | 2184delA |
| c.2125OT | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |

(continued)

| Mutation cDNA Name | Mutation Protein Name | Mutation Legacy Name |
|---|---|---|
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547OA | p.Tyr849X | Y849X |
| c.2551C>T | p.Arg851X | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG |  | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |

(continued)

| Mutation cDNA Name | Mutation Protein Name | Mutation Legacy Name |
|---|---|---|
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |

(continued)

| Mutation cDNA Name | Mutation Protein Name | Mutation Legacy Name |
|---|---|---|
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.3718-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.3764oA | p.Ser1255X | S1255X |
| c.3773_3774insT | p.Leu1258PhefsX7 | 3905insT |
| c.3808G>A | p.Asp1270Asn | D1270N |
| c.3846G>A | p.Trp1282X | W1282X |
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

MODULATORS OF CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATOR

This application claims priority to U.S. Provisional Application 62/657,513, filed Apr. 13, 2018, the disclosure of which is incorporated herein by reference in its entirety.

This disclosure provides modulators of Cystic Fibrosis Transmembrane Conductance Regulator (CFTR), pharmaceutical compositions containing at least one such modulator, methods of treatment of cystic fibrosis by administering such modulators and pharmaceutical compositions, and processes for making such modulators.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for novel treatments of CFTR mediated diseases.

One aspect of the invention provides novel compounds, including compounds of Formulae (1), (1-3)-(1-11), (1-14), (2), and (3), Compounds (1-1), (1-2), (1-12), (1-13), Compounds (2-1)-(2-12), Compounds (3-1)-(3-3), and Compounds (4-1)-(4-5), pharmaceutically acceptable salts thereof, and deuterated derivatives of any of the foregoing wherein at least one carbon atom is replaced by a silicon atom, a boron atom, or a germanium atom.

For example, disclosed herein are compounds of Formula (1):

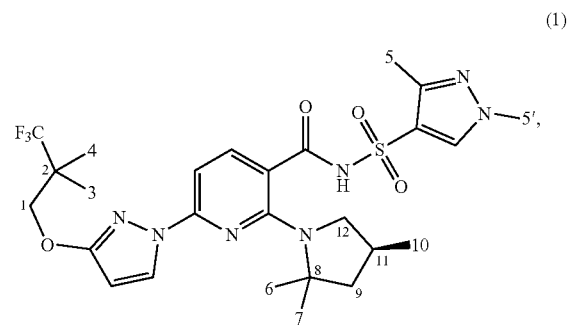

(1)

pharmaceutically acceptable salts thereof, and deuterated derivatives of any of the foregoing,
wherein:
at least one of the carbon atoms at positions 2 and 8 of Formula (1) is replaced by a silicon atom;
at least one of the methyl groups at positions 3, 4, 5, 5', 6, 7, and 10 of Formula (1) is replaced by a group chosen from —Si(R)$_3$ groups, —Si(R)$_2$(OR) groups, and —Si(R)(OR)$_2$ groups;

at least one of the methylene groups at positions 1, 9, and 12 of Formula (1) is replaced by a group chosen from >Si(R)$_2$ groups and >Si(R)(OR) groups; and/or the methine group at position 11 of Formula (1) is replaced by a group chosen from ≡Si(R) groups and ≡Si(OR) groups; and wherein each R, which may be identical or different, is independently chosen from hydrogen and $C_1$-$C_4$ alkyl groups.

Another embodiment provides compounds of Formula (2) and pharmaceutically acceptable salts and deuterated derivatives thereof:

(2)

wherein:

X is selected from —Si(CH$_3$)$_3$,

Z is selected from and wherein each compound of Formula (2) contains at least one Si atom. In some embodiments, the compound of Formula (2) is selected from Compounds (2-1)-(2-12) and pharmaceutically acceptable salts and deuterated derivatives thereof.

A further embodiment of the invention includes compounds of Formula (3) and pharmaceutically acceptable salts and deuterated derivatives thereof:

(3)

wherein:

X is selected from —Ge(CH$_3$)$_3$, and

Z is selected from

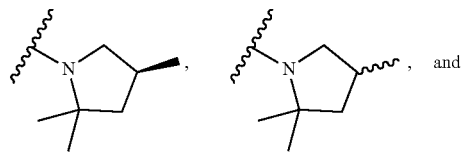 and

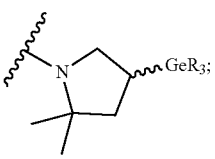

wherein each compound of Formula (3) contains at least one Ge atom. In some embodiments, the compound of Formula (3) is selected from Compounds (3-1), (3-2), (3-3) and pharmaceutically acceptable salts and deuterated derivatives thereof.

Other embodiments of the invention include Compounds (4-1), (4-2), (4-3), and (4-4):

(4-1)
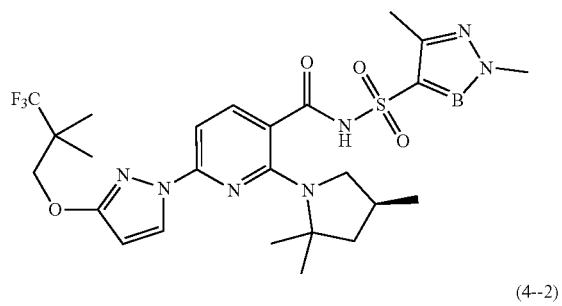

(4-2)
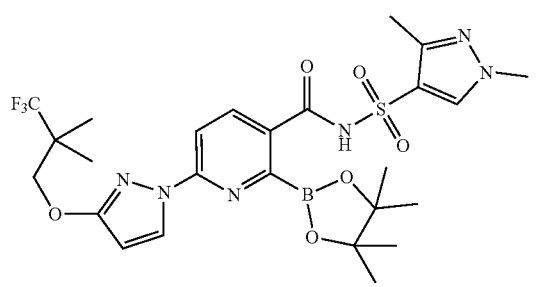

(4-3)
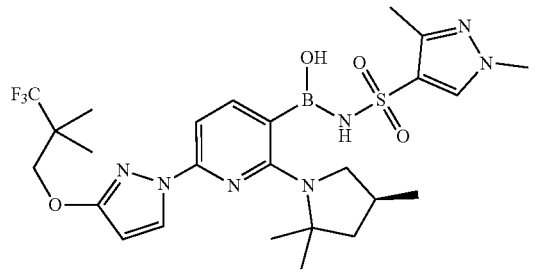

(4-4)
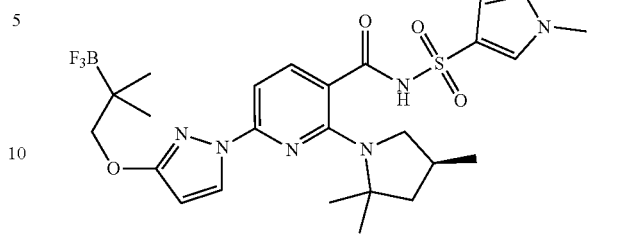

(4-5)
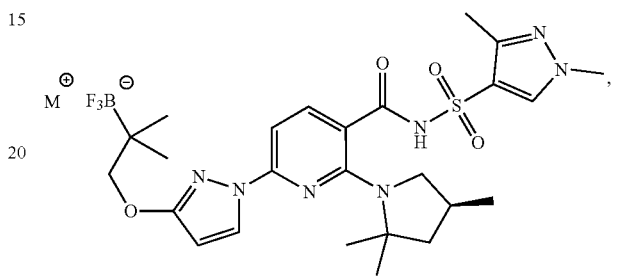

wherein M is a metal ion,
and pharmaceutically acceptable salts and deuterated derivatives thereof.

In some embodiments, M in Compound (4-5) is potassium or sodium. In some embodiments, M is potassium. In some embodiments, M is sodium.

Another aspect of the invention provides pharmaceutical compositions comprising at least one compound chosen from the novel compounds disclosed herein, pharmaceutically acceptable salts thereof, and deuterated derivatives of any of the foregoing, and at least one pharmaceutically acceptable carrier, which compositions may further include at least one additional active pharmaceutical ingredient. Thus, another aspect of the invention provides methods of treating the CFTR-mediated disease cystic fibrosis comprising administering at least one of compound chosen from the novel compounds disclosed herein, pharmaceutically acceptable salts thereof, and deuterated derivatives of any of the foregoing, and at least one pharmaceutically acceptable carrier, optionally as part of a pharmaceutical composition comprising at least one additional component, to a subject in need thereof.

In certain embodiments, the pharmaceutical compositions of the invention comprise at least one compound chosen from Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5) and pharmaceutically acceptable salts and deuterated derivatives thereof. In some embodiments, compositions comprising at least one compound chosen from the Formulae (1), (1-3)-(1-11), (1-14), (2), and (3), Compounds (1-1), (1-2), (1-12), (1-13), Compounds (2-1)-(2-12), Compounds (3-1), (3-2), (3-3), and pharmaceutically acceptable salts and deuterated derivatives thereof may optionally further comprise (a) at least one compound chosen from Compound (II) and pharmaceutically acceptable salts and deuterated derivatives thereof; (b) at least one compound chosen from Compound (III) and pharmaceutically acceptable salts and deuterated derivatives thereof, such as Compound (III-d); and/or (c) at least one compound chosen from Compound (IV) and pharmaceutically acceptable salts and deuterated derivatives thereof.

Compound (II) can be depicted as having the following structure:

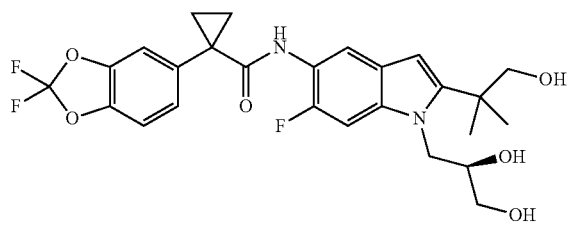 [SMILES: CC(C)(CO)c1cc2cc(NC(=O)C3(c4ccc5c(c4)OC(F)(F)O5)CC3)c(F)cc2n1C[C@@H](O)CO]

A chemical name for Compound II is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

Compound (III) can be depicted as having the following structure:

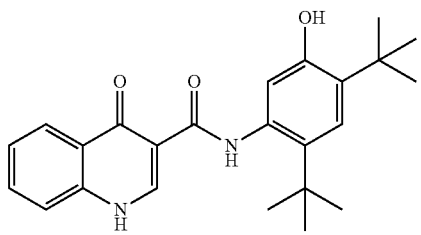 [SMILES: CC(C)(C)c1cc(C(C)(C)C)c(NC(=O)c2c[nH]c3ccccc3c2=O)cc1O]

A chemical name for Compound (III) is N-(5-hydroxy-2,4-di-tert-butyl-phenyl)-4-oxo-1H-quinoline-3-carboxamide.

Compound (III-d) can be depicted as having the following structure:

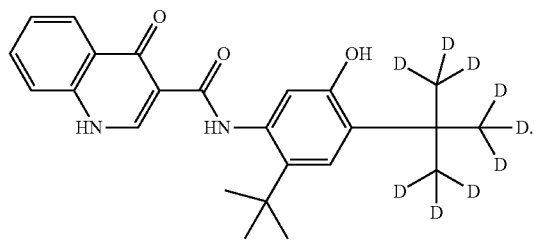

A chemical name for Compound (III-d) is N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide.

Compound (IV) is depicted as having the following structure:

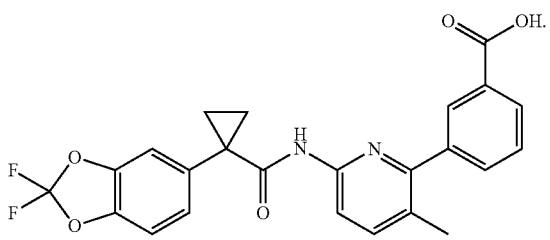 [SMILES: Cc1ccc(NC(=O)C2(c3ccc4c(c3)OC(F)(F)O4)CC2)nc1-c1cccc(C(=O)O)c1]

A chemical name for Compound IV is 3-(6-(1-(2,2-difluorobenzo[d][1,3]dioxol-5-yl)cyclopropanecarboxamido)-3-methylpyridin-2-yl)benzoic acid.

Another aspect of the invention provides methods of treating the CFTR-mediated disease cystic fibrosis comprising administering at least one compound chosen from the novel compounds disclosed herein, pharmaceutically acceptable salts thereof, and deuterated derivatives of any of the foregoing, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II), N-[2,4-bis(1,1-dimethylethyl)-5-hydroxyphenyl]-1,4-dihydro-4-oxoquinoline-3-carboxamide (Compound III) or N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d), and 3-(6-(1-(2,2-difluorobenzo[d][1,3]dioxol-5-yl)cyclopropane carboxamido)-3-methylpyridin-2-yl)benzoic acid (Compound IV), optionally as part of at least one pharmaceutical composition comprising at least one additional component, to a patient in need thereof.

BRIEF DESCRIPTION OF THE DRAWING

FIG. 1 is a representative list of CFTR genetic mutations.

DEFINITIONS

As used herein, "—Si(R)$_3$ groups", "—Si(R)$_2$(OR) groups", and "—Si(R)(OR)$_2$ groups" refer to monovalent groups having three substituents, wherein the "-" symbols represent the point of attachment from the silicon atom to the compound.

As used herein, ">Si(R)$_2$ groups" and >Si(R)(OR) groups" refer to divalent groups having two substituents, wherein the ">" symbols represent the two points of attachment from the silicon atom to the compound.

As used herein, "Si(R) groups" and "Si(OR) groups" refer to trivalent groups having one substituent and the "≡" symbols represent the three points of attachment from the silicon atom to the compound.

As used herein, "Compounds (2-1)-(2-12)" refers to each of Compounds (2-1), (2-2), (2-3), (2-4), (2-5), (2-6), (2-7), (2-8), (2-9), (2-10), (2-11), and (2-12). Similarly, reference to "Formulae (1-3)-(1-11)" is meant to include each of the Formulae (1-3), (1-4), (1-5), (1-6), (1-7), (1-8), (1-9), (1-10), and (1-11).

As used herein, the term "alkyl" refers to a saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted.

The term "alkoxy" as used herein refers to an alkyl or cycloalkyl covalently bonded to an oxygen atom. Alkoxy groups may be substituted or unsubstituted.

As used herein, "cycloalkyl" refers to a cyclic, bicyclic, tricyclic, or polycyclic non-aromatic hydrocarbon groups having 3 to 12 carbons (such as, for example 3-10 carbons). "Cycloalkyl" groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, and dispiro[2.0.2.1]heptane. Cycloalkyl groups may be substituted or unsubstituted.

"Substituted," whether preceded by the term "optionally" or not, indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

As used herein, "deuterated derivative(s)" means the same chemical structure, but with one or more hydrogen atoms replaced by a deuterium atom.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compound I, Compound II, and their pharmaceutically acceptable salts thereof disclosed herein are CFTR correctors.

As used herein, the term "CFTR potentiator" refers to a compound that increases the channel activity of CFTR protein located at the cell surface, resulting in enhanced ion transport. Compound III and Compound III-d disclosed herein are CFTR potentiators.

As used herein, the term "active pharmaceutical ingredient" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describe pharmaceutically acceptable salts in detail in *J. Pharmaceutical Sciences*, 1977, 66, 1-19. A "free base" form of a compound, for example, does not contain an ionically bonded salt.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The phrase "and pharmaceutically acceptable salts and deuterated derivatives thereof" is used interchangeably with "and pharmaceutically acceptable salts thereof and deuterated derivatives of any of the forgoing" in reference to one or more compounds or formulae of the invention. These phrases are intended to encompass pharmaceutically acceptable salts of any one of the referenced compounds, deuterated derivatives of any one of the referenced compounds, and pharmaceutically acceptable salts of those deuterated derivatives.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

As used herein, the term "solvent" refers to any liquid in which the product is at least partially soluble (solubility of product >1 g/l).

As used herein, the term "room temperature" or "ambient temperature" means 15° C. to 30° C.

It will be appreciated that certain compounds of this invention may exist as separate stereoisomers or enantiomers and/or mixtures of those stereoisomers or enantiomers.

Certain compounds disclosed herein may exist as tautomers and both tautomeric forms are intended, even though only a single tautomeric structure is depicted. For example, a description of Compound A is understood to include its tautomer Compound B and vice versa, as well as mixtures thereof:

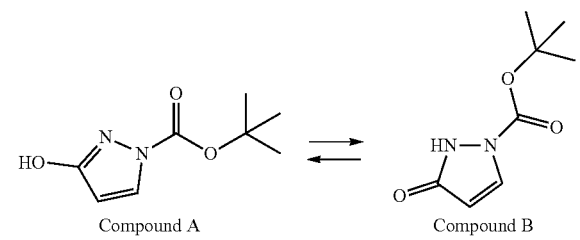

Compound A                    Compound B

Each of compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof can be independently administered once daily, twice daily, or three times daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered once daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered twice daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered with at least one compound chosen from Compound (II) and pharmaceutically acceptable salts thereof once daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered with at least one compound chosen from Compound (II) and pharmaceutically acceptable salts thereof twice daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered with at least one compound chosen from Compound (III), Compound (III-d), and pharmaceutically acceptable salts thereof once daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered with at least one compound chosen from Compound (III) and pharmaceutically acceptable salts thereof twice daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and (4-1)-(4-5), and pharmaceutically acceptable salts and deuterated derivatives thereof, is administered with at least one compound chosen from Compound (IV) and pharmaceutically acceptable salts thereof once daily. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered with at least one compound chosen from Compound IV and pharmaceutically acceptable salts thereof twice daily. In some embodiments, a deuterated derivative of Compound (II), (III), and/or (IV) or a pharmaceutically acceptable salt thereof is employed in any one of these embodiments. In some embodiments, the deuterated derivative of Compound (III) is Compound (III-d).

In some embodiments, 10 mg to 1,500 mg of a novel compound disclosed herein, a pharmaceutically acceptable salt thereof, or a deuterated derivative of such compound or salt are administered daily.

One of ordinary skill in the art would recognize that, when an amount of "a compound, a pharmaceutically acceptable salt thereof, or a deuterated derivative of any of the foregoing" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "10 mg of at least one compound chosen from compounds of Formula (1), pharmaceutically acceptable salts thereof, and deuterated derivatives of any of the foregoing" includes 10 mg of a compound of Formula (1) and a concentration of a pharmaceutically acceptable salt of compounds of Formula (1) equivalent to 10 mg of compounds of Formula (1).

As stated above, disclosed herein are compounds of Formula (1):

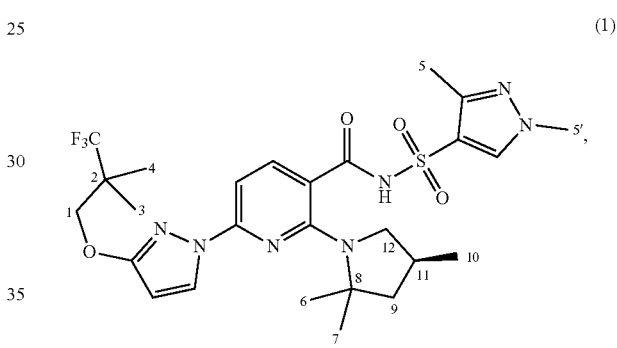

(1)

pharmaceutically acceptable salts thereof, and deuterated derivatives of any of the foregoing,
wherein:
at least one of the carbon atoms at positions 2 and 8 of Formula (1) is replaced by a silicon atom;
at least one of the methyl groups at positions 3, 4, 5, 5', 6, 7, and 10 of Formula (1) is replaced by a group chosen from —Si(R)$_3$ groups, —Si(R)$_2$(OR) groups, and —Si(R)(OR)$_2$ groups;
at least one of the methylene groups at positions 1, 9, and 12 of Formula (1) is replaced by a group chosen from >Si(R)$_2$ groups and >Si(R)(OR) groups; and/or
the methine group at position 11 of Formula (1) is replaced by a group chosen from Si(R) groups and Si(OR) groups; and
wherein each R, which may be identical or different, is independently chosen from hydrogen, hydroxyl, and $C_1$-$C_4$ alkyl groups. In some embodiments, each R may be identical or different, and is independently chosen from hydrogen and $C_1$-$C_4$ alkyl groups.

In some embodiments, at least one of the carbon atoms at positions 2 and 8 of Formula (1) is replaced by a silicon atom. In some embodiments, the carbon atoms at position 2 of Formula (1) is replaced by a silicon atom. In some embodiments, the carbon atoms at position 8 of Formula (1) is replaced by a silicon atom. In some embodiments, the carbon atoms at positions 2 and 8 of Formula (1) are both replaced by a silicon atom.

In some embodiments, at least one of the methyl groups at positions 3, 4, 5, 5', 6, 7, and 10 of Formula (1) is replaced by a group chosen from —Si(R)₃ groups, —Si(R)₂(OR) groups, and —Si(R)(OR)₂ groups. In some embodiments, the methyl groups at position 3 of Formula (1) is replaced by a group chosen from —Si(R)₃ groups, —Si(R)₂(OR) groups, and —Si(R)(OR)₂ groups. In some embodiments, the methyl groups at position 4 of Formula (1) is replaced by a group chosen from —Si(R)₃ groups, —Si(R)₂(OR) groups, and —Si(R)(OR)₂ groups. In some embodiments, the methyl groups at position 5 of Formula (1) is replaced by a group chosen from —Si(R)₃ groups, —Si(R)₂(OR) groups, and —Si(R)(OR)₂ groups. In some embodiments, the methyl groups at position 5' of Formula (1) is replaced by a group chosen from —Si(R)₃ groups, —Si(R)₂(OR) groups, and —Si(R)(OR)₂ groups. In some embodiments, the methyl groups at position 6 of Formula (1) is replaced by a group chosen from —Si(R)₃ groups, —Si(R)₂(OR) groups, and —Si(R)(OR)₂ groups. In some embodiments, the methyl groups at position 7 of Formula (1) is replaced by a group chosen from —Si(R)₃ groups, —Si(R)₂(OR) groups, and —Si(R)(OR)₂ groups. In some embodiments, the methyl groups at position 10 of Formula (1) is replaced by a group chosen from —Si(R)₃ groups, —Si(R)₂(OR) groups, and —Si(R)(OR)₂ groups. In some embodiments, the methyl groups at positions 3, 4, 5, 5', 6, 7, and 10 of Formula (1) are replaced by a group chosen from —Si(R)₃ groups, —Si(R)₂(OR) groups, and —Si(R)(OR)₂ groups.

In some embodiments, at least one of the methylene groups at positions 1, 9, and 12 of Formula (1) is replaced by a group chosen from >Si(R)₂ groups and >Si(R)(OR) groups. In some embodiments, the methylene groups at position 1 of Formula (1) is replaced by a group chosen from >Si(R)₂ groups and >Si(R)(OR) groups. In some embodiments, the methylene groups at position 12 of Formula (1) is replaced by a group chosen from >Si(R)₂ groups and >Si(R)(OR) groups. In some embodiments, at least two of the methylene groups at positions 1, 9, and 12 of Formula (1) are replaced by a group chosen from >Si(R)₂ groups and >Si(R)(OR) groups. In some embodiments, at least three the methylene groups at positions 1, 9, and 12 of Formula (1) is replaced by a group chosen from >Si(R)₂ groups and >Si(R)(OR) groups.

In some embodiments, at least one of the methylene groups at positions 1, 9, and 12 of Formula (1) is replaced by an >Si(R)₂ group. In some embodiments, the methylene groups at position 1 of Formula (1) is replaced by an >Si(R)₂ group. In some embodiments, the methylene groups at position 12 of Formula (1) is replaced by an >Si(R)₂ group. In some embodiments, at least two of the methylene groups at positions 1, 9, and 12 of Formula (1) are replaced by an >Si(R)₂ group. In some embodiments, at least three the methylene groups at positions 1, and 12 of Formula (1) is replaced by an >Si(R)₂ group.

In some embodiments, at least one of the methylene groups at positions 1, 9, and 12 of Formula (1) is replaced by an >Si(R)(OR) group. In some embodiments, the methylene groups at position 12 of Formula (1) is replaced by an >Si(R)(OR) group. In some embodiments, at least two of the methylene groups at positions 1, 9, and 12 of Formula (1) are replaced by an >Si(R)(OR) group. In some embodiments, at least three the methylene groups at positions 1, 9, and 12 of Formula (1) is replaced by an >Si(R)(OR) group.

In some embodiments, the methine group at position 11 of Formula (1) is replaced by a group chosen from Si(R) groups and Si(OR) groups. In some embodiments, the methine group at position 11 of Formula (1) is replaced by an Si(R) group. In some embodiments, the methine group at position 11 of Formula (1) is replaced by an Si(OR) group.

In some embodiments, the novel compound is chosen from compounds of Compound (1-1):

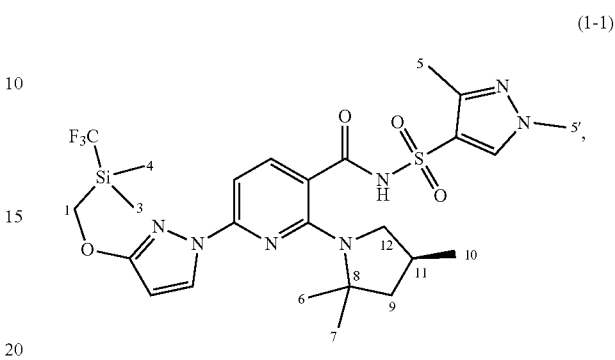

(1-1)

and pharmaceutically acceptable salts and deuterated derivatives thereof.

In some embodiments, the novel compound is chosen from Compound (1-2):

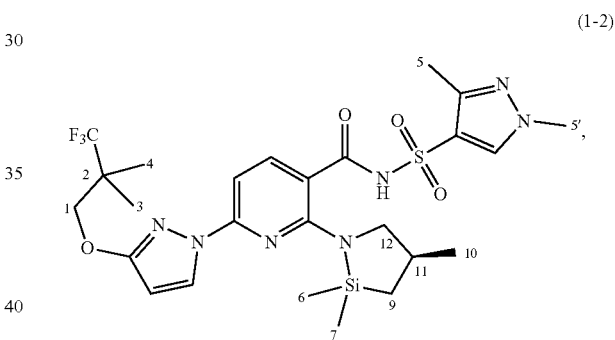

(1-2)

and pharmaceutically acceptable salts and deuterated derivatives thereof.

In some embodiments, the novel compound is chosen from compounds of Formula (1-3), compounds of Formula (1-4), compounds of Formula (1-5), compounds of Formula (1-6), compounds of Formula (1-7), compounds of Formula (1-8), compounds of Formula (1-9), compounds of Formula (1-10), compounds of Formula (1-11):

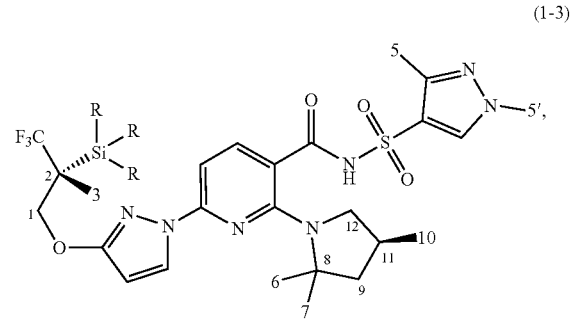

(1-3)

(1-4)
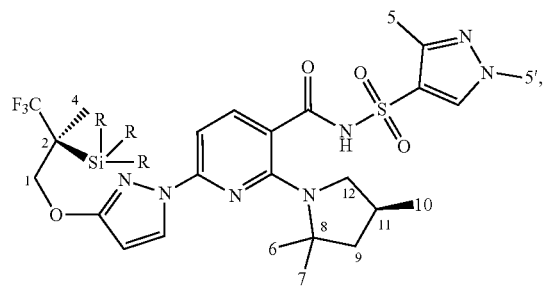

(1-5)
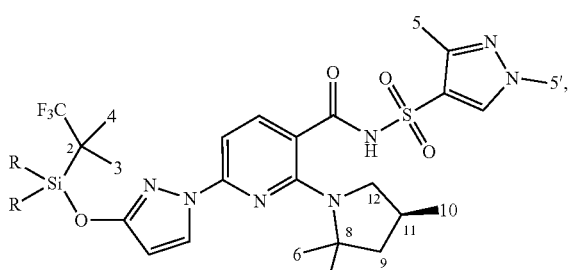

(1-6)
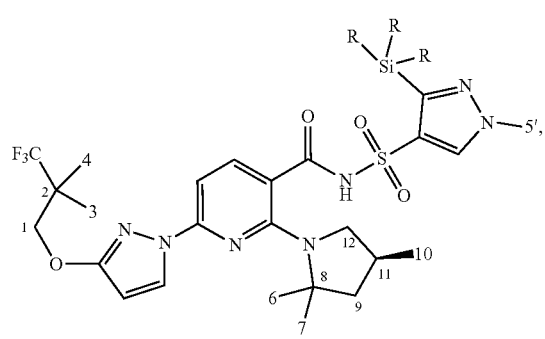

(1-7)
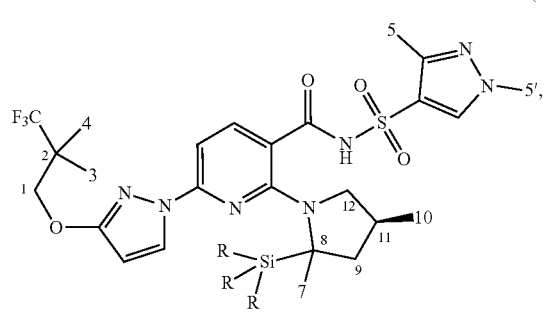

(1-8)
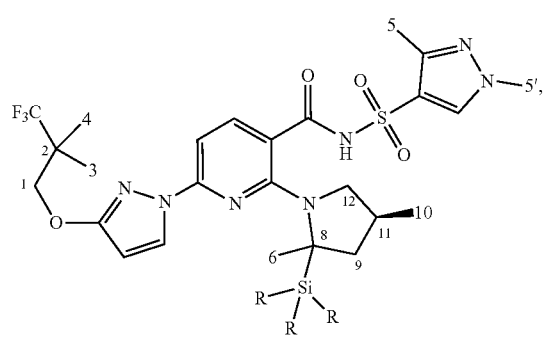

(1-9)
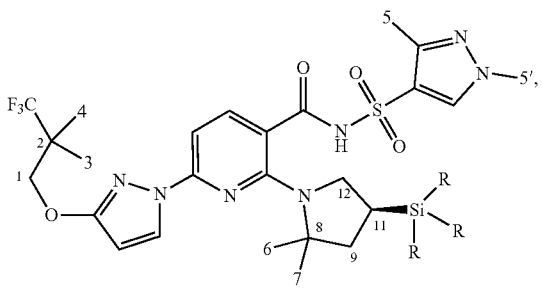

(1-10)
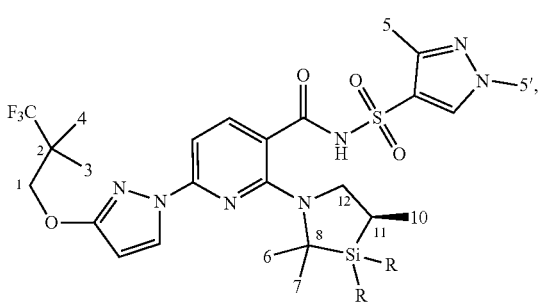

(1-11)
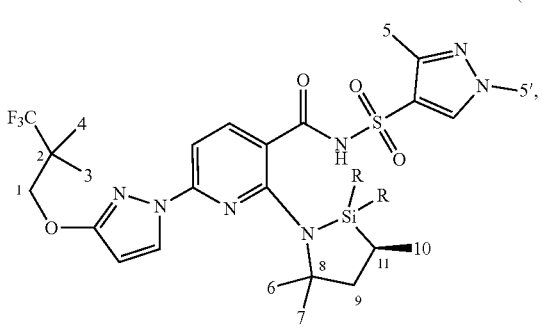

wherein each R is independently chosen from hydrogen, hydroxyl, —O(C$_1$-C$_4$ alkyl), and C$_1$-C$_4$ alkyl groups, and pharmaceutically acceptable salts thereof, and deuterated derivatives of any of the foregoing.

In some embodiments, each R is independently chosen from hydrogen and C$_1$-C$_4$ alkyl groups. In some embodiments, at least one hydrogen atom of at least one R group in the novel compounds disclosed herein is replaced by a deuterium atom. In some embodiments, each R is independently chosen from C$_1$ alkyl groups and C$_2$ alkyl groups. In some embodiments, each R is independently —CH$_3$ or —CD$_3$. In some embodiments, each R is independently —CH$_3$.

In some embodiments, the novel compound is chosen from Compounds (1-12) and (1-13):

(1-12)

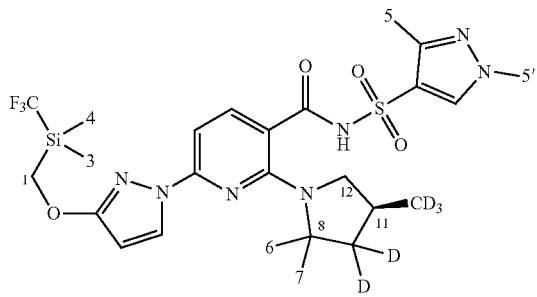

(1-13)

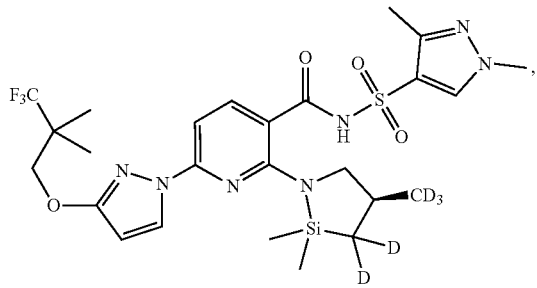

and pharmaceutically acceptable salts and deuterated derivatives thereof.

In some embodiments, the novel compound is chosen from compounds of Formula (1-14):

(1-14)

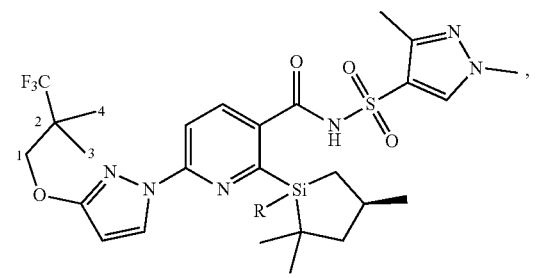

wherein R is —OH, —O(C$_1$-C$_4$ alkyl), or a C$_1$-C$_4$ alkyl group, and pharmaceutically acceptable salts and deuterated derivatives thereof. In some embodiments, R is —OH. In some embodiments, R is a —C$_1$-C$_4$ alkyl group. In some embodiments, R is a —O(C$_1$-C$_4$ alkyl) group.

Isomeric mixtures and enantioenriched (e.g., >90% ee, >95% ee, or >98% ee) isomers are included in the scope of the present disclosure.

In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and (4-1)-(4-5), and pharmaceutically acceptable salts and deuterated derivatives thereof, can be administered in combination with at least one additional active pharmaceutical ingredient. In some embodiments, at least one additional active pharmaceutical ingredient is chosen from:

(a) Compound (II):

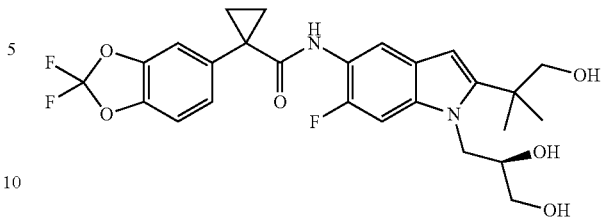

and pharmaceutically acceptable salts thereof (wherein a chemical name for Compound (II) is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide);

(b) Compound (III):

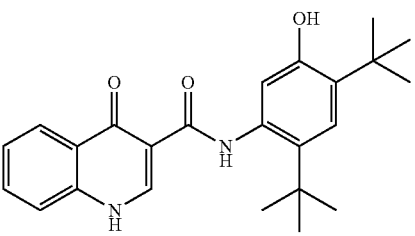 [SMILES: CC(C)(C)c1cc(C(C)(C)C)c(NC(=O)c2c[nH]c3ccccc3c2=O)cc1O]

and pharmaceutically acceptable salts thereof (wherein a chemical name for Compound (III) is N-(5-hydroxy-2,4-di-tert-butyl-phenyl)-4-oxo-1H-quinoline-3-carboxamide);

(c) Compound (III-d) can be depicted as having the following structure:

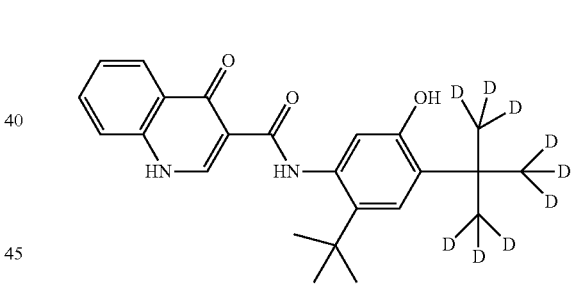

(wherein a chemical name for Compound (III-d) is N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide); and (d) Compound (IV):

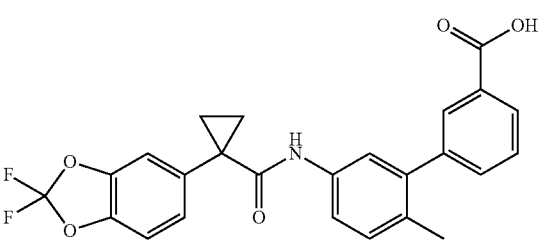 [SMILES: Cc1ccc(NC(=O)C2(c3ccc4c(c3)OC(F)(F)O4)CC2)cc1-c1cccc(C(=O)O)c1]
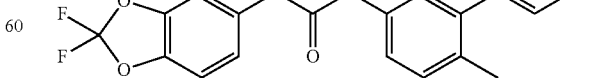

and pharmaceutically acceptable salts thereof (wherein a chemical name for Compound IV is 3-(6-(1-(2,2-difluorobenzo[d][1,3]dioxol-5-yl)cyclopropanecarboxamido)-3-methylpyridin-2-yl)benzoic acid).

In certain embodiments, at least one compound chosen from Compounds (2-1) (2-12), (3-1), (3-2), (3-3) and pharmaceutically acceptable salts and deuterated derivatives thereof, can be administered in combination with at least one additional active pharmaceutical ingredient. In some embodiments, the at least one additional active pharmaceutical ingredient is chosen from Compounds II, III, and pharmaceutically acceptable salts and deuterated derivatives thereof, including Compound III-d and pharmaceutically acceptable salts thereof.

Suitable pharmaceutically acceptable salts are, for example, those disclosed in S. M. Berge, et al. *J. Pharmaceutical Sciences*, 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered in combination with at least one compound chosen from Compound (II), pharmaceutically acceptable salts and deuterated derivatives thereof. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered in combination with at least one compound chosen from Compound (III) and pharmaceutically acceptable salts thereof. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered in combination with at least one compound chosen from Compound (III-d) and pharmaceutically acceptable salts thereof. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered in combination with at least one compound chosen from Compound (IV) and pharmaceutically acceptable salts thereof. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered in combination with Compounds (II) or a pharmaceutically acceptable salt or deuterated derivative thereof and at least one compound chosen from Compound (III), Compound (III-d), and pharmaceutically acceptable salts thereof. In some embodiments, at least one compound chosen from compounds of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), and pharmaceutically acceptable salts and deuterated derivatives thereof, is administered in combination with at least one compound chosen from Compound (III) and pharmaceutically acceptable salts thereof, and deuterated derivatives of any of the foregoing and at least one compound chosen from Compound (IV) and pharmaceutically acceptable salts and deuterated derivatives thereof.

Any of the novel compounds disclosed herein, such as for example, Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), pharmaceutically acceptable salts thereof, and deuterated derivatives of such compounds and salts can be comprised in a single pharmaceutical composition or separate pharmaceutical compositions optionally in combination with other additional active pharmaceutical ingredient(s) (e.g., Compound (II), (III), (III-d), or (IV), or a pharmaceutically acceptable salt or deuterated derivative of such Compound or salt). Such pharmaceutical compositions can be administered once daily or multiple times daily, such as, e.g., twice daily. In some embodiments, the disclosure features a pharmaceutical composition comprising at least one compound chosen from any of the compounds disclosed herein and pharmaceutically acceptable salts thereof, and at least one pharmaceutically acceptable carrier.

In some embodiments, the disclosure features a pharmaceutical composition comprising at least one compound chosen from Compounds (2-1)-(2-12), (3-1), (3-2), (3-3), and pharmaceutically acceptable salts and deuterated derivatives thereof; at least one compound chosen from Compound (II) and pharmaceutically acceptable salts thereof; and at least one pharmaceutically acceptable carrier.

In some embodiments, the disclosure features a pharmaceutical composition comprising at least one compound chosen from Compounds (2-1)-(2-12), (3-1), (3-2), (3-3), and pharmaceutically acceptable salts and deuterated derivatives thereof; at least one compound chosen from Compound (III) and pharmaceutically acceptable salts thereof; and at least one pharmaceutically acceptable carrier.

In some embodiments, the disclosure features a pharmaceutical composition comprising at least one compound chosen from Compounds (2-1)-(2-12), (3-1), (3-2), (3-3), and pharmaceutically acceptable salts and deuterated derivatives thereof; at least one compound chosen from Compound (II) and pharmaceutically acceptable salts thereof; at least one compound chosen from Compound (III), Compound (III-d), and pharmaceutically acceptable salts thereof; and at least one pharmaceutically acceptable carrier.

In some embodiments, the disclosure features a pharmaceutical composition comprising at least one compound chosen from Compounds (2-1)-(2-12), (3-1), (3-2), (3-3), and pharmaceutically acceptable salts and deuterated derivatives thereof; at least one compound chosen from Compound (III), Compound (III-d), and pharmaceutically acceptable salts thereof; at least one compound chosen from Compound (IV) and pharmaceutically acceptable salts thereof; and at least one pharmaceutically acceptable carrier.

In some embodiments, pharmaceutical compositions disclosed herein comprise at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises (i) a compound of Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), or a pharmaceutically acceptable salt thereof, or a deuterated derivative of such compound or salt; and (ii) at least two additional active pharmaceutical ingredients, one of which is a CFTR corrector and one of which is a CFTR potentiator.

In some embodiments, at least one additional active pharmaceutical ingredient is selected from mucolytic agents, bronchodilators, antibiotics, anti-infective agents, and anti-inflammatory agents.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure, including a pharmaceutical composition comprising combinations described previously, can be employed in combination therapies; that is, the compositions can be administered concurrently with, prior to, or subsequent to, at least one additional active pharmaceutical ingredient or medical procedures.

Pharmaceutical compositions comprising these combinations are useful for treating cystic fibrosis.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

It will also be appreciated that a pharmaceutical composition of this disclosure, including a pharmaceutical composition comprising any of the combinations described previously, can be employed in combination therapies; that is, the compositions can be administered concurrently with, prior to, or subsequent to, at least one active pharmaceutical ingredients or medical procedures.

In some embodiments, the methods of the disclosure employ administering to a patient in need thereof at least one compound chosen from Formulae (1), (1-3)-(1-11), (1-14), (2), and (3), Compounds (1-1), (1-2), (1-12), (1-13), Compounds (2-1)-(2-12), Compounds (3-1), (3-2), (3-3), and Compounds (4-1)-(4-5), pharmaceutically acceptable salts and deuterated derivatives thereof, and at least one compound chosen from Compound (II), Compound (III), Compound (III-d), Compound (IV), and pharmaceutically acceptable salts of any of the foregoing. In some embodiments, the methods disclosed herein employ at least one compound chosen from Compounds (2-1)-(2-12), (3-1), (3-2), (3-3), and pharmaceutically acceptable salts and deuterated derivatives thereof, and at least one compound chosen from Compound (II), Compound (III), Compound (III-d), Compound (IV), and pharmaceutically acceptable salts thereof.

Any suitable pharmaceutical compositions known in the art can be used for the novel compounds disclosed herein, Compound (II), Compound (III), Compound (IV), and pharmaceutically acceptable salts thereof. Some exemplary pharmaceutical compositions for Compound (I) and its pharmaceutically acceptable salts are described in the Examples. Some exemplary pharmaceutical compositions for Compound (II) and its pharmaceutically acceptable salts can be found in WO 2011/119984 and WO 2014/015841, all of which are incorporated herein by reference. Some exemplary pharmaceutical compositions for Compound (III) and its pharmaceutically acceptable salts can be found in WO 2007/134279, WO 2010/019239, WO 2011/019413, WO 2012/027731, and WO 2013/130669, all of which are incorporated herein by reference. Some exemplary pharmaceutical compositions for Compound (IV) and its pharmaceutically acceptable salts can be found in WO 2010/037066, WO 2011/127241, WO 2013/112804, and WO 2014/071122, all of which are incorporated herein by reference.

In some embodiments, a pharmaceutical composition comprising at least one compound chosen from compounds of Formulae (1) (including Formulae (1-3)-(1-11), and (1-14)), (2), and (3) (e.g., at least one of Compounds (1-1), (1-2), (1-12), (1-13), (2-2)-(2-15), and (3-1)-(3-4)), and pharmaceutically acceptable salts and deuterated derivatives thereof, is administered with a pharmaceutical composition comprising Compound (II) and Compound (III). In some embodiments, a pharmaceutical composition comprising at least one compound chosen from Formulae (1), (1-3)-(1-11), (1-14), (2), and (3), Compounds (1-1), (1-2), (1-12), (1-13), Compounds (2-1)-(2-12), Compounds (3-1), (3-2), (3-3), and pharmaceutically acceptable salts and deuterated derivatives thereof, is administered with a pharmaceutical composition comprising Compound (II) and Compound (III-d). Pharmaceutical compositions comprising Compound (II) and Compound (III) are disclosed in PCT Publication No. WO 2015/160787, incorporated herein by reference. An exemplary embodiment is shown in the following Table:

TABLE 2

Exemplary Tablet Comprising 100 mg of Compound II and 150 mg of Compound III.

| | Ingredient | Amount per tablet (mg) |
|---|---|---|
| Intra-granular | Compound II SDD (spray dried dispersion) (80 wt % Compound II, 20 wt % HPMC) | 125 |
| | Compound III SDD (80 wt % Compound III, 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadry | 17.7 |
| Total coated Tablet | | 609.6 |

In some embodiments, a pharmaceutical composition comprising at least one compound chosen from the novel compounds disclosed herein and pharmaceutical salts thereof is administered with a pharmaceutical composition comprising Compound (III). Pharmaceutical compositions comprising Compound (III) are disclosed in PCT Publication No. WO 2010/019239, incorporated herein by reference. An exemplary embodiment is shown in the following Table:

TABLE 3

Ingredients for Exemplary Tablet of Compound III.

| Tablet Formulation | Percent Dose % Wt./Wt. | Dose (mg) | Batch (g) |
|---|---|---|---|
| Compound III SDD (80 wt % Compound III, 19.5 wt % HPMCAS-HG; 0.5 wt % sodium lauryl sulfate) | 34.09% | 187.5 | 23.86 |
| Microcrystalline cellulose | 30.51% | 167.8 | 21.36 |
| Lactose | 30.40% | 167.2 | 21.28 |
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

Additional pharmaceutical compositions comprising Compound (III) are disclosed in PCT Publication No. WO 2013/130669, incorporated herein by reference. Exemplary mini-tablets (~2 mm diameter, ~2 mm thickness, each mini-tablet weighing about 6.9 mg) was formulated to have approximately 50 mg of Compound (III) per 26 mini-tablets and approximately 75 mg of Compound (III) per 39 mini-tablets using the amounts of ingredients recited in Table 4, below.

TABLE 4

Ingredients for mini-tablets for 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Compound III SDD (80 wt % Compound III, 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

Pharmaceutical compositions comprising Compound (III-d) can be made in a similar manner as those for Compound (III).

In some embodiments, the pharmaceutical compositions are a tablet. In some embodiments, the tablets are suitable for oral administration.

These combinations are useful for treating cystic fibrosis.

A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes.

In some embodiments, disclosed herein methods of treating, lessening the severity of, or symptomatically treating cystic fibrosis in a patient comprising administering an effective amount of a compound, pharmaceutically acceptable salt thereof, or a deuterated analog of any of the foregoing; or a pharmaceutical composition, of this disclosure to a patient, such as a human, wherein said patient has cystic fibrosis. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation.

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance.

In some embodiments, the patient is heterozygous and has an F508del mutation on one allele and a mutation on the other allele selected from Table 5:

TABLE 5

CFTR Mutations
Mutation

| | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C | 3600 + 2insT |
| 405 + 1G→A | 1249 − 1G→A | 1811 + 1.6kbA→G | (G970R) | 3850 − 1G→A |
| 405 + 3A→C | 1341 + 1G→A | 1811 + 1643G→T | 3120G→A | 4005 + 1G→A |
| 406 − 1G→A | 1525 − 2A→G | 1812 − 1G→A | 3120 + 1G→A | 4374 + 1G→T |
| 621 + 1G→T | 1525 − 1G→A | 1898 + 1G→A | 3121 − 2A→G | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365-366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |

TABLE 5-continued

| CFTR Mutations Mutation | | | | |
|---|---|---|---|---|
| 849delG | 1548delG | 2585delT | 3349insT | 4326delTC |
| 935delA | 1609del CA | 2594delGT | 3659delC | |
| CFTRdele1 | | CFTRdele16-17b | 1461ins4 | |
| CFTRdele2 | | CFTRdele17a, 17b | 1924del7 | |
| CFTRdele2, 3 | | CFTRdele17a-18 | 2055del9→A | |
| CFTRdele2-4 | | CFTRdele19 | 2105-2117del13insAGAAA | |
| CFTRdele3-10, 14b-16 | | CFTRdele19-21 | 2372del8 | |
| CFTRdele4-7 | | CFTRdele21 | 2721del11 | |
| CFTRdele4-11 | | CFTRdele22-24 | 2991del32 | |
| CFTR50kbdel | | CFTRdele22,23 | 3667ins4 | |
| CFTRdup6b-10 | | 124del23bp | 4010del4 | |
| CFTRdele11 | | 602del14 | 4209TGTT→AA | |
| CFTRdele13, 14a | | 852del22 | | |
| CFTRdele14b-17b | | 991del5 | | |
| A46D | V520F | Y569D | N1303K | |
| G85E | A559T | L1065P | | |
| R347P | R560T | R1066C | | |
| L467P | R560S | L1077P | | |
| I507del | A561E | M1101K | | |

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

In some embodiments of the methods of treating cystic fibrosis disclosed herein, the absolute change in patient's percent predicted forced expiratory volume in one second (ppFEV$_1$) after 15 days of administration of at least one compound chosen from Compound (I) and pharmaceutically acceptable salts thereof, at least one compound chosen from Compound (II) and pharmaceutically acceptable salts thereof, and at least one compound chosen from Compound (III) or (III-d) and pharmaceutically acceptable salts thereof ranges from 3% to 40% relative to the ppFEV1 of the patient prior to said administration.

In some embodiments of the methods of treating cystic fibrosis disclosed herein, the absolute change in patient's percent predicted forced expiratory volume in one second (ppFEV$_1$) after 29 days of administration of at least one compound chosen from compounds of Formula (1), (2) and (3), and pharmaceutically acceptable salts thereof and deuterated derivatives thereof, at least one compound chosen from Compound (II) and pharmaceutically acceptable salts thereof, and at least one compound chosen from Compound (III) and pharmaceutically acceptable salts thereof ranges from 3% to 40% relative to the ppFEV1 of the patient prior to said administration. In some embodiments, the absolute change ppFEV$_1$ after 29 days ranges from 4% to 40% relative to the ppFEV1 of the patient prior to administration. In some embodiments, the absolute change ppFEV$_1$ after 29 days ranges from 6% to 40% relative to the ppFEV1 of the patient prior to administration. In some embodiments, the absolute change ppFEV$_1$ after 29 days ranges from 7% to 40% relative to the ppFEV1 of the patient prior to administration.

In some embodiments of the methods of treating cystic fibrosis disclosed herein, the absolute change in the patient's sweat chloride after 15 days of administration of at least one compound chosen from compounds of Formulae (1), (2), and (3), and pharmaceutically acceptable salts and deuterated derivatives thereof, at least one compound chosen from Compound (II) and pharmaceutically acceptable salts thereof, and at least one compound chosen from Compound (III) or (III-d) and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −3 to −65 mmol/L. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −20 to −65 mmol/L. In some embodiments, the absolute change in sweat chloride of said patient ranges from −30 to −65 mmol/L. In some embodiments, the absolute change in sweat chloride of said patient ranges from −38 to −65 mmol/L. In some embodiments of the methods of treating cystic fibrosis disclosed herein, the absolute change in the patient's sweat chloride after 29 days of administration of at least one compound chosen from compounds of Formulae (1), (2), and (3), and pharmaceutically acceptable salts and deuterated derivatives thereof, at least one compound chosen from Compound (II) and pharmaceutically acceptable salts thereof, and at least one compound chosen from Compound (III) or (III-d) and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −3 to −65 mmol/L. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −20 to −65 mmol/L. In some embodiments, the absolute change in sweat chloride of said patient ranges from −30 to −65 mmol/L. In some embodiments, the absolute change in sweat chloride of said patient ranges from −38 to −65 mmol/L.

In some embodiments of the methods of treating cystic fibrosis disclosed herein, the absolute change in the patient's sweat chloride after 29 days of administration of at least one compound chosen from compounds of Formulae (1), (2), and (3), and pharmaceutically acceptable salts and deuterated derivatives thereof, at least one compound chosen from Compound (II) and pharmaceutically acceptable salts thereof, and at least one compound chosen from Compound (III) and pharmaceutically acceptable salts thereof ranges from −2 to −65 mmol/L from baseline, i.e., relative to the sweat chloride of the patient prior to said administration. In some embodiments, the absolute change in sweat chloride of said patient ranges from −5 to −65 mmol/L. In some embodiments, the absolute change in sweat chloride of said patient ranges from −10 to −65 mmol/L. In some embodiments, the absolute change in sweat chloride of said patient ranges from −2 to −65 mmol/L.

In some embodiments, the triple combinations are administered to a patient who has one F508del mutation and one minimal function mutation, and who has not taken any of said at least one compound chosen from compounds of Formulae (1), (2), and (3), and pharmaceutically acceptable salts and deuterated derivatives thereof, at least one compound chosen from Compound (II) and pharmaceutically acceptable salts thereof, and at least one compound chosen from Compound (III) or (III-d) and pharmaceutically acceptable salts thereof.

In some embodiments, the triple combinations are administered to a patient has two copies of F508del mutation, and wherein patient has taken at least one compound chosen from Compound (II) and pharmaceutically acceptable salts thereof, and at least one compound chosen from Compound (III) or (III-d) and pharmaceutically acceptable salts thereof, but not any of said at least one compound chosen from compounds of Formulae (1), (2), and (3), and pharmaceutically acceptable salts and deuterated derivatives thereof.

In some embodiments, the absolute change in patient's ppFEV$_1$ after 15 days of administration of at least one compound chosen from compounds of Formulae (1), (2), and (3), and pharmaceutically acceptable salts and deuterated derivatives thereof, and optionally, at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 35% relative to the ppFEV1 of the patient prior to said administration.

In some embodiments, the absolute change in patient's ppFEV$_1$ after 29 days of administration of at least one compound chosen from compounds of Formulae (1), (2), and (3), and pharmaceutically acceptable salts and deuterated derivatives thereof, and optionally, at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof ranges from 3% to 35% relative to the ppFEV1 of the patient prior to said administration.

In some embodiments, the absolute change in a patient's ppFEV$_1$ relative to the ppFEV1 of the patient prior to such administration of the triple combinations can be calculated as (postbaseline value-baseline value). The baseline value is defined as the most recent non-missing measurement collected before the first dose of study drug in the Treatment Period (Day 1).

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which, in some embodiments, are referred to as Compound I', Compound II', Compound III', Compound III-d or Compound IV'. In some embodiments, Compound I', Compound II', Compound III', Compound III-d, Compound IV', or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^3H$)- and/or carbon-14 ($^{14}C$)-labelled compounds are particularly useful for various types of assays, such as substrate tissue distribution assays, due to relatively simple preparation and excellent detectability. For example, deuterium ($^2H$)-labelled ones are therapeutically useful with potential therapeutic advantages over the non-$^2H$-labelled compounds. In general, deuterium ($^2H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2H$)-labelled ones. In some specific embodiments, the isotope-labelled compounds and salts are deuterium ($^2H$)-labelled, wherein one or more hydrogen atoms therein have been replaced by deuterium. In chemical structures, deuterium is represented as "D."

The deuterium ($^2H$)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. For a further discussion, see S. L. Harbeson and R. D. Tung, *Deuterium In Drug Discovery and Development*, Ann. Rep. Med. Chem. 2011, 46, 403-417, which is incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

In some embodiments, Compound III' as used herein includes the deuterated compound disclosed in U.S. Pat. No. 8,865,902 (which is incorporated herein by reference), and CTP-656.

In some embodiments, Compound III' is Compound (III-d):

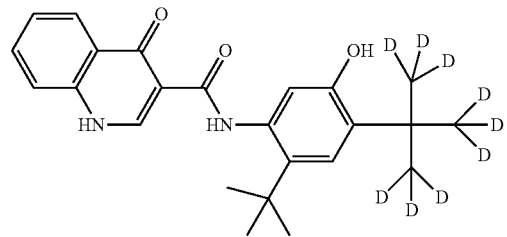 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

The novel compounds disclosed herein (e.g., compounds of Formula (1) (including Formulae (1-3)-(1-11), (1-14)), Formula (2), and Formula (3), Compounds (1-1), (1-2), (1-12), (1-13), (2-2)-(2-15), (3-1)-(3-4), and (4-1)-(4-5), and pharmaceutically acceptable salts and deuterated derivatives thereof) can be prepared by suitable methods known in the art. For example, they can be prepared in accordance with procedures described in WO2016/057572 and by the exemplary syntheses described below. For example, deuterated derivatives of the novel compounds disclosed herein and pharmaceutically acceptable salts thereof can be prepared in a similar manner as those for non-deuterated compounds and pharmaceutically acceptable salts thereof by employing intermediates and/or reagents where one or more hydrogen atoms are replaced with deuterium. For example, see T. G. Gant "Using deuterium in drug discovery: leaving the label in the drug" J. Med. Chem. 2014, 57, 3595-3611, the relevant portions of which are incorporated herein by reference. For example, Si incorporated compounds described herein can be prepared in a similar manner as those for non-Si compounds and pharmaceutically acceptable salts thereof by employing intermediates and/or reagents where one or more Si units (e.g., Si, —Si(R)₃, —Si(R)₂(OR), —Si(R)(OR)₂, >Si(R)₂, >Si(R)(OR), ≡Si(R) and ≡Si(OR) groups) by employing Si chemistry known in the art. For example, see International Patent Application Publication Nos. WO2017223188 and WO2017177124, *Journal of Organic Chemistry* 1971, 36, 3120-3126, and *Organometallics* 1991, 10, 2095-6, the relevant portions of which are incorporated herein by reference. For example, boron (B) incorporated compounds described herein can be prepared in a similar manner as those for non-B compounds and pharmaceutically acceptable salts thereof by employing intermediates and/or reagents where one or more B units by employing B chemistry known in the art. For example, see S. J. Baker et al., "Therapeutic potential of boron-containing compounds," *Future Med. Chem.*, 2009, 1(7), 1275-1288 and F. Issa et al., "Boron in Drug Discovery: Carboranes as Unique Pharmacophores in Biologically Active Compounds", *Chem. Rev.* 2011, 111, 5701-5722, the relevant portions of each of which are incorporated herein by reference.

In some embodiments, compounds of Formulae (1) (including Formulae (1-3)-(1-11), (1-14)), (2), and (3), Compounds (1-1), (1-2), (1-12), (1-13), (2-2)-(2-15), (3-1)-(3-4), and (4-1)-(4-5), and pharmaceutically acceptable salts and deuterated derivatives thereof, are prepared as depicted in Schemes 1-4, wherein the variables therein are each and independently are as those for Formulae (1) and (1-3)-(1-11) above, and wherein each Ph is phenyl; each $R^a$ is independently chosen from $C_1$-$C_4$ alkyl groups; and each $X^a$ is independently chosen from F or Cl. Suitable condition(s) known in the art can be employed for each step depicted in the schemes.

In some embodiments, as shown in Scheme 1, the methods comprise reacting a compound of Formula (F-1) or a salt thereof with a compound of Formula (G-1) or a salt thereof to generate a compound of Formula (1), a pharmaceutically acceptable salt thereof, or a deuterated derivative of any of the foregoing.

Any suitable conditions, such as those for a nucleophilic reaction of amine, known in the art can be used. In some embodiments, the reaction depicted in Scheme 1 is performed in the presence of a base, such as a metal carbonate (e.g., $Na_2CO_3$ or $K_2CO_3$).

In some embodiments, a salt of a compound of Formula (G-1) is employed. In some embodiments, an HCl salt of a compound of Formula (G-1) is employed.

A compound of Formula (F-1) or a salt thereof and a compound of Formula (G-1) or a salt thereof can be prepared by any suitable method known in the art, for example, those in WO2016/57572 and those in the exemplary syntheses described below in the Examples.

In some embodiments, as shown in Scheme 2, a compound of Formula (F-2), a pharmaceutically acceptable salt thereof, or a deuterated derivative of any of the foregoing is prepared by a method that comprises reacting a compound of Formula (D-1) or a salt thereof with a compound of Formula (E-1) or a salt thereof. In some embodiments, compounds of Formula (D-1), salts thereof, or deuterated derivatives of any of the foregoing are prepared by a method that comprises reacting a compound of Formula (A-1) or a salt thereof with a compound of Formula (B-1) or a salt thereof to generate a compound of Formula (C-1) or a salt thereof; and hydrolyzing the —C(O)OR$^a$ of compound of Formula (C-1) to generate a compound of Formula (D-1) or a salt thereof. Any suitable conditions known in the art can be used for steps (a), (b), and (c) of Scheme 2 below, such as those for a coupling reaction between carboxylic acid and sulfonamide or those for an acylation of sulfonamide for step (a), those for hydrolysis of ester for step (b), and those for a nucleophilic reaction of amine for step (c).

In some embodiments, step (a) of Scheme 2 below is performed in the presence of a base. In some specific embodiments, step (a) is performed in the presence of a non-nucleophilic base. In some embodiments, in step (a), the reaction of a compound of Formula (D-1) or a salt thereof with a compound of Formula (E-1) or a salt thereof comprises reacting a compound of Formula (D-1) or a salt thereof with a coupling reagent, such as carbonyl diimidazole (CDI), and subsequently with a compound of Formula (E-1) or a salt thereof in the presence of a base, such as a non-nucleophilic base. In some embodiments, a compound of Formula (D-1) or a salt thereof is reacted with CDI prior to the reaction with a compound of Formula (E-1) or a salt thereof, and then subsequently with a compound of Formula (E-1) or a salt thereof in the presence of a base, such as DBU (1,8-Diazabicyclo(5.4.0)undec-7-ene).

In some embodiments, step (b) of Scheme 2 below is performed in the presence of a base. In some embodiments, step (b) is performed in the presence of an aqueous base, such as aqueous hydroxide. In some embodiments, step (b) is performed in the presence of an aqueous metal hydroxide, such as aqueous NaOH.

In some embodiments, step (c) of Scheme 2 below is performed in the presence of a base. In some embodiments, step (c) is performed in the presence of a metal carbonate (e.g., $Na_2CO_3$ or $K_2CO_3$).

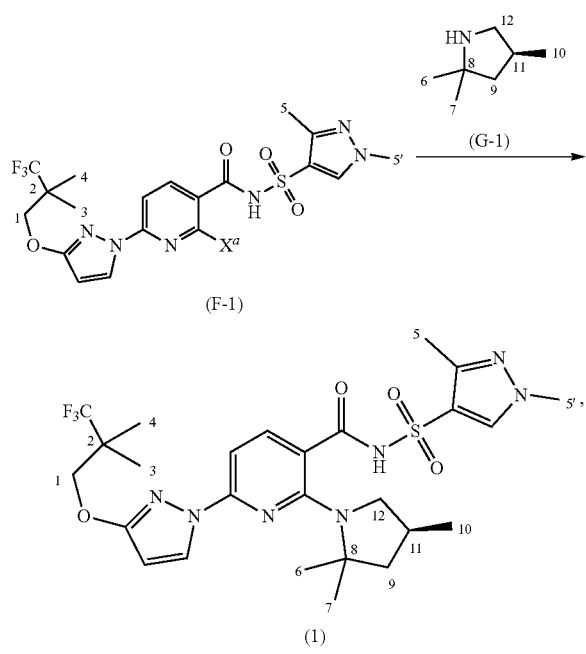

Scheme 1

Scheme 2

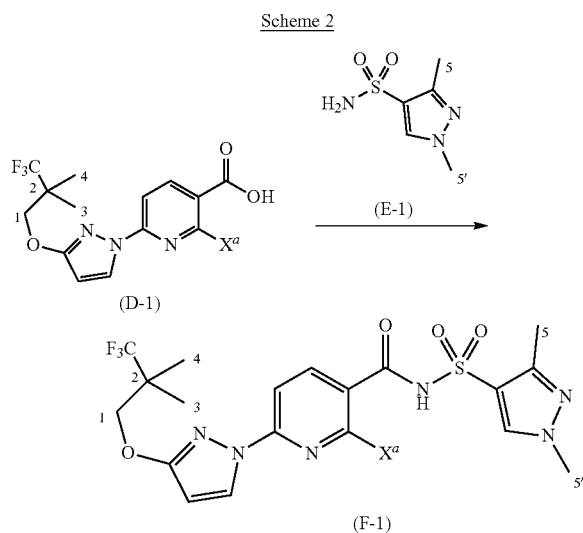

In some embodiments, compounds of Formula (D-1) or salts thereof, or their deuterated derivatives are prepared by a method that comprises reacting a compound of Formula (A-1) or a salt thereof with a compound of Formula (B-1) or a salt thereof to generate a compound of formula (C-1) or a salt thereof; and hydrolyzing the —C(O)OR$^a$ of compound of Formula (C-1) or salt thereof to generate a compound of formula (D-1) or a salt thereof, as shown in Scheme 3.

Scheme 3

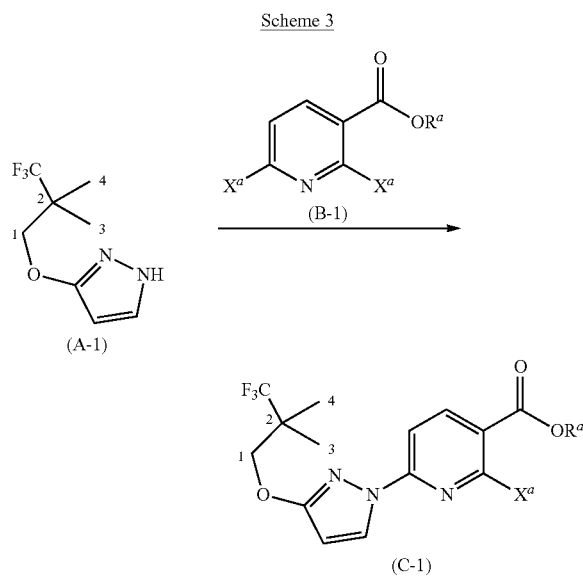

Any suitable conditions known in the art can be used for steps (a-1), (b-1), and (c-1) of Scheme 4 below, such as those for a coupling reaction between carboxylic acid and sulfonamide or those for an acylation of sulfonamide for step (a-1), those for hydrolysis of ester for step (b-1), and those for a nucleophilic reaction of amine for step (c-1).

In some embodiments, step (a-1) of Scheme 4 below is performed in the presence of a base. In some embodiments, step (a-1) of Scheme 4 below is performed in the presence of a non-nucleophilic base. In some embodiments, in step (a-1), the reaction of a compound of Formula (D-1) or a salt thereof with a compound of Formula (E-1) or a salt thereof comprises reacting a compound of Formula (D-1) or a salt thereof with a coupling reagent, such as carbonyl diimidazole (CDI), and subsequently with a compound of Formula (E-1) or a salt thereof in the presence of a base, such as a non-nucleophilic base. In some embodiments, (i) a compound of Formula (D-1) or a salt thereof is reacted with CDI prior to the reaction with a compound of Formula (E-1) or a salt thereof, and then subsequently (ii) the reaction product of step (i) is reacted with a compound of Formula (E-1) or a salt thereof in the presence of a base, such as DBU (1,8-diazabicyclo(5.4.0)undec-7-ene).

In some embodiments, step (b-1) of Scheme 4 below is performed in the presence of a base. In some embodiments, step (b-1) is performed in the presence of an aqueous base, such as aqueous hydroxide. In some embodiments, step (b-1) is performed in the presence of an aqueous metal hydroxide, such as aqueous NaOH.

In some embodiments, step (c-1) of Scheme 4 below is performed in the presence of a base. In some embodiments, step (c-1) is performed in the presence of a metal carbonate (e.g., $Na_2CO_3$ or $K_2CO_3$).

Scheme 4

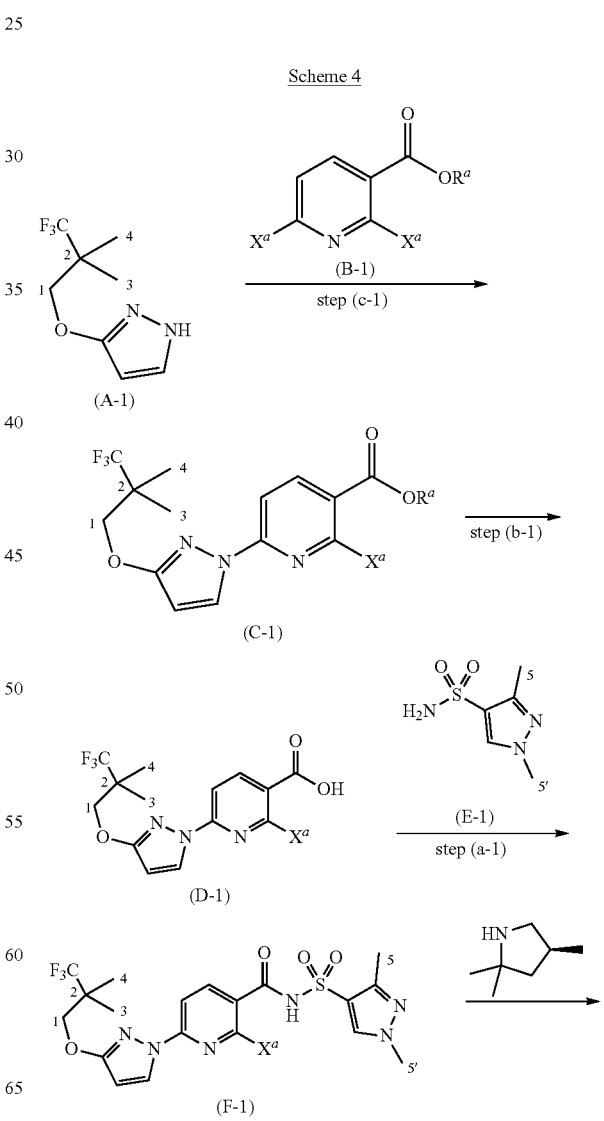

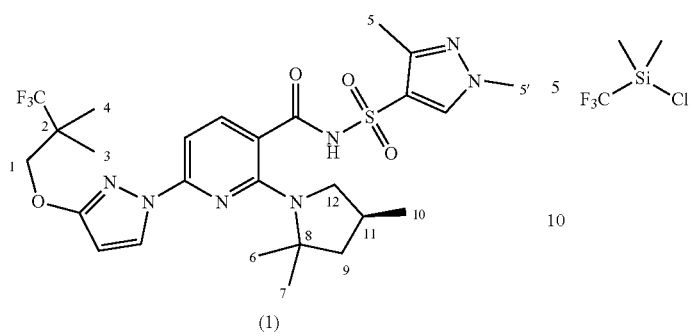

(1)

In Scheme 4, $R^a$ is chosen from $C_1$-$C_4$ alkyl groups; and each $X^a$ is independently chosen from F or Cl.

In some embodiments, Si-containing compounds of Formula (A-1) (e.g., compound of Formula (A-1a) and compound of Formula (A-1b)) can be made by employing Si chemistry known in the art, such as *Organometallics* 1991, 10, 2095-6 (the relevant portions of which are incorporated herein by reference). In one embodiment, compounds of Formula (A-1a) can be prepared as shown in Scheme 5.

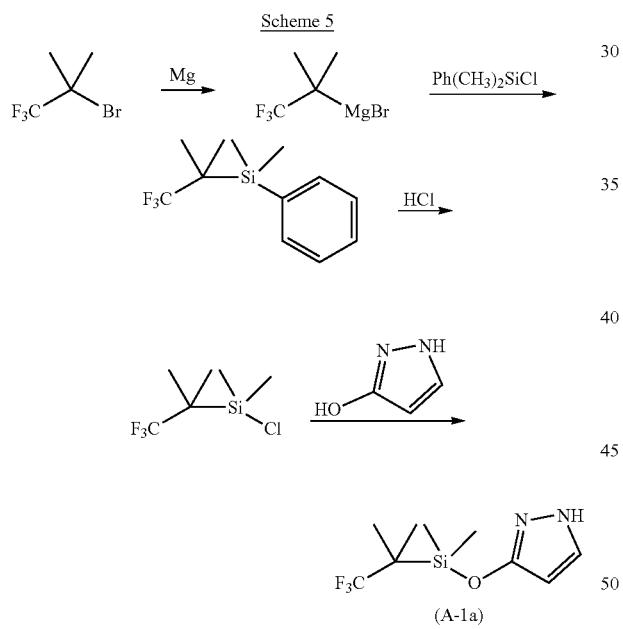

(A-1a)

In one specific embodiment, 2-bromo-1,1,1-trifluoro-2-methylpropane (1 eq.) is reacted with excess magnesium turnings to provide (1,1,1-trifluoro-2-methylpropan-2-yl)magnesium bromide which can be reacted with chlorodimethyl(phenyl)silane (1 eq.) to give dimethyl(phenyl)(1,1,1-trifluoro-2-methylpropan-2-yl)silane. Treatment of dimethyl (phenyl)(1,1,1-trifluoro-2-methylpropan-2-yl)silane with HCl can provide chlorodimethyl(1,1,1-trifluoro-2-methylpropan-2-yl)silane which can be reacted with 1H-pyrazol-3-ol to give 3-((dimethyl(1,1,1-trifluoro-2-methylpropan-2-yl)silyl)oxy)-1H-pyrazole (A-1a).

In one embodiment, compounds of Formula (A-1b) can be prepared as shown in Scheme 6.

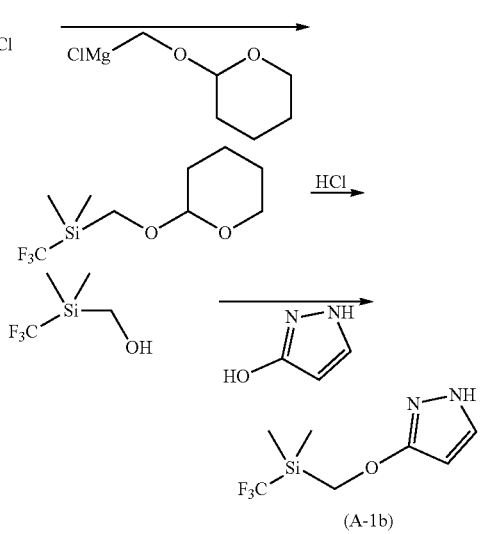

(A-1b)

In some embodiments, chlorodimethyl(trifluoromethyl)silane can be made as described in *Tetrahedron Letters* 1984, 25(21), 2195-8 (the relevant portions of which are incorporated herein by reference). Chlorodimethyl(trifluoromethyl)silane can be reacted with (2-((tetrahydro-2H-pyran-2-yl)oxy)ethyl)magnesium chloride (e.g., 1 eq.) to yield dimethyl (((tetrahydro-2H-pyran-2-yl)oxy)methyl)(trifluoromethyl)silane. Acid-catalyzed deprotection of dimethyl (((tetrahydro-2H-pyran-2-yl)oxy)methyl)(trifluoromethyl)silane can produce (dimethyl(trifluoromethyl)silyl)methanol which can be subjected to Mitsunobu conditions in the presence of 1H-pyrazol-3-ol to provide 3-((dimethyl(trifluoromethyl)silyl)methoxy)-1H-pyrazole.

In some embodiments, Si-containing compounds of Formula (G-1) (e.g., compound of Formula (G-1a)) can be made by employing Si chemistry known in the art, such as *Journal of Organic Chemistry* 1971, 36, 3120-3126 (the relevant portions of which are incorporated herein by reference). In some embodiments, a compound of Formula (G-1a) may be prepared as shown in Scheme 7. In some embodiments 3-((dimethyl(trifluoromethyl)silyl)methoxy)-1H-pyrazole may be reacted with ammonia.

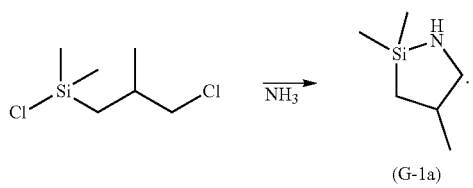

(G-1a)

Compounds of Formula (4-1), (4-2), (4-3), and (4-4) may be made by methods known to those of ordinary skill in the art.

In some embodiments, a compound of Formula (4-2) can be prepared according to reactions such as those in Scheme 8.

Scheme 8

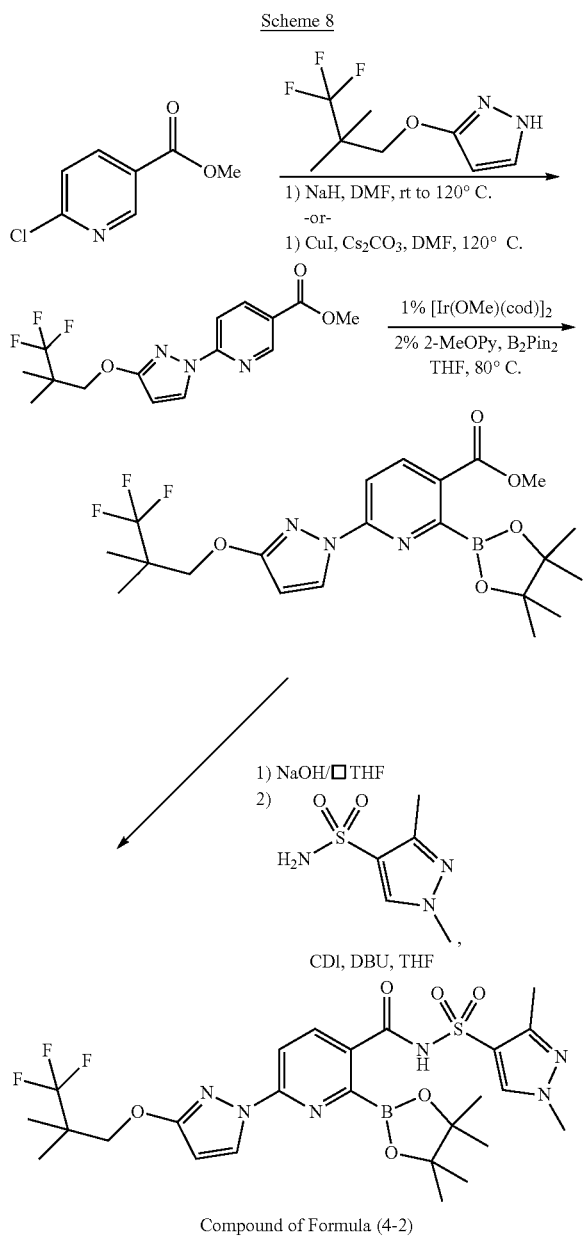

Compound of Formula (4-2)

3-(3,3,3-trifluoro-2,2-dimethylpropoxy)-1H-pyrazole, prepared as described herein, can be treated with sodium hydride and DMF. Methyl 6-chloronicotinate is added and stirred at room temperature to an elevated temperature, for example, 120° C., which can provide methyl 6-(3-(3,3,3-trifluoro-2,2-dimethylpropoxy)-1H-pyrazol-1-yl)nicotinate.

Following a procedure from US Published Patent Application No. 20150065743A1 (the relevant portions of which are incorporated herein by reference), the iridium catalyst, the ligand, bispinacol diboron, and THF can be pre-stirred under a nitrogen atmosphere. methyl 6-(3-(3,3,3-trifluoro-2,2-dim ethyl propoxy)-1H-pyrazol-1-yl)nicotinate can be added and stirred at, for example, 80° C., which can provide methyl 2-(4,4,5,5-tetramethyl-1,3,2-dioxaborolan-2-yl)-6-(3-(3,3,3-trifluoro-2,2-dimethylpropoxy)-1H-pyrazol-1-yl) nicotinate. Saponification of the methyl ester using sodium hydroxide (e.g., 1N) in THF can provide the acid which can be pretreated with CDI in THF and then treated with 1,3-dimethyl-1H-pyrazole-4-sulfonamide and DBU (e.g., for 3 hours) which can provide a compound of Formula (4-2), N-((1,3-dimethyl-1H-pyrazol-4-yl)sulfonyl)-2-(4,4,5,5-tetramethyl-1,3,2-dioxaborolan-2-yl)-6-(3-(3,3,3-trifluoro-2,2-dimethylpropoxy)-1H-pyrazol-1-yl)nicotinamide.

In some embodiments, a compound of Formula (4-3) can be prepared according to reactions such as those in Scheme 9.

Scheme 9

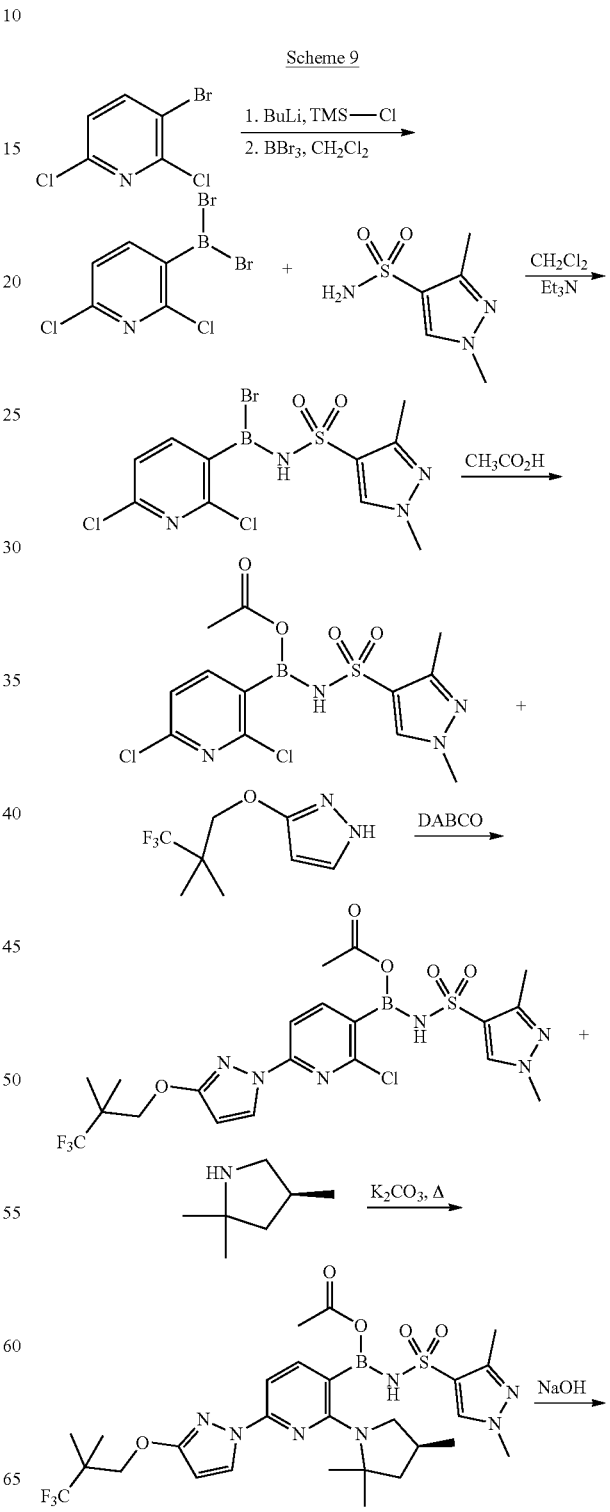

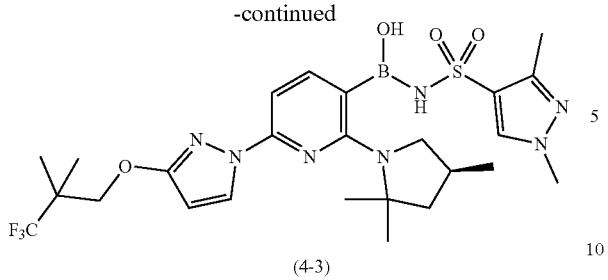

(4-3)

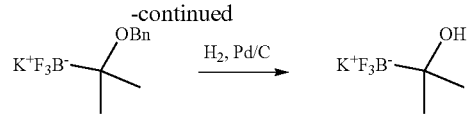

As shown in Scheme 9, 3-bromo-2,6-dichloropyridine can be reacted with butyl lithium (BuLi) then with trimethylsilyl chloride (TMS-Cl) followed by boron tribromide (BBr$_3$) in dichloromethane (CH$_2$Cl$_2$). See, e.g., Helten, *Journal of the American Chemical Society* 2017 139(16), 5692-5695, the relevant portions of which are incorporated herein by reference. Such reactions can provide 2,6-dichloro-3-(dibromoboranyl)pyridine. Treatment of 2,6-dichloro-3-(dibromoboranyl)pyridine with 1,3-dimethyl-11H-pyrazole-4-sulfonamide in, for example, dichloromethane (CH$_2$Cl$_2$) with or without trimethylamine (Et$_3$N) can provide N-(bromo(2,6-dichloropyridin-3-yl)boranyl)-1,3-dimethyl-11H-pyrazole-4-sulfonamide which can be further treated with acetic acid (CH$_3$CO$_2$H) to yield N-(acetoxy(2,6-dichloropyridin-3-yl)boranyl)-1,3-dimethyl-1H-pyrazole-4-sulfonamide. Coupling of N-(acetoxy(2,6-dichloropyridin-3-yl)boranyl)-1,3-dimethyl-11H-pyrazole-4-sulfonamide and 3-(3,3,3-trifluoro-2,2-dimethylpropoxy)-1H-pyrazole in the presence of 1,4-diazabicyclo[2.2.2]octane (DABCO) can provide N-(acetoxy(2-chloro-6-(3-(3,3,3-trifluoro-2,2-dimethylpropoxy)-1H-pyrazol-1-yl)pyridin-3-yl)boranyl)-1,3-dimethyl-1H-pyrazole-4-sulfonamide which can then be coupled with (S)-2,2,4-trimethylpyrrolidine under basic conditions to yield N-(acetoxy(6-(3-(3,3,3-trifluoro-2,2-dimethylpropoxy)-1H-pyrazol-1-yl)-2-((S)-2,2,4-trimethylpyrrolidin-1-yl)pyridin-3-yl)boranyl)-1,3-dimethyl-1H-pyrazole-4-sulfonamide. N-(acetoxy(6-(3-(3,3,3-trifluoro-2,2-dimethylpropoxy)-1H-pyrazol-1-yl)-2-((S)-2,2,4-trimethylpyrrolidin-1-yl)pyridin-3-yl)boranyl)-1,3-dimethyl-1H-pyrazole-4-sulfonamide can be hydrolyzed under aqueous basic conditions in a manner similar to that reported in Ballmer et al., *Organic Syntheses* 2009, 86, 344-359 (the relevant portions of which are incorporated herein by reference), which can provide N-(hydroxy(6-(3-(3,3,3-trifluoro-2,2-dimethylpropoxy)-1H-pyrazol-1-yl)-2-((S)-2,2,4-trimethylpyrrolidin-1-yl)pyridin-3-yl)boranyl)-1,3-dimethyl-1H-pyrazole-4-sulfonamide.

In some embodiments, a compound of Formula (4-4) can be prepared according to reactions including those previously disclosed and those in Schemes 10 and 11 below.

Scheme 10

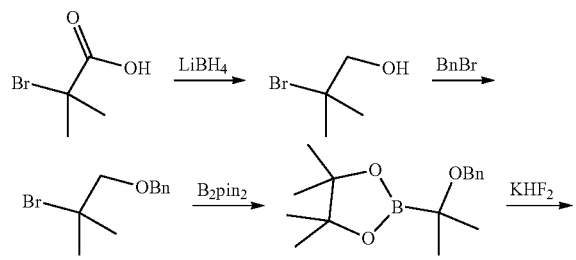

As proposed in Scheme 10, 2-bromo-2-methylpropanoic acid can be reacted with lithium borohydride to provide 2-bromo-2-methylpropan-1-ol. 2-bromo-2-methylpropan-1-ol can be reacted with benzyl bromide which can produce ((2-bromo-2-methylpropoxy)methyl)benzene followed by conversion to the pinacol ester with bis(pinacolato)diboron which, in turn, can yield 2-(2-(benzyloxy)propan-2-yl)-4,4,5,5-tetramethyl-1,3,2-dioxaborolane. Following the procedure in Oliveira, et. al., *Magnetic Resonance in Chemistry* 2009, 47, 873-8 (the relevant portions of which are incorporated herein by reference), 2-(2-(benzyloxy)propan-2-yl)-4,4,5,5-tetramethyl-1,3,2-dioxaborolane can be reacted with excess potassium hydrogen fluoride in methanol to provide potassium (2-(benzyloxy)propan-2-yl)trifluoroborate. Treatment of potassium (2-(benzyloxy)propan-2-yl)trifluoroborate with palladium on carbon and excess hydrogen can provide potassium trifluoro(2-hydroxypropan-2-yl)borate.

As depicted in Scheme 11, potassium (S)-(1-((1-(5-(((1,3-dimethyl-1H-pyrazol-4-yl)sulfonyl)carbamoyl)-6-(2,2,4-trimethylpyrrolidin-1-yl)pyridin-2-yl)-1H-pyrazol-3-yl)oxy)-2-methylpropan-2-yl)trifluoroborate can be reacted with TMSCl using a procedure such as that disclosed in Bagutski, et al., *Angew. Chem. Int. Ed.* 2011, 50, 1080-1083 (the relevant portions of which are incorporated herein by reference), which can provide a compound of Formula (4-4), (S)-6-(3-(2-(difluoroboranyl)-2-methylpropoxy)-1H-pyrazol-1-yl)-N-((1,3-dimethyl-1H-pyrazol-4-yl)sulfonyl)-2-(2,2,4-trimethylpyrrolidin-1-yl)nicotinamide.

Scheme 11

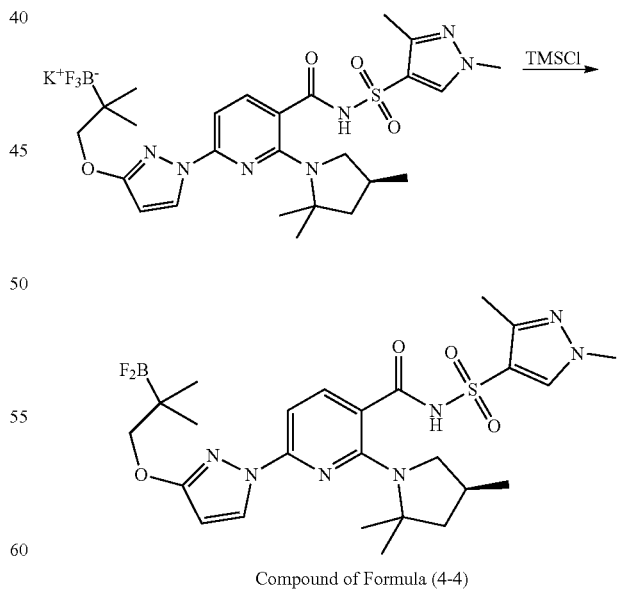

Compound of Formula (4-4)

In some embodiments, a compound of Formula (1-14) wherein R is C$_1$-C$_4$ alkyl can be prepared according to reactions including those previously disclosed and those in Scheme 12.

Scheme 12

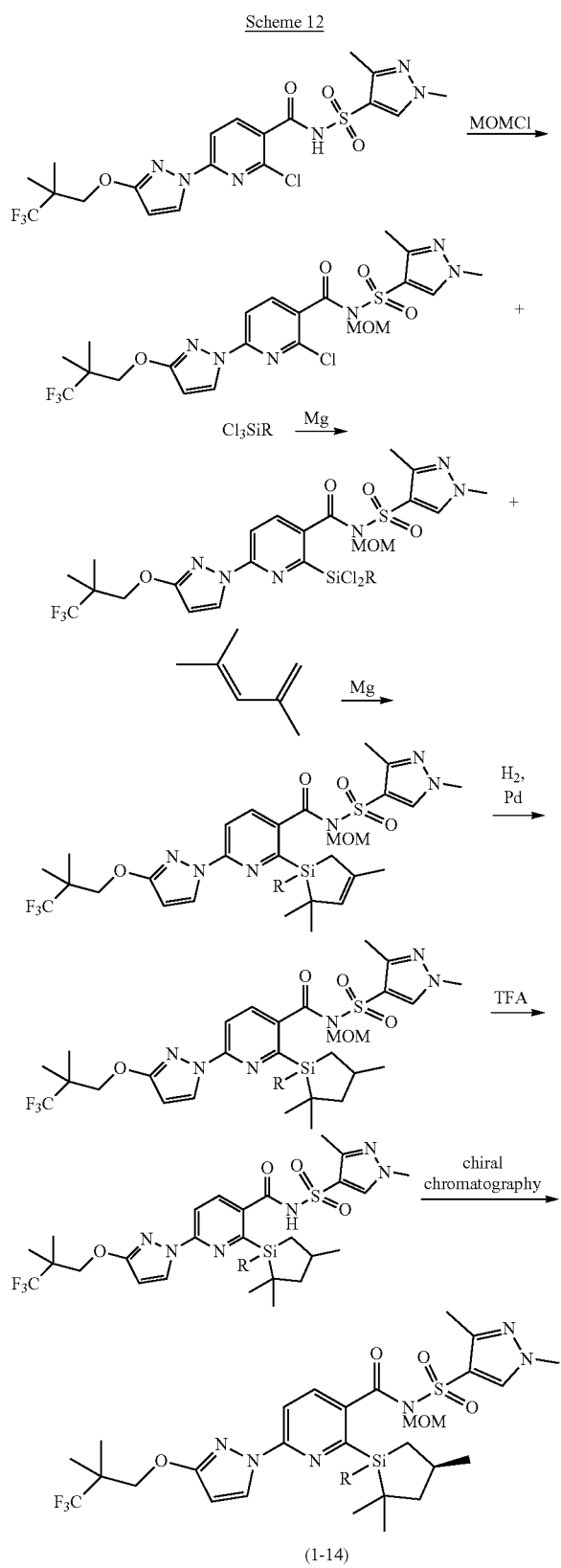

(1-14)

As proposed in Scheme 12, a compound of Formula (D-1) where X' is Cl can be protected using chloromethyl methyl ether to provide a compound of Formula (Q-1). A compound of Formula (Q-1) can be treated with magnesium followed by trichloro(methyl)silane to provide a compound of Formula (Q-2). Treatment of a compound of Formula (Q-2) with magnesium and 2,4-dimethylpenta-1,3-diene and subsequent hydrogenation according to the method reported by Nagao, Yukinori et al. (Nippon Kagaku Kaishi, 2000, 6, 411-417, (the relevant portions of which are incorporated herein by reference) can yield a compound of Formula (Q-4). A compound of Formula (Q-4) can be treated with trifluoroacetic acid to remove the MOM protecting group followed by treatment with diisobutylaluminum hydride according to the procedure reported by Tour, J. et al. (*Journal* of Organometallic Chemistry, 1992, 429, 301-310 (the relevant portions of which are incorporated herein by reference) to provide a racemic mixture of compounds of Formula (Q-5). Chiral preparatory chromatography utilizing a chiral stationary phase can separate the racemic mixture to provide the desired single enantiomer, a compound of Formula (1-14).

Additional embodiments include:

1. A compound of Formula (1):

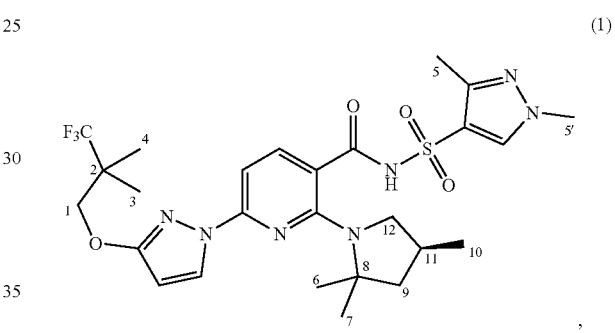

(1)

or a pharmaceutically acceptable salt or deuterated derivative thereof, wherein:

at least one of the carbon atoms at positions 2 and 8 of Formula (1) is replaced by a silicon atom;

at least one of the methyl groups at positions 3, 4, 5, 5', 6, 7, and 10 of Formula (1) is replaced by a group chosen from —Si(R)$_3$ groups, —Si(R)$_2$(OR) groups, and —Si(R)(OR)$_2$ groups;

at least one of the methylene groups at positions 1, 9, and 12 of Formula (1) is replaced by a group chosen from >Si(R)$_2$ groups and >Si(R)(OR) groups; and/or the methine group at position 11 of Formula (1) is replaced by a group chosen from Si(R) groups and Si(OR) groups; and wherein each R, which may be identical or different, is independently chosen from hydrogen, hydroxyl, and C$_1$-C$_4$ alkyl groups.

2. A compound according to embodiment 1, a pharmaceutically acceptable salt thereof, or a deuterated derivative of any of the foregoing, wherein at least one of the carbon atoms at positions 2 and 8 of Formula (1) is replaced by a silicon atom.

3. A compound according to embodiment 1, a pharmaceutically acceptable salt thereof, or a deuterated derivative of any of the foregoing, wherein at least one of the methyl groups at positions 3, 4, 5, 5', 6, 7, and 10 of Formula (1) is replaced by a group chosen from —Si(R)$_3$ groups, —Si(R)$_2$(OR) groups, and —Si(R)(OR)$_2$ groups.

4. A compound according to embodiment 1, a pharmaceutically acceptable salt thereof, or a deuterated derivative of any of the foregoing, wherein at least one of the methylene groups at positions 1, 9, and 12 of Formula (1) is replaced by a group chosen from >Si(R)$_2$ groups and >Si(R)(OR) groups.

5. A compound according to embodiment 1, a pharmaceutically acceptable salt thereof, or a deuterated derivative of any of the foregoing, wherein the methine group at position 11 of Formula (1) is replaced by a group chosen from Si(R) groups and Si(OR) groups.

6. A compound according to embodiment 1 chosen from Compound (1-1):

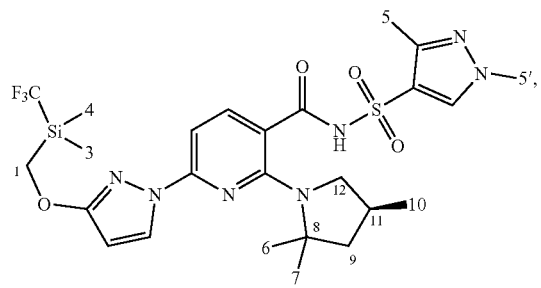

(1-1)

and pharmaceutically acceptable salts and deuterated derivatives thereof.

7. A compound according to embodiment 1 chosen from Compound (1-2):

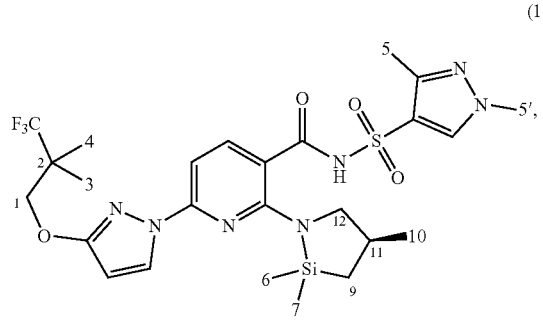

(1-2)

and pharmaceutically acceptable salts and deuterated derivatives thereof.

8. A compound according to embodiment 1 chosen from compounds of Formula (1-3), compounds of Formula (1-4), compounds of Formula (1-5), compounds of Formula (1-6), compounds of Formula (1-7), compounds of Formula (1-8), compounds of Formula (1-9), compounds of Formula (1-10), compounds of Formula (1-11):

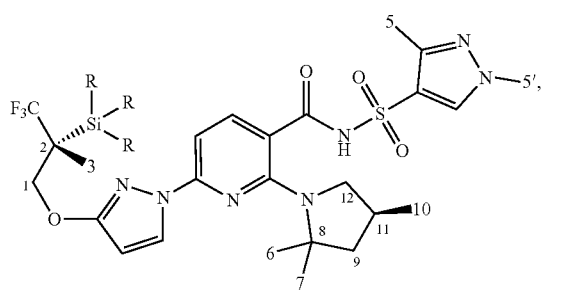

(1-3)

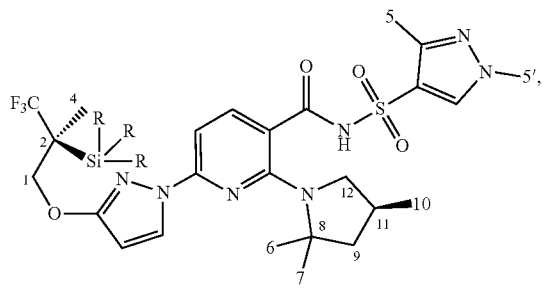

(1-4)

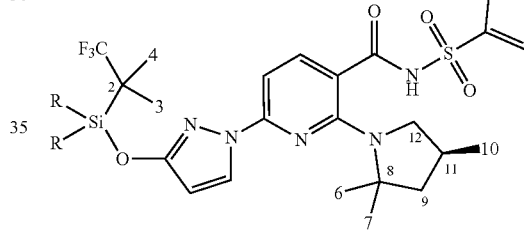

(1-5)

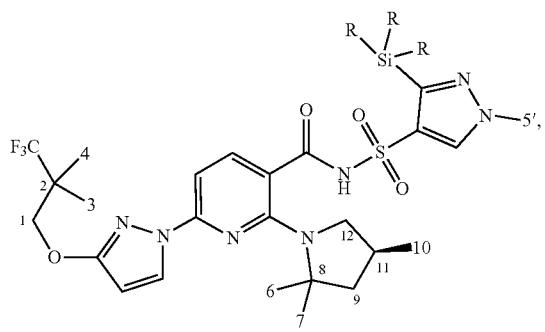

(1-6)

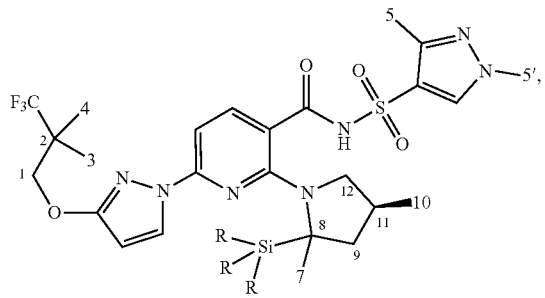

(1-7)

-continued (1-8)
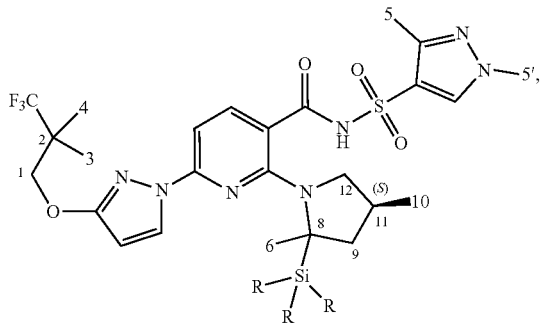

(1-9)
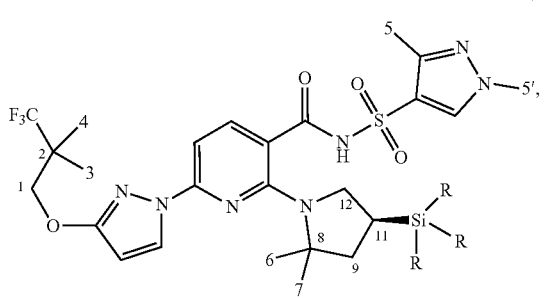

(1-10)
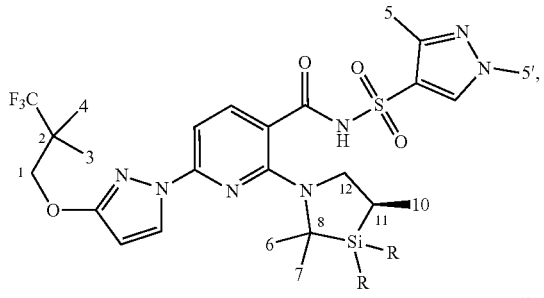

(1-11)
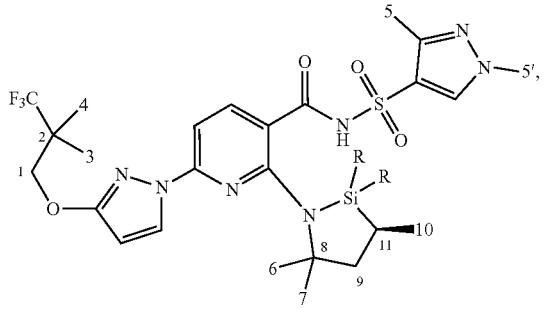

wherein each R is independently chosen from hydrogen, hydroxyl, —O(C$_1$-C$_4$ alkyl), and C$_1$-C$_4$ alkyl groups,
and pharmaceutically acceptable salts and deuterated derivatives thereof.

9. A compound according to embodiment 1, a pharmaceutically acceptable salt thereof, or a deuterated derivative of any of the foregoing, wherein at least one hydrogen atom of at least one R group is replaced by a deuterium atom.

10. A compound according to embodiment 1, a pharmaceutically acceptable salt thereof, or a deuterated derivative of any of the foregoing, wherein each R is independently chosen from C$_1$ alkyl groups and C$_2$ alkyl groups.

11. A compound according to embodiment 1, a pharmaceutically acceptable salt thereof, or a deuterated derivative of any of the foregoing, wherein each R is independently —CH$_3$ or —CD$_3$.

12. A compound according to embodiment 1, a pharmaceutically acceptable salt thereof, or a deuterated derivative of any of the foregoing, wherein each R is independently —CH$_3$.

13. A compound according to embodiment 1 chosen from Compounds (1-12) and (1-13):

(1-12)
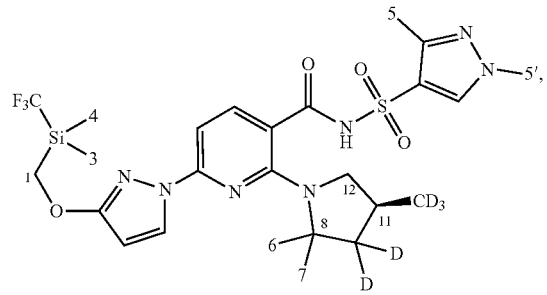

(1-13)
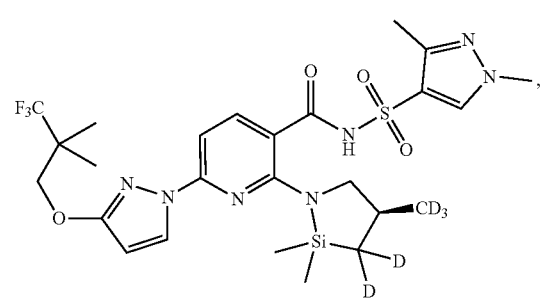

and pharmaceutically acceptable salts and deuterated derivatives thereof.

14. A compound of Formula (1-14):

(1-14)
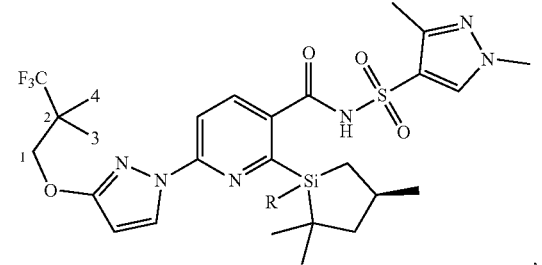

wherein R is H, —OH, —O(C$_1$-C$_4$ alkyl), or a C$_1$-C$_4$ alkyl group, or a pharmaceutically acceptable salt or deuterated derivative thereof.

15. A compound according to embodiment 14, a pharmaceutically acceptable salt thereof, or a deuterated derivative of any of the foregoing, wherein R is a C$_1$-C$_4$ alkyl group.

16. A pharmaceutical composition comprising:
(a) at least one compound chosen from compounds according to any one of embodiments 1-15, pharmaceutically acceptable salts thereof, and deuterated derivatives of any of the foregoing;

(b) at least one pharmaceutically acceptable carrier; and optionally one or more of:

(c) (i) a compound selected from Compound (II):

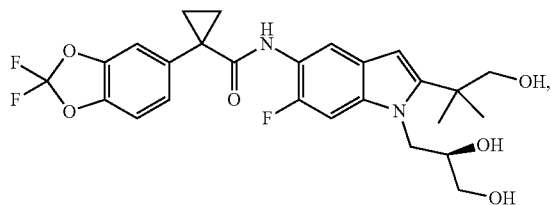 [SMILES: CC(C)(CO)c1cc2cc(NC(=O)C3(c4ccc5c(c4)OC(F)(F)O5)CC3)c(F)cc2n1C[C@@H](O)CO]

and pharmaceutically acceptable salts and deuterated derivatives thereof; and (ii) a compound selected from Compound (III), Compound (III-d):

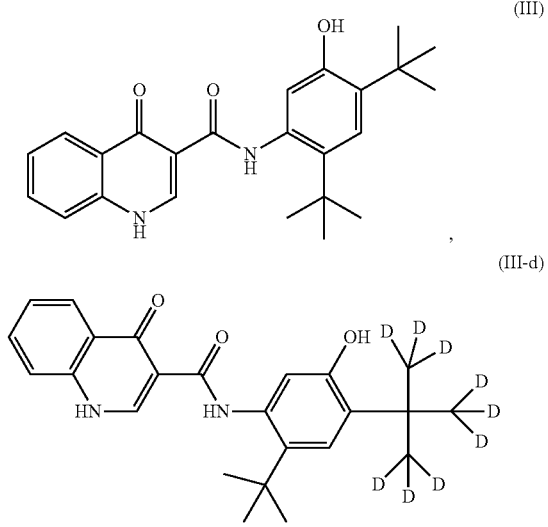

and pharmaceutically acceptable salts and deuterated derivatives thereof.

17. A method of treating cystic fibrosis comprising administering to a patient in need thereof a pharmaceutical composition according to claim 16 or at least one compound chosen from compounds according to any one of embodiments 1-15, pharmaceutically acceptable salts thereof, and deuterated derivatives of any of the foregoing.

18. A method of preparing a compound of Formula (1):

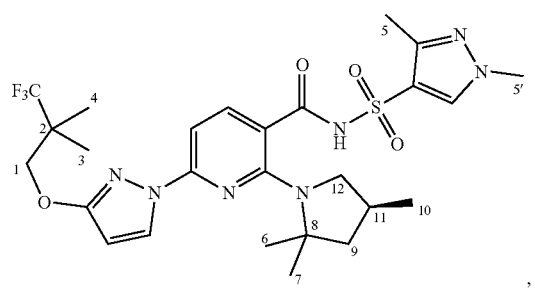

a pharmaceutically acceptable salt thereof, or a deuterated derivative of any of the foregoing, comprising reacting a compound of Formula (F-1) or a salt thereof with a compound of Formula (G-1) or a salt thereof to generate said compound having Formula (1), a pharmaceutically acceptable salt thereof, or a deuterated derivative of any of the foregoing:

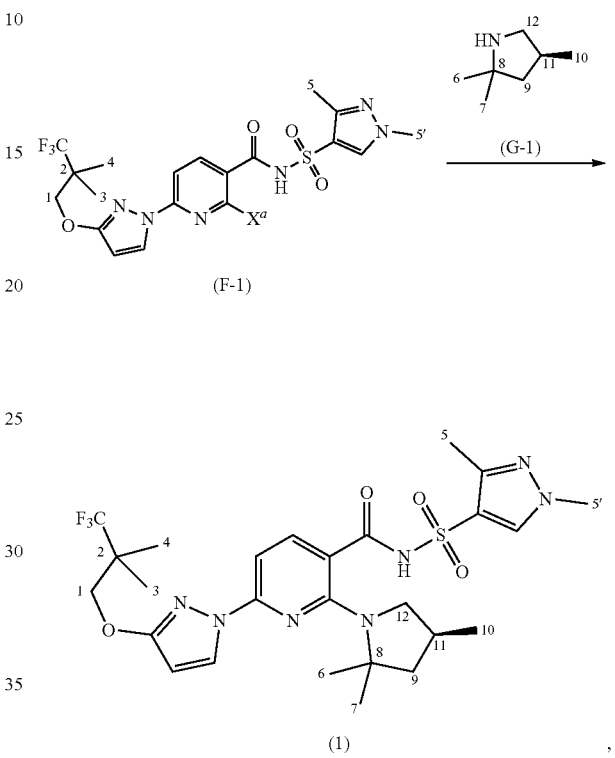

wherein, in each of Formulae (F-1), (G-1) and (1), independently, at least one of the carbon atoms at positions 2 and 8 of Formula (1) is replaced by a silicon atom;

at least one of the methyl groups at positions 3, 4, 5, 5', 6, 7, and 10 of Formula (1) is replaced by a group chosen from —Si(R)$_3$ groups, —Si(R)$_2$(OR) groups, and —Si(R)(OR)$_2$ groups;

at least one of the methylene groups at positions 1, 9, and 12 of Formula (1) is replaced by a group chosen from >Si(R)$_2$ groups and >Si(R)(OR) groups; and/or the methine group at position 11 of Formula (1) is replaced by a group chosen from ≡Si(R) groups and ≡Si(OR) groups;

wherein each R, which may be identical or different, is independently chosen from hydrogen and C$_1$-C$_4$ alkyl groups; and wherein X$^a$ in Formula (F-1) is F or Cl.

19. The method of embodiment 18, wherein said reacting a compound of Formula (F-1) or a salt thereof with a compound of Formula (G-1) or a salt thereof is performed in the presence of a base.

20. A method of preparing a compound of Formula (F-1):

(F-1)

a salt thereof, or a deuterated derivative of any of the foregoing, comprising reacting a compound of Formula (D-1) with a compound of Formula (E-1) or a salt thereof, wherein Ph is phenyl, to generate a compound of Formula (F-1) or a salt thereof:

(D-1)

(E-1)

(F-1)

wherein, in each of Formulae (D-1) and (F-1), independently, the carbon atom at position 2 is replaced by a silicon atom; and/or at least one of the methylene groups at positions 1, 3, and 4 is replaced by a group chosen from >Si(R)$_2$ groups and >Si(R)(OR) groups; and wherein each R, which may be identical or different, is independently chosen from hydrogen and $C_1$-$C_4$ alkyl groups; and each $X^a$ in each of Formulae (D-1) and (F-1) is independently F or Cl.

21. The method of embodiment 20, wherein said reacting a compound of Formula (D-1) or a salt thereof with a compound of Formula (E-1) or a salt thereof is performed in the presence of a base.

22. The method of embodiment 20, wherein said reacting a compound of Formula (D-1) or a salt thereof with a compound of Formula (E-1) or a salt thereof comprises reacting a compound of Formula (D-1) with a coupling reagent and subsequently with a compound of Formula (E-1) in the presence of a base.

23. A method of preparing a compound of Formula (D-1):

(D-1)

a salt thereof, or a deuterated derivative of any of the foregoing, comprising:
(i) reacting a compound of Formula (A-1) or a salt thereof with a compound of Formula (B-1) or a salt thereof to generate a compound of Formula (C-1) or a salt thereof:

(A-1)

(B-1)

(C-1)

and
(ii) hydrolyzing the —C(O)OR$^a$ group of a compound of Formula (C-1) or a salt thereof to generate a compound of Formula (D-1) or a salt thereof, wherein, in each Formulae (A-1), (C-1), and (D-1), independently, the carbon atom at position 3 is replaced by a silicon atom; and/or at least one of the methylene groups at positions 1, 3, and 4 is replaced by a group chosen from >Si(R)$_2$ groups and —Si(R)(OR) groups; and wherein each R, which may be identical or different, is independently chosen from hydrogen and $C_1$-$C_4$ alkyl groups;

each R$^a$, which may be identical or different, in each of Formulae (B-1) and (C-1) is independently chosen from $C_1$-$C_4$ alkyl groups; and each $X^a$, which may be identical or different, in each of Formulae (B-1), (C-1), and (D-1) is independently F or Cl.

24. The method of embodiment 23, wherein the hydrolysis of the —C(O)OR$^a$ group is performed in the presence of a base or an acid.

25. The method of embodiment 24, wherein $R^a$ is ethyl or t-butyl.

26. The method of embodiment 23, wherein said reacting a compound of Formula (A-1) or a salt thereof with a compound of Formula (B-1) or a salt thereof is performed in the presence of a base.

27. A compound chosen from:

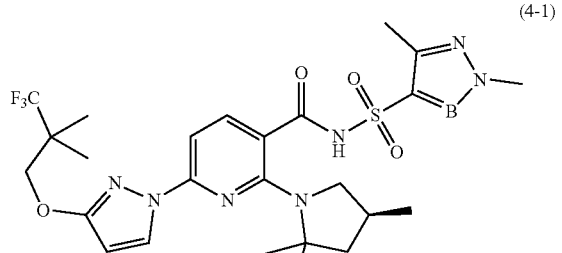
(4-1)

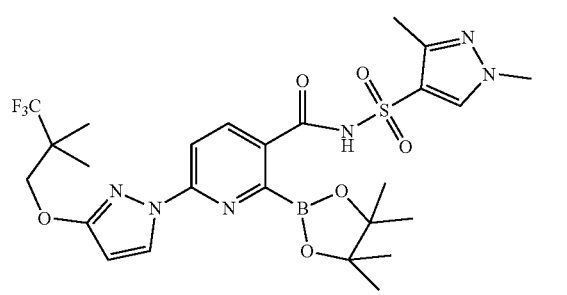
(4-2)

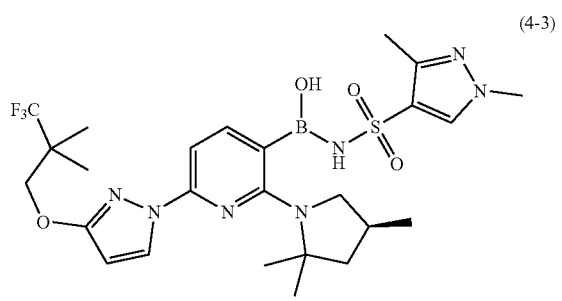
(4-3)

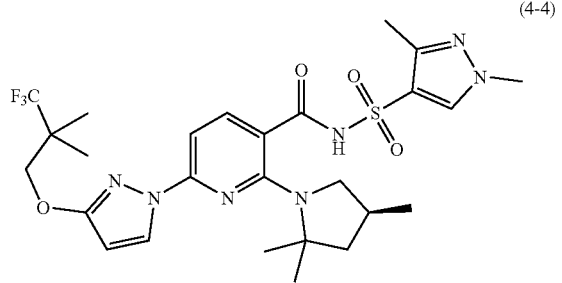
(4-4)

and pharmaceutically acceptable salts and deuterated derivatives thereof.

28. A compound chosen from:

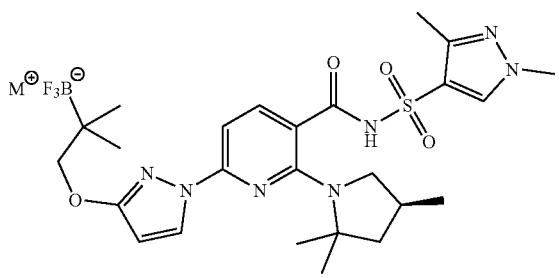
(4-5)

and deuterated derivatives thereof, wherein M is a metal ion.

29. A compound according to embodiment 28, wherein M is chosen from potassium and sodium.

30. A pharmaceutical composition comprising:
(a) at least one compound chosen from compounds of any one of embodiments 27-29, pharmaceutically acceptable salts thereof, and deuterated derivatives of any of the foregoing;
(b) at least one pharmaceutically acceptable carrier; and optionally one or more of:
(c) (i) a compound chosen from Compound (II):

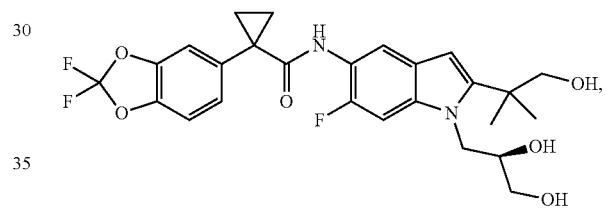

and pharmaceutically acceptable salts and deuterated derivatives thereof; and
(ii) a compound chosen from Compound (III), Compound (III-d):

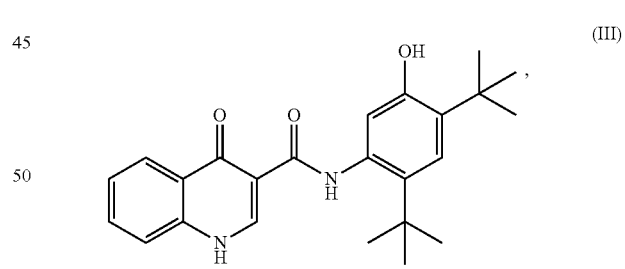
(III)

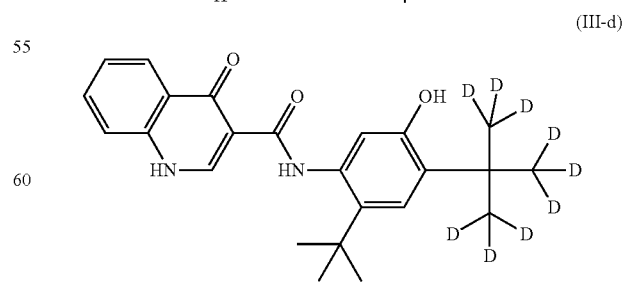
(III-d)

are pharmaceutically acceptable salts and deuterated derivatives thereof.

31. A method of treating cystic fibrosis comprising administering to a patient in need thereof a pharmaceutical composition according to embodiment 30 or a compound chosen from compounds of any one of embodiments 27-29, pharmaceutically acceptable salts thereof, and deuterated derivatives of any of the foregoing.

32. A compound Formula (2):

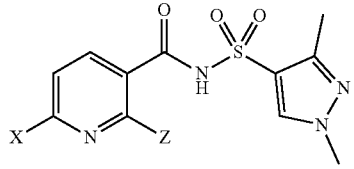
(2)

wherein:

X is selected from —Si(CH$_3$)$_3$,

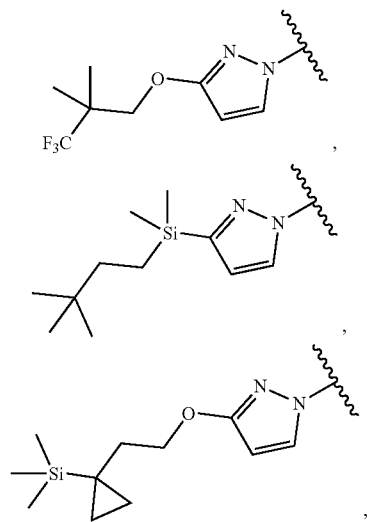

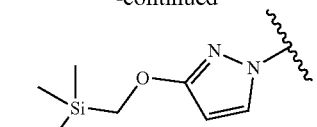

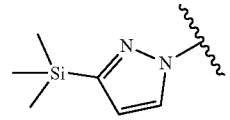, 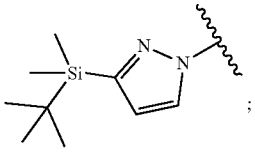;

Z is selected from

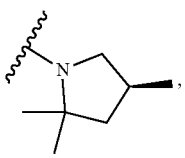, 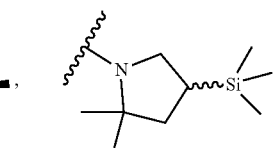, and

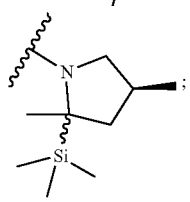;

and wherein each compound of Formula (2) contains at least one Si atom, or a pharmaceutically acceptable salt or deuterated derivative thereof.

33. The compound of embodiment 32, wherein the compound is chosen from:

Compound (2-1)

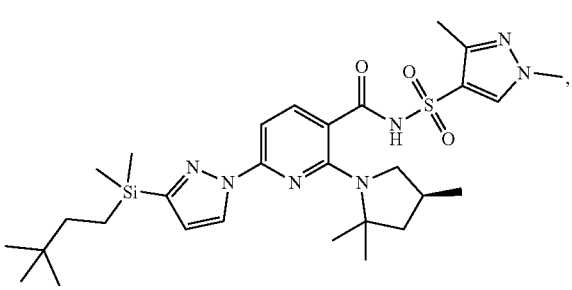

Compound (2-2)

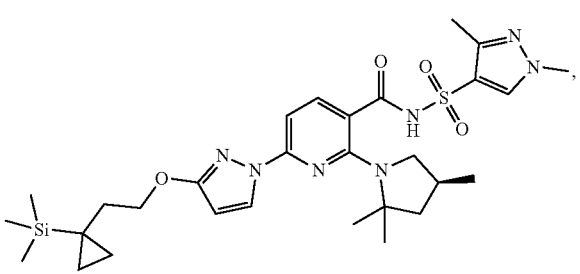

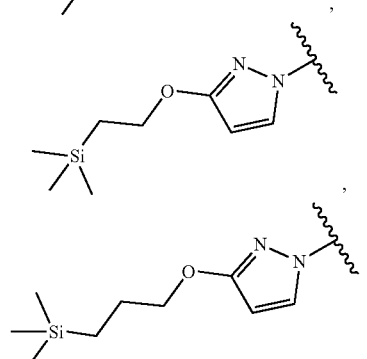

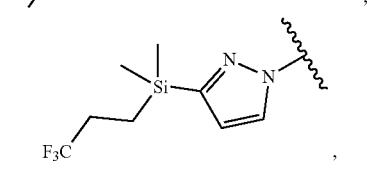

Compound (2-3)
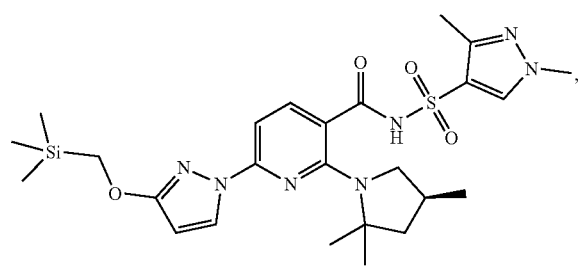

Compound (2-4)
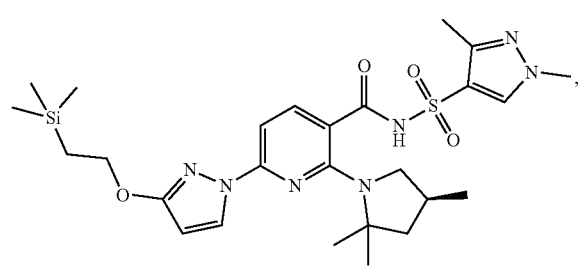

Compound (2-5)
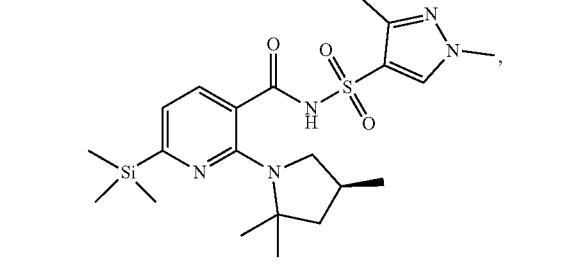

Compound (2-6)
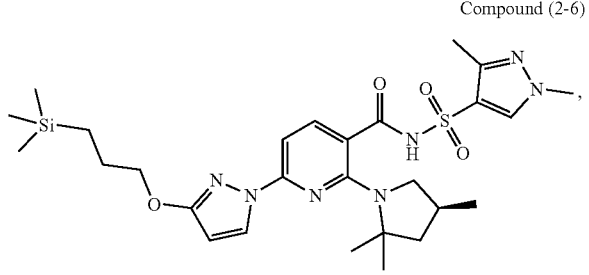

Compound (2-7)
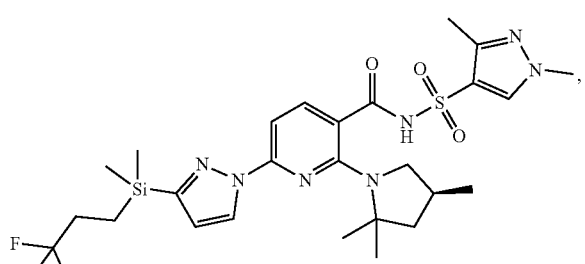

Compound (2-8)
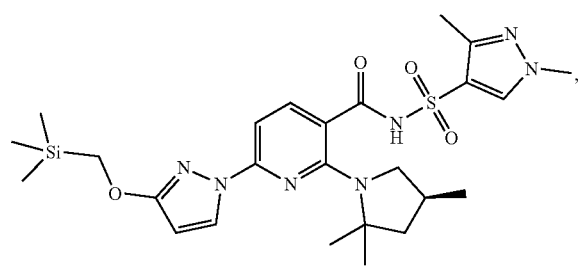

Compound (2-9)
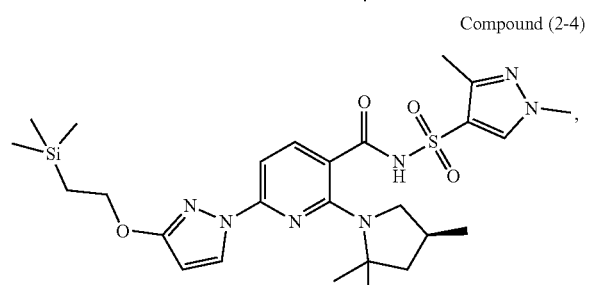

Compound (2-10)
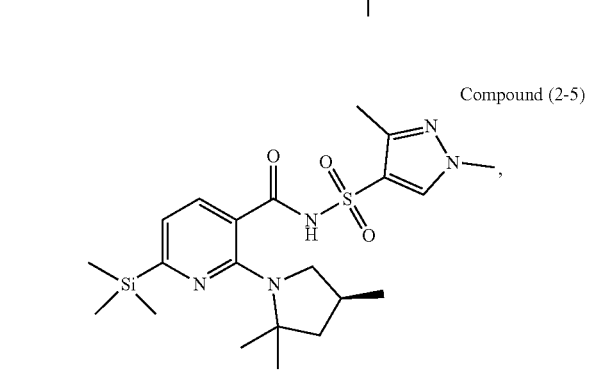

Compound (2-11)
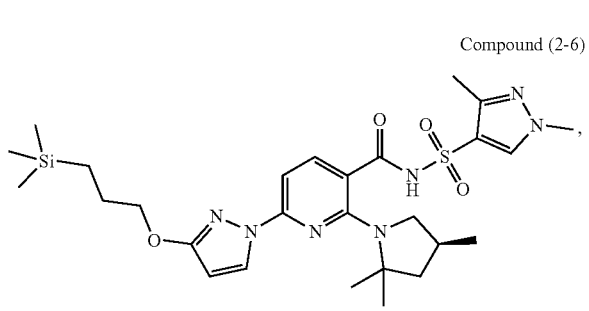

Compound (2-12)
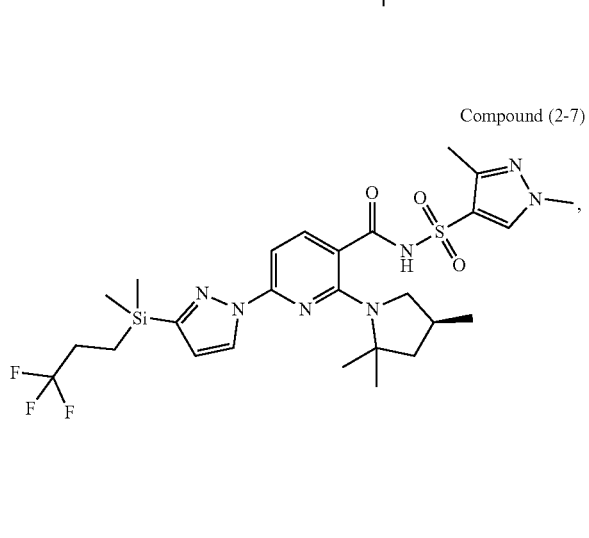

and pharmaceutically acceptable salts and deuterated derivatives thereof.

34. The compound of embodiment 32 or 33, wherein at least one hydrogen is replaced by deuterium.

35. The compound of any one of embodiments 32 to 34, wherein the compound is a pharmaceutically acceptable salt.

36. Compound (2-8) in the form of a single stereoisomer or a mixture of stereoisomers.

37. Compound (2-9) in the form of a single enantiomer or a mixture of enantiomers.

38. A compound of Formula (3):

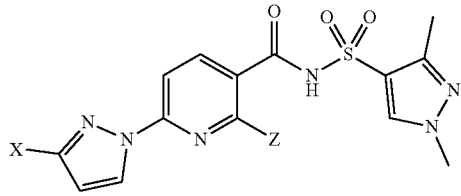

wherein:

X is selected from —Ge(CH$_3$)$_3$,

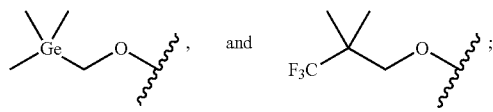

Z is selected from

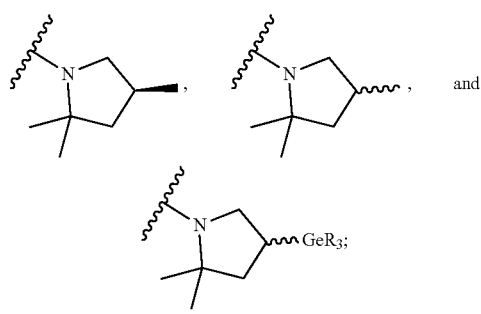

and wherein each compound of Formula (3) contains at least one Ge atom, or a pharmaceutically acceptable salts or deuterated derivative thereof.

39. The compound of embodiment 38, wherein the compound is chosen from:

Compound (3-1)

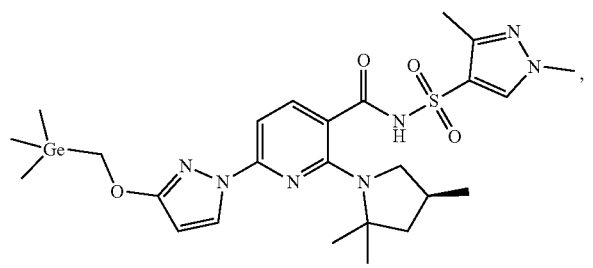

Compound (3-2)

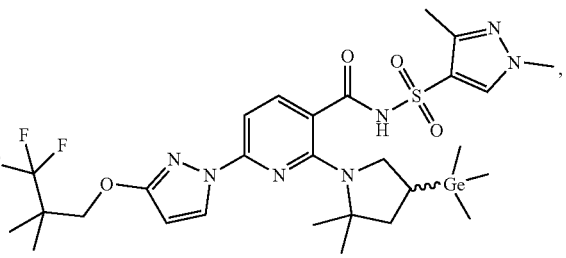

Compound (3-3)

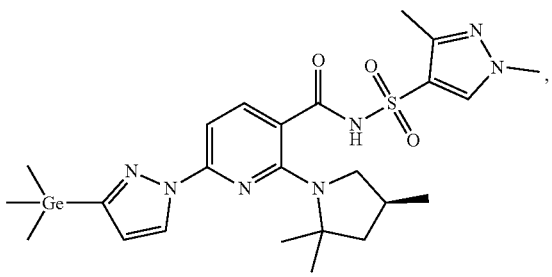

40. The compound of embodiment 38 or 39, wherein at least one hydrogen is replaced by deuterium.

41. The compound of any one of embodiments 38 to 40, wherein the compound is a pharmaceutically acceptable salt.

42. Compound (3-2) in the form of a single stereoisomer or a mixture of stereoisomers.

43. A pharmaceutical composition comprising:

(a) at least one compound chosen from compounds of any one of embodiments 32-37;

(b) at least one pharmaceutically acceptable carrier; and optionally one or more of:

(c) (i) a compound chosen from Compound (II):

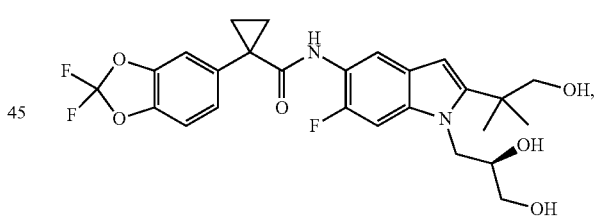

and pharmaceutically acceptable salts and deuterated derivatives thereof; and (ii) a compound chosen from Compound (III), Compound (III-d):

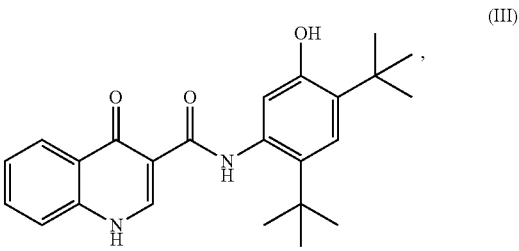

-continued (III-d)

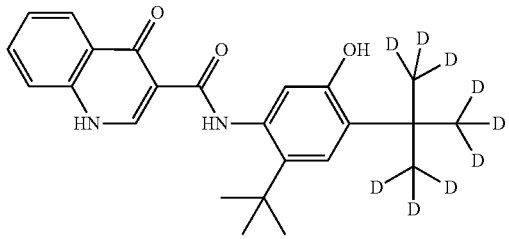

and pharmaceutically acceptable salts and deuterated derivatives thereof.

44. A pharmaceutical composition comprising a compound of any one of embodiments 32-42 and a pharmaceutically acceptable carrier.

45. The pharmaceutical composition of embodiment 44, further comprising at least one compound selected from Compound (II), Compound (III), Compound (III-d), and pharmaceutically acceptable salts thereof.

46. The pharmaceutical composition of embodiment 45, wherein the composition comprises Compound (II) and Compound (III).

47. The pharmaceutical composition of embodiment 45, wherein the composition comprises Compound (II) and Compound (III-d).

48. A pharmaceutical composition comprising a compound of any one of embodiments 38-42 and a pharmaceutically acceptable carrier.

49. The pharmaceutical composition of embodiment 48, further comprising at least one compound selected from Compound (II), Compound (III), Compound (III-d), and pharmaceutically acceptable salts thereof.

50. The pharmaceutical composition of embodiment 49, wherein the composition comprises Compound (II) and Compound (III).

51. The pharmaceutical composition of embodiment 49, wherein the composition comprises Compound (II) and Compound (III-d).

52. A method of treating cystic fibrosis comprising administering to a patient in need thereof, a pharmaceutical composition according to any one of embodiments 43-51 or a compound chosen from compounds of any one of embodiments 32-42.

53. The pharmaceutical composition according to any one of embodiments 43-51 or the compound according to of any one of embodiments 32-42 for use in the treatment of cystic fibrosis.

54. The pharmaceutical composition according to any one of embodiments 43-51 or the compound according to any one of embodiments 32-42 for use in the manufacture of a medicament for the treatment of cystic fibrosis.

55. The pharmaceutical composition according to claim 16 or the compound according to any one of embodiments 1-15 for use in the treatment of cystic fibrosis.

56. The pharmaceutical composition according to claim 16 or the compound according to any one of embodiments 1-15 for use in the manufacture of a medicament for the treatment of cystic fibrosis.

57. The pharmaceutical composition according to embodiment 30 or the compound according to any one of embodiments 27-29 for use in the treatment of cystic fibrosis.

58. The pharmaceutical composition according to embodiment 30 or the compound according to any one of embodiments 27-29 for use in the manufacture of a medicament for the treatment of cystic fibrosis.

59. A compound chosen from:
N-(1,3-dimethylpyrazol-4-yl)sulfonyl-6-[3-(3,3,3-trifluoro-2,2-dimethyl-propoxy)pyrazol-1-yl]-2-[(4 S)-2,2,4-trimethylpyrrolidin-1-yl]-5-trimethyl silyl-pyridine-3-carboxamide N-(1-methyl-3-trimethylsilyl-pyrazol-4-yl)sulfonyl-6-[3-[2-[1-(trifluoromethyl)cyclopropyl]ethoxy]pyrazol-1-yl]-2-[(4 S)-2,2,4-trimethylpyrrolidin-1-yl]pyridine-3-carboxamide N-(1-methyl-3-trimethylsilyl-pyrazol-4-yl)sulfonyl-6-[3-(3,3,3-trifluoro-2,2-dimethyl-propoxy)pyrazol-1-yl]-2-[(4 S)-2,2,4-trimethylpyrrolidin-1-yl]pyridine-3-carboxamide N-(1,3-dimethylpyrazol-4-yl)sulfonyl-6-[3-(3,3,3-trifluoro-2,2-dimethyl-propoxy)pyrazol-1-yl]-2-trimethylsilyl-pyridine-3-carboxamide;

and pharmaceutically acceptable salts and deuterated derivatives thereof.

60. The compound of embodiment 59, for use in the treatment of cystic fibrosis.

61. The compound of embodiment 59, for use in the manufacture of a medicament for the treatment of cystic fibrosis.

General Experimental Procedures

The following abbreviations are used in this disclosure:
ACN: Acetonitrile
Boc anhydride ((Boc)2O): Di-tert-butyl dicarbonate
CDI: Carbonyl diimidazole
COMU: (1-Cyano-2-ethoxy-2-oxoethylidenaminooxy)dimethylamino-morpholino-carbenium hexafluorophosphate
DABCO: 1,4-Diazabicyclo[2.2.2]octane
DBU: 1,8-Diazabicyclo(5.4.0)undec-7-ene
DCM: Dichloromethane
DI water: Deionized water
DIAD: Diisopropyl azodicarboxylate
DIEA (DIPEA; N,N-diisopropylethylamine)
DMA: N,N-Dimethylacetamide
DMAP: 4-Dimethylaminopyridine
DMF: N,N-Dimethylformamide
DMSO: Dimethyl sulfoxide
EDC: 1-Ethyl-3-(3-dimethylaminopropyl)carbodiimide
Et2O: Diethyl ether
EtOAc: Ethyl acetate
EtOH: Ethanol
HATU: 1-[Bis(dimethylamino)methylene]-1H-1,2,3-triazolo[4,5-b]pyridinium 3-oxid hexafluorophosphate
HPLC: High performance liquid chromatography
HMPA: Hexamethylphosphoramide
IPA: Isoproanol
LAH: Lithium luminium hydride, LiAlH4
LC: Liquid chromatography
LDA: Lithium diisopropylamide
MeCN: Acetonitrile
MeOH: Methanol
MTBE: Methyl tert-butyl ether
MeTHF or 2-MeTHF: 2-Methyltetrahydrofuran
NMP: N-Methyl-2-pyrrolidone
NMM: N-Methylmorpholine
Pd(dppf)Cl2: [1,1'-Bis(diphenylphosphino)ferrocene]dichloropalladium(II)
PTFE: Polytetrafluoroethylene
rt: Room temperature
SFC: Supercritical fluid chromatography
TBS-Cl: tert-Butyldimethylsilyl chloride
TEA: Triethylamine
TFA: Trifluoroacetic acid THF: Tetrahydrofuran
TMS: Trimethylsilyl
TMSCl: Trimethylsilyl chloride
TPPO-DIAD complex: a complex of triphenylphosphine oxide with diisopropyl azodicarboxylate
p-TsOH: p-Toluenesulfonic Acid
UPLC: Ultra Performance Liquid Chromatography Procedures for the Synthesis of Common Intermediates Reagents and starting materials were obtained by commercial sources unless otherwise stated and were used without purification. Proton and carbon NMR spectra were acquired on either a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters. Final purity of compounds was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30m×0.25 mm×0.25 um_df) column, with a 2.0 mL/min flow rate ($H_2$ carrier gas), at an injection temperature of 220° C. and an oven temperature of 120° C., 15 minutes.

Part A: Synthesis of (4S)-2,2,4-trimethylpyrrolidine Hydrochloride

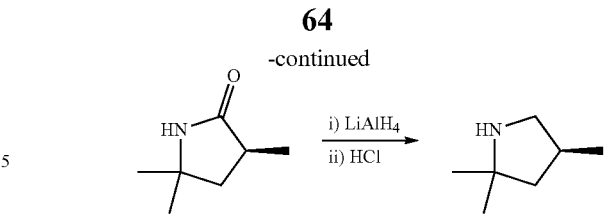

Step 1: Synthesis of methyl-2,4-dimethyl-4-nitro-pentanoate

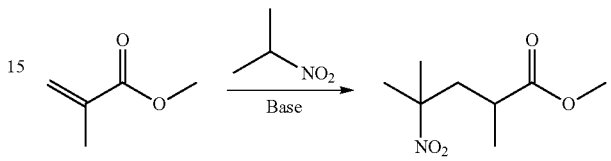

Tetrahydrofuran (THF, 4.5 L) was added to a 20 L glass reactor and stirred under $N_2$ at room temperature. 2-Nitropropane (1.5 kg, 16.83 mol) and 1,8-diazabicyclo[5.4.0]undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. This was dried with $MgSO_4$ and filtered to afford methyl-2,4-dimethyl-4-nitro-pentanoate as a clear green oil (3.16 kg, 99% yield). $^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of Methyl (2S)-2,4-dimethyl-4-nitro-pentanoate

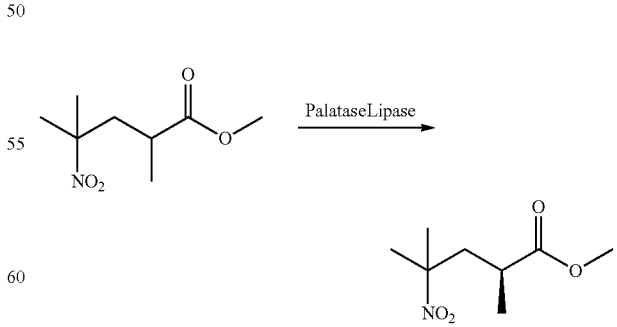

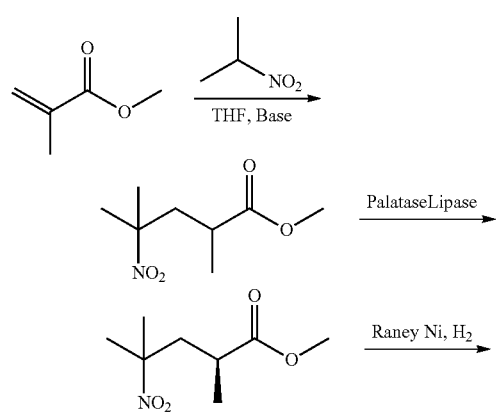

A reactor was charged with purified water (2090 L; 10 vol) and then potassium phosphate monobasic (27 kg, 198.4 moles; 13 g/L for water charge). The pH of the reactor contents was adjusted to pH 6.5 (±0.2) with 20% (w/v)

potassium carbonate solution. The reactor was charged with racemic methyl-2,4-dimethyl-4-nitro-pentanoate (209 kg; 1104.6 moles), and Palatase 20000L lipase (13 L, 15.8 kg; 0.06 vol).

The reaction mixture was adjusted to 32±2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000 L). The combined organic extracts were washed with aqueous $Na_2CO_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of (3S)-3,5,5-trimethylpyrrolidin-2-one

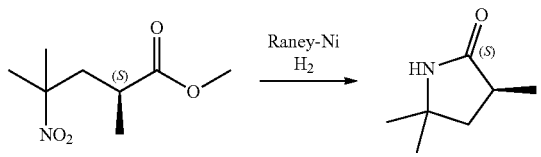

A 20 L reactor was purged with $N_2$. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with $H_2$ and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white crystalline solid (2.042 kg, 16.1 mol, 87%). $^1$H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine Hydrochloride

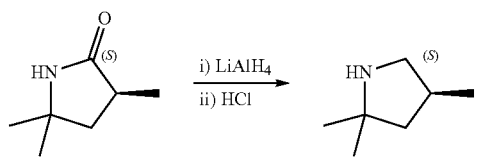

A glass lined 120 L reactor was charged with lithium aluminium hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv water with 1.4 equiv sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/N2 bleed) to afford (4S)-2,2,4-trimethylpyrrolidine.HCl as a white, crystalline solid (6.21 kg, 75% yield). $^1$H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Part B: Synthesis of N-(benzenesulfonyl)-2-chloro-6-[3-[2-[1-(trifluoromethyl)cyclopropyl]ethoxy]pyrazol-1-yl]pyridine-3-carboxamide

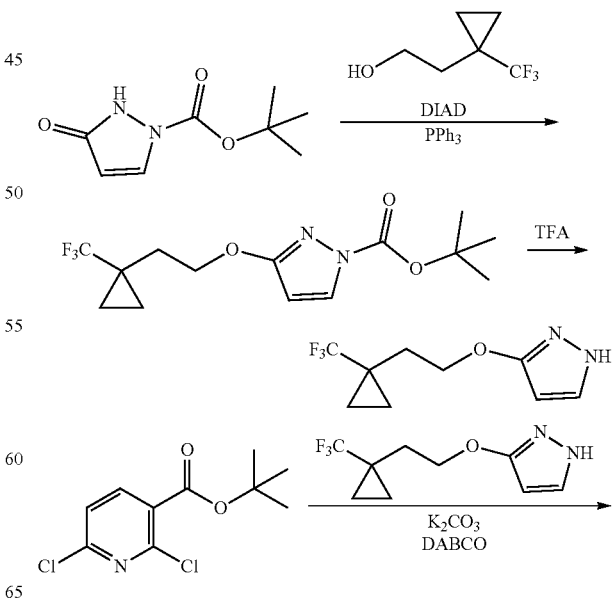

-continued

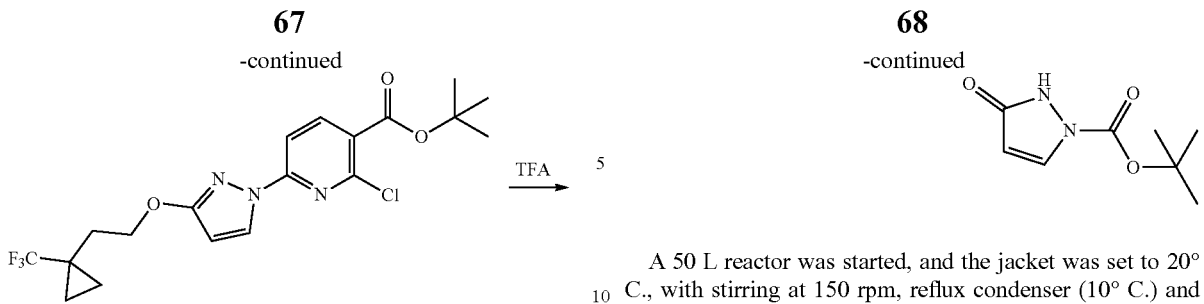

TFA →

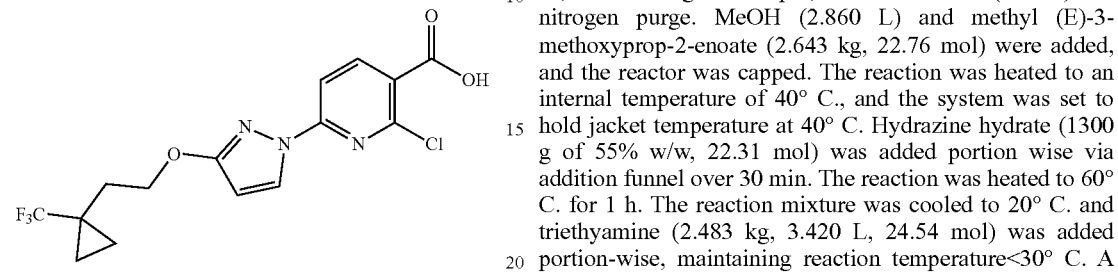

Synthesis of Starting Materials

Synthesis of Tert-Butyl 2,6-dichloropyridine-3-carboxylate

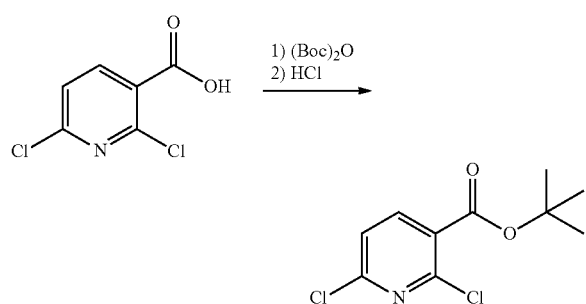

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and stirred overnight at room temperature. At this point, HCl 1N (400 mL) was added, and the mixture was stirred vigorously for about 10 minutes. The product was extracted with ethyl acetate (2×300 mL), and the combined organic layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m/z calc. 247.02, found 248.1 (M+1)+; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Synthesis of Tert-Butyl 3-oxo-2,3-dihydro-1H-pyrazole-1-carboxylate

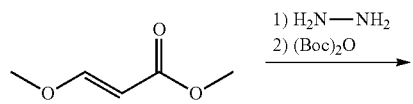

-continued

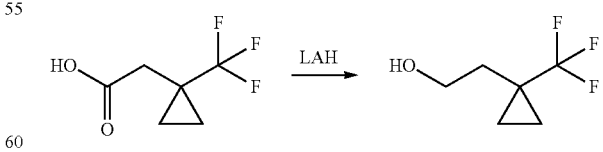

A 50 L reactor was started, and the jacket was set to 20° C., with stirring at 150 rpm, reflux condenser (10° C.) and nitrogen purge. MeOH (2.860 L) and methyl (E)-3-methoxyprop-2-enoate (2.643 kg, 22.76 mol) were added, and the reactor was capped. The reaction was heated to an internal temperature of 40° C., and the system was set to hold jacket temperature at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethyamine (2.483 kg, 3.420 L, 24.54 mol) was added portion-wise, maintaining reaction temperature<30° C. A solution of Boc anhydride (di-tert-butyl dicarbonate) (4.967 kg, 5.228 L, 22.76 mol) in MeOH (2.860 L) was added portion-wise maintaining temperature<45° C. The reaction mixture was stirred at 20° C. for 16 h. The reaction solution was partially concentrated to remove MeOH, resulting in a clear, light amber oil. The resulting oil was transferred to the 50 L reactor, stirred and water (7.150 L) and heptane (7.150 L) were added. The additions caused a small amount of the product to precipitate. The aqueous layer was drained into a clean container, and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol) and added dropwise. The jacket was set to 0° C. to absorb the quench exotherm. After the addition was complete (pH=5), the reaction mixture was stirred for 1 h. The solid was collected by filtration and washed with water (7.150 L), and washed a second time with water (3.575 L). The crystalline solid was transferred into a 20 L rotovap bulb, and heptane (7.150 L) was added. The mixture was slurried at 45° C. for 30 mins, and 1-2 volumes of solvent were distilled off. The slurry in the rotovap flask was filtered, and the solids were washed with heptane (3.575 L). The solid was further dried in vacuo (50° C., 15 mbar) to give tert-butyl 5-oxo-1H-pyrazole-2-carboxylate (2921 g, 71%) as a coarse, crystalline solid. $^1$H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Synthesis of 2-[1-(trifluoromethyl)cyclopropyl]ethanol

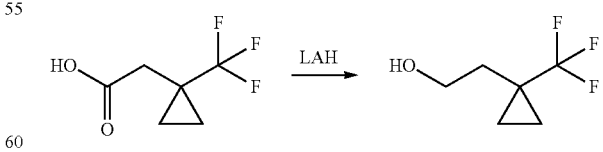

To a solution of lithium aluminum hydride (293 mg, 7.732 mmol) in THF (10.00 mL) in an ice-bath, 2-[1-(trifluoromethyl)cyclopropyl]acetic acid (1.002 g, 5.948 mmol) in THF (3.0 mL) was added dropwise over a period of 30 minutes keeping the reaction temperature below 20° C. The mixture was allowed to gradually warm to ambient temperature and was stirred for 18 h. The mixture was cooled with an ice-bath and sequentially quenched with water (294 mg, 295 μL, 16.36 mmol), NaOH (297 μL of 6 M, 1.784 mmol), and then water (884.0 μL, 49.07 mmol) to afford a granular solid in the mixture. The solid was filtered off using celite, and the precipitate was washed with ether. The filtrate was further dried with MgSO₄ and filtered and concentrated in vacuo to afford the product with residual THF and ether. The mixture was taken directly into the next step without further purification.

Step 1: tert-Butyl 3-[2-[1-(trifluoromethyl)cyclopropyl]ethoxy]pyrazole-1-carboxylate

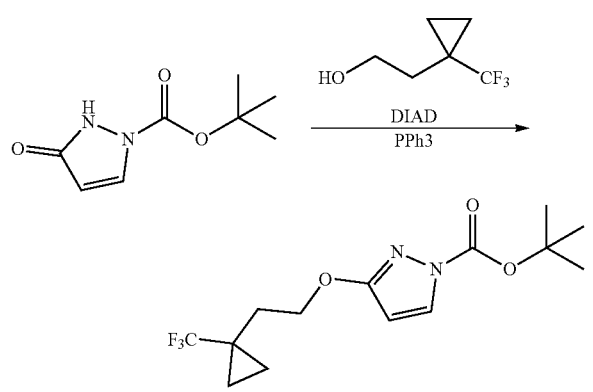

tert-Butyl 5-oxo-1H-pyrazole-2-carboxylate (1.043 g, 5.660 mmol), 2-[1-(trifluoromethyl)cyclopropyl]ethanol (916 mg, 5.943 mmol), and triphenyl phosphine (1.637 g, 6.243 mmol) were combined in THF (10.48 mL) and the reaction was cooled in an ice-bath. Diisopropyl azodicarboxylate (1.288 g, 1.254 mL, 6.368 mmol) was added dropwise to the reaction mixture, and the reaction was allowed to warm to room temperature for 16 hours. The mixture was evaporated, and the resulting material was partitioned between ethyl acetate (30 mL) and 1N sodium hydroxide (30 mL). The organic layer was separated, washed with brine (30 mL), dried over sodium sulfate, and concentrated. The crude material was purified by silica gel chromatography eluting with a gradient of ethyl acetate in hexanes (0-30%) to give tert-butyl 3-[2-[1-(trifluoromethyl)cyclopropyl]ethoxy]pyrazole-1-carboxylate (1.03 g, 57%). ESI-MS m/z calc. 320.13, found 321.1 (M+1)⁺; Retention time: 0.72 minutes.

Step 2: 3-[2-[1-(Trifluoromethyl)cyclopropyl]ethoxy]-1H-pyrazole

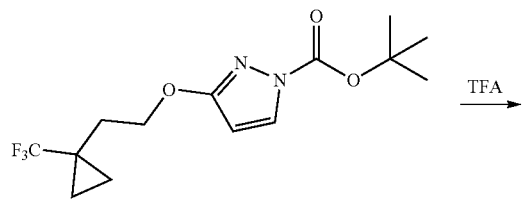

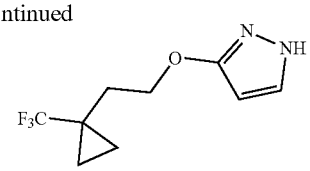

tert-Butyl-3-[2-[1-(trifluoromethyl)cyclopropyl]ethoxy]pyrazole-1-carboxylate (1.03 g, 3.216 mmol) was dissolved in dichloromethane (10.30 mL) with trifluoroacetic acid (2.478 mL, 32.16 mmol), and the reaction was stirred at room temperature for 2 hours. The reaction was evaporated, and the resulting oil was partitioned between ethyl acetate (10 mL) and a saturated sodium bicarbonate solution. The organic layer was separated, washed with brine, dried over sodium sulfate, and evaporated to give 3-[2-[1-(trifluoromethyl)cyclopropyl]ethoxy]-1H-pyrazole (612 mg, 86%). ESI-MS m/z calc. 220.08, found 221.0 (M+1)⁺; Retention time: 0.5 minutes. ¹H NMR (400 MHz, DMSO-d6) δ 11.86 (s, 1H), 7.50 (t, J=2.1 Hz, 1H), 5.63 (t, J=2.3 Hz, 1H), 4.14 (t, J=7.1 Hz, 2H), 2.01 (t, J=7.1 Hz, 2H), 0.96-0.88 (m, 2H), 0.88-0.81 (m, 2H).

Step 3: tert-Butyl 2-chloro-6-[3-[2-[1-(trifluoromethyl)cyclopropyl]ethoxy]pyrazol-1-yl]pyridine-3-carboxylate

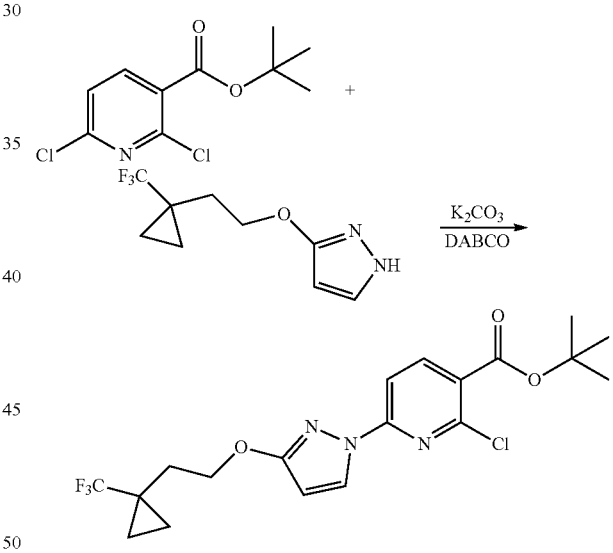

tert-Butyl 2,6-dichloropyridine-3-carboxylate (687 mg, 2.770 mmol), 3-[2-[1-(trifluoromethyl)cyclopropyl]ethoxy]-1H-pyrazole (610 mg, 2.770 mmol), and freshly ground potassium carbonate (459 mg, 3.324 mmol) were combined in anhydrous DMSO (13.75 mL). 1,4-diazabicyclo[2.2.2]octane (DABCO (1,4-diazabicyclo[2.2.2]octane), 62 mg, 0.5540 mmol) was added, and the mixture was stirred at room temperature under nitrogen for 16 hours. The reaction mixture was diluted with water (20 mL) and stirred for 15 minutes. The resulting solid was collected and washed with water. The solid was dissolved in dichloromethane and dried over magnesium sulfate. The mixture was filtered and concentrated to give tert-butyl 2-chloro-6-[3-[2-[1-(trifluoromethyl)cyclopropyl]ethoxy]pyrazol-1-yl]pyridine-3-carboxylate (1.01 g, 84%). ESI-MS m/z calc. 431.12, found 432.1 (M+1)+; Retention time: 0.88 minutes.

Step 4: 2-Chloro-6-[3-[2-[1-(trifluoromethyl)cyclopropyl]ethoxy]pyrazol-1-yl]pyridine-3-carboxylic Acid

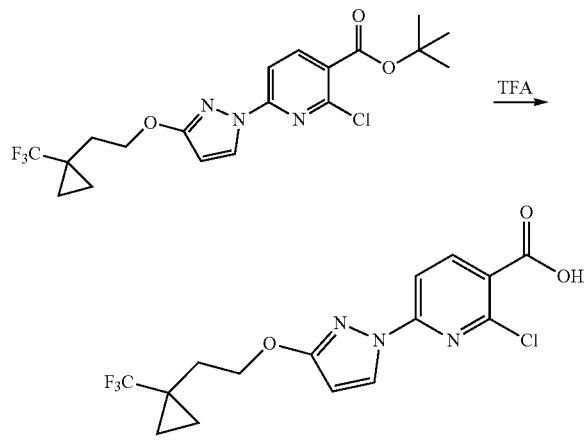

tert-Butyl 2-chloro-6-[3-[2-[1-(trifluoromethyl)cyclopropyl]ethoxy]pyrazol-1-yl]pyridine-3-carboxylate (1.01 g, 2.339 mmol) and trifluoroacetic acid (1.8 mL, 23.39 mmol) were combined in dichloromethane (10 mL) and heated at 40° C. for 3 h. The reaction was concentrated. Hexanes were added, and the mixture was concentrated again to give 2-chloro-6-[3-[2-[1-(trifluoromethyl)cyclopropyl]ethoxy]pyrazol-1-yl]pyridine-3-carboxylic acid (873 mg, 99%) ESI-MS m/z calc. 375.06, found 376.1 (M+1)+; Retention time: 0.69 minutes.

Part C: Preparation of 2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide

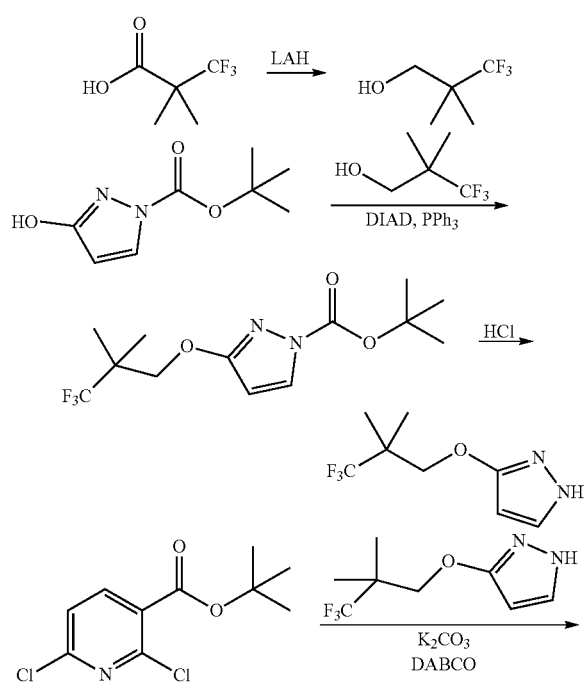

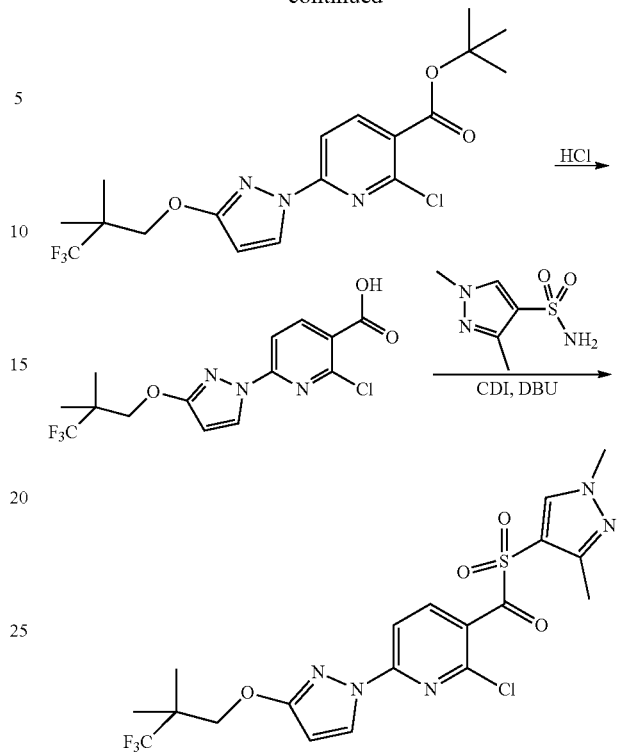

Step 1: 3,3,3-Trifluoro-2,2-dimethyl-propan-1-ol

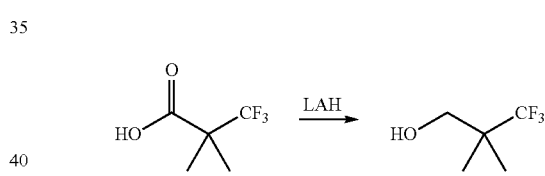

A 1 L 3 neck round bottom flask was fitted with a mechanical stirrer, a cooling bath, an addition funnel, and a J-Kem temperature probe. The vessel was charged with lithium aluminum hydride (LAH) pellets (6.3 g, 0.1665 mol) under a nitrogen atmosphere. The vessel was then charged with tetrahydrofuran (200 mL) under a nitrogen atmosphere. The mixture was allowed to stir at room temperature for 0.5 hours to allow the pellets to dissolve. The cooling bath was then charged with crushed ice in water and the reaction temperature was lowered to 0° C. The addition funnel was charged with a solution of 3,3,3-trifluoro-2,2-dimethyl-propanoic acid (20 g, 0.1281 mol) in tetrahydrofuran (60 mL) and the clear pale yellow solution was added drop wise over 1 hour. After the addition was complete the mixture was allowed to slowly warm to room temperature and stirring was continued for 24 hours. The suspension was cooled to 0° C. with a crushed ice-water in the cooling bath and then quenched by the very slow and drop wise addition of water (6.3 mL), followed by sodium hydroxide solution (15 weight %; 6.3 mL) and then finally with water (18.9 mL). The reaction temperature of the resulting white suspension was recorded at 5° C. The suspension was stirred at ~5° C. for 30 minutes and then filtered through a 20 mm layer of Celite. The filter cake was washed with tetrahydrofuran (2×100 mL). The filtrate was dried over sodium sulfate (150 g) and then filtered. The filtrate was concentrated under reduced pressure to provide a clear colorless oil (15 g) containing a mixture of the product 3,3,3-trifluoro-2,2-dimethyl-propan-1-ol in THF (73% weight of product ~10.95 g, and 27 wt. % THF as determined by 1H-NMR). The distillate from the rotary evaporation was distilled at atmospheric pressure using a 30 cm Vigreux column to provide 8.75 g of a residue containing 60% weight of THF and 40% weight of product (~3.5 g). The estimated total amount of product is 14.45 g (79% yield). 1H NMR (400 MHz, DMSO-d6) δ 4.99 (t, J=5.7 Hz, 1H), 3.38 (dd, J=5.8, 0.9 Hz, 2H), 1.04 (d, J=0.9 Hz, 6H).

Step 2: tert-Butyl 3-(3,3,3-trifluoro-2,2-dimethyl-propoxy)pyrazole-1-carboxylate

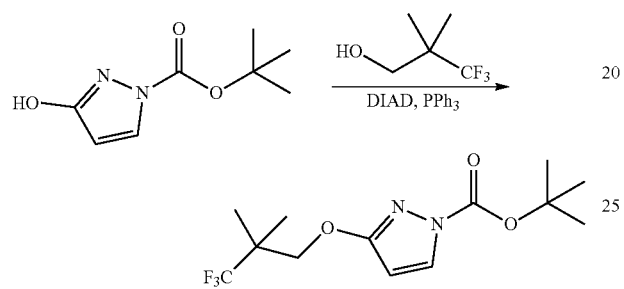

A mixture of 3,3,3-trifluoro-2,2-dimethyl-propan-1-ol (10 g, 70.36 mmol) and tert-butyl 3-hydroxypyrazole-1-carboxylate (12.96 g, 70.36 mmol) in toluene (130 mL) was treated with triphenyl phosphine (20.30 g, 77.40 mmol) followed by isopropyl N-isopropoxycarbonyliminocarbamate (14.99 mL, 77.40 mmol) and the mixture was stirred at 110° C. for 16 hours. The yellow solution was concentrated under reduced pressure, diluted with heptane (100 mL) and the precipitated triphenylphosphine oxide was removed by filtration and washed with heptane/toluene 4:1 (v:v) (100 mL). The yellow filtrate was evaporated and the residue purified by silica gel chromatography with a linear gradient of ethyl acetate in hexane (0-40%) to give tert-butyl 3-(3,3,3-trifluoro-2,2-dimethyl-propoxy)pyrazole-1-carboxylate (12.3 g, 57%) as an off white solid. ESI-MS m/z calc. 308.13477, found 309.0 (M+1)$^+$; Retention time: 1.84 minutes. $^1$H NMR (400 MHz, DMSO-d6) δ 8.10 (d, J=3.0 Hz, 1H), 6.15 (d, J=3.0 Hz, 1H), 4.18 (s, 2H), 1.55 (s, 9H), 1.21 (s, 6H).

Step 3: 3-(3,3,3-Trifluoro-2,2-dimethyl-propoxy)-1H-pyrazole

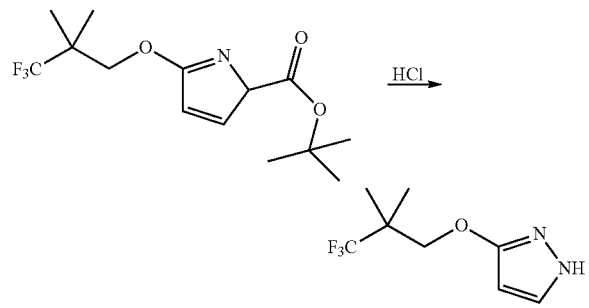

tert-Butyl 3-(3,3,3-trifluoro-2,2-dimethyl-propoxy)pyrazole-1-carboxylate (13.5 g, 43.79 mmol) was treated with 4 M hydrogen chloride in dioxane (54.75 mL, 219.0 mmol) and the mixture was stirred at 45° C. for 1 hour. The reaction mixture was evaporated to dryness and the residue was extracted with 1 M aqueous NaOH (100 mL) and methyl tert-butyl ether (100 mL), washed with brine (50 mL) and extracted with methyl tert-butyl ether (50 mL). The combined organic phases were dried, filtered and evaporated to give 3-(3,3,3-trifluoro-2,2-dimethyl-propoxy)-1H-pyrazole (9.0 g, 96%) as an off white waxy solid. ESI-MS m/z calc. 208.08235, found 209.0 (M+1)$^+$; Retention time: 1.22 minutes. $^1$H NMR (400 MHz, DMSO-d6) δ 11.91 (s, 1H), 7.52 (d, J=2.2 Hz, 1H), 5.69 (t, J=2.3 Hz, 1H), 4.06 (s, 2H), 1.19 (s, 6H).

Step 4: tert-Butyl 2-chloro-6-[3-(3,3,3-trifluoro-2,2-dimethyl-propoxy)pyrazol-1-yl]pyridine-3-carboxylate

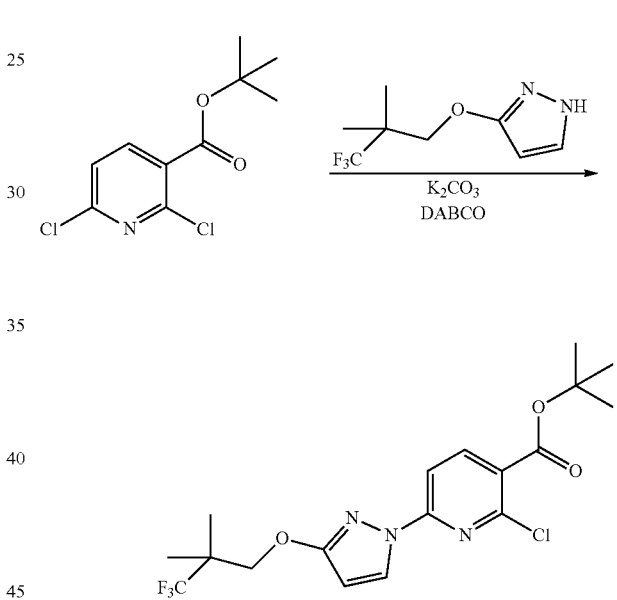

To a solution of tert-butyl 2,6-dichloropyridine-3-carboxylate (10.4 g, 41.9 mmol) and 3-(3,3,3-trifluoro-2,2-dimethyl-propoxy)-1H-pyrazole (9.0 g, 41.93 mmol) in DMF (110 mL) were added potassium carbonate (7.53 g, 54.5 mmol) and 1,4-diazabicyclo[2.2.2]octane (706 mg, 6.29 mmol) and the mixture was stirred at room temperature for 16 hours. The creamy suspension was cooled in a cold water bath and cold water (130 mL) was slowly added. The thick suspension was stirred at room temperature for 1 hour, filtered and washed with plenty of water to give tert-butyl 2-chloro-6-[3-(3,3,3-trifluoro-2,2-dimethyl-propoxy)pyrazol-1-yl]pyridine-3-carboxylate (17.6 g, 99%) as an off white solid. ESI-MS m/z calc. 419.12234, found 420.0 (M+1)$^+$; Retention time: 2.36 minutes. $^1$H NMR (400 MHz, DMSO-d6) δ 8.44 (d, J=2.9 Hz, 1H), 8.31 (d, J=8.4 Hz, 1H), 7.76 (d, J=8.4 Hz, 1H), 6.26 (d, J=2.9 Hz, 1H), 4.27 (s, 2H), 1.57 (s, 9H), 1.24 (s, 6H).

Step 5: 2-Chloro-6-[3-(3,3,3-trifluoro-2,2-dimethyl-propoxy)pyrazol-1-yl]pyridine-3-carboxylic Acid

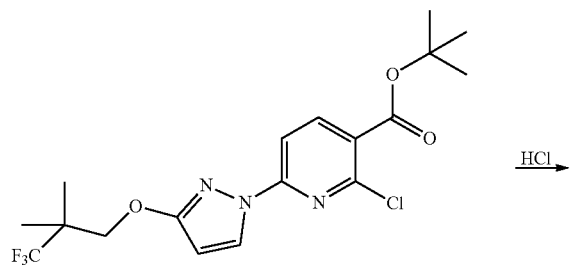

vacuum at 45-50° C. with a nitrogen bleed overnight to give 2-chloro-6-[3-(3,3,3-trifluoro-2,2-dimethyl-propoxy)pyrazol-1-yl]pyridine-3-carboxylic acid (13.7 g, 91%) as an off white solid. ESI-MS m/z calc. 363.05975, found 364.0 (M+1)+; Retention time: 1.79 minutes. $^1$H NMR (400 MHz, DMSO-d6) δ 13.61 (s, 1H), 8.44 (d, J=2.9 Hz, 1H), 8.39 (d, J=8.4 Hz, 1H), 7.77 (d, J=8.4 Hz, 1H), 6.25 (d, J=2.9 Hz, 1H), 4.28 (s, 2H), 1.24 (s, 6H).

Step 6: 2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide

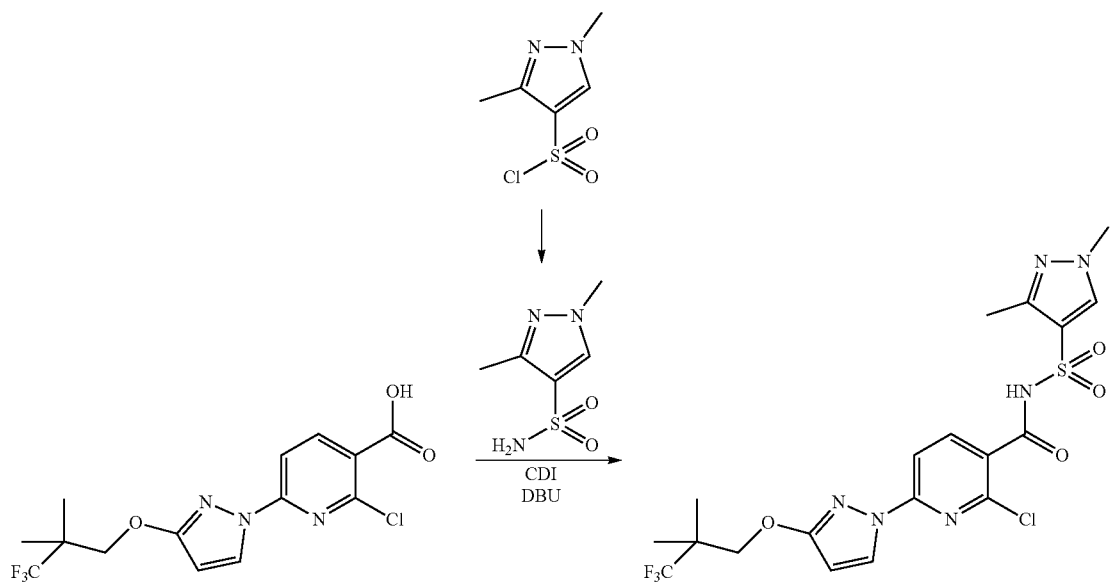

-continued

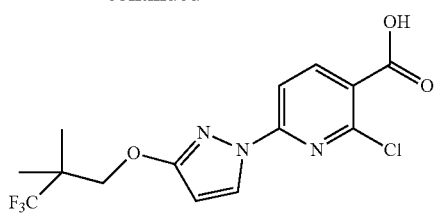

tert-Butyl 2-chloro-6-[3-(3,3,3-trifluoro-2,2-dimethyl-propoxy)pyrazol-1-yl]pyridine-3-carboxylate (17.6 g, 40.25 mmol) was suspended in isopropanol (85 mL), treated with hydrochloric acid (34 mL of 6 M, 201 mmol) and heated to reflux for 3 hours (went almost completely into solution at reflux and started to precipitate again). The suspension was diluted with water (51 mL) at reflux and left to cool to room temperature under stirring for 2.5 h. The solid was collected by filtration, washed with isopropanol/water 1:1 (v:v) (50 mL), plenty of water and dried in a drying cabinet under 2-Chloro-6-[3-(3,3,3-trifluoro-2,2-dimethyl-propoxy) pyrazol-1-yl]pyridine-3-carboxylic acid (100 mg, 0.2667 mmol) and CDI (512 mg, 3.158 mmol) were combined in THF (582.0 μL) and the mixture was stirred at room temperature. Meanwhile, 1,3-dimethylpyrazole-4-sulfonyl chloride (62 mg, 0.3185 mmol) was combined with ammonia (in methanol) in a separate vial, instantly forming a white solid. After stirring for an additional 20 min, the volatiles were removed by evaporation, and 1 mL of dichloromethane was added to the solid residue, and was also evaporated. DBU (100 μL, 0.6687 mmol) was then added and the mixture stirred at 60° C. for 5 minutes, followed by addition of THF (1 mL) which was subsequently evaporated. The contents of the vial containing the CDI activated carboxylic acid in THF were then added to the vial containing the newly formed sulfonamide and DBU, and the reaction mixture was stirred for 4 hours at room temperature. The reaction mixture was diluted with 10 mL of ethyl acetate, and washed with 10 mL solution of citric acid (1 M). The aqueous layer was extracted with ethyl acetate (2×10 mL) and the combined organics were washed with brine, dried over sodium sulfate, and concentrated to give 2-chloro-N-(1,3-dimethylpyrazol-4-yl)sulfonyl-6-[3-(3,3,3-trifluoro-2,2-dimethyl-propoxy)

pyrazol-1-yl]pyridine-3-carboxamide as a white solid (137 mg, 99%) that was used in the next step without further purification. ESI-MS m/z calc. 520.09076, found 521.1 (M+1)$^+$; Retention time: 0.68 minutes.

General UPLC/HPLC Analytical Methods

LC method A: Analytical reverse phase UPLC using an Acquity UPLC BEH C$_{18}$ column (50×2.1 mm, 1.7 μm particle) made by Waters (pn: 186002350), and a dual gradient run from 1-99% mobile phase B over 2.9 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C.

LC method B: Merckmillipore Chromolith SpeedROD C$_{18}$ column (50×4.6 mm) and a dual gradient run from 5-100% mobile phase B over 6 minutes. Mobile phase A=water (0.1% CF$_3$CO$_2$H). Mobile phase B=acetonitrile (0.1% CF$_3$CO$_2$H).

LC method C: Merckmillipore Chromolith SpeedROD C$_{18}$ column (50×4.6 mm) and a dual gradient run from 5-100% mobile phase B over 12 minutes. Mobile phase A=water (0.1% CF$_3$CO$_2$H). Mobile phase B=acetonitrile (0.1% CF$_3$CO$_2$H).

LC method D: Acquity UPLC BEH C$_{18}$ column (30×2.1 mm, 1.7 μm particle) made by Waters (pn: 186002349), and a dual gradient run from 1-99% mobile phase B over 1.0 minute. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 μL, and column temperature=60° C.

LC method E: Luna column C$_{18}$ (2) 50×3 mm, 3 μm. run: 2.5 min. Mobile phase: Initial 95% H$_2$O containing 0.1% formic acid/5% MeCN containing 0.1% formic acid, linear gradient to 95% MeCN containing 0.1% formic acid over 1.3 min, hold 1.2 min at 95% MeCN containing 0.1% formic acid. Temperature: 45° C., Flow: 1.5 mL/min.

LC method F: SunFire column C$_{18}$ 75×4.6 mm 3.5 μm, run: 6 min. Mobile phase conditions: Initial 95% H$_2$O+0.1% formic acid/5% MeCN+0.1% formic acid, linear gradient to 95% MeCN for 4 min, hold for 2 min at 95% MeCN. T: 45° C., Flow: 1.5 mL/min.

LC method G: Analytical reverse phase UPLC using an Acquity UPLC BEH C$_{18}$ column (50×2.1 mm, 1.7 μm particle) made by Waters (pn: 186002350), and a dual gradient run from 30-99% mobile phase B over 2.9 minutes. Mobile phase A=H$_2$O (0.05% CF$_3$CO$_2$H). Mobile phase B=MeCN (0.035% CF$_3$CO$_2$H). Flow rate=1.2 mL/min, injection volume=1.5 μL, and column temperature=60° C.

LC method H: Water Cortex 2.7μ C$_{18}$ (3.0 mm×50 mm) column, Temp: 55° C.; Flow: 1.2 mL/min; Mobile phase: 100% water with 0.1% trifluoroacetic(TFA) acid then 100% acetonitrile with 0.1% TFA acid, gradient 5% to 100% B over 4 min, with stay at 100% B for 0.5 min, equilibration to 5% B over 1.5 min.

LC method I: Reverse phase UPLC using an Acquity UPLC BEH Cis column (30×2.1 mm, 1.7 μm particle) made by Waters (pn: 186002349), and a dual gradient run from 30-99% mobile phase B over 1.0 minutes. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 μL, and column temperature=60° C.

Example 1: Preparation of N-(1,3-dimethylpyrazol-4-yl)sulfonyl-2-(2,2-dimethyl-4-trimethylsilyl-pyrrolidin-1-yl)-6-[3-(3,3,3-trifluoro-2,2-dimethyl-propoxy)pyrazol-1-yl]pyridine-3-carboxamide (Compound (2-8))

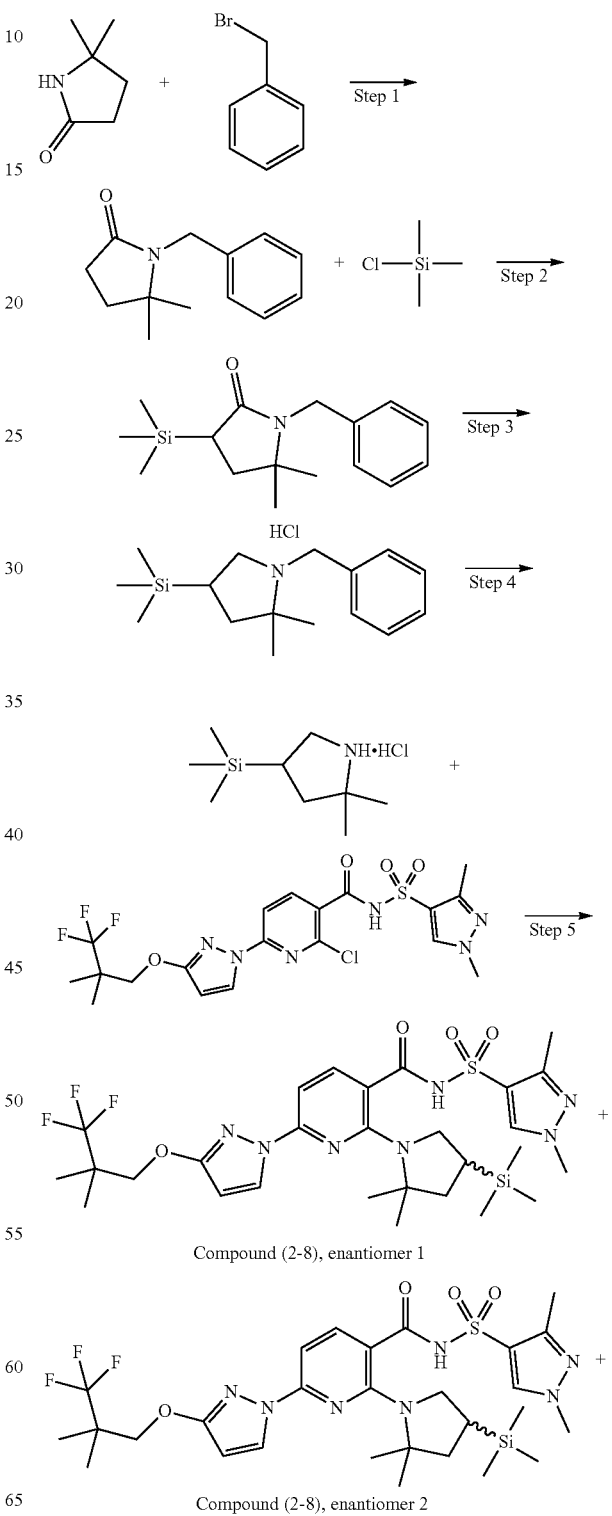

Compound (2-8), enantiomer 1

Compound (2-8), enantiomer 2

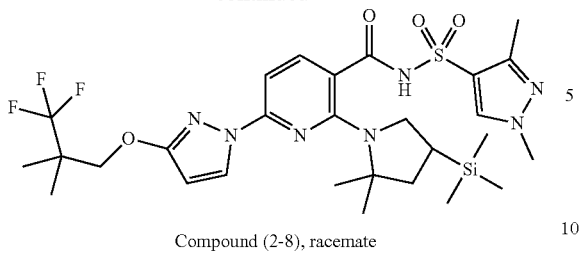

Compound (2-8), racemate

Step 1: 1-Benzyl-5,5-dimethyl-pyrrolidin-2-one

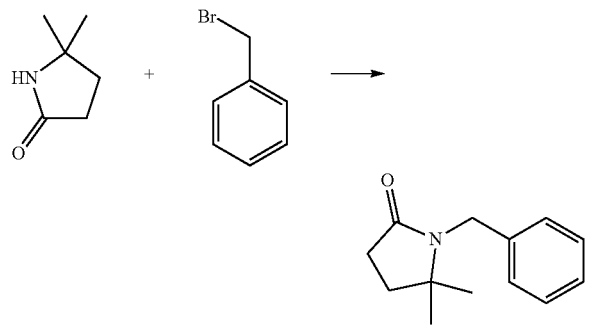

To a stirred suspension of sodium hydride (60% dispersion in mineral oil, 936 mg, 23.40 mmol) in anhydrous DMF (35 mL) was added dropwise a solution of 5,5-dimethylpyrrolidin-2-one (2.36 g, 20.86 mmol) in anhydrous DMF (3 mL) over 3 min at 0° C. (ice-water bath) under nitrogen. The reaction was stirred at that temperature for 1.5 h, then benzyl bromide (2.8 mL, 23.54 mmol, neat) was added through syringe over 3 min. The reaction was left in the ice-bath for 45 min and then stirred at room temperature for approximately 3 hours. The reaction was quenched with aqueous ammonium chloride (75 mL) and water (50 mL) and extracted with EtOAc (3×50 mL). The combined organics were washed with brine (50 mL), dried over anhydrous sodium sulfate, filtered and concentrated under reduced pressure. The crude product was purified by silica gel chromatography (80 g silica gel column, 5-80% EtOAc in hexanes over 30 min-ELSD detection, the product eluted around 40-70% EA) to give 1-benzyl-5,5-dimethyl-pyrrolidin-2-one (3.75 g, 88%) as a colorless oil. ¹H NMR (400 MHz, DMSO-$d_6$) δ 7.32-7.24 (m, 4H), 7.24-7.17 (m, 1H), 4.32 (s, 2H), 2.35 (t, J=7.9 Hz, 2H), 1.82 (t, J=7.9 Hz, 2H), 1.08 (s, 6H). ESI-MS m/z calc. 203.13101, found 204.56 (M+1)⁺; Retention time: 1.2 minutes (LC method A).

Step 2: 1-Benzyl-5,5-dimethyl-3-trimethylsilyl-pyrrolidin-2-one

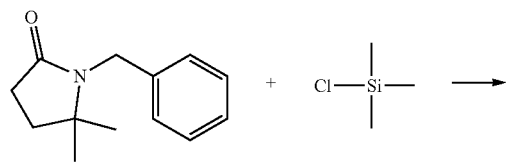

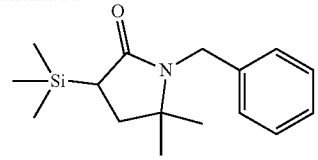

A 100 mL flask was charged under nitrogen with anhydrous THF (1 mL) and LDA (1.1 mL of 2 M solution in THF/heptane/ethylbenzene, 2.200 mmol). The mixture was stirred and cooled down to −78° C. and a solution of 1-benzyl-5,5-dimethyl-pyrrolidin-2-one (408 mg, 2.007 mmol) in anhydrous THF (1 mL) was added dropwise. After 25 min at this temperature, TMSCl (1.5 mL, 11.82 mmol) (neat) was added dropwise. The mixture was stirred in the cooling bath at −78° C. for 2 h. The cooling bath was removed and the mixture was quenched with aqueous saturated ammonium chloride (40 mL) and water (20 mL). The product was extracted with EtOAc (2×30 mL). The combined extracts were dried over sodium sulfate and the solvents evaporated. The crude was dissolved in DCM and purified by flash chromatography on silica gel (40 g column) using a gradient of ethyl acetate (0 to 50% over 15 min.) in hexanes. The product eluted around 30-40% EA. Evaporation of the solvents gave 1-benzyl-5,5-dimethyl-3-trimethylsilyl-pyrrolidin-2-one (393 mg, 71%) as a colorless oil that slowly solidified into a white solid. ¹H NMR (400 MHz, DMSO-$d_6$) δ 7.36-7.11 (m, 5H), 4.46 (d, J=15.7 Hz, 1H), 4.13 (d, J=15.7 Hz, 1H), 2.11 (t, J=10.0 Hz, 1H), 1.94 (dd, J=12.6, 9.5 Hz, 1H), 1.62 (dd, J=12.6, 10.5 Hz, 1H), 1.07 (s, 3H), 1.07 (s, 3H), 0.08 (s, 9H). ESI-MS m/z calc. 275.17053, found 276.16 (M+1)⁺; Retention time: 1.87 minutes (LC method A).

Step 3: (1-Benzyl-5,5-dimethyl-pyrrolidin-3-yl)-trimethyl-silane (Hydrochloride Salt)

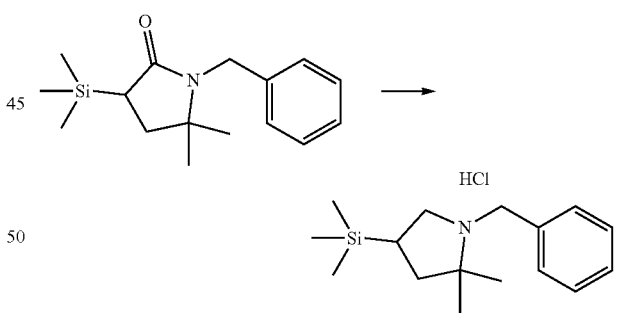

A 100 mL flask was charged under nitrogen with 1-benzyl-5,5-dimethyl-3-trimethylsilyl-pyrrolidin-2-one (1.097 g, 3.98 mmol) and anhydrous THF (15 mL). A solution of LAH (2M in THF, 5.3 mL, 10.60 mmol) was added dropwise (effervescence). At the end of the addition, the reaction was stirred in a dry bath at 65° C. for 17 h. The mixture was cooled down in ice and water (0.3 mL, 16.65 mmol) was added dropwise followed by aqueous 2M NaOH (0.32 mL, 0.6400 mmol) and water (1 mL, 55.51 mmol). The slurry was stirred at room temperature for 15 min. The solid was filtered out on a pad of celite and washed with THF. The filtrate was evaporated. The residue was dissolved in DMSO/MeOH. The solution was microfiltered through a 0.45 µM PTFE syringe filter disc and purified by reverse phase preparative HPLC (C$_{18}$) using a gradient of acetonitrile in water (1 to 99% over 15 min) and HCl as a modifier. Evaporation gave (1-benzyl-5,5-dimethyl-pyrrolidin-3-yl)-trimethyl-silane (hydrochloride salt) (36 mg, 3%) as a colorless film. The product was used for the next step without any further purification. ESI-MS m/z calc. 261.19128, found 262.17 (M+1)$^+$; Retention time: 1.12 minutes (LC method A).

Step 4: (5,5-Dimethylpyrrolidin-3-yl)-trimethyl-silane (Hydrochloride Salt)

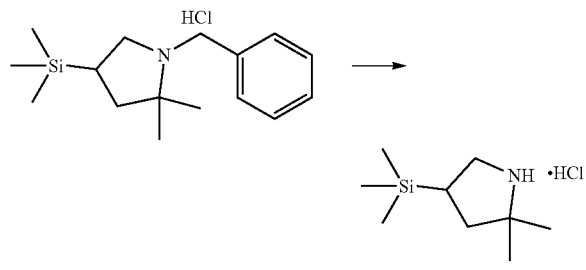

A 100 mL flask was charged with (1-benzyl-5,5-dimethyl-pyrrolidin-3-yl)-trimethyl-silane (hydrochloride salt) (25 mg, 0.084 mmol), methanol (5 mL) and Pd(OH)$_2$ (20% w/w on carbon, 60 mg, 0.085 mmol). After purging by bubbling nitrogen, the mixture was stirred under hydrogen atmosphere (balloon) for 19 h. 1N aq. HCl was added (10 mL) and additional methanol (20 mL). The mixture was degassed and filtered through a pad of celite. Evaporation of the solvents gave 23 mg of crude material. The material was dissolved in DMSO (1 mL). The solution was microfiltered through a 0.45 µM PTFE syringe filter disc and purified by reverse phase preparative HPLC (C$_{18}$) using a gradient of acetonitrile in water (1 to 99% over 15 min) and HCl as a modifier. Evaporation gave (5,5-dimethylpyrrolidin-3-yl)-trimethyl-silane (hydrochloride salt) (10 mg, 57%) as a colorless resin that slowly crystallized. ESI-MS m/z calc. 171.14433, found 172.19 (M+1)$^+$; Retention time: 0.88 minutes (LC method A).

Step 5: N-(1,3-dimethylpyrazol-4-yl)sulfonyl-2-(2,2-dimethyl-4-trimethylsilyl-pyrrolidin-1-yl)-6-[3-(3,3,3-trifluoro-2,2-dimethyl-propoxy)pyrazol-1-yl]pyridine-3-carboxamide (Compound (2-8), Enantiomer 1 and Enantiomer 2)

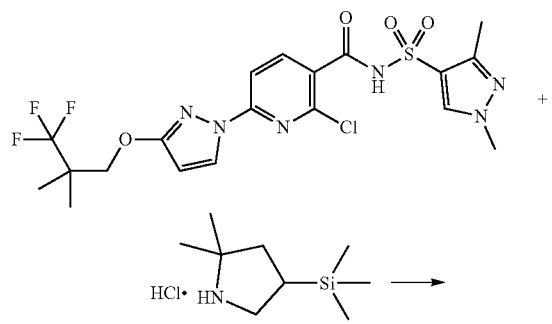

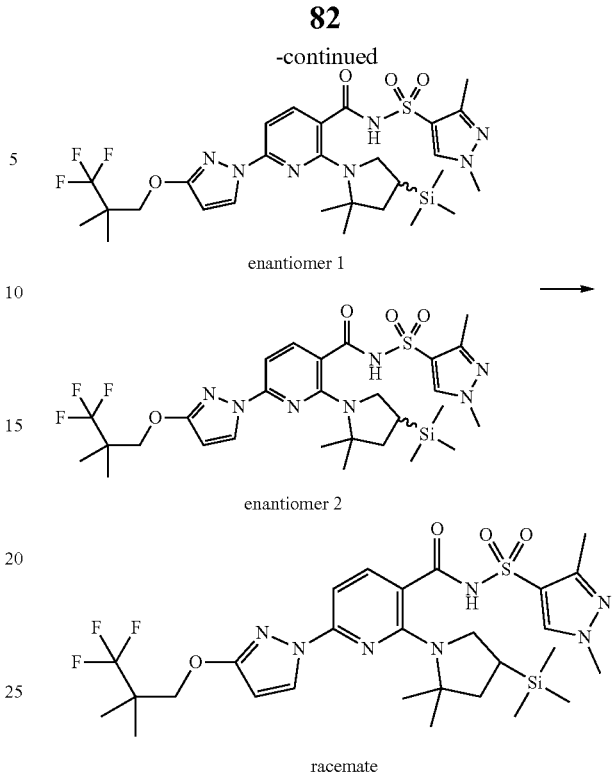

An HPLC vial was charged with (5,5-dimethylpyrrolidin-3-yl)-trimethyl-silane (hydrochloride salt) (29 mg, 0.14 mmol), 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (40 mg, 0.077 mmol), K$_2$CO$_3$ (60 mg, 0.43 mmol) (325 mesh) and NMP (250 µL). The vial was capped and stirred at 145° C. for 23 hours. The mixture was diluted with DMSO (1 mL). The suspension was microfiltered through a Whatman 0.45 µM PTFE syringe filter disc and purified by reverse phase preparative HPLC (C$_{18}$) using a gradient of acetonitrile in water (1 to 99% over 15 min) and HCl as a modifier. The pure fractions were evaporated and the residue was triturated in DCM/hexanes. Evaporation gave racemic N-(1,3-dimethylpyrazol-4-yl)sulfonyl-2-(2,2-dimethyl-4-trimethylsilyl-pyrrolidin-1-yl)-6-[3-(3,3,3-trifluoro-2,2-dimethyl-propoxy)pyrazol-1-yl]pyridine-3-carboxamide (33 mg, 66%) as a tan solid. $^1$H NMR (400 MHz, DMSO-d6) δ 12.31 (s, 1H), 8.36 (s, 1H), 8.24 (d, J=2.8 Hz, 1H), 7.72 (d, J=8.2 Hz, 1H), 6.91 (d, J=8.2 Hz, 1H), 6.18 (d, J=2.8 Hz, 1H), 4.23 (s, 2H), 3.79 (s, 3H), 3.19 (t, J=11.5 Hz, 1H), 2.60 (t, J=9.0 Hz, 1H), 2.33 (s, 3H), 1.81 (dd, J=12.0, 5.2 Hz, 1H), 1.63 (d, J=13.6 Hz, 1H), 1.59 (s, 3H), 1.55 (s, 3H), 1.44 (m, 1H), 1.23 (s, 6H), −0.07 (s, 9H). ESI-MS m/z calc. 655.25836, found 656.25 (M+1)$^+$; Retention time: 2.35 minutes (LC method A).

The two enantiomers were separated by chiral SFC using a ChiralPaq iG (250×10 mm), 5 µM column at 35° C.; Mobile phase: 38% MeOH (no modifier), 62% CO$_2$; flow: 10 mL/min; concentration: 23 mg/mL in MeOH (no modifier); injection volume: 70 µL; pressure: 134 bar; wavelength: 276 nM. For each compound, the solvents were evaporated to give the separated enantiomers as white solids.

Compound (2-8), enantiomer 1: N-(1,3-Dimethylpyrazol-4-yl)sulfonyl-2-(2,2-dimethyl-4-trimethylsilyl-pyrrolidin-1-yl)-6-[3-(3,3,3-trifluoro-2,2-dimethyl-propoxy)pyrazol-1- yl]pyridine-3-carboxamide (11 mg, 43%). ESI-MS m/z calc. 655.25836, found 656.32 (M+1)⁺; Retention time: 2.38 minutes (LC method A).

Compound (2-8), enantiomer 2: N-(1,3-Dimethylpyrazol-4-yl)sulfonyl-2-(2,2-dimethyl-4-trimethylsilyl-pyrrolidin-1-yl)-6-[3-(3,3,3-trifluoro-2,2-dimethyl-propoxy)pyrazol-1-yl]pyridine-3-carboxamide (11 mg, 44%). ESI-MS m/z calc. 655.25836, found 656.26 (M+1)⁺; Retention time: 2.38 minutes (LC method A).

Compound (2-8), racemate: A DMSO stock solution of N-(1,3-dimethylpyrazol-4-yl)sulfonyl-2-(2,2-dimethyl-4-trimethylsilyl-pyrrolidin-1-yl)-6-[3-(3,3,3-trifluoro-2,2-dimethyl-propoxy)pyrazol-1-yl]pyridine-3-carboxamide (0.2 mL of 10 mM, 0.0020 mmol) (Compound (2-8), enantiomer 1) was combined with a DMSO stock solution of N-(1,3-dimethylpyrazol-4-yl)sulfonyl-2-(2,2-dimethyl-4-trimethylsilyl-pyrrolidin-1-yl)-6-[3-(3,3,3-trifluoro-2,2-dimethyl-propoxy)pyrazol-1-yl]pyridine-3-carboxamide (0.2 mL of 10 mM, 0.0020 mmol) (Compound (2-8), enantiomer 2) to make a racemic mixture of N-(1,3-dimethylpyrazol-4-yl)sulfonyl-2-(2,2-dimethyl-4-trimethyl silyl-pyrrolidin-1-yl)-6-[3-(3,3,3-trifluoro-2,2-dimethyl-propoxy)pyrazol-1-yl]pyridine-3-carboxamide. ESI-MS m/z calc. 655.25836, found 656.5 (M+1)⁺; Retention time: 2.33 minutes (LC method A).

Example 2: Preparation of N-(1,3-dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide (Compound (3-2))

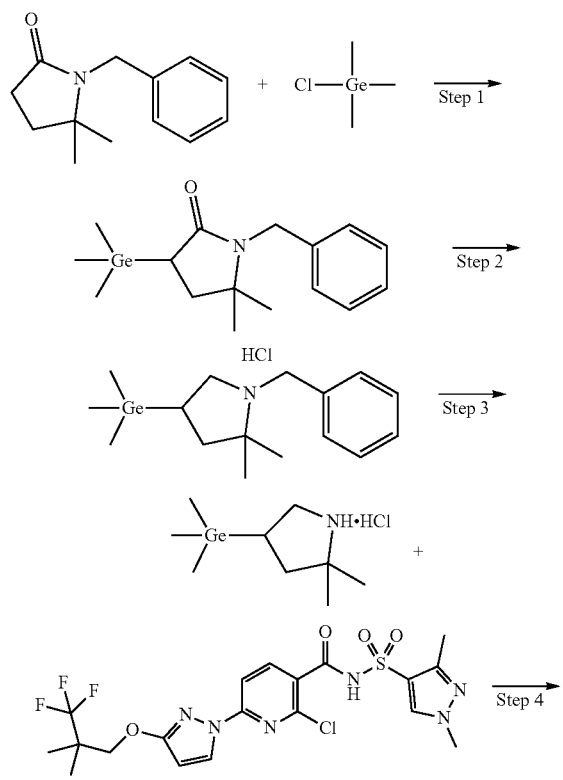

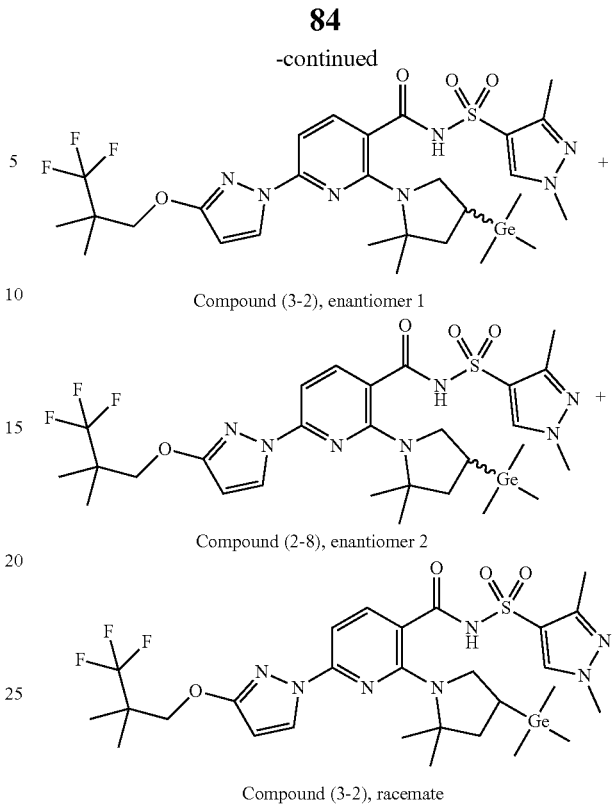

Compound (3-2), enantiomer 1

Compound (2-8), enantiomer 2

Compound (3-2), racemate

Step 1: 1-Benzyl-5,5-dimethyl-3-trimethylgermyl-pyrrolidin-2-one

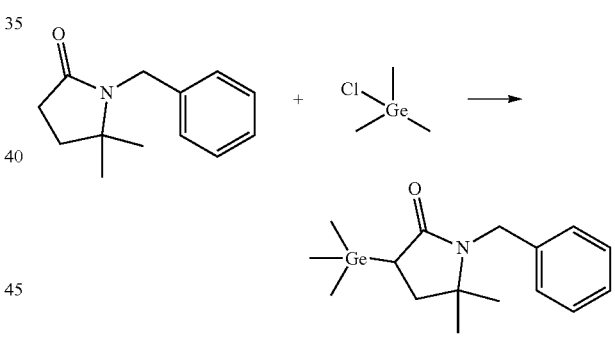

A 100 mL flask was charged under nitrogen with anhydrous THF (10 mL) and LDA (5.5 mL of 2 M solution in THF/heptane/ethylbenzene, 11.00 mmol). The mixture was stirred and cooled down to −78° C. and a solution of 1-benzyl-5,5-dimethyl-pyrrolidin-2-one (2.02 g, 9.937 mmol) in anhydrous THF (7 mL) was added dropwise over 5 min. After approximately 30 min at this temperature, chloro(trimethyl)germane (6.0 mL, 48.56 mmol) (neat) was added dropwise. The mixture was stirred in the cooling bath at −78° C. for approximately 3 h. The acetone dry-ice cooling bath was replaced by ice-water and the mixture was quenched with aqueous saturated ammonium chloride (40 mL) and water (20 mL). The product was extracted with EtOAc (2×25 mL). The combined extracts were dried over sodium sulfate and the solvents evaporated. The crude was dissolved in DCM and purified by flash chromatography on silica gel (120 g column) using a gradient of ethyl acetate (0 to 40% over 30 min, ELSD collection) in hexanes. The product eluted around 20-30% EA. Evaporation gave 1-benzyl-5,5-dimethyl-3-trimethylgermyl-pyrrolidin-2-one (1.958 g, 62%) as a colorless oil that slowly solidified. ¹H NMR (400 MHz, DMSO-$d_6$) δ 7.42-7.09 (m, 5H), 4.45 (d, J=15.6 Hz, 1H), 4.15 (d, J=15.6 Hz, 1H), 2.27 (t, J=9.5 Hz, 1H), 2.00 (dd, J=12.7, 9.7 Hz, 1H), 1.63 (dd, J=12.7, 9.4 Hz, 1H), 1.08 (s, 3H), 1.06 (s, 3H), 0.21 (s, 9H). ESI-MS m/z calc. 321.1148, found 322.09 (M+1)⁺; Retention time: 1.9 minutes (LC method A).

Step 2: (1-Benzyl-5,5-dimethyl-pyrrolidin-3-yl)-trimethyl-germane (Hydrochloride Salt)

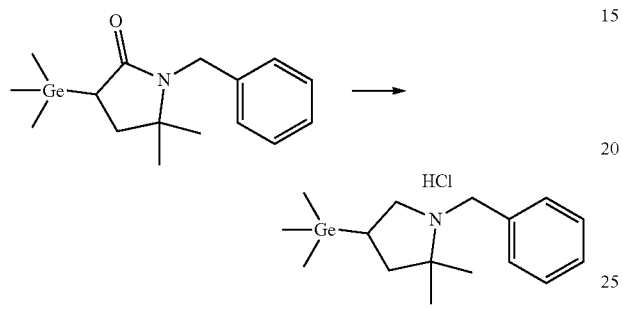

A 100 mL flask was charged under nitrogen with 1-benzyl-5,5-dimethyl-3-trimethylgermyl-pyrrolidin-2-one (1.947 g, 6.08 mmol) and anhydrous THF (20 mL). A solution of LiAlH₄ (8 mL of 2 M in THF, 16.00 mmol) was added dropwise (effervescence). At the end of the addition, the reaction was stirred in a dry bath at 65° C. for 16 h. The mixture was cooled down to room temperature, diluted with THF, cooled down in ice and water (500 µL, 27.75 mmol) was added dropwise followed by aqueous NaOH (500 µL of 2 M, 1.000 mmol) and water (1.5 mL, 83.26 mmol). The slurry was stirred at room temperature for 30 min. The solid was filtered out on a pad of celite and washed with THF. The filtrate was evaporated. The residue was dissolved in DMSO. The solution was microfiltered through a Whatman 0.45 µM PTFE syringe filter disc and purified by reverse phase preparative HPLC ($C_{18}$) using a gradient of acetonitrile in water (1 to 99% over 15 min) and HCl as a modifier. Evaporation gave (1-benzyl-5,5-dimethyl-pyrrolidin-3-yl)-trimethyl-germane (hydrochloride salt) (86 mg, 4%). The material was used for the next step without any further purification. ESI-MS m/z calc. 307.13553, found 308.11 (M+1)⁺; Retention time: 1.11 minutes (LC method A).

Step 3: (5,5-Dimethylpyrrolidin-3-yl)-trimethyl-germane (Hydrochloride Salt)

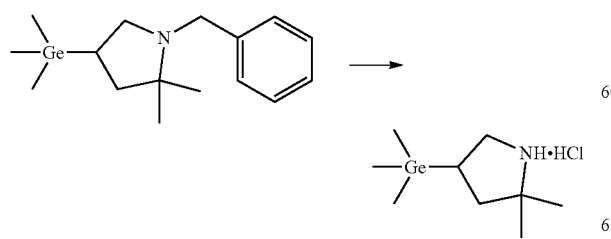

A 100 mL flask was charged with (1-benzyl-5,5-dimethyl-pyrrolidin-3-yl)-trimethyl-germane (hydrochloride salt) (95 mg, 0.2774 mmol), methanol (20 mL) and Pd(OH)₂ (191 mg of 20% w/w, 0.2720 mmol) (on carbon, 20% by weight). After purging by bubbling nitrogen, the mixture was stirred under hydrogen atmosphere (balloon) for 5 h. 1N aq. HCl was added (10 mL) and additional methanol (20 mL). The mixture was degassed and filtered through a pad of celite. After evaporation, the residue was dissolved in MeOH (1 mL). The solution was microfiltered through a Whatman 0.45 µM PTFE syringe filter disc and purified by reverse phase preparative HPLC ($C_{18}$) using a gradient of acetonitrile in water (1 to 99% over 15 min) and HCl as a modifier. Evaporation gave (5,5-dimethylpyrrolidin-3-yl)-trimethyl-germane (hydrochloride salt) (53 mg, 76%) as a colorless film. ESI-MS m/z calc. 217.08858, found 218.08 (M+1)⁺; Retention time: 0.89 minutes (LC method A).

Step 4: N-(1,3-Dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide (Compound (3-2), Enantiomer 1 and Enantiomer 2)

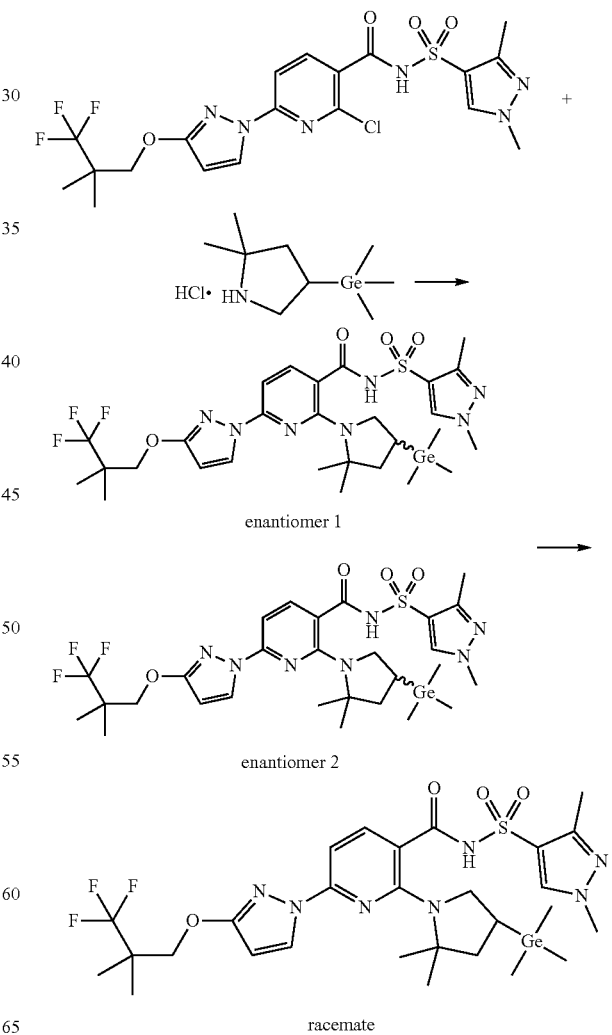

An HPLC vial was charged with (5,5-dimethylpyrrolidin-3-yl)-trimethyl-germane (hydrochloride salt) (26 mg, 0.10 mmol), 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (28 mg, 0.054 mmol), K$_2$CO$_3$ (45 mg, 0.33 mmol) (325 mesh) and NMP (200 µL). The vial was capped and stirred at 145° C. for 19 h. The mixture was diluted with DMSO (1 mL). The suspension was microfiltered through a Whatman 0.45 PTFE syringe filter disc and purified by reverse phase preparative HPLC (C$_{18}$) using a gradient of acetonitrile in water (1 to 99% over 15 min) and HCl as a modifier. The pure fractions were evaporated and the residue triturated in DCM/hexanes. Evaporation gave racemic N-(1,3-dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide (26.2 mg, 70%) as a tan solid. $^1$H NMR (400 MHz, DMSO-d$_6$) δ 12.30 (s, 1H), 8.35 (s, 1H), 8.24 (d, J=2.8 Hz, 1H), 7.71 (d, J=8.2 Hz, 1H), 6.91 (d, J=8.2 Hz, 1H), 6.18 (d, J=2.7 Hz, 1H), 4.23 (s, 2H), 3.80 (s, 3H), 3.20 (t, J=10.7 Hz, 1H), 2.71-2.60 (m, 1H), 2.33 (s, 3H), 1.93-1.79 (m, 1H), 1.70-1.60 (m, 2H), 1.59 (s, 3H), 1.56 (s, 3H), 1.23 (s, 6H), 0.06 (s, 9H). ESI-MS m/z calc. 701.20264, found 702.189 (M+1)$^+$; Retention time: 2.4 minutes (LC method A)

The two enantiomers were separated by chiral SFC using a ChiralPak IG (250×10 mm), 5 µM column at 35° C.; Mobile phase: 32% MeOH (no modifier), 68% CO$_2$; flow: 10 mL/min; concentration: 23 mg/mL in MeOH no modifier; injection volume: 70 µL; pressure: 136 bar; wavelength: 276 nM. For each compound, the solvents were evaporated to give the separated enantiomers as white solids.

Compound (3-2), enantiomer 1: N-(1,3-Dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide (8.9 mg, 47%). ESI-MS m/z calc. 701.20264, found 702.24 (M+1)$^+$; Retention time: 2.39 minutes (LC method A).

Compound (3-2), enantiomer 2: N-(1,3-Dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide (9.3 mg, 49%). ESI-MS m/z calc. 701.20264, found 702.24 (M+1)$^+$; Retention time: 2.39 minutes (LC method A).

Compound (3-2), racemate: A DMSO stock solution of N-(1,3-dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide (200 µL of 10 mM, 0.002 mmol) (compound (3-2), enantiomer 1) was combined with a DMSO stock solution of N-(1,3-dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide (200.0 µL of 10 mM, 0.002 mmol) (compound (3-2), enantiomer 2) to make a racemic mixture of N-(1,3-dimethylpyrazol-4-yl)sulfonyl-2-(2,2-dimethyl-4-trimethylgermyl-pyrrolidin-1-yl)-6-[3-(3,3,3-trifluoro-2,2-dimethyl-propoxy)pyrazol-1-yl]pyridine-3-carboxamide. ESI-MS m/z calc. 701.20264, found 702.5 (M+1)$^+$; Retention time: 2.36 minute (LC method A).

Example 3: Preparation of N-(1,3-dimethylpyrazol-4-yl)sulfonyl-2-[(4S)-2,2,4-trimethylpyrrolidin-1-yl]-6-(3-trimethylsilylpyrazol-1-yl)pyridine-3-carboxamide (Compound (2-12))

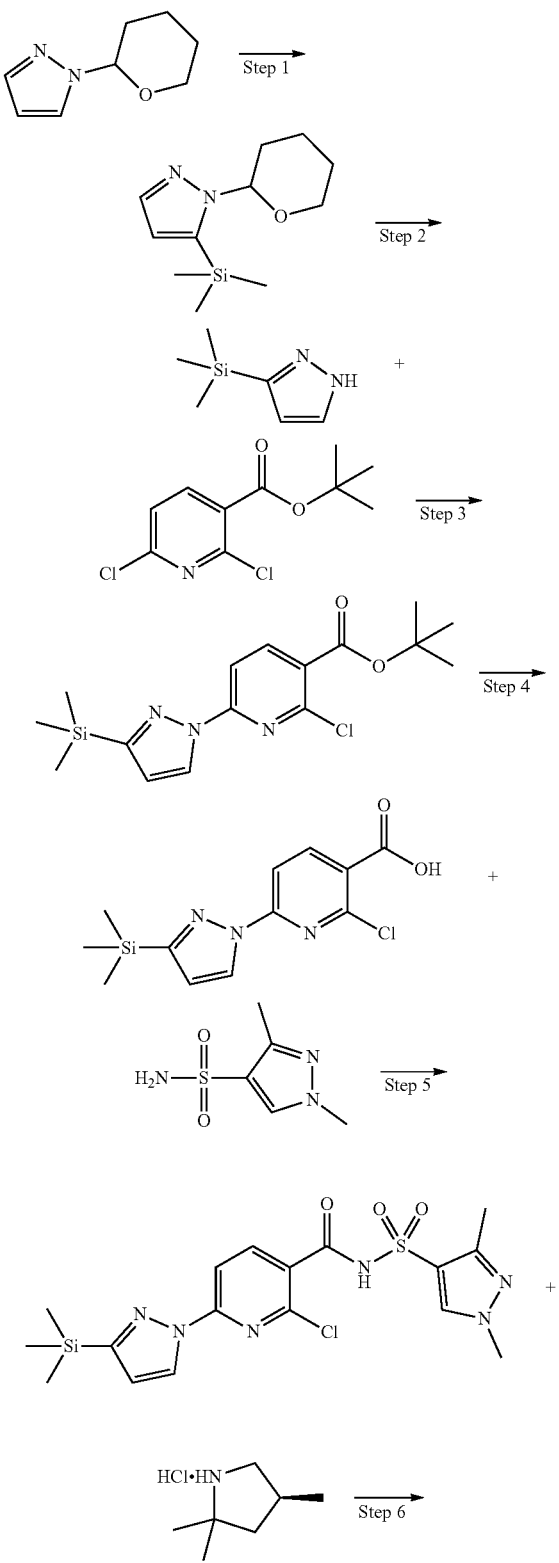

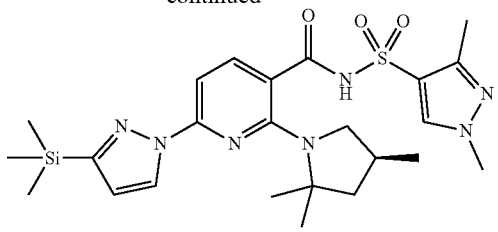

Step 1: Trimethyl-(2-tetrahydropyran-2-ylpyrazol-3-yl)silane

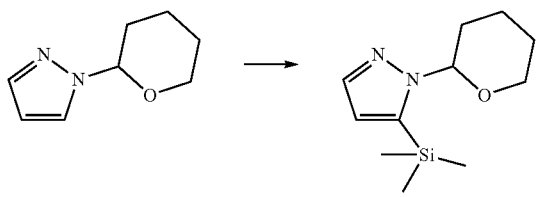

1-Tetrahydropyran-2-ylpyrazole (5.85 g, 38.44 mmol) was dissolved in THF (35 mL) and cooled to −35° C. n-Butyl lithium (18.5 mL of 2.5 M in hexanes, 46.25 mmol) was added dropwise and the solution was stirred for an additional 1 h at −35° C. Chloro(trimethyl)silane (5.4 mL, 42.55 mmol) was added dropwise and the reaction was allowed to warm to room temperature and stir for 3 h. At this point, 100 mL of a saturated aqueous ammonium chloride solution was added and the mixture was extracted with ether. The organics were separated, washed with brine, dried over magnesium sulfate and evaporated. The crude material was purified by silica gel chromatography eluting with 0-50% ethyl acetate in hexanes to give trimethyl-(2-tetrahydropyran-2-ylpyrazol-3-yl)silane (6.88 g, 80%) as a clear oil. $^1$H NMR (400 MHz, DMSO-$d_6$) δ 7.47 (d, J=1.6 Hz, 1H), 6.42 (d, J=1.7 Hz, 1H), 5.30 (dd, J=9.4, 2.3 Hz, 1H), 3.92-3.84 (m, 1H), 3.65-3.55 (m, 1H), 2.31-2.19 (m, 1H), 2.01-1.88 (m, 2H), 1.76-1.62 (m, 1H), 1.57-1.48 (m, 2H), 0.29 (s, 9H). ESI-MS m/z calc. 224.13449, found 225.3 (M+1)$^+$; Retention time: 0.66 minutes (LC method D).

Step 2: Trimethyl(1H-pyrazol-3-yl)silane

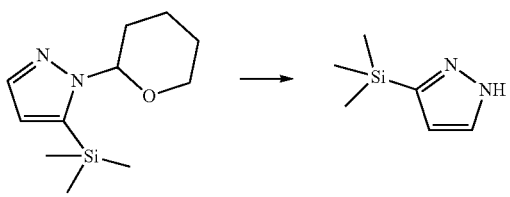

Trimethyl-(1-tetrahydropyran-2-ylpyrazol-3-yl)silane (6.88 g, 30.66 mmol) was dissolved in a mixture of ethanol (7.5 mL) and aqueous 6 N HCl (15 mL, 90.00 mmol) and heated at 50° C. for 4 h. A saturated aqueous NaHCO$_3$ solution was added to quench the acid, and the resulting solution was extracted with ethyl acetate two times. The organics were combined, washed with brine, dried over magnesium sulfate and evaporated. The crude material was purified by silica gel chromatography eluting with 0-100% ethyl acetate in hexanes to give trimethyl(1H-pyrazol-3-yl)silane (3.48 g, 81%) as a white solid. $^1$H NMR (400 MHz, DMSO-$d_6$) δ 12.78 (s, 1H), 7.49 (s, 1H), 6.38 (s, 1H), 0.26 (s, 9H). ESI-MS m/z calc. 140.07698, found 141.5 (M+1)$^+$; Retention time: 0.41 minutes (LC method D).

Step 3: Tert-Butyl 2-chloro-6-(3-trimethylsilylpyrazol-1-yl)pyridine-3-Carboxylate

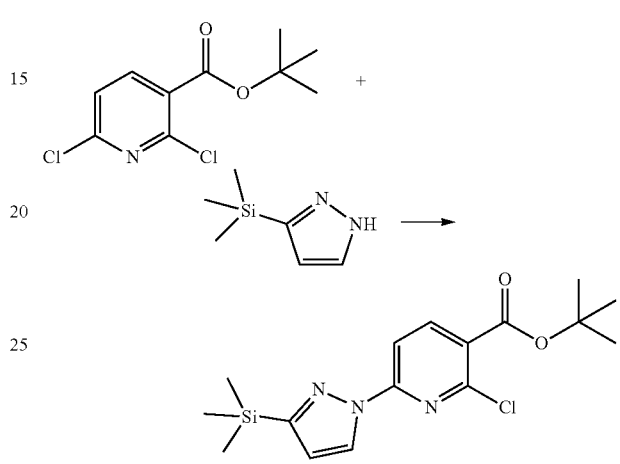

tert-Butyl 2,6-dichloropyridine-3-carboxylate (1.68 g, 6.77 mmol), trimethyl(1H-pyrazol-3-yl)silane (950 mg, 6.77 mmol), DABCO (154 mg, 1.37 mmol), and potassium carbonate (1.12 g, 8.10 mmol) were combined in DMSO (20 mL) under nitrogen and stirred at room temperature for 16 h. The reaction was diluted with water (60 mL) and stirred for 30 min. The resulting white solid was collected via filtration and washed with water. The solid was further dried to give tert-butyl 2-chloro-6-(3-trimethylsilylpyrazol-1-yl)pyridine-3-carboxylate (2.16 g, 91%) as a white solid. $^1$H NMR (400 MHz, DMSO-$d_6$) δ 8.58 (d, J=2.6 Hz, 1H), 8.36 (d, J=8.4 Hz, 1H), 7.99 (d, J=8.4 Hz, 1H), 6.76 (d, J=2.6 Hz, 1H), 1.57 (s, 9H), 0.31 (s, 9H). ESI-MS m/z calc. 351.11697, found 353.2 (M+2)$^+$; Retention time: 0.94 minutes (LC method D).

Step 4: 2-Chloro-6-(3-trimethylsilylpyrazol-1-yl)pyridine-3-carboxylic Acid

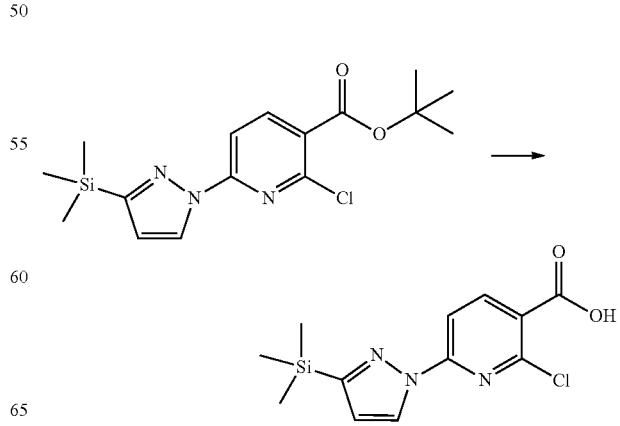

In a 50 mL flask, to a stirred solution of tert-butyl 2-chloro-6-(3-trimethylsilylpyrazol-1-yl)pyridine-3-carboxylate (540 mg, 1.53 mmol) in anhydrous dichloromethane (10 mL) was added trifluoroacetic acid (2.5 mL, 32.45 mmol) at ambient temperature under nitrogen. The reaction was stirred at ambient temperature overnight (12 h). The volatiles were removed under reduced pressure and the crude viscous residue was subjected to three cycles of addition and evaporation with dichloromethane-hexanes (1:1 ratio, 20 mL in each cycle) to obtain a solid. After further drying under high vacuum the desired 2-chloro-6-(3-trimethylsilylpyrazol-1-yl)pyridine-3-carboxylic acid (454 mg, 100%) was obtained as an off-white solid. It was used in the subsequent amide coupling reaction. $^1$H NMR (400 MHz, Chloroform-d) δ 8.58 (d, J=2.6 Hz, 1H), 8.46 (d, J=8.5 Hz, 1H), 8.08 (d, J=8.5 Hz, 1H), 6.59 (d, J=2.6 Hz, 1H), 0.34 (s, 9H) (carboxylic acid proton was not seen). ESI-MS m/z calc. 295.05438, found 296.0 (M+1)$^+$; Retention time: 1.77 minutes (LC method A).

Step 5: 2-Chloro-N-(1,3-dimethylpyrazol-4-yl)sulfonyl-6-(3-trimethylsilylpyrazol-1-yl)pyridine-3-carboxamide

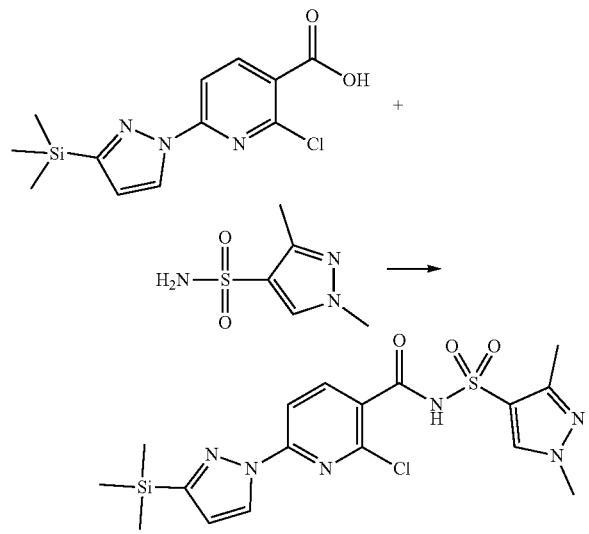

In a 50 mL flask, to a stirred solution of 2-chloro-6-(3-trimethylsilylpyrazol-1-yl)pyridine-3-carboxylic acid (195 mg, 0.66 mmol) in anhydrous tetrahydrofuran (2 mL) was added CDI (170 mg, 1.05 mmol) under nitrogen and stirred at room temperature for 4 h. Then 1,3-dimethylpyrazole-4-sulfonamide (135 mg, 0.77 mmol) and DBU (500 μL, 3.34 mmol) were added in that order and the solution was stirred at room temperature for 14 h (overnight). Then aqueous 10% citric acid (20 mL) was added carefully. The suspension was extracted with ethyl acetate (2×25 mL). The combined organics were further washed with 10% citric acid (20 mL), followed by brine (20 mL). The organics were dried over anhydrous sodium sulfate, filtered and concentrated under reduced pressure. The crude material 2-chloro-N-(1,3-dimethylpyrazol-4-yl)sulfonyl-6-(3-trimethylsilylpyrazol-1-yl)pyridine-3-carboxamide (330 mg, 71%) was obtained as off-white solid and used in the subsequent step without further purification. $^1$H NMR (400 MHz, Chloroform-d) δ 9.34 (s, 1H), 8.51 (d, J=2.7 Hz, 1H), 8.31 (d, J=8.5 Hz, 1H), 8.10 (d, J=8.4 Hz, 1H), 8.08 (s, 1H), 6.58 (d, J=2.6 Hz, 1H), 3.89 (s, 3H), 2.50 (s, 3H), 0.33 (s, 9H). ESI-MS m/z calc. 452.08536, found 453.0 (M+1)$^+$; Retention time: 1.74 minutes (LC method A).

Step 6: N-(1,3-Dimethylpyrazol-4-yl)sulfonyl-2-[(4S)-2,2,4-trimethylpyrrolidin-1-yl]-6-(3-trimethylsilylpyrazol-1-yl)pyridine-3-carboxamide (Compound (2-12))

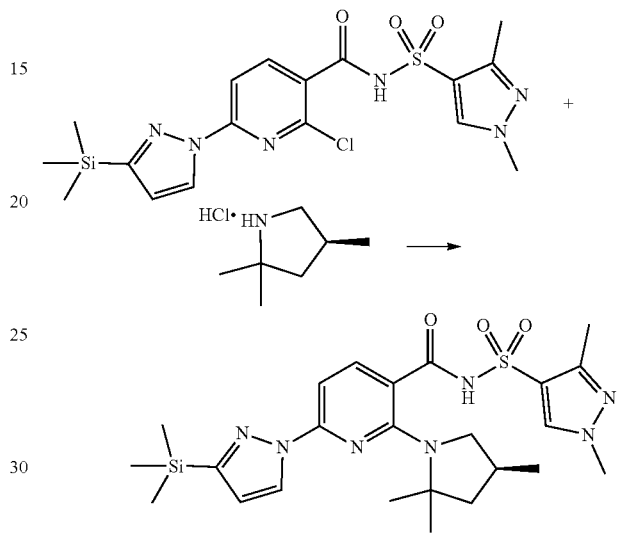

In a 20 mL microwave tube, to a stirred solution of 2-chloro-N-(1,3-dimethylpyrazol-4-yl)sulfonyl-6-(3-trimethylsilylpyrazol-1-yl)pyridine-3-carboxamide (300 mg, 0.53 mmol) in anhydrous dimethyl sulfoxide (4 mL) were added potassium carbonate (370 mg, 2.68 mmol) and (4S)-2,2,4-trimethylpyrrolidine (hydrochloride salt) (240 mg, 1.60 mmol), in that order, under nitrogen at ambient temperature. The tube was capped under nitrogen and the heterogeneous mixture was stirred at 130° C. for 20 h in an oil-bath. The reaction was allowed to cool to ambient temperature and partitioned between ethyl acetate (30 mL) and cold 10% aqueous citric acid solution (20 mL). The organics were separated and the aqueous was re-extracted with ethyl acetate (20 mL). The combined organics were further washed with 10% aqueous citric acid (20 mL), followed by brine (20 mL). The organics were dried over anhydrous sodium sulfate, filtered and concentrated under reduced pressure. The crude material was purified from silica gel chromatography (40 g silica gel column, eluting with 5-80% ethyl acetate in hexanes over 30 min; compound eluted at 45% ethyl acetate) to furnish desired N-(1,3-dimethylpyrazol-4-yl)sulfonyl-2-[(4S)-2,2,4-trimethylpyrrolidin-1-yl]-6-(3-trimethylsilylpyrazol-1-yl)pyridine-3-carboxamide (179 mg, 63%) as a white solid. $^1$H NMR (400 MHz, DMSO-d$_6$) δ 12.40 (s, 1H), 8.39 (d, J=2.5 Hz, 1H), 8.38 (s, 1H), 7.78 (d, J=8.2 Hz, 1H), 7.15 (d, J=8.2 Hz, 1H), 6.70 (d, J=2.5 Hz, 1H), 3.81 (s, 3H), 2.55 (t, J=10.4 Hz, 1H), 2.44 (dd, J=10.2, 7.1 Hz, 1H), 2.33 (s, 3H), 2.26-2.12 (m, 1H), 1.88 (dd, J=11.9, 5.6 Hz, 1H), 1.58 (s, 3H), 1.55 (s, 3H), 1.43 (t, J=12.2 Hz, 1H), 0.82 (d, J=6.3 Hz, 3H), 0.29 (s, 9H). ESI-MS m/z calc. 529.2291, found 530.2 (M+1)$^+$; Retention time: 2.1 minutes (LC method A).

Example 4: Preparation of 6-[3-[tert-butyl(dimethyl)silyl]pyrazol-1-yl]-N-(1,3-dimethylpyrazol-4-yl)sulfonyl-2-[(4S)-2,2,4-trimethylpyrrolidin-1-yl]pyridine-3-carboxamide (Compound (2-10))

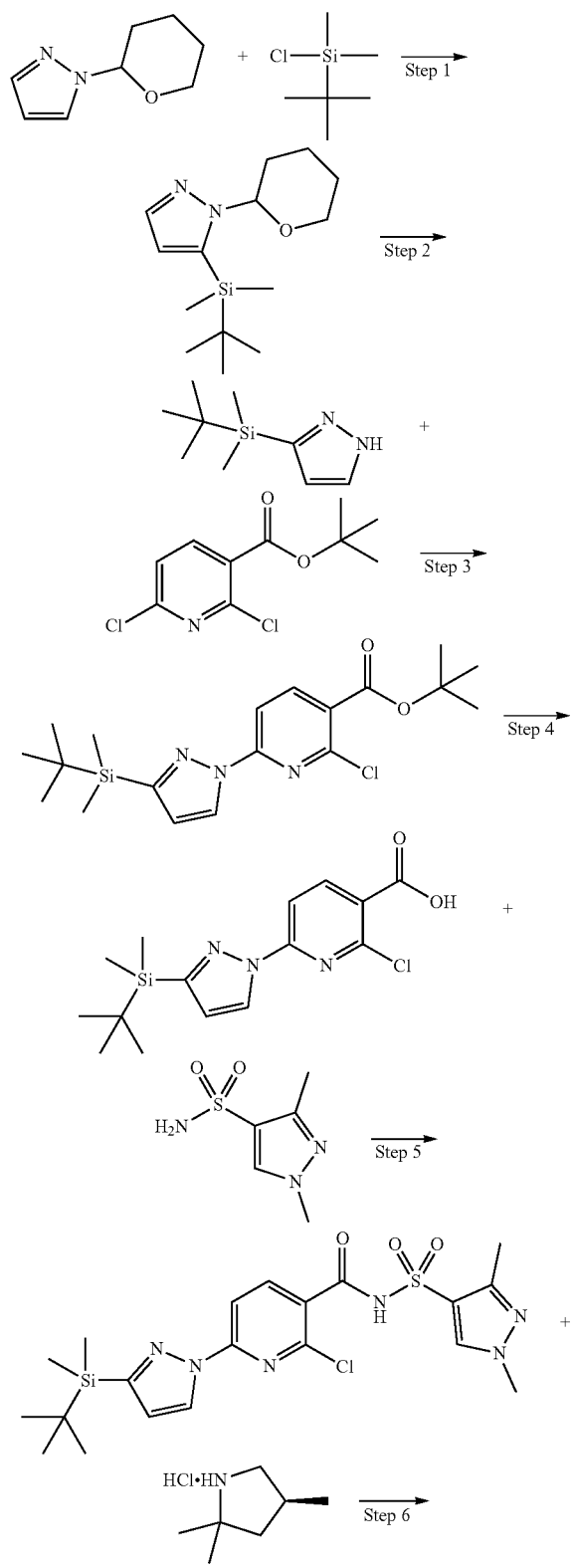

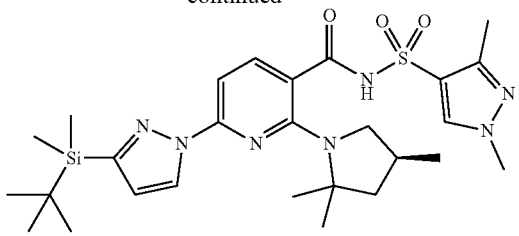

Step 1: tert-Butyl-dimethyl-(2-tetrahydropyran-2-ylpyrazol-3-yl)silane

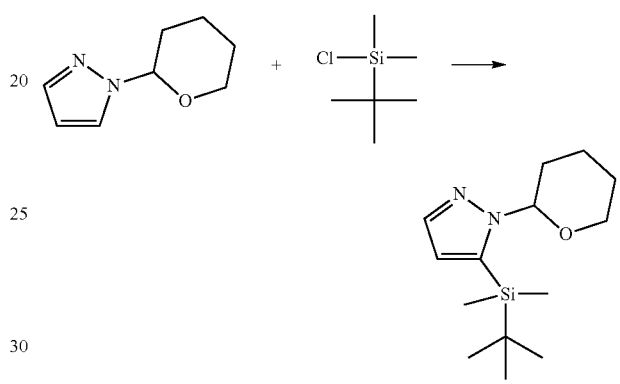

1-Tetrahydropyran-2-ylpyrazole (5.065 g, 33.28 mmol) was dissolved in THF (30 mL) and cooled to −35° C. n-Butyl lithium (16 mL of 2.5 M solution in hexanes, 40.00 mmol) was added dropwise and the solution was stirred for an additional 1 h at −35° C. A solution of tert-butyl-chloro-dimethyl-silane (5.1 g, 33.84 mmol) in THF (7 mL) was added dropwise and the reaction was allowed to warm to room temperature and stir for 3 h. At this point, a saturated ammonium chloride solution was added until pH was ~7 and the mixture was extracted with ether. The organics were separated, washed with brine, dried over magnesium sulfate and evaporated to give tert-butyl-dimethyl-(2-tetrahydropyran-2-ylpyrazol-3-yl)silane (8.41 g, 95%) as an orange oil. $^1$H NMR (400 MHz, DMSO-$d_6$) δ 7.53 (d, J=1.6 Hz, 1H), 6.43 (d, J=1.7 Hz, 1H), 5.23 (dd, J=10.1, 2.4 Hz, 1H), 3.96-3.85 (m, 1H), 3.63-3.48 (m, 1H), 2.43-2.29 (m, 1H), 2.02-1.92 (m, 1H), 1.84-1.75 (m, 1H), 1.73-1.56 (m, 1H), 1.56-1.47 (m, 2H), 0.88 (s, 9H), 0.32 (s, 3H), 0.30 (s, 3H). ESI-MS m/z calc. 266.18143, found 267.3 (M+1)$^+$; Retention time: 0.79 minutes (LC method D).

Step 2: tert-Butyl-dimethyl-(1H-pyrazol-3-yl)silane

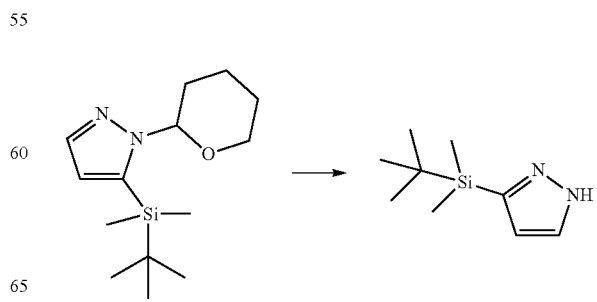

tert-Butyl-dimethyl-(1-tetrahydropyran-2-ylpyrazol-3-yl)silane (8.4 g, 31.53 mmol) was dissolved in a mixture of aqueous 6M HCl (16 mL 96.00 mmol), ethanol (8 mL) and heated at 50° C. for 3 h. A saturated aqueous NaHCO₃ solution was added to quench the acid, and the resulting solution was extracted with ethyl acetate two times. The organics were combined, washed with brine, dried over magnesium sulfate and evaporated. The crude material was purified by silica gel chromatography eluting with 0-100% ethyl acetate in hexanes to give tert-butyl-dimethyl-(1H-pyrazol-3-yl)silane (3.85 g, 67%) as a white solid. ¹H NMR (400 MHz, DMSO-d₆) δ 12.77 (s, 1H), 7.52 (s, 1H), 6.40 (d, J=1.6 Hz, 1H), 0.85 (s, 9H), 0.25 (s, 6H). ESI-MS m/z calc. 182.12393, found 183.6 (M+1)⁺; Retention time: 0.57 minutes (LC method D).

Step 3: tert-Butyl 6-[3-[tert-butyl(dimethyl)silyl]pyrazol-1-yl]-2-chloro-pyridine-3-carboxylate

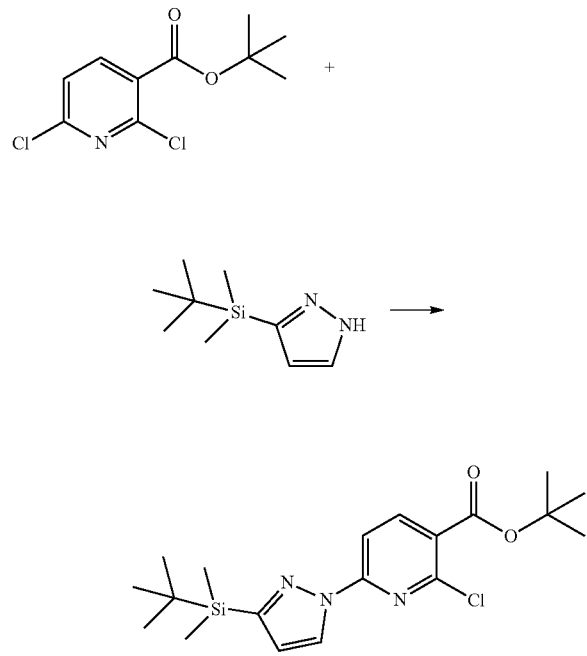 [SMILES: CC(C)(C)OC(=O)c1ccc(Cl)nc1Cl ; CC(C)(C)[Si](C)(C)c1cc[nH]n1 ; CC(C)(C)OC(=O)c1ccc(-n2ccc([Si](C)(C)C(C)(C)C)n2)nc1Cl]

tert-Butyl 2,6-dichloropyridine-3-carboxylate (1.348 g, 5.43 mmol), tert-butyl-dimethyl-(1H-pyrazol-3-yl)silane (984 mg, 5.40 mmol), DABCO (124 mg, 1.105 mmol), and potassium carbonate (921 mg, 6.66 mmol) were combined in anhydrous DMSO (25 mL) and stirred at room temperature under nitrogen for 16 h. The reaction mixture was diluted with water and stirred for 15 min. The resulting solid was collected and washed with water. The solid was further dried to give tert-butyl 6-[3-[tert-butyl(dimethyl)silyl]pyrazol-1-yl]-2-chloro-pyridine-3-carboxylate (1.624 g, 76%) as a white solid. ¹H NMR (400 MHz, DMSO-d₆) δ 8.59 (d, J=2.6 Hz, 1H), 8.37 (d, J=8.4 Hz, 1H), 7.98 (d, J=8.4 Hz, 1H), 6.74 (d, J=2.6 Hz, 1H), 1.57 (s, 9H), 0.94 (s, 9H), 0.28 (s, 6H). ESI-MS m/z calc. 393.16394, found 394.3 (M+1)⁺; Retention time: 0.8 minutes (LC method D).

Step 4: 6-[3-[tert-Butyl(dimethyl)silyl]pyrazol-1-yl]-2-chloro-pyridine-3-carboxylic Acid

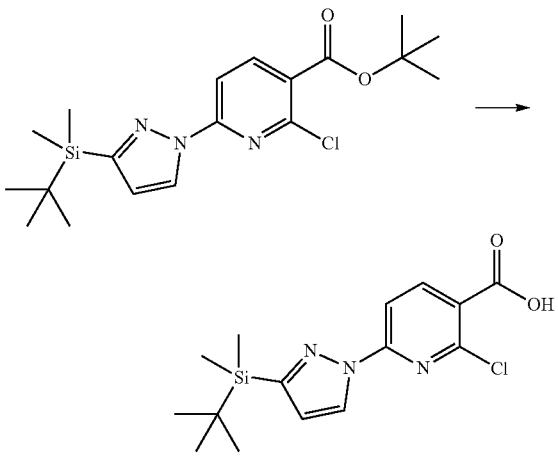

tert-Butyl 6-[3-[tert-butyl(dimethyl)silyl]pyrazol-1-yl]-2-chloro-pyridine-3-carboxylate (200 mg, 0.51 mmol) was dissolved into a solution of HCl (2.0 mL of 6 M in 1,4-dioxane, 12.00 mmol). The solution was allowed to stir at room temperature overnight. To the obtained white slurry was added additional HCl (1.0 mL of 6 M in 1,4-dioxane, 6.000 mmol). The reaction mixture was then stirred at 55° C. for 3 hours. The reaction mixture was diluted with EtOAc (75 mL) and washed with water (3×75 mL) and brine (1x 75 mL). The organic layer was dried over sodium sulfate, filtered and concentrated under reduced pressure. The crude product was chromatographed on a 12 gram silica gel column eluting with a 0-100% EtOAc/hexane gradient over 20 minutes; product eluted at 25% EtOAc/hexane. 6-[3-[tert-Butyl(dimethyl)silyl]pyrazol-1-yl]-2-chloro-pyridine-3-carboxylic acid (161 mg, 94%) was obtained as a white solid. ¹H NMR (400 MHz, DMSO-d₆) δ 13.71 (s, 1H), 8.60 (d, J=2.6 Hz, 1H), 8.45 (d, J=8.4 Hz, 1H), 7.99 (d, J=8.4 Hz, 1H), 6.74 (d, J=2.6 Hz, 1H), 0.94 (s, 9H), 0.29 (s, 6H). ESI-MS m/z calc. 337.10132, found 338.2 (M+1)⁺; Retention time: 2.15 minutes (LC method A).

Step 5: 6-[3-[tert-Butyl(dimethyl)silyl]pyrazol-1-yl]-2-chloro-N-(1,3-dimethylpyrazol-4-yl)sulfonyl-pyridine-3-carboxamide

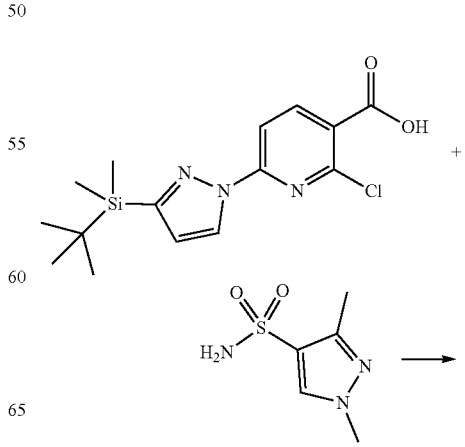

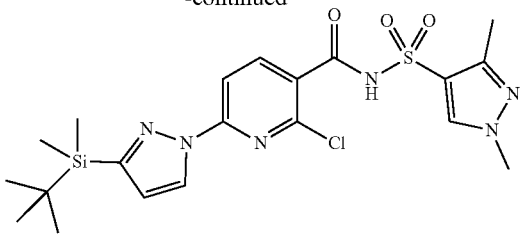

6-[3-[tert-Butyl(dimethyl)silyl]pyrazol-1-yl]-2-chloro-pyridine-3-carboxylic acid (100 mg, 0.30 mmol) and CDI (72 mg, 0.44 mmol) were dissolved in THF (2 mL). The solution was allowed to stir at room temperature for 2 hours. 1,3-Dimethylpyrazole-4-sulfonamide (68 mg, 0.39 mmol) was added followed by DBU (133 μL, 0.89 mmol). The reaction mixture was allowed to stir at room temperature overnight. The reaction mixture was diluted with EtOAc (50 mL) and washed with 10% aqueous citric acid solution (1×50 mL) and brine (1x 50 mL). The organic layer was dried over sodium sulfate, filtered and concentrated under reduced pressure. 6-[3-[tert-Butyl(dimethyl)silyl]pyrazol-1-yl]-2-chloro-N-(1,3-dimethylpyrazol-4-yl)sulfonyl-pyridine-3-carboxamide (136 mg, 93%) was obtained as a yellow solid. $^1$H NMR (400 MHz, DMSO-d$_6$) δ 12.78 (s, 1H), 8.58 (d, J=2.6 Hz, 1H), 8.40 (s, 1H), 8.14 (d, J=8.3 Hz, 1H), 7.95 (d, J=8.3 Hz, 1H), 6.73 (d, J=2.6 Hz, 1H), 3.84 (s, 3H), 2.35 (s, 3H), 0.94 (s, 9H), 0.28 (s, 6H). ESI-MS m/z calc. 494.13232, found 495.2 (M+1)$^+$; Retention time: 2.07 minutes (LC method A).

Step 6: 6-[3-[tert-Butyl(dimethyl)silyl]pyrazol-1-yl]-N-(1,3-dimethylpyrazol-4-yl)sulfonyl-2-[(4S)-2,2,4-trimethylpyrrolidin-1-yl]pyridine-3-carboxamide (Compound (2-10))

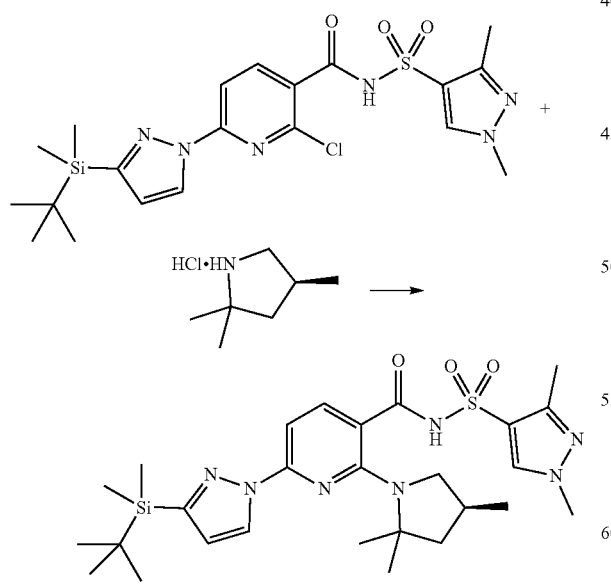

6-[3-[tert-Butyl(dimethyl)silyl]pyrazol-1-yl]-2-chloro-N-(1,3-dimethylpyrazol-4-yl)sulfonyl-pyridine-3-carboxamide (138 mg, 0.28 mmol) was combined with (4S)-2,2,4-trimethylpyrrolidine (hydrochloride salt) (100 mg, 0.67 mmol) and dissolved in DMSO (1 mL). Finely ground potassium carbonate (193 mg, 1.40 mmol) was added, and the reaction mixture was capped and stirred overnight at 130° C. The reaction mixture was diluted with dichloromethane (10 mL) and injected directly onto a 24 gram silica gel column. The product was eluted with a 0-30% EtOAc/hexane gradient over 20 minutes; product eluted at isocratic 30% EtOAc/hexane. 6-[3-[tert-Butyl(dimethyl)silyl]pyrazol-1-yl]-N-(1,3-dimethylpyrazol-4-yl)sulfonyl-2-[(4S)-2,2,4-trimethylpyrrolidin-1-yl]pyridine-3-carboxamide (56 mg, 35%) was obtained as a white solid. $^1$H NMR (400 MHz, DMSO-d$_6$) δ 12.40 (s, 1H), 8.40 (d, J=2.5 Hz, 1H), 8.37 (s, 1H), 7.78 (d, J=8.2 Hz, 1H), 7.14 (d, J=8.2 Hz, 1H), 6.68 (d, J=2.5 Hz, 1H), 3.81 (s, 3H), 2.56 (t, J=10.4 Hz, 1H), 2.45 (t, J=8.7 Hz, 1H), 2.33 (s, 3H), 2.21 (td, J=11.8, 6.5 Hz, 1H), 1.88 (dd, J=12.0, 5.5 Hz, 1H), 1.58 (s, 3H), 1.55 (s, 3H), 1.43 (t, J=12.1 Hz, 1H), 0.94 (s, 9H), 0.82 (d, J=6.3 Hz, 3H), 0.27 (s, 3H), 0.26 (s, 3H). ESI-MS m/z calc. 571.27606, found 572.4 (M+1)$^+$; Retention time: 2.04 minutes (LC method G).

Example 5: Preparation of N-(1-methyl-3-trimethylsilyl-pyrazol-4-yl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

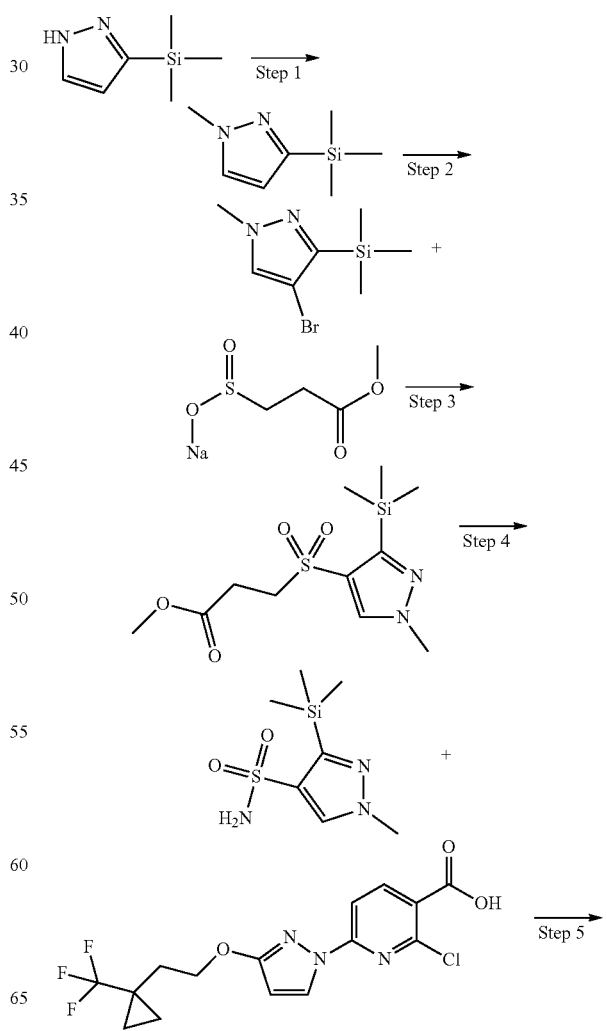

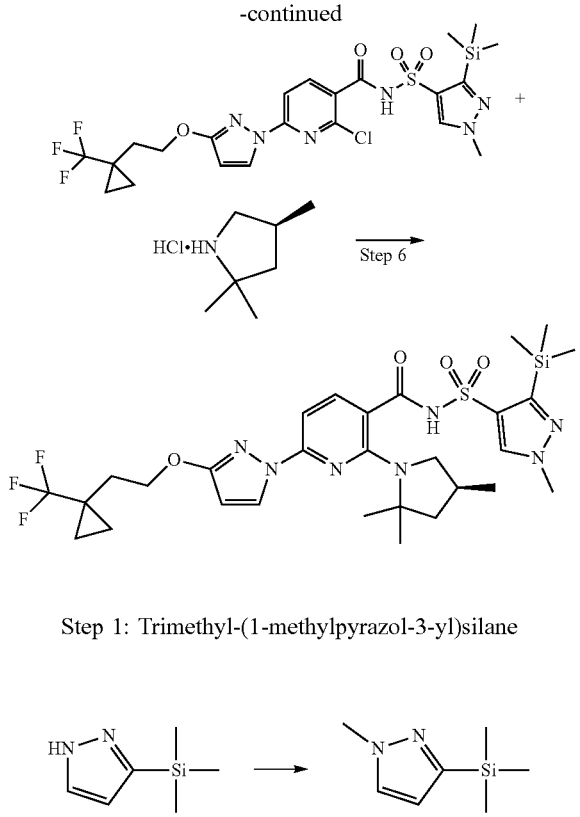

Step 1: Trimethyl-(1-methylpyrazol-3-yl)silane

Trimethyl(1H-pyrazol-3-yl)silane (519 mg, 3.70 mmol) and potassium carbonate (1.125 g, 8.14 mmol) were combined with acetone (6 mL) in a screwcap vial, and iodomethane (260 μL, 4.18 mmol) was added. The reaction mixture was heated to 40° C. with vigorous stirring for 72 hours, then an additional iodomethane (70 μL, 1.124 mmol) was added and the reaction was returned to 40° C. for another 24 hours. The reaction mixture was then cooled to room temperature and was partitioned between DI water (30 mL) and diethyl ether (30 mL). The layers were separated, and the aqueous was extracted an additional 30 mL of diethyl ether. The combined organics were washed with brine, dried over sodium sulfate, and concentrated to give a colorless oil, trimethyl-(1-methylpyrazol-3-yl)silane (535 mg, 94%). $^1$H NMR (400 MHz, Chloroform-d) δ 7.38 (d, J=2.1 Hz, 1H), 6.37 (d, J=2.1 Hz, 1H), 3.96 (s, 3H), 0.29 (s, 9H). ESI-MS m/z calc. 154.09262, found 155.5 (M+1)$^+$; Retention time: 0.41 minutes (LC method D).

Step 2: (4-Bromo-1-methyl-pyrazol-3-yl)-trimethyl-silane

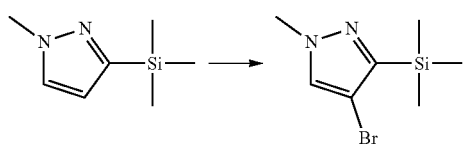

Bromine (180 μL, 3.49 mmol) was combined in DCM (6 mL) with sodium carbonate (750 mg, 7.08 mmol) at 0° C. Trimethyl-(1-methylpyrazol-3-yl)silane (535 mg, 3.47 mmol) was added dropwise by syringe as a solution in DCM (1 mL). The reaction was stirred for an additional 20 minutes at 0° C. then poured into 20 mL water and the layers were separated. The aqueous was extracted an additional time with 15 mL dichloromethane. The combined organics were washed with brine, dried over sodium sulfate and concentrated. The resulting crude material contained >50% desilylated dibromo material, and was further purified by chromatography on silica gel (1-99% ethyl acetate in hexanes), to give as a colorless liquid, (4-bromo-1-methyl-pyrazol-3-yl)-trimethyl-silane (141 mg, 17%). $^1$H NMR (400 MHz, Chloroform-d) δ 7.40 (s, 1H), 3.91 (s, 3H), 0.35 (s, 9H). ESI-MS m/z calc. 232.00314, found 233.1 (M+1)$^+$; Retention time: 0.67 minutes (LC method D).

Step 3: Methyl 3-(1-methyl-3-trimethylsilyl-pyrazol-4-yl)sulfanylpropanoate

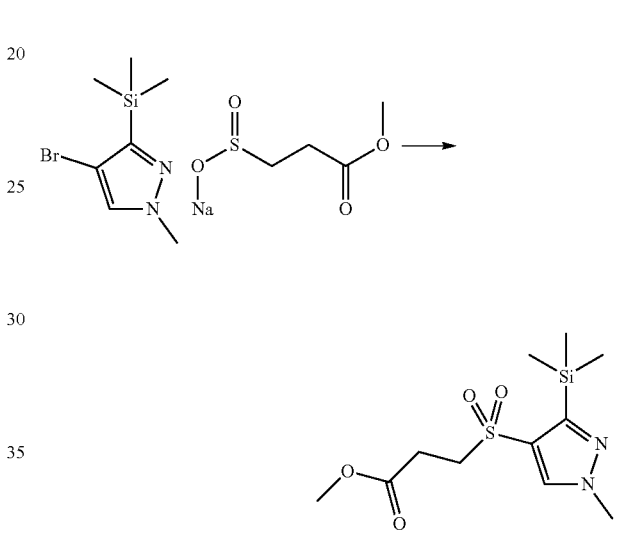

(4-Bromo-1-methyl-pyrazol-3-yl)-trimethyl-silane (141 mg, 0.60 mmol), (3-methoxy-3-oxo-propyl)sulfinyloxysodium (211 mg, 1.21 mmol) and copper(I) iodide (350 mg, 1.84 mmol) were combined in degassed DMSO (850 μL). Nitrogen was bubbled through the reaction for another 5 min and then it was sealed and heated to 80° C. for 16 hours, giving only low conversion. The reaction temperature was increased to 110° C. for 22 hours and during this time the reaction went from a cloudy brown solution to a clear orange, and finally a dark black. The reaction was cooled to room temperature and diluted with ethyl acetate (25 mL) and NH$_4$Cl (10 mL). The aqueous was extracted with 2×20 mL ethyl acetate and the combined organics were washed with brine (30 mL). The organics were dried over sodium sulfate and evaporated. The crude material was purified by silica gel chromatography eluting with 0-100% ethyl acetate in hexanes to give methyl 3-(1-methyl-3-trimethylsilyl-pyrazol-4-yl)sulfanylpropanoate (40 mg, 22%). $^1$H NMR (400 MHz, Chloroform-d) δ 7.87 (s, 1H), 3.96 (s, 3H), 3.67 (s, 3H), 3.47-3.36 (m, 2H), 2.78 (dd, J=8.3, 7.1 Hz, 2H), 0.38 (s, 9H). ESI-MS m/z calc. 304.0913, found 305.6 (M+1)$^+$; Retention time: 0.54 minutes (LC method D).

Step 4: 1-Methyl-3-trimethylsilyl-pyrazole-4-sulfonamide

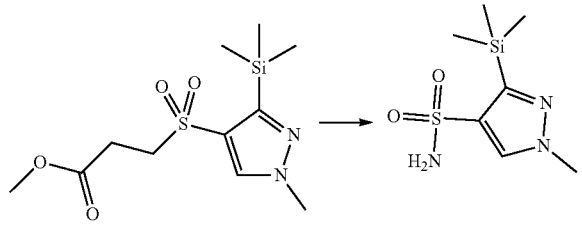

Methyl 3-(1-methyl-3-trimethylsilyl-pyrazol-4-yl)sulfanylpropanoate (40 mg, 0.13 mmol) was dissolved in THF (600 μL) and 25% NaOMe in methanol (30 μL of 25% w/v, 0.14 mmol) was added. The reaction was stirred for 5 min and evaporated. Hexane was added and the mixture evaporated again, giving a white solid, which was used in the next step without further purification. 1-Methyl-3-trimethylsilyl-pyrazole-4-sulfinate (Sodium salt) (32 mg, 101%) ESI-MS m/z calc. 217.0467, found 219.1 (M+2)$^+$; Retention time: 0.36 minutes. The product was dissolved in dichloromethane (500 μL) and N-chlorosuccinimide (18 mg, 0.13 mmol) was added. The reaction was stirred for 30 min at room temperature. The reaction mixture was added slowly to an ice bath cooled solution of ammonia in methanol (1 mL of 7 M, 7.00 mmol). After 10 minutes it was removed from the ice bath and was stirred for another 60 min at room temperature. The reaction mixture was partitioned between 25 mL ethyl acetate and 15 mL water. The organics were separated, and the aqueous was extracted an additional 2×15 mL ethyl acetate, washed with brine, dried over sodium sulfate, and evaporated. This product was used in the next step without additional purification. 1-Methyl-3-trimethylsilyl-pyrazole-4-sulfonamide (25 mg, 82%). $^1$H NMR (400 MHz, Chloroform-d) δ 7.88 (s, 1H), 4.66 (s, 2H), 3.94 (s, 3H), 0.39 (s, 9H). ESI-MS m/z calc. 233.06543, found 234.5 (M+1)$^+$; Retention time: 0.41 minutes (LC method D).

Step 5: 2-Chloro-N-(1-methyl-3-trimethylsilyl-pyrazol-4-yl)sulfonyl-6-[3-[2-[1-(trifluoromethyl)cyclopropyl]ethoxy]pyrazol-1-yl]pyridine-3-carboxamide

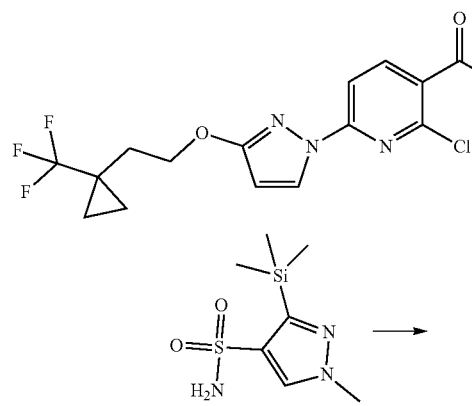

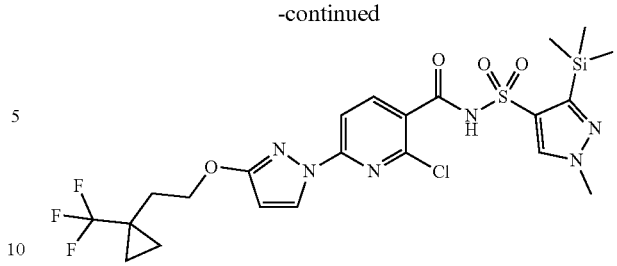

2-Chloro-6-[3-[2-[1-(trifluoromethyl)cyclopropyl] ethoxy]pyrazol-1-yl]pyridine-3-carboxylic acid (12 mg, 0.032 mmol) was combined with CDI (7 mg, 0.043 mmol) in THF (200 and stirred at room temperature for 45 minutes. DBU (14 μL, 0.094 mmol) was added, followed by 1-methyl-3-trimethylsilyl-pyrazole-4-sulfonamide (7 mg, 0.030 mmol), and stirring was continued for 16 hours at room temperature. The reaction mixture was then partitioned between aqueous 1M citric acid (15 mL) and ethyl acetate (25 mL). The layers were separated, and the aqueous was extracted an additional 2×15 mL ethyl acetate. The combined organics were washed with water and brine, dried over sodium sulfate and concentrated to give a slightly yellow solid, which was used in the next step without additional purification, 2-chloro-N-(1-methyl-3-trimethylsilyl-pyrazol-4-yl)sulfonyl-6-[3-[2-[1-(trifluoromethyl)cyclopropyl] ethoxy]pyrazol-1-yl]pyridine-3-carboxamide (22 mg, 82%). ESI-MS m/z calc. 590.1146, found 591.0 (M+1)$^+$; Retention time: 0.79 minutes (LC method D).

Step 6: N-(1-Methyl-3-trimethylsilyl-pyrazol-4-yl) sulfonyl-6-[3-[2-[1-(trifluoromethyl)cyclopropyl] ethoxy]pyrazol-1-yl]-2-[(4S)-2,2,4-trimethylpyrrolidin-1-yl]pyridine-3-carboxamide

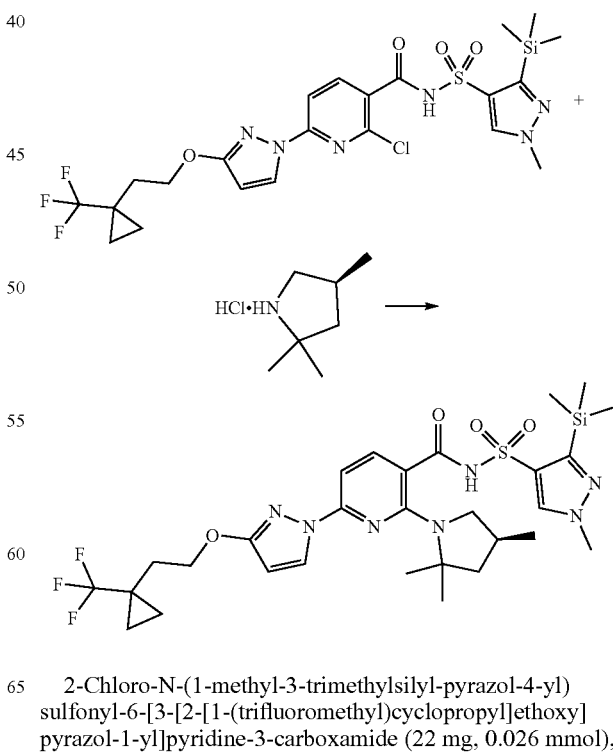

2-Chloro-N-(1-methyl-3-trimethylsilyl-pyrazol-4-yl) sulfonyl-6-[3-[2-[1-(trifluoromethyl)cyclopropyl]ethoxy] pyrazol-1-yl]pyridine-3-carboxamide (22 mg, 0.026 mmol), (4S)-2,2,4-trimethylpyrrolidine (hydrochloride salt) (32 mg, 0.21 mmol), and potassium carbonate (60 mg, 0.43 mmol) were combined in DMSO (200 µL) and heated at 130° C. for 16 h. The reaction was cooled to room temperature and partitioned between 15 mL 1M citric acid and 15 mL ethyl acetate. The aqueous and organic layers were separated, and the aqueous layer was extracted two additional times with 15 mL ethyl acetate. The organics were combined, washed with brine, dried over sodium sulfate and concentrated. The resulting solid was purified by silica gel chromatography eluting with 0-100% ethyl acetate in hexanes. Fractions containing pure product were concentrated to give a white solid. N-(1-Methyl-3-trimethylsilyl-pyrazol-4-yl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (2.3 mg, 13%). ESI-MS m/z calc. 667.25836, found 668.3 (M+1)+; Retention time: 2.41 minutes (LC method A).

Example 6: Preparation of N-(1-Methyl-3-trimethylsilyl-pyrazol-4-yl)sulfonyl-6-[13-(3,3,3-trifluoro-2,2-dimethyl-propoxy)pyrazol-1-yl]-2-[(4S)-2,2,4-trimethylpyrrolidin-1-yl]pyridine-3-carboxamide

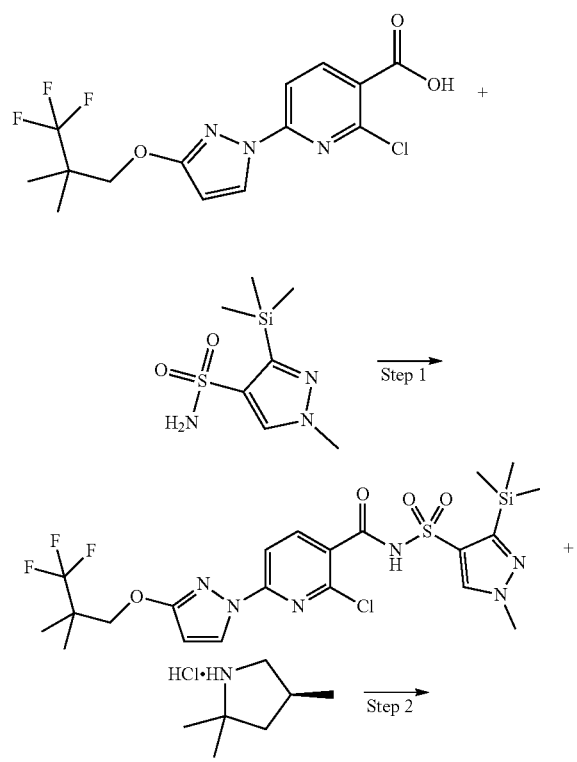

Step 1: 2-Chloro-N-(1-methyl-3-trimethylsilyl-pyrazol-4-yl)sulfonyl-6-[3-(3,3,3-trifluoro-2,2-dimethyl-propoxy)pyrazol-1-yl]pyridine-3-carboxamide

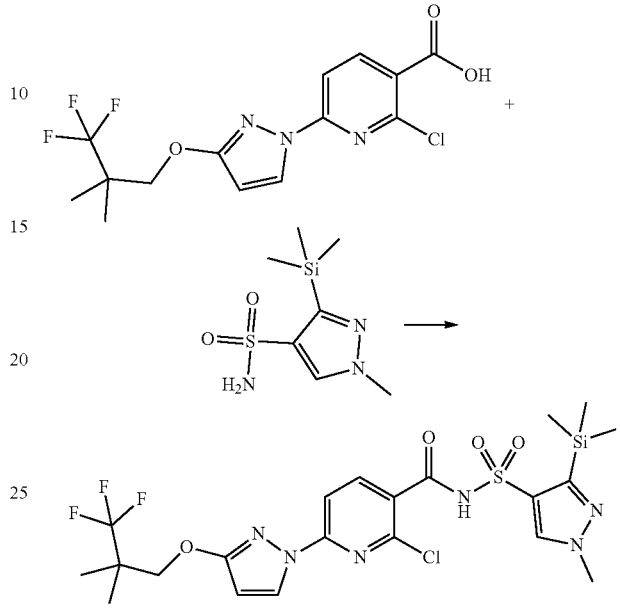

2-Chloro-6-[3-(3,3,3-trifluoro-2,2-dimethyl-propoxy)pyrazol-1-yl]pyridine-3-carboxylic acid (24 mg, 0.066 mmol) was combined with CDI (14 mg, 0.086 mmol) in THF (0.25 mL), and stirred at room temperature for 45 minutes. DBU (30 µL, 0.20 mmol) was added, followed by 1-methyl-3-trimethylsilyl-pyrazole-4-sulfonamide (15 mg, 0.06428 mmol), and stirring was continued for 16 hours at room temperature. The reaction mixture was then partitioned between aqueous 1M citric acid (15 mL) and ethyl acetate (25 mL). The layers were separated, and the aqueous was extracted an additional 2×15 mL ethyl acetate. The combined organics were washed with water and brine, dried over sodium sulfate and concentrated to give a slightly yellow solid, which was used in the next step without additional purification, 2-chloro-N-(1-methyl-3-trimethylsilyl-pyrazol-4-yl)sulfonyl-6-[3-(3,3,3-trifluoro-2,2-dimethyl-propoxy)pyrazol-1-yl]pyridine-3-carboxamide (42 mg, 93%). ESI-MS m/z calc. 578.1146, found 579.3 (M+1)+; Retention time: 0.82 minutes (LC method D).

Step 2: N-(1-Methyl-3-trimethylsilyl-pyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide

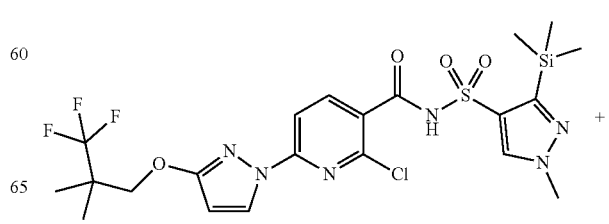

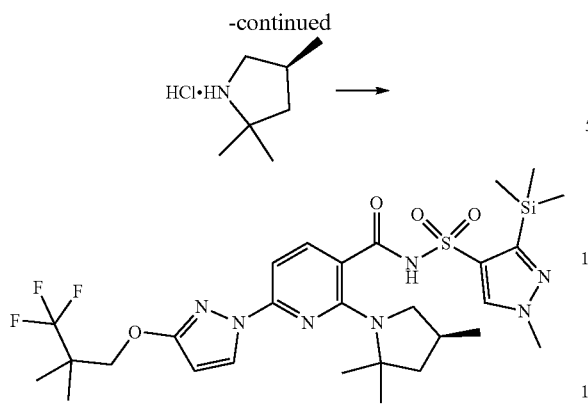

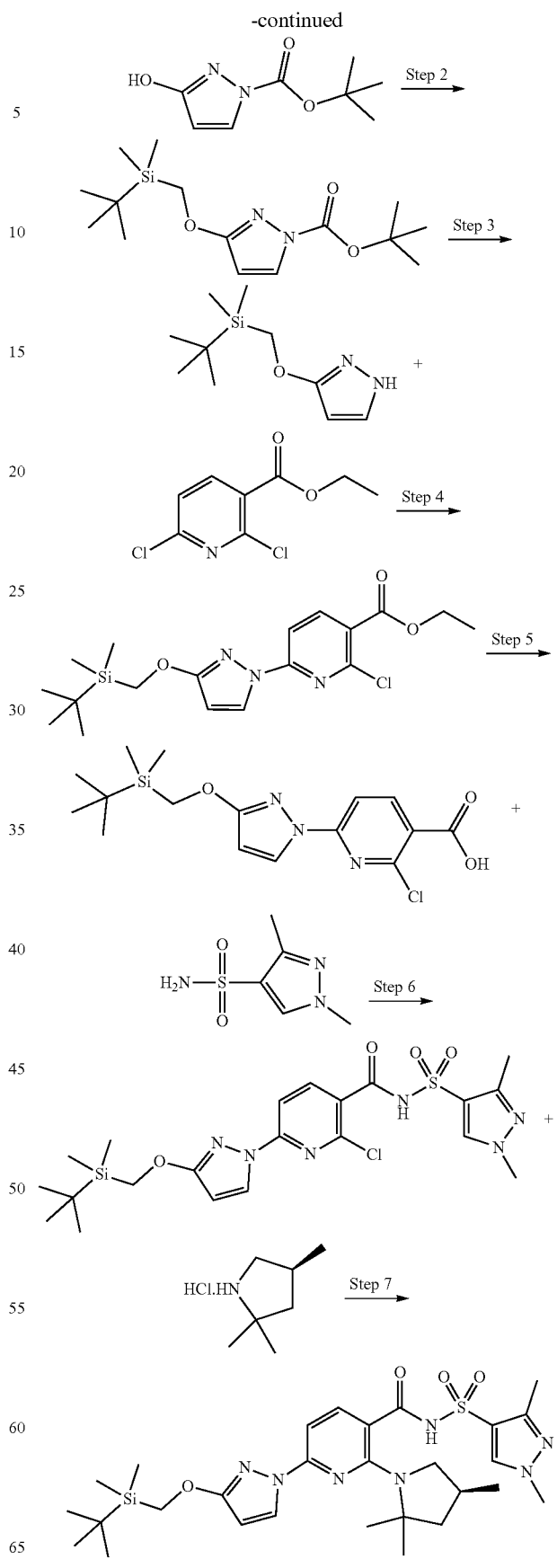

2-Chloro-N-(1-methyl-3-trimethylsilyl-pyrazol-4-yl)sulfonyl-6-[3-(3,3,3-trifluoro-2,2-dimethyl-propoxy)pyrazol-1-yl]pyridine-3-carboxamide (42 mg, 0.062 mmol), (4S)-2,2,4-trimethylpyrrolidine (hydrochloride salt) (48 mg, 0.32 mmol), and potassium carbonate (90 mg, 0.65 mmol) were combined in DMSO (200 μL) and heated at 130° C. for 16 h. The reaction was cooled to room temperature, and 1 mL of water was added. After 15 minutes stirring, the contents of the vial were allowed to settle, the liquid portion was removed by pipet and the remaining solids were dissolved with 20 mL ethyl acetate, and then washed with 15 mL 1M citric acid. The aqueous and organic layers were separated, and the aqueous layer was extracted two additional times with 15 mL ethyl acetate. The organics were combined, washed with brine, dried over sodium sulfate and concentrated. The resulting solid was purified silica gel chromatography eluting with 0-100% ethyl acetate in hexanes. Fractions containing pure product were concentrated to give a white solid. N-(1-Methyl-3-trimethylsilyl-pyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (12 mg, 29%). $^1$H NMR (400 MHz, DMSO-$d_6$) δ 12.33 (s, 1H), 8.55 (s, 1H), 8.21 (d, J=2.8 Hz, 1H), 7.69 (d, J=8.2 Hz, 1H), 6.92 (d, J=8.2 Hz, 1H), 6.16 (d, J=2.7 Hz, 1H), 4.23 (s, 2H), 3.92 (s, 3H), 2.55 (t, J=10.4 Hz, 2H), 2.16 (s, 1H), 1.87 (dd, J=11.9, 5.6 Hz, 1H), 1.56 (s, 3H), 1.53 (s, 3H), 1.41 (t, J=12.1 Hz, 1H), 1.23 (s, 6H), 0.77 (d, J=6.3 Hz, 3H), 0.32 (s, 9H). ESI-MS m/z calc. 655.25836, found 656.3 (M+1)$^+$; Retention time: 2.43 minutes (LC method A).

Example 7: Preparation of 6-[3-[[tert-butyl(dimethyl)silyl]methoxy]pyrazol-1-yl]-N-(1,3-dimethylpyrazol-4-yl)sulfonyl-2-[(4S)-2,2,4-trimethylpyrrolidin-1-yl]pyridine-3-carboxamide (Compound (2-11))

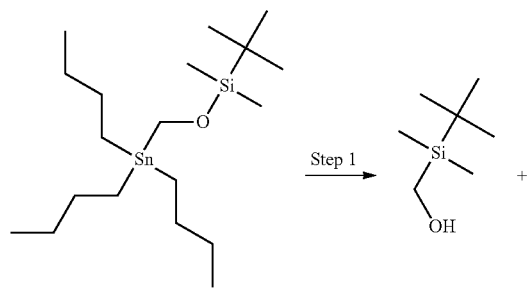

Step 1: [Tert-Butyl(Dimethyl)Silyl]Methanol

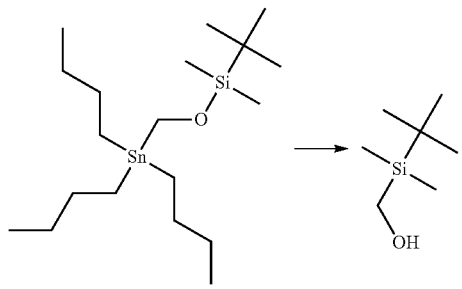

In a heat gun-dried round-bottom flask under nitrogen, n-butyl lithium (1 mL, 1.600 mmol, 1.6 M solution in hexanes) was combined with N,N,N',N'-tetramethylethane-1,2-diamine (200 µL, 1.325 mmol) in anhydrous THF (8 mL) at 0° C. in an ice-water bath. tert-Butyl-dimethyl-(tributylstannylmethoxy)silane (500 mg, 1.149 mmol) was then added dropwise by syringe over 1 minute. The reaction mixture was stirred for 2 minutes at 0° C. then quenched with acetic acid (200 µL, 3.517 mmol). The reaction mixture was then diluted with a saturated aqueous solution of sodium bicarbonate (10 mL), water (10 mL) and ethyl acetate (15 mL) and warmed to room temperature. The layers were separated and the aqueous phase was extracted by an additional 2×15 mL ethyl acetate. The combined organics were washed with brine, dried over sodium sulfate, and concentrated to give a colorless oil. This crude material was purified by chromatography on silica gel (1-70% ethyl acetate in hexanes gradient, with an initial hexane flush) to give as a white solid, [tert-butyl(dimethyl)silyl]methanol (95 mg, 57%). $^1$H NMR (400 MHz, Chloroform-d) δ 3.46 (s, 2H), 0.90 (s, 9H), 0.00 (s, 6H). (alcohol OH not visible)

Step 2: tert-Butyl 3-[[tert-butyl)dimethyl)silyl]methoxy]pyrazole-1-carboxylate

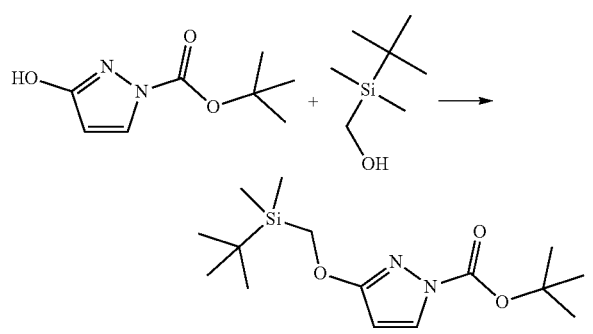

tert-Butyl 3-hydroxypyrazole-1-carboxylate (220 mg, 1.194 mmol), [tert-butyl(dimethyl)silyl]methanol (190 mg, 1.299 mmol), and triphenylphosphine (345 mg, 1.315 mmol) were combined in THF (2.5 mL) and cooled to 0° C. DIAD (255 µL, 1.317 mmol) was added dropwise and the reaction mixture was warmed to room temperature for 16 hours. The reaction mixture was then partitioned between 30 mL 1M NaOH (aq) and ethyl acetate (30 mL). The layers were separated and the aqueous phase was extracted with an additional 2×30 mL ethyl acetate. The combined organics were washed with brine, dried over sodium sulfate and concentrated. The resulting crude material was purified by flash chromatography on silica gel, eluting with a gradient of 0-50% ethyl acetate in hexanes (initially very shallow, compound eluted just before 10%) to give as a colorless oil, tert-butyl 3-[[tert-butyl(dimethyl) silyl]methoxy]pyrazole-1-carboxylate (242 mg, 65%). $^1$H NMR (400 MHz, Chloroform-d) δ 7.81 (d, J=2.7 Hz, 1H), 5.85 (d, J=2.8 Hz, 1H), 4.06 (s, 2H), 1.61 (s, 9H), 0.94 (s, 9H), 0.06 (s, 6H). ESI-MS m/z calc. 312.18692, found 313.3 (M+1)$^+$; Retention time: 0.88 minutes (LC method D).

Step 3: tert-Butyl-dimethyl-(1H-pyrazol-3-yloxymethyl)silane

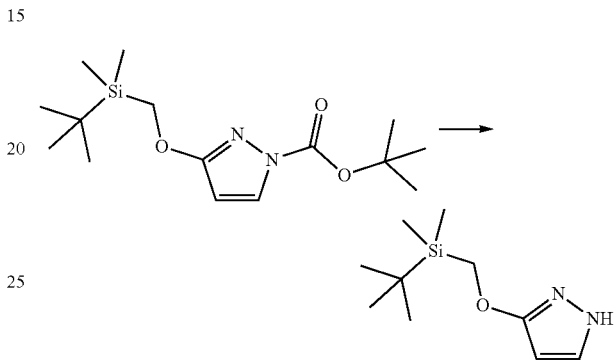

tert-Butyl 3-[[tert-butyl(dimethyl)silyl]methoxy]pyrazole-1-carboxylate (242 mg, 0.7744 mmol) was combined in DCM (2.5 mL) with TFA (750 µL, 9.735 mmol) at room temperature and stirred for 15 minutes. The reaction mixture was then evaporated under reduced pressure. The crude material was dissolved in 15 mL ethyl acetate and washed with 15 mL of saturated sodium bicarbonate. The aqueous layer was extracted with an additional 2×10 mL ethyl acetate, and the combined organics were washed with brine, dried over sodium sulfate, and concentrated to give a colorless oil. tert-Butyl-dimethyl-(1H-pyrazol-3-yloxymethyl)silane (161 mg, 98%). $^1$H NMR (400 MHz, Chloroform-d) δ 7.35 (d, J=2.4 Hz, 1H), 5.73 (d, J=2.5 Hz, 1H), 3.92 (s, 2H), 0.95 (s, 9H), 0.08 (s, 6H) (NH not visible). ESI-MS m/z calc. 212.13449, found 213.6 (M+1)$^+$; Retention time: 0.66 minutes (LC method D).

Step 4: Ethyl 6-[3-[[tert-butyl)dimethyl)silyl]methoxy]pyrazol-1-yl]-2-chloro-pyridine-3-carboxylate

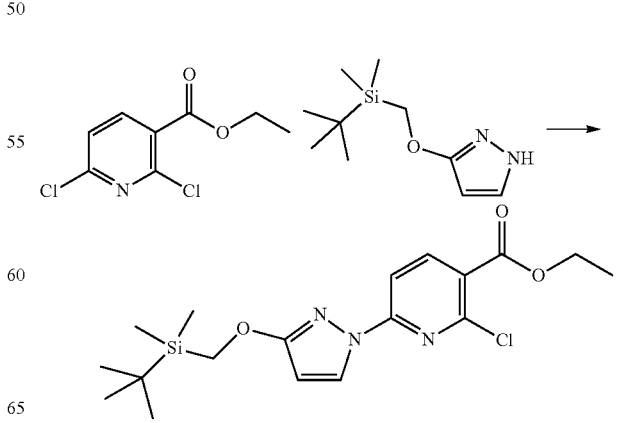

A round bottom flask was charged under nitrogen with tert-butyl-dimethyl-(1H-pyrazol-3-yloxymethyl)silane (160 mg, 0.7534 mmol), ethyl 2,6-dichloropyridine-3-carboxylate (170 mg, 0.7725 mmol), K$_2$CO$_3$ (160 mg, 1.158 mmol) (freshly ground in a mortar) and anhydrous DMF (1.5 mL). DABCO (15 mg, 0.1337 mmol) was added and the mixture was stirred at room temperature under nitrogen for 8 hours. The reaction mixture was diluted with ethyl acetate (50 mL) and water (50 mL) and the two phases were separated. The aqueous phase was further extracted with ethyl acetate (2×30 mL), and the combined extracts were washed with brine and dried over sodium sulfate, after which the solvent was removed under reduced pressure. The material was subjected to flash chromatography on silica gel using an initially shallow gradient of 0-40% ethyl acetate in hexanes. The pure fractions were combined and the solvents removed under reduced pressure to provide a white solid; ethyl 6-[3-[[tert-butyl(dimethyl)silyl]methoxy]pyrazol-1-yl]-2-chloro-pyridine-3-carboxylate (194 mg, 63%). $^1$H NMR (400 MHz, Chloroform-d) δ 8.35 (dd, J=2.9, 0.9 Hz, 1H), 8.27 (dd, J=8.4, 0.8 Hz, 1H), 7.73 (dd, J=8.5, 0.8 Hz, 1H), 5.97 (dd, J=2.9, 0.8 Hz, 1H), 4.41 (q, J=7.2 Hz, 2H), 4.05 (s, 2H), 1.42 (dd, J=7.6, 6.8 Hz, 3H), 0.97 (d, J=0.9 Hz, 9H), 0.10 (s, 6H). ESI-MS m/z calc. 395.1432, found 396.2 (M+1)$^+$; Retention time: 0.88 minutes (LC method D).

Step 5: 6-[3-[[tert-Butyl(dimethyl)silyl]methoxy] pyrazol-1-yl]-2-chloro-pyridine-3-carboxylic Acid

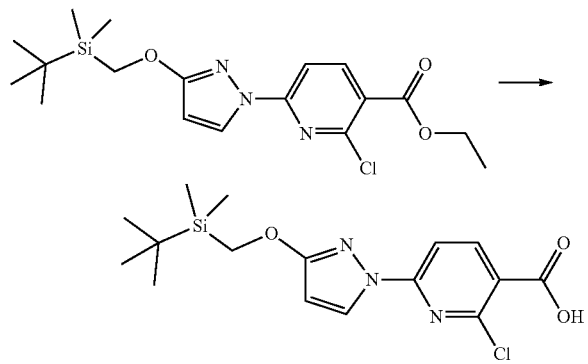

Ethyl 6-[3-[[tert-butyl(dimethyl)silyl]methoxy]pyrazol-1-yl]-2-chloro-pyridine-3-carboxylate (197 mg, 0.4975 mmol) was combined with tetrahydrofuran (1.5 mL) and methanol (1.5 mL). Sodium hydroxide (2M aqueous, 500 μL, 1.000 mmol) was added dropwise, and the reaction mixture was vigorously stirred at room temperature for 45 minutes. The reaction mixture was then partitioned between 1M HCl (30 mL) and ethyl acetate (30 mL). The layers were separated and the aqueous phase was extracted an additional 2×25 mL ethyl acetate. The combined organics were washed with brine, dried over sodium sulfate, and concentrated to give a white powder, 6-[3-[[tert-butyl(dimethyl)silyl] methoxy]pyrazol-1-yl]-2-chloro-pyridine-3-carboxylic acid (170 mg, 93%). $^1$H NMR (400 MHz, DMSO-d$_6$) δ 13.59 (s, 1H), 8.40 (d, J=2.9 Hz, 1H), 8.38 (d, J=8.5 Hz, 1H), 7.74 (d, J=8.4 Hz, 1H), 6.20 (d, J=2.9 Hz, 1H), 4.07 (s, 2H), 0.94 (s, 9H), 0.07 (s, 6H). ESI-MS m/z calc. 367.1119, found 368.1 (M+1)$^+$; Retention time: 0.86 minutes (LC method D).

Step 6: 6-[3-[[tert-Butyl(dimethyl)silyl]methoxy] pyrazol-1-yl]-2-chloro-N-(1,3-dimethylpyrazol-4-yl) sulfonyl-pyridine-3-carboxamide

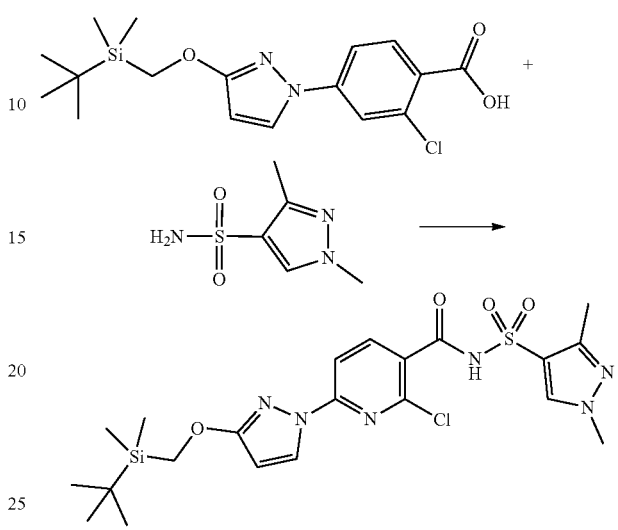

6-[3-[[tert-Butyl(dimethyl)silyl]methoxy]pyrazol-1-yl]-2-chloro-pyridine-3-carboxylic acid (79 mg, 0.21 mmol) was combined with CDI (42 mg, 0.26 mmol) in THF (480 μL) and stirred at room temperature for 45 minutes. 1,3-Dimethylpyrazole-4-sulfonamide (41 mg, 0.24 mmol) was then added, followed by DBU (48 μL, 0.32 mmol), and the reaction was stirred at room temperature for 16 hours. The reaction mixture was then partitioned between 1M aqueous citric acid (30 mL) and ethyl acetate (30 mL). The layers were separated and the aqueous was extracted an additional 2×20 mL ethyl acetate. The combined organics were washed with water, brine, dried over sodium sulfate and concentrated to give 6-[3-[[tert-butyl(dimethyl)silyl]methoxy]pyrazol-1-yl]-2-chloro-N-(1,3-dimethylpyrazol-4-yl)sulfonyl-pyridine-3-carboxamide (127 mg, 96%) as a white solid, which was used in the next step without further purification. ESI-MS m/z calc. 524.1429, found 525.5 (M+1)$^+$; Retention time: 0.66 minutes (LC method I).

Step 7: 6-[3-[[tert-Butyl(dimethyl)silyl]methoxy] pyrazol-1-yl]-N-(1,3-dimethylpyrazol-4-yl)sulfonyl-2-[(4S)-2,2,4-trimethylpyrrolidin-1-yl]pyridine-3-carboxamide (Compound (2-11))

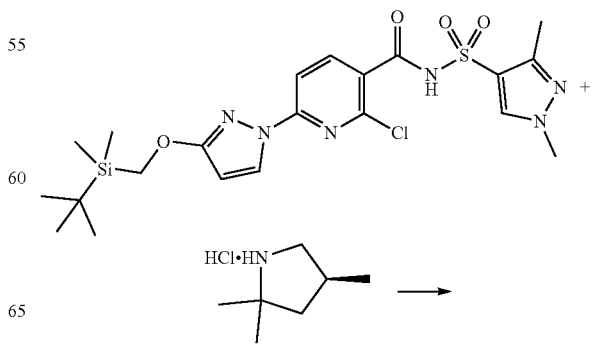

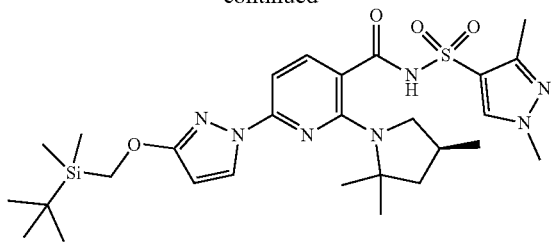

6-[3-[[tert-Butyl(dimethyl)silyl]methoxy]pyrazol-1-yl]-2-chloro-N-(1,3-dimethylpyrazol-4-yl)sulfonyl-pyridine-3-carboxamide (127 mg, 0.21 mmol), (4S)-2,2,4-trimethylpyrrolidine (hydrochloride salt) (160 mg, 1.07 mmol), and potassium carbonate (300 mg, 2.17 mmol) were combined in DMSO (450 μL) and heated at 130° C. for 16 h. The reaction was cooled to room temperature, and 1 mL of water was added. After 15 minutes stirring, the contents of the vial were allowed to settle, the liquid portion was removed by pipet and the remaining solids were dissolved with 20 mL ethyl acetate, then washed with 15 mL 1M citric acid. The aqueous and organic layers were separated, and the aqueous layer was extracted two additional times with 15 mL ethyl acetate. The organics were combined, washed with brine, dried over sodium sulfate and concentrated. The resulting solid was purified first by silica gel chromatography eluting with 0-10% methanol in dichloromethane followed by silica gel chromatography eluting with 0-100% ethyl acetate in hexanes. Fractions containing pure product were concentrated to give a white solid. 6-[3-[[tert-Butyl(dimethyl)silyl]methoxy]pyrazol-1-yl]-N-(1,3-dimethylpyrazol-4-yl)sulfonyl-2-[(4S)-2,2,4-trimethylpyrrolidin-1-yl]pyridine-3-carboxamide (53 mg, 42%). $^1$H NMR (400 MHz, DMSO-d$_6$) δ 12.33 (s, 1H), 8.36 (s, 1H), 8.18 (d, J=2.7 Hz, 1H), 7.73 (d, J=8.2 Hz, 1H), 6.92 (d, J=8.2 Hz, 1H), 6.11 (d, J=2.8 Hz, 1H), 4.02 (s, 2H), 3.80 (s, 3H), 2.56 (t, J=10.5 Hz, 1H), 2.42 (t, J=8.6 Hz, 1H), 2.32 (s, 3H), 2.18 (dp, J=18.0, 6.2 Hz, 1H), 1.88 (dt, J=12.0, 5.9 Hz, 1H), 1.56 (s, 3H), 1.53 (s, 3H), 1.42 (t, J=12.1 Hz, 1H), 0.94 (s, 9H), 0.82 (dd, J=6.6, 3.6 Hz, 3H), 0.06 (s, 6H). ESI-MS m/z calc. 601.2866, found 602.3 (M+1)$^+$; Retention time: 2.46 minutes (LC method A).

Example 8: Preparation N-(1,3-dimethylpyrazol-4-yl)sulfonyl-6-[3-(3,3,3-trifluoro-2,2-dimethyl-propoxy)pyrazol-1-yl]-2-trimethylsilyl-pyridine-3-carboxamide

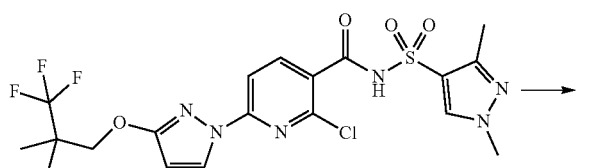

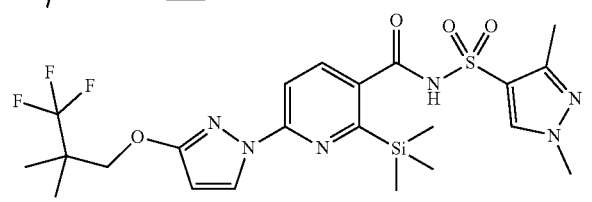

In a 5-mL microwave vial, hexamethyldisilane (40 μL, 0.19 mmol) was mixed with freshly distilled HMPA (30 μL) and cooled to 0° C. A diethoxymethane solution of MeLi (60 μL of 3.1 M, 0.19 mmol) was added dropwise, and the resulting dark red solution was stirred at 0° C. for 3 min. This solution was then diluted with Et$_2$O (70 μL). A solution of 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (27.7 mg, 0.053 mmol) in THF (70 μL) was then added dropwise. After stirring at 0° C. for 10 min, the reaction mixture was warmed to room temperature and stirred for 30 min then at 70° C. for 15 h. It was then cooled to room temperature, quenched with MeOH (600 μL), filtered, and purified by reverse-phase preparative chromatography using a Cis column and a gradient eluent of 1 to 99% acetonitrile in water containing 5 mM hydrochloric acid. The desired product (2.1 mg in ~80% purity) was repurified by preparative TLC (SiO$_2$, 1:1 EtOAc:hexanes) to give N-(1,3-dimethylpyrazol-4-yl)sulfonyl-6-[3-(3,3,3-trifluoro-2,2-dimethyl-propoxy)pyrazol-1-yl]-2-trimethylsilyl-pyridine-3-carboxamide (0.5 mg, 2%). $^1$H NMR (400 MHz, chloroform-d) δ 8.47 (s, 1H), 8.44 (s, 1H), 8.37 (d, J=2.8 Hz, 1H), 8.09 (s, 1H), 8.00 (s, 1H), 5.99 (d, J=2.8 Hz, 1H), 4.25 (s, 2H), 3.89 (s, 3H), 2.48 (s, 3H), 1.28 (s, 6H), 0.25 (s, 9H). ESI-MS m/z calc. 558.16925, found 559.1 (M+1)$^+$; Retention time: 2.07 minutes (LC method A.)

Example 9: Preparation of N-(1,3-dimethylpyrazol-4-yl)sulfonyl-2-[(4S)-2,4-dimethyl-2-trimethylsilyl-pyrrolidin-1-yl]-6-[3-(3,3,3-trifluoro-2,2-dimethyl-propoxy)pyrazol-1-yl]pyridine-3-carboxamide (Compound (2-9))

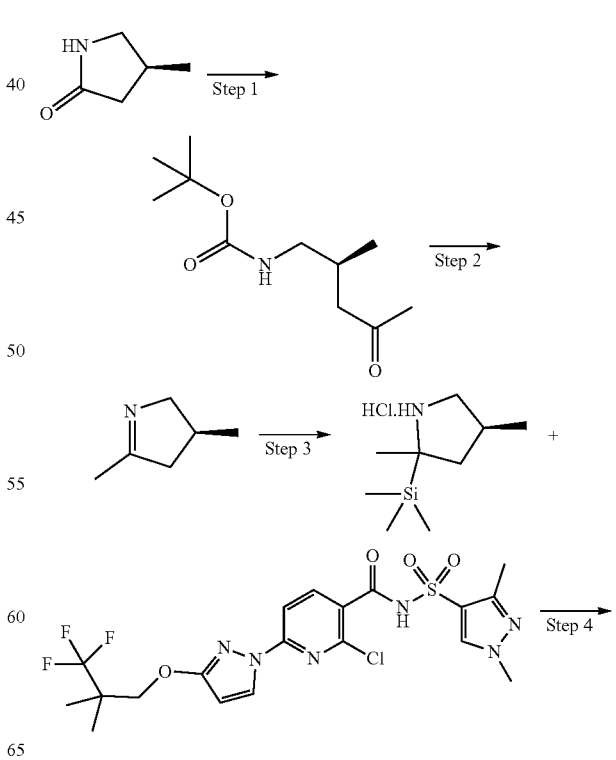

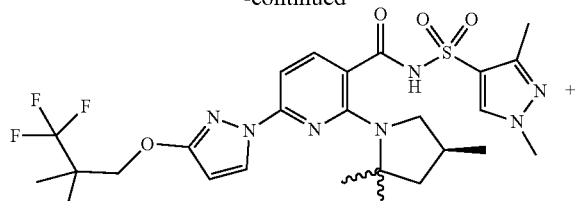

Compound (2-9) stereoisomer 1

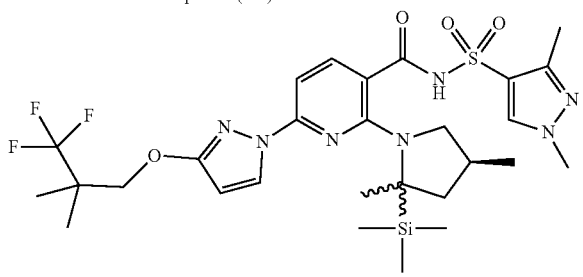

Compound (2-9) stereoisomer 2

Step 1: Tert-Butyl N-[(2S)-2-methyl-4-oxo-pentyl]carbamate

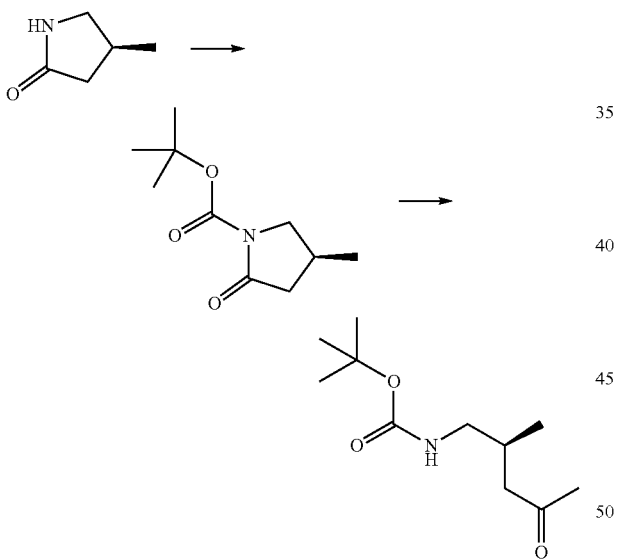

In a 100-mL round-bottomed flask, (4S)-4-methylpyrrolidin-2-one (1.0481 g, 10.04 mmol) was mixed with Boc$_2$O (2.65 g, 12.14 mmol) and MeCN (40 mL), to which DMAP (0.1268 g, 1.04 mmol) was added in one portion. The resulting solution was stirred at room temperature for 2 h, after which it was evaporated in vacuo to give 2.18 g (>100% yield) of a dark orange transparent liquid. The crude product was dissolved in THF (15 mL), and cooled to 0° C. under N2 atmosphere. An Et$_2$O solution of MeMgBr (4.5 mL of 3.0 M, 13.50 mmol) was added dropwise, and the resulting mixture was stirred at 0° C. for 3 h. After this time, it was quenched at 0° C. with a saturated aqueous NH$_4$C$_1$ solution (15 mL) and warmed to room temperature. H$_2$O (30 mL) was added, and the resulting mixture was extracted with ethyl acetate (3×40 mL). The combined organic extracts was washed with water (80 mL) and saturated aqueous sodium chloride solution (80 mL), then dried over sodium sulfate, filtered, and evaporated in vacuo. Purification by silica gel chromatography (80 g of silica) using a gradient eluent of 0 to 70% ethyl acetate in hexanes gave a clear liquid, tert-butyl N-[(2S)-2-methyl-4-oxo-pentyl]carbamate (1.249 g, 58%). $^1$H NMR (400 MHz, chloroform-d) δ 4.85-4.41 (bs, 1H), 3.08-2.92 (m, 2H), 2.48 (dd, J=16.4, 5.9 Hz, 1H), 2.27 (dd, J=16.4, 7.3 Hz, 1H), 2.23-2.14 (m, 1H), 2.14 (s, 3H), 1.44 (s, 9H), 0.92 (d, J=6.7 Hz, 3H). ESI-MS m/z calc. 215.15215, found 216.2 (M+1)$^+$; Retention time: 1.11 minutes (LC method A).

Step 2: (3S)-3,5-Dimethyl-3,4-dihydro-2H-pyrrole

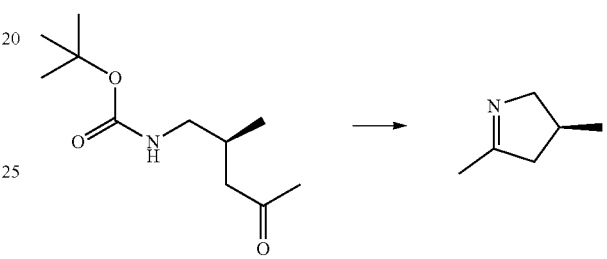

In a 250-mL round-bottomed flask, tert-butyl N-[(2S)-2-methyl-4-oxo-pentyl]carbamate (3.5869 g, 16.66 mmol) was mixed with CH$_2$C$_{12}$ (30 mL), and TFA (10 mL, 129.8 mmol) was added. The resulting solution was stirred at room temperature for 20 h, after which aqueous NaOH (200 mL of 1.0 M, 200.0 mmol) was added. The mixture was extracted with diethyl ether (3×100 mL). The combined organic extracts was washed with water (200 mL) and saturated aqueous sodium chloride solution (200 mL), then dried over sodium sulfate, filtered, and evaporated in vacuo. This gave a dark orange oil: (3S)-3,5-dimethyl-3,4-dihydro-2H-pyrrole (1.0228 g, 63%). $^1$H NMR (400 MHz, chloroform-d) δ 3.96-3.85 (m, 1H), 3.41-3.32 (m, 1H), 2.65 (dd, J=17.0, 8.8 Hz, 1H), 2.45-2.31 (m, 1H), 2.09 (dd, J=17.1, 5.4 Hz, 1H), 2.00 (s, 3H), 1.01 (d, J=6.9 Hz, 3H).

Step 3: [(4S)-2,4-Dimethylpyrrolidin-2-yl]-trimethyl-silane (Hydrochloride Salt)

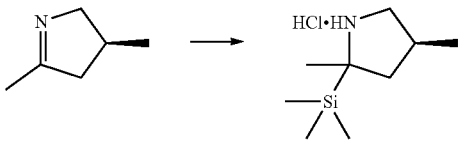

In a 250-mL round-bottomed flask, hexamethyldisilane (14 mL, 68.38 mmol) was mixed with freshly distilled HMPA (10 mL) and cooled to 0° C. A diethoxymethane solution of MeLi (20 mL of 3.1 M, 62.00 mmol) was added dropwise, and the resulting dark red solution was stirred at 0° C. for 3 min. A solution of (3S)-3,5-dimethyl-3,4-dihydro-2H-pyrrole (869.0 mg, 8.94 mmol) in Et$_2$O (22 mL) was then added dropwise. After stirring at 0° C. for 5 min, the reaction mixture was quenched with water (75 mL) and mixed with Et$_2$O (75 mL). The layers were separated, and the organic layer was washed with water (3×50 mL) and saturated aqueous sodium chloride solution (75 mL), then dried over magnesium sulfate, filtered, and evaporated in vacuo. ~2 g of crude product was obtained. It was diluted with MeOH (5.0 mL), filtered, and purified by reverse-phase preparative chromatography using a $C_{18}$ column and a gradient eluent of 1 to 50% acetonitrile in water containing 5 mM hydrochloric acid to give [(4S)-2,4-dimethylpyrrolidin-2-yl]-trimethyl-silane (hydrochloride salt) (101.5 mg, 5%). $^1$H NMR (400 MHz, chloroform-d) δ 9.55 (s, 1H), 9.04 (s, 1H), 3.58-3.46 (m, 1H), 2.94-2.75 (m, 1H), 2.41-2.24 (m, 2H), 1.50 (s, 3H), 1.35-1.25 (m, 1H), 1.13 (d, J=6.2 Hz, 3H), 0.27 (s, 9H). ESI-MS m/z calc. 171.14433, found 172.2 (M+1)$^+$; Retention time: 0.6 minutes (LC method A).

Step 4: N-(1,3-Dimethylpyrazol-4-yl)sulfonyl-2-[(4S)-2,4-dimethyl-2-trimethylsilyl-pyrrolidin-1-yl]-6-[3-(3,3,3-trifluoro-2,2-dimethyl-propoxy)pyrazol-1-yl]pyridine-3-carboxamide (Compound (2-9), stereoisomer 1 and stereoisomer 2)

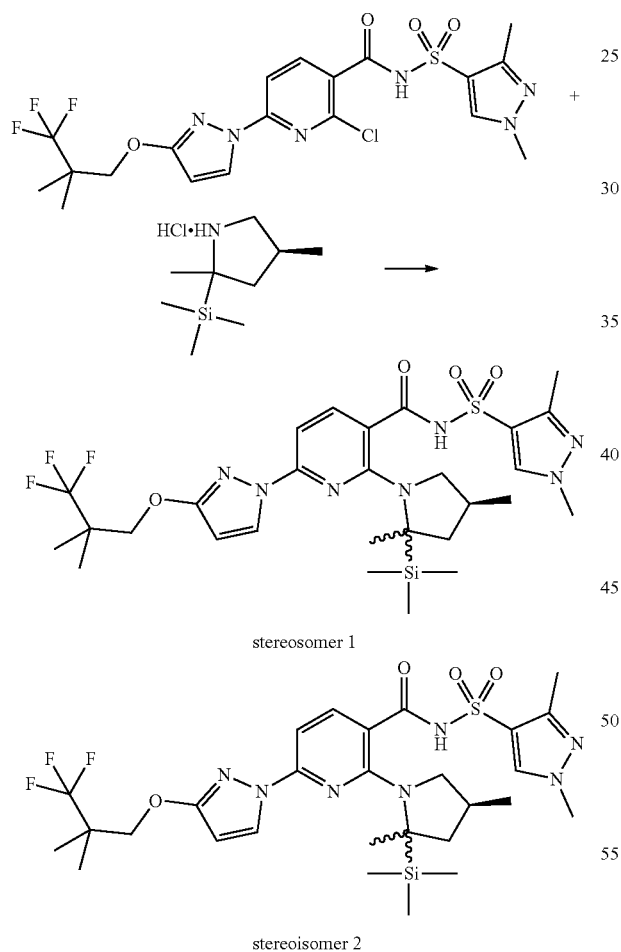

In a 3-mL vial, 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (51.4 mg, 0.099 mmol), [(4S)-2,4-dimethylpyrrolidin-2-yl]-trimethyl-silane (hydrochloride salt) (35.9 mg, 0.17 mmol) and $K_2CO_3$ (100.2 mg, 0.72 mmol) were mixed with DMSO (500 The resulting mixture was stirred vigorously at 170° C. for 16 h. It was cooled to room temperature, then 1 N HCl solution (1.5 mL) was added, followed by EtOAc (1.5 mL). The phases were vigorously mixed and then allowed to settle into two layers. The organic layer was filtered and purified by reverse-phase preparative chromatography using a $C_{18}$ column and a gradient eluent of 50 to 99% acetonitrile in water containing 5 mM hydrochloric acid to give 2 products:

Compound (2-9) stereoisomer 1: more polar, major diastereomer. N-(1,3-Dimethylpyrazol-4-yl)sulfonyl-2-[(4S)-2,4-dimethyl-2-trimethylsilyl-pyrrolidin-1-yl]-6-[3-(3,3,3-trifluoro-2,2-dimethyl-propoxy)pyrazol-1-yl]pyridine-3-carboxamide (16.1 mg, 25%). 1H NMR (400 MHz, DMSO-$d_6$) δ 12.40 (s, 1H), 8.35 (s, 1H), 8.10 (d, J=2.7 Hz, 1H), 7.73 (d, J=8.2 Hz, 1H), 6.88 (d, J=8.2 Hz, 1H), 6.12 (d, J=2.7 Hz, 1H), 4.21 (s, 2H), 3.79 (s, 3H), 2.64-2.55 (m, 1H), 2.32 (s, 3H), 2.16 (dd, J=12.0, 5.3 Hz, 1H), 1.98-1.89 (m, 1H), 1.62 (s, 3H), 1.31 (t, J=12.0 Hz, 1H), 1.22 (s, 6H), 0.84 (d, J=6.3 Hz, 3H), 0.84-0.78 (m, 1H), −0.15 (s, 9H). ESI-MS m/z calc. 655.25836, found 656.3 (M+1)$^+$; Retention time: 2.33 minutes (LC method A).

Compound (2-9) stereoisomer 2: less polar, minor diastereomer. N-(1,3-Dimethylpyrazol-4-yl)sulfonyl-2-[(4S)-2,4-dimethyl-2-trimethylsilyl-pyrrolidin-1-yl]-6-[3-(3,3,3-trifluoro-2,2-dimethyl-propoxy)pyrazol-1-yl]pyridine-3-carboxamide (4.7 mg, 7%). $^1$H NMR (400 MHz, DMSO-$d_6$) δ 12.34 (s, 1H), 8.42-8.27 (bs, 1H), 8.17-8.12 (m, 1H), 7.73-7.65 (m, 1H), 6.90-6.82 (m, 1H), 6.13-6.07 (m, 1H), 4.26-4.16 (m, 2H), 3.78 (s, 3H), 2.52-2.49 (m, 1H), 2.34-2.30 (m, 1H), 2.30 (s, 3H), 2.20-2.14 (m, 1H), 1.65 (s, 3H), 1.49 (t, J=11.8 Hz, 1H), 1.22 (s, 6H), 0.88-0.83 (m, 1H), 0.81 (d, J=6.1 Hz, 3H), −0.05 (s, 9H). ESI-MS m/z calc. 655.25836, found 656.3 (M+1)$^+$; Retention time: 2.38 minutes (LC method A).

Example 10: Preparation of N-(1,3-dimethylpyrazol-4-yl)sulfonyl-6-[3-[dimethyl(3,3,3-trifluoropropyl)silyl]pyrazol-1-yl]-2-[(4S)-2,2,4-trimethylpyrrolidin-1-yl]pyridine-3-carboxamide (Compound (2-7))

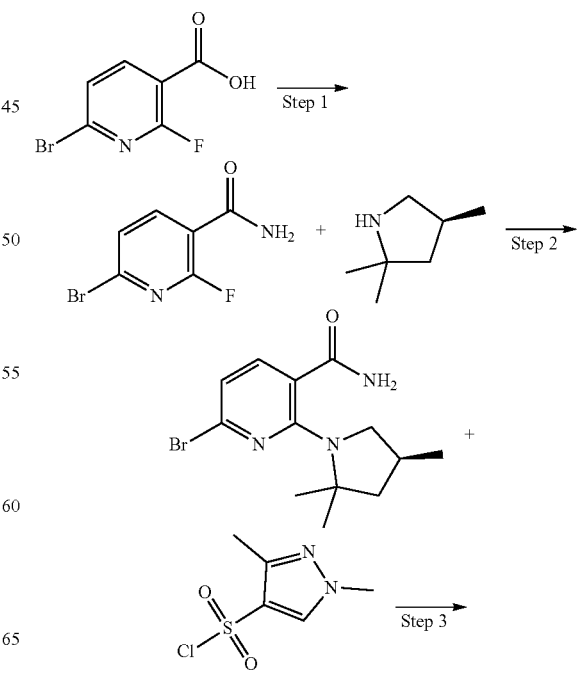

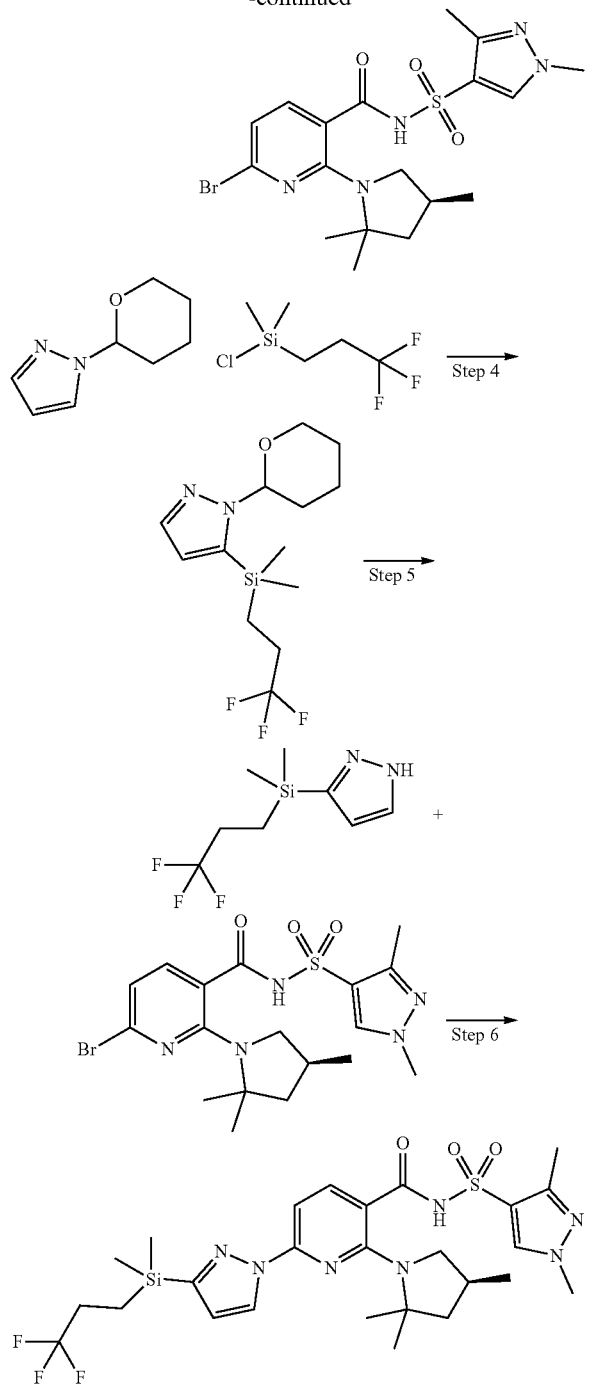

Step 1: 6-Bromo-2-fluoro-pyridine-3-carboxamide

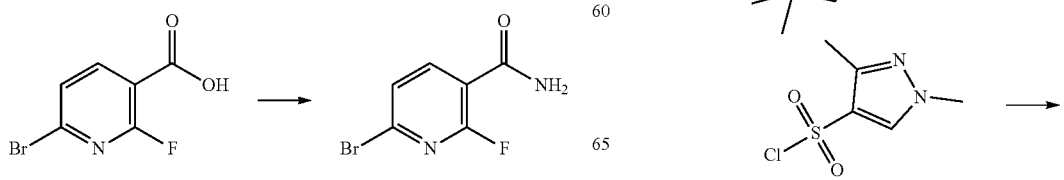

To a solution of 6-bromo-2-fluoro-pyridine-3-carboxylic acid (24.7 g, 106.66 mmol) and Boc$_2$O (33 g, 146.67 mmol) in 2-MeTHF (250 mL) was added NMM (13.80 g, 15 mL, 136.44 mmol). The mixture was stirred for 30 min at room temperature and then NH$_4$HCO$_3$ (15 g, 189.74 mmol) was added. The reaction mixture was stirred for 20 hours at room temperature. Water (200 mL) and EtOAc (100 mL) were added and the mixture was stirred for 10 min. The two phases were separated. The organic layer was washed with saturated sodium bicarbonate, brine, dried over sodium sulfate and concentrated to give 6-bromo-2-fluoro-pyridine-3-carboxamide (23.5 g, 96%) as a light color solid. ESI-MS m/z calc. 217.9491, found 219.3 (M+1)$^+$; Retention time: 2.33 minutes (LC method B).

Step 2: 6-Bromo-2-[(4S)-2,2,4-trimethylpyrrolidin-1-yl]pyridine-3-carboxamide

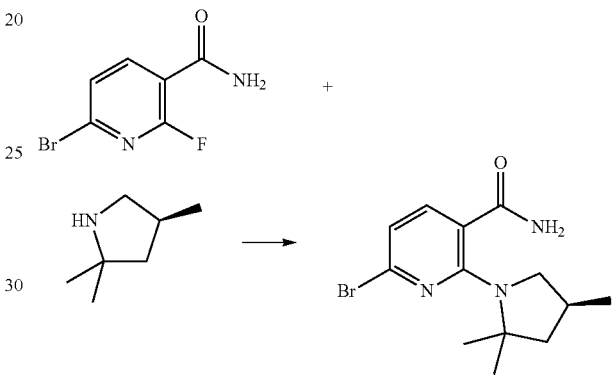

To a solution of 6-bromo-2-fluoro-pyridine-3-carboxamide (23.5 g, 101.94 mmol) and (4S)-2,2,4-trimethylpyrrolidine (18.5 g, 160.16 mmol) in ACN (200 mL) was added K$_2$CO$_3$ (38 g, 274.95 mmol). The reaction mixture was stirred at room temperature for 20 hours. Water (400 mL) was added and stirred for 2 hours with air blowing off most solvent ACN (final volume ~450 mL). The formed solid was collected to give 6-bromo-2-[(4S)-2,2,4-trimethylpyrroli-din-1-yl]pyridine-3-carboxamide (28.3 g, 87%) as a beige color solid. ESI-MS m/z calc. 311.0633, found 312.5 (M+1)$^+$; Retention time: 3.55 minutes (LC method B).

Step 3: 6-Bromo-N-(1,3-dimethylpyrazol-4-yl)sulfonyl-2-[(4S)-2,2,4-trimethylpyrrolidin-1-yl]pyridine-3-carboxamide

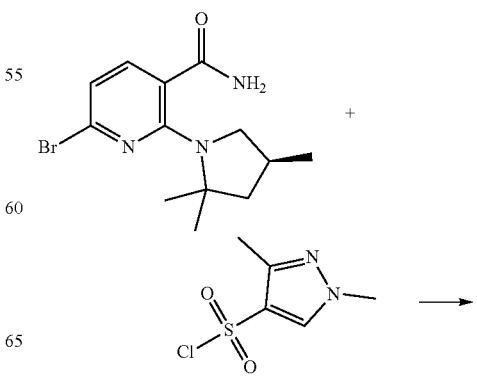

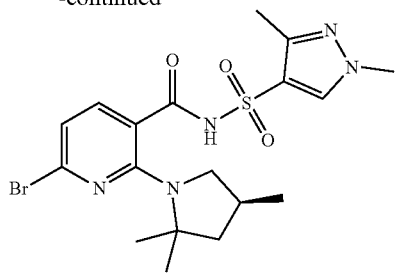

To a 3-neck 100 mL round bottom flask was added 6-bromo-2-[(4S)-2,2,4-trimethylpyrrolidin-1-yl]pyridine-3-carboxamide (3.05 g, 9.76 mmol), 1,3-dimethylpyrazole-4-sulfonyl chloride (3.23 g, 16.59 mmol) and 2-Me-THF (21 mL) and the contents were purged with nitrogen. The reaction mixture was cooled down to 0-5° C. under ice bath. Lithium tert-amoxide (3.1 M solution in heptane, 10.7 mL, 33.18 mmol) was added to the mixture while keeping the internal temperature below 5° C. The reaction mixture was stirred below 5° C. for 1.5 h, then for 3.5 h at room temperature. Water (20 mL) was added to the mixture and the reaction was stirred at room temperature for 30 min. MeTHF (5 mL) was added, followed by aqueous 1M HCl until pH<2. The aqueous layer was separated and organic layer was dried over sodium sulfate. After evaporation, the residue was triturated and stirred in DCM/heptane (1:3, v:v) for 15 min. The solid was collected by filtration to give 6-bromo-N-(1,3-dimethylpyrazol-4-yl)sulfonyl-2-[(4S)-2,2,4-trimethylpyrrolidin-1-yl]pyridine-3-carboxamide (4.27 g, 93%). ESI-MS m/z calc. 469.0783, found 470.0 (M+1)+ Retention time: 2.51 minutes.

Step 4: Dimethyl-(2-tetrahydropyran-2-ylpyrazol-3-yl)-(3,3,3-trifluoropropyl)silane

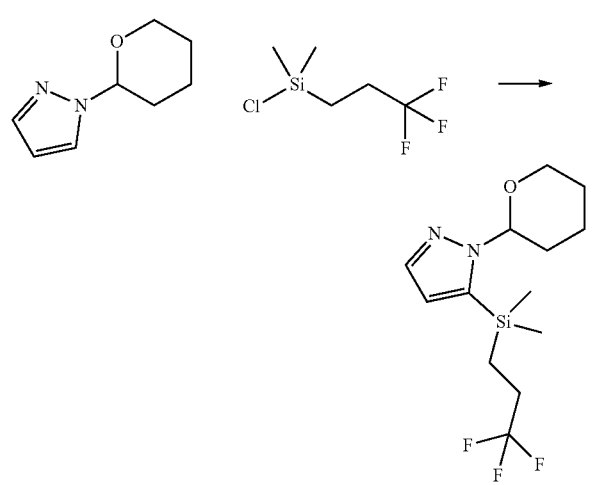

1-Tetrahydropyran-2-ylpyrazole (4.0 g, 26.28 mmol) was dissolved in THF (24 mL). The solution was cooled to −35° C. for the slow dropwise addition of n-butyl lithium (12.6 mL of 2.5 M solution in hexanes, 31.50 mmol). Stirring was continued at −35° C. for 1 hour. Chloro-dimethyl-(3,3,3-trifluoropropyl)silane (5.0 mL, 29.29 mmol) was then added dropwise, and the reaction mixture was allowed to warm to room temperature. After stirring overnight at room temperature, the reaction mixture was diluted with EtOAc (75 mL). It was washed with saturated aqueous ammonium chloride (lx 75 mL), water (lx 75 mL) and brine (1×75 mL). The organic layer was dried over sodium sulfate, filtered and concentrated under reduced pressure. The crude product was chromatographed on an 80 gram silica gel column eluting with a 0-50% EtOAc/hexane gradient over 50 minutes; the product eluted at 15% EtOAc/hexanes. Dimethyl-(2-tetrahydropyran-2-ylpyrazol-3-yl)-(3,3,3-trifluoropropyl)silane (7.56 g, 94%) was obtained as a clear colorless oil. $^1$H NMR (400 MHz, DMSO-d$_6$) δ 7.51 (d, J=1.6 Hz, 1H), 6.47 (d, J=1.6 Hz, 1H), 5.31 (dd, J=9.4, 2.4 Hz, 1H), 3.85 (ddt, J=11.5, 4.6, 2.4 Hz, 1H), 3.67-3.58 (m, 1H), 2.31-2.19 (m, 1H), 2.11 (ddtd, J=16.9, 13.8, 11.1, 5.8 Hz, 2H), 2.02-1.91 (m, 2H), 1.76-1.63 (m, 1H), 1.53 (ddt, J=10.9, 7.9, 3.7 Hz, 2H), 0.99-0.92 (m, 2H), 0.34 (s, 3H), 0.33 (s, 3H). ESI-MS m/z calc. 306.1375, found 307.2 (M+1)+; Retention time: 1.87 minutes (LC method A).

Step 5: Dimethyl-(1H-pyrazol-3-yl)-(3,3,3-trifluoropropyl)silane

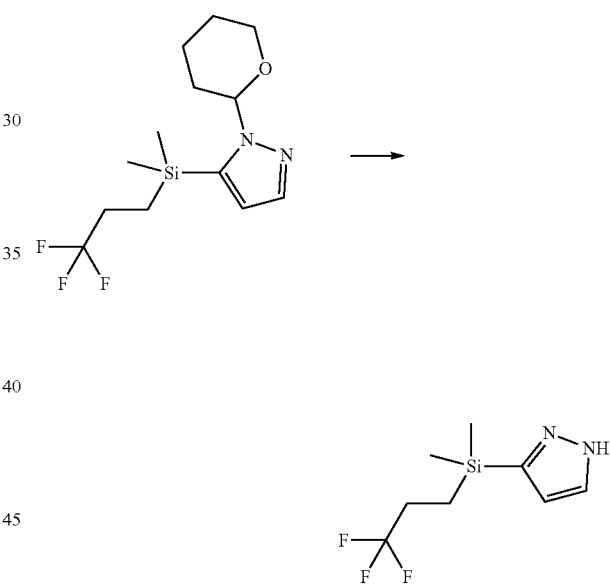

Dimethyl-(2-tetrahydropyran-2-ylpyrazol-3-yl)-(3,3,3-trifluoropropyl)silane (7.56 g, 24.67 mmol) was dissolved into a solution of hydrochloric acid (19 mL of 4 M, 76.00 mmol) in 1,4-dioxane. The reaction mixture was allowed to stir overnight at 50° C. Volatiles were removed under reduced pressure. The remaining oil was dissolved in EtOAc (75 mL) and washed with saturated aqueous sodium bicarbonate solution (2×75 mL) and brine (1×75 mL). The organic layer was dried over sodium sulfate, filtered and concentrated under reduced pressure. The crude product was then chromatographed on a 40 gram silica gel column eluting with a 0-40% EtOAc/hexane gradient over 40 minutes. Dimethyl-(1H-pyrazol-3-yl)-(3,3,3-trifluoropropyl)silane (3.83 g, 70%) was obtained as a yellow oil. $^1$H NMR (400 MHz, DMSO-d$_6$) δ 12.86 (s, 1H), 7.52 (s, 1H), 6.44 (d, J=1.6 Hz, 1H), 2.24-2.07 (m, 2H), 0.97-0.86 (m, 2H), 0.31 (s, 6H). ESI-MS m/z calc. 222.08002, found 223.2 (M+1)+; Retention time: 1.37 minutes (LC method A).

Step 6: N-(1,3-Dimethylpyrazol-4-yl)sulfonyl-6-[3-[dimethyl(3,3,3-trifluoropropyl)silyl]pyrazol-1-yl]-2-[(4S)-2,2,4-trimethylpyrrolidin-1-yl]pyridine-3-carboxamide (Compound (2-7))

Example 11: Preparation of N-(1,3-dimethylpyrazol-4-yl)sulfonyl-2-[(4S)-2,2,4-trimethylpyrrolidin-1-yl]-6-trimethylsilyl-pyridine-3-carboxamide (Compound (2-5))

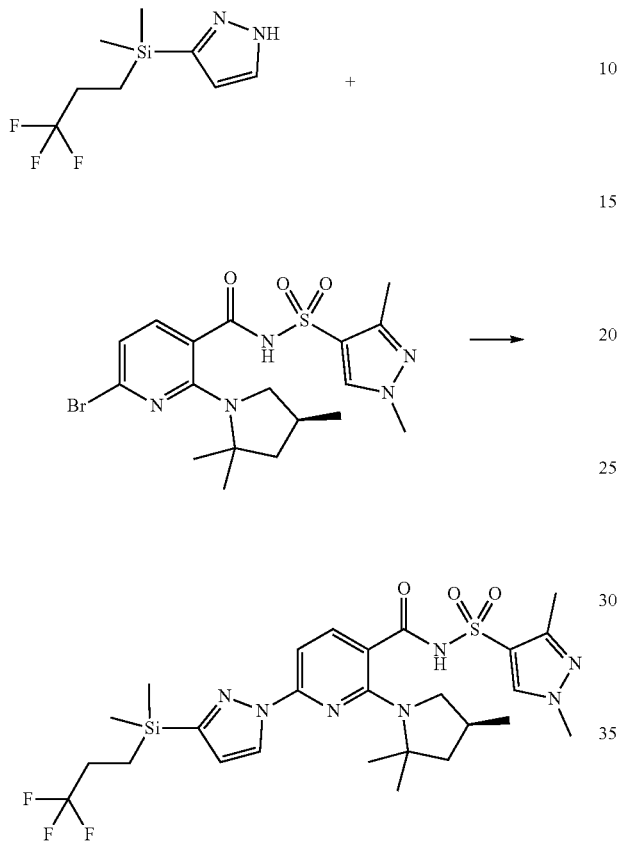

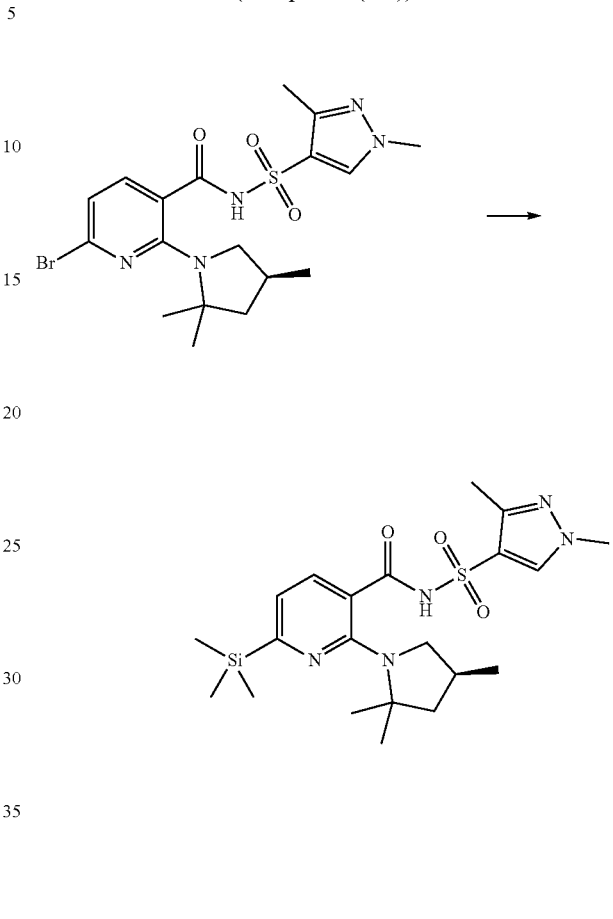

Dimethyl-(1H-pyrazol-3-yl)-(3,3,3-trifluoropropyl)silane (75 mg, 0.34 mmol), 6-bromo-N-(1,3-dimethylpyrazol-4-yl)sulfonyl-2-[(4S)-2,2,4-trimethylpyrrolidin-1-yl]pyridine-3-carboxamide (159 mg, 0.34 mmol), potassium carbonate (93 mg, 0.67 mmol) and racemic trans-N1,N2-dimethylcyclohexane-1,2-diamine (29 mg, 0.20 mmol) were combined in DMF (0.5 mL). Copper(I) iodide (7 mg, 0.037 mmol) was added under nitrogen gas. The reaction mixture was capped and allowed to stir overnight at 115° C. After cooling to room temperature, the reaction mixture was diluted with dichloromethane (6 mL) and filtered. The filtrate was injected directly onto a 24 gram silica gel column and eluted with a 0-100% EtOAc/hexanes gradient over 20 minutes. The product eluted at 50% EtOAc/hexanes. N-(1,3-dimethylpyrazol-4-yl)sulfonyl-6-[3-[dimethyl(3,3,3-trifluoropropyl)silyl]pyrazol-1-yl]-2-[(4S)-2,2,4-trimethylpyrrolidin-1-yl]pyridine-3-carboxamide (59.5 mg, 29%) was obtained as a white solid. $^1$H NMR (400 MHz, DMSO-$d_6$) δ 12.40 (s, 1H), 8.41 (d, J=2.5 Hz, 1H), 8.38 (s, 1H), 7.79 (d, J=8.2 Hz, 1H), 7.13 (d, J=8.2 Hz, 1H), 6.75 (d, J=2.5 Hz, 1H), 3.81 (s, 3H), 2.56 (t, J=10.3 Hz, 1H), 2.44 (t, J=8.5 Hz, 1H), 2.33 (s, 3H), 2.31-2.14 (m, 3H), 1.88 (dd, J=12.0, 5.6 Hz, 1H), 1.58 (s, 3H), 1.55 (s, 3H), 1.43 (t, J=12.2 Hz, 1H), 1.00-0.92 (m, 2H), 0.82 (d, J=6.3 Hz, 3H), 0.33 (s, 6H). ESI-MS m/z calc. 611.2322, found 612.2 (M+1)$^+$; Retention time: 2.37 minutes (LC method A).

6-Bromo-N-(1,3-dimethylpyrazol-4-yl)sulfonyl-2-[(4S)-2,2,4-trimethylpyrrolidin-1-yl]pyridine-3-carboxamide (102 mg, 0.22 mmol), tris(dibenzylideneacetone)dipalladium(0) (10.2 mg, 0.011 mmol), dicyclohexyl-(2-phenylphenyl)phosphane (14.1 mg, 0.04 mmol), water (20 μL, 1.11 mmol), and KF (73.6 mg, 1.27 mmol) were combined in dioxane (0.6 mL) under nitrogen and stirred at 100° C. for 15 min. Trimethyl(trimethylsilyl)silane (70 μL, 0.34 mmol) was added and the reaction was heated at 100° C. for an additional 48 h. The reaction mixture was partitioned between ethyl acetate and a 10% citric acid solution. The organics were separated, washed with brine, dried over sodium sulfate and evaporated. The crude material was purified by preparative HPLC utilizing a gradient of 1-99% acetonitrile in 5 mM aq HCl to yield N-(1,3-dimethylpyrazol-4-yl)sulfonyl-2-[(4S)-2,2,4-trimethylpyrrolidin-1-yl]-6-trimethylsilyl-pyridine-3-carboxamide (hydrochloride salt) (5.4 mg, 5%) as a yellow solid.

$^1$H NMR (400 MHz, DMSO-$d_6$) δ 12.32 (s, 1H), 8.37 (s, 0.7H), 8.33 (br s, 0.3H), 7.98 (br s, 0.3H), 7.46 (d, J=7.4 Hz, 0.7H), 6.79 (d, J=7.4 Hz, 1H), 3.80 (s, 3H), 2.47-2.36 (m, 1H), 2.35-2.24 (m, 4H), 2.24-2.10 (m, 1H), 1.82 (dd, J=11.9, 5.6 Hz, 1H), 1.56-1.46 (m, 6H), 1.39 (t, J=11.9 Hz, 1H), 0.96 (s, 1H, one proton of CH$_3$), 0.80 (d, J=6.3 Hz, 2H, two protons of CH$_3$), 0.23 (s, 9H). There appeared to be different protonation states that led to splitting of some of the peaks in the NMR spectrum. ESI-MS m/z calc. 463.20734, found 464.1 (M+1)$^+$; Retention time: 1.71 minutes (LC method A).

Example 12: Preparation of 6-[3-[3,3-dimethylbutyl)dimethyl)silyl]pyrazol-1-yl]-N-(1,3-dimethylpyrazol-4-yl)sulfonyl-2-[(4S)-2,2,4-trimethylpyrrolidin-1-yl]pyridine-3-carboxamide (Compound (2-1))

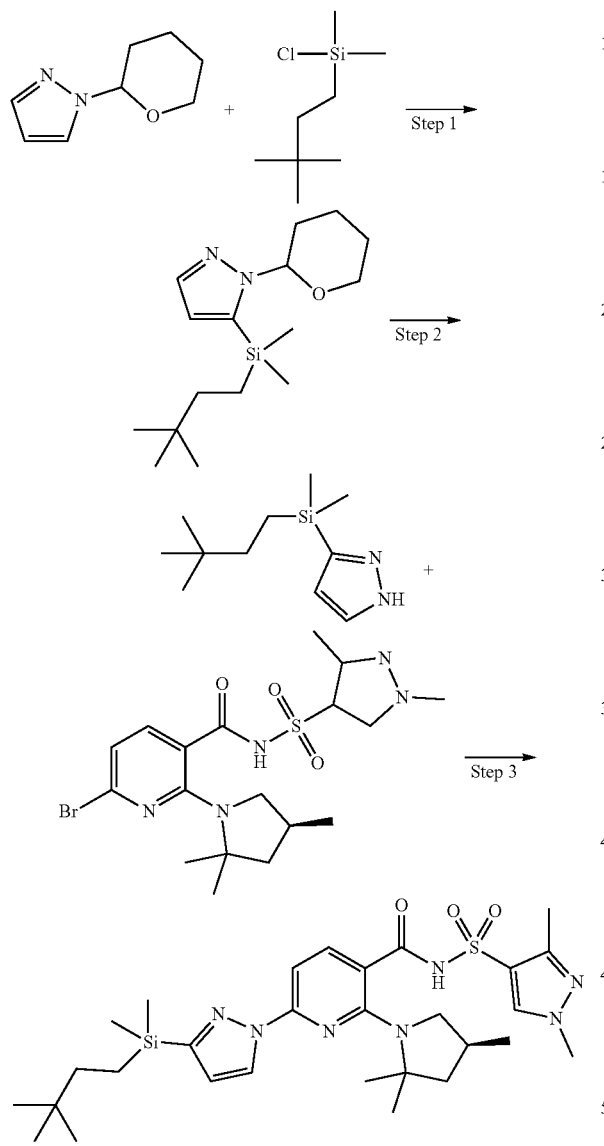

Step 1: 3,3-Dimethylbutyl-dimethyl-(2-tetrahydropyran-2-ylpyrazol-3-yl)silane

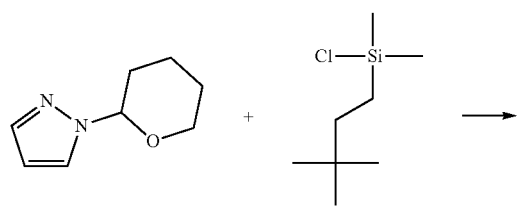

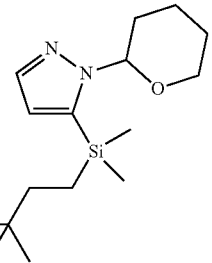

To a stirred solution of 1-tetrahydropyran-2-ylpyrazole (3 g, 19.71 mmol) in anhydrous tetrahydrofuran (25 mL) was added n-butyllithium (1.6 M in hexanes) (15 mL, 24.00 mmol) dropwise from a dropping funnel over 6 min at −35° C. under nitrogen. After the addition was complete, the resulting solution was stirred for an additional 1 h at −35° C. Then a solution of chloro-(3,3-dimethylbutyl)-dimethyl-silane (3.90 g, 21.82 mmol) in anhydrous tetrahydrofuran (1 mL) was added dropwise from the dropping funnel over 5 min. After the end of the addition, the reaction was stirred for an additional 10 min at that temperature, and then the bath was removed and allowed to warm to room temperature. Then after stirring for another 3 h, saturated ammonium chloride solution (30 mL) was added and the mixture was extracted with ether (3×30 mL). The combined organics were washed with brine (20 mL), dried over sodium sulfate, filtered and concentrated under reduced pressure. The crude material (light orange light oil) was used in the subsequent step without further purification. 3,3-Dimethylbutyl-dimethyl-(2-tetrahydropyran-2-ylpyrazol-3-yl)silane (5.79 g, 100%). $^1$H NMR (400 MHz, Chloroform-d) δ 7.57 (d, J=1.7 Hz, 1H), 6.39 (d, J=1.7 Hz, 1H), 5.29 (dd, J=9.8, 2.6 Hz, 1H), 4.08-3.98 (m, 1H), 3.62 (td, J=11.2, 2.6 Hz, 1H), 2.57-2.42 (m, 1H), 2.13-2.07 (m, 1H), 2.03-1.96 (m, 1H), 1.77-1.63 (m, 2H), 1.61-1.56 (m, 1H), 1.19-1.12 (m, 2H), 0.85 (s, 9H), 0.76-0.70 (m, 2H), 0.30 (s, 6H). ESI-MS m/z calc. 294.21274, found 295.2 (M+1)$^+$; Retention time: 2.21 minutes (LC method A).

Step 2: 3,3-Dimethylbutyl-dimethyl-(1H-pyrazol-3-yl)silane

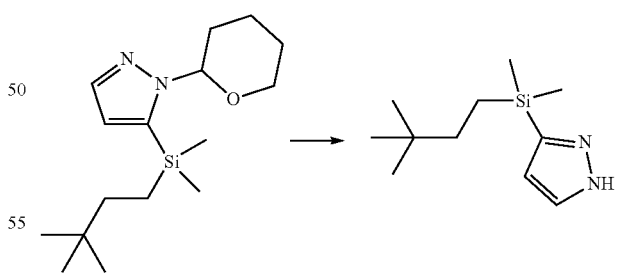

To a stirred solution of 3,3-dimethylbutyl-dimethyl-(2-tetrahydropyran-2-ylpyrazol-3-yl)silane (5.2 g, 17.66 mmol) in ethanol (15 mL) was added aqueous hydrochloric acid (11 mL of 5.0 M, 55.00 mmol) and stirred at 50° C. for 4 h. The reaction was allowed to cool to ambient temperature and a saturated aq. NaHCO$_3$ solution was added slowly (vigorous CO$_2$ gas evolution) to quench the acid, and the resulting solution was extracted with ethyl acetate (3×30 mL). The combined organics were washed with brine (20 mL), dried over sodium sulfate, filtered and concentrated under reduced pressure. The crude material (thick oil) upon standing at ambient temperature became a brownish solid. It was used in the subsequent reaction without further purification. 3,3-Dimethylbutyl-dimethyl-(1H-pyrazol-3-yl)silane (3.64 g, 98%). $^1$H NMR (400 MHz, Methanol-$d_4$) δ 8.18 (d, J=2.4 Hz, 1H), 6.84 (d, J=2.4 Hz, 1H), 1.22-1.15 (m, 2H), 0.87 (s, 9H), 0.86-0.79 (m, 2H), 0.39 (s, 6H). ESI-MS m/z calc. 210.15523, found 211.1 (M+1)$^+$; Retention time: 1.66 minutes (LC method A).

Step 3: 6-[3-[3,3-Dimethylbutyl(dimethyl)silyl]pyrazol-1-yl]-N-(1,3-dimethylpyrazol-4-yl)sulfonyl-2-[(4S)-2,2,4-trimethylpyrrolidin-1-yl]pyridine-3-carboxamide (Compound (2-1))

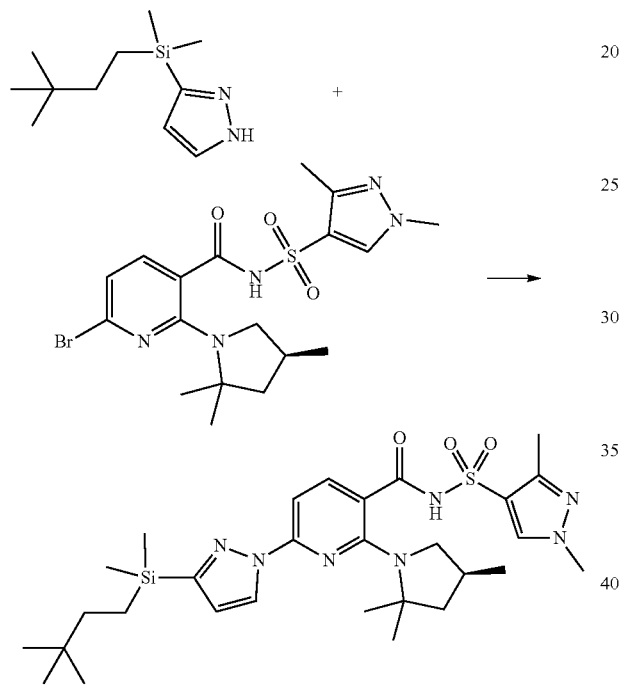

In a 4 mL vial, 3,3-dimethylbutyl-dimethyl-(1H-pyrazol-3-yl)silane (77 mg, 0.37 mmol), 6-bromo-N-(1,3-dimethylpyrazol-4-yl)sulfonyl-2-[(4S)-2,2,4-trimethylpyrrolidin-1-yl]pyridine-3-carboxamide (172 mg, 0.37 mmol), racemic trans-N1,N2-dimethylcyclohexane-1,2-diamine (54 mg, 0.38 mmol), and potassium carbonate (140 mg, 1.01 mmol) (325 mesh) were combined in anhydrous DMF (500 The mixture was sparged with nitrogen for 5 min. Copper (I) iodide (8 mg, 0.042 mmol) was added under nitrogen gas. The reaction vial was capped, and the reaction mixture was allowed to stir at 115° C. for 17 h. After cooling to room temperature, the reaction mixture was diluted with dichloromethane (6 mL). The mixture was injected directly onto a 24 gram silica gel column eluting with a 0-30% EtOAc/hexanes gradient over 30 min then 30-60% over 10 min. the product eluted around 40% EtOAc/hexanes. After evaporation of the solvents, 67 mg of impure product was isolated and dissolved in DMSO (2 mL). The solution was microfiltered through a Whatman 0.45 µM PTFE syringe filter disc and purified by reverse phase preparative HPLC ($C_{18}$) using a gradient of acetonitrile in water (30 to 99% over 15 min) and HCl as a modifier. Evaporation gave 6-[3-[3,3-dimethylbutyl(dimethyl) silyl]pyrazol-1-yl]-N-(1,3-dimethylpyrazol-4-yl)sulfonyl-2-[(4S)-2,2,4-trimethylpyrrolidin-1-yl]pyridine-3-carboxamide (41.2 mg, 18%) as a white solid. 1H NMR (400 MHz, DMSO-$d_6$) δ 12.39 (s, 1H), 8.42-8.34 (m, 2H), 7.78 (d, J=8.2 Hz, 1H), 7.14 (d, J=8.2 Hz, 1H), 6.68 (d, J=2.5 Hz, 1H), 3.81 (s, 3H), 2.56 (t, J=10.4 Hz, 1H), 2.44 (t, J=8.6 Hz, 1H), 2.33 (s, 3H), 2.26-2.12 (m, 1H), 1.88 (dd, J=12.0, 5.6 Hz, 1H), 1.58 (s, 3H), 1.55 (s, 3H), 1.43 (t, J=12.2 Hz, 1H), 1.26-1.16 (m, 2H), 0.89-0.78 (m, 12H), 0.74-0.63 (m, 2H), 0.27 (s, 6H). ESI-MS m/z calc. 599.3074, found 600.3 (M+1)$^+$; Retention time: 2.23 minutes (LC method G).

Example 13: Preparation of N-(1,3-dimethylpyrazol-4-yl)sulfonyl-2-[(4S)-2,2,4-trimethylpyrrolidin-1-yl]-6-[3-(trimethylsilylmethoxy)pyrazol-1-yl]pyridine-3-carboxamide (Compound (2-3))

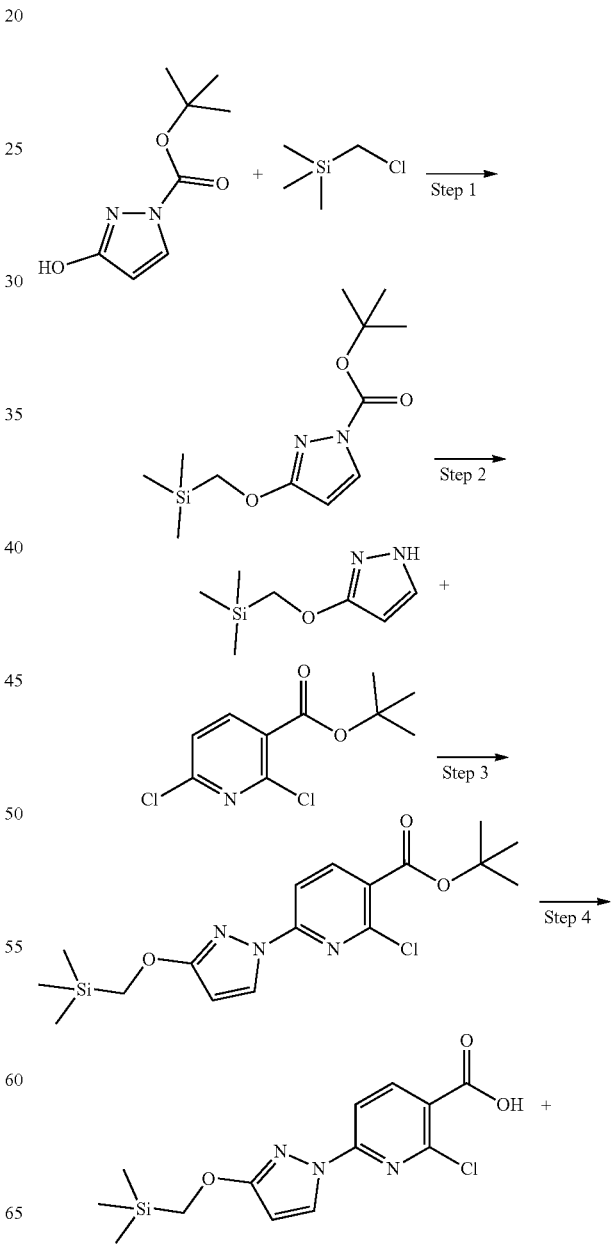

1H), 3.98 (s, 2H), 1.61 (s, 9H), 0.11 (s, 9H). ESI-MS m/z calc. 270.14, found 270.9 (M+1)⁺; Retention time: 6.62 minutes (LC method C).

Step 2: Trimethyl(1H-pyrazol-3-yloxymethyl)silane

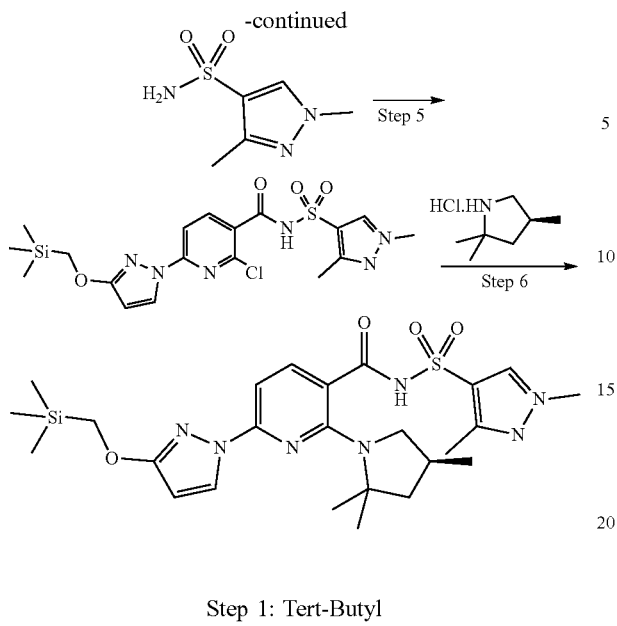

Step 1: Tert-Butyl 3-(trimethylsilylmethoxy)pyrazole-1-carboxylate

Into a solution of tert-butyl 3-(trimethylsilylmethoxy) pyrazole-1-carboxylate (2.146 g, 7.78 mmol) in DCM (24 mL) was added TFA (12 mL, 155.76 mmol). The reaction was stirred at rt for 2 hours. All the volatiles were removed under vacuum to furnish trimethyl(1H-pyrazol-3-yloxymethyl)silane (trifluoroacetate salt) (3.03 g, 100%) as a clear oil. $^1$H NMR (250 MHz, Chloroform-d) δ 7.72 (d, J=2.9 Hz, 1H), 5.95 (d, J=2.9 Hz, 1H), 3.92 (s, 2H), 0.17 (s, 9H). ESI-MS m/z calc. 170.0875, found 171.3 (M+1)⁺, Retention time: 3.85 minutes (LC method C).

Step 3: tert-Butyl 2-chloro-6-[3-(trimethylsilylmethoxy)pyrazol-1-yl]pyridine-3-carboxylate

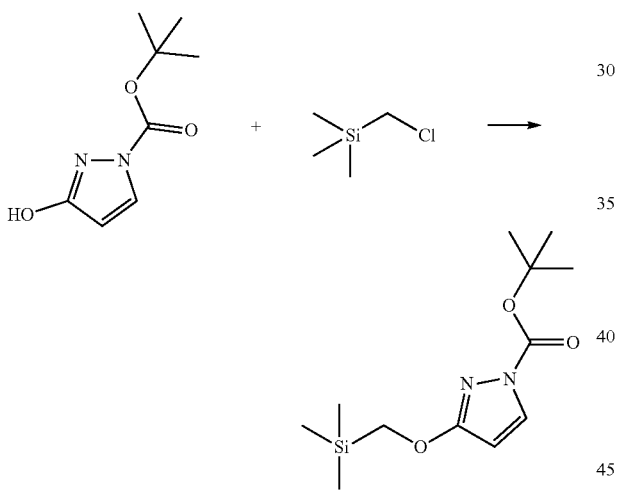

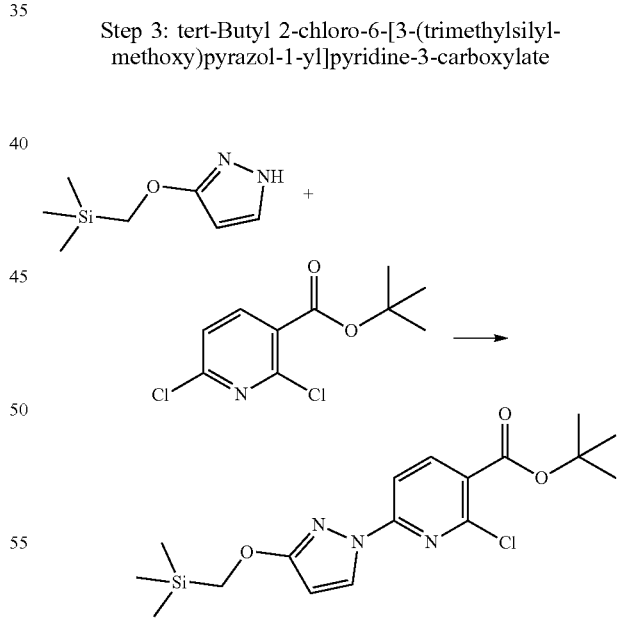

A 5 mL microwave vial was charged with tert-butyl 3-hydroxypyrazole-1-carboxylate (2 g, 10.86 mmol), chloromethyl(trimethyl)silane (1.6 mL, 11.46 mmol), potassium carbonate (3.00 g, 21.71 mmol) and DMA (20 mL). The reaction was heated at 120° C. for 16 hours. The reaction was diluted with water (50 mL) and ethyl acetate (50 mL). After separation of the two layers, the aqueous layer was extracted with ethyl acetate (2×50 mL). The combined organic layers were washed with brine (3×50 mL), dried over anhydrous sodium sulfate and concentrated under vacuum. The residue was dissolved in THF (20 mL). TEA (4.6 mL, 33.00 mmol) and Boc₂O (4.75 g, 21.764 mmol) were added to the reaction mixture, followed by a catalytic amount of DMAP (157 mg, 1.285 mmol). The reaction was stirred at rt for 16 hours. All the volatiles were removed under vacuum. The residue was purified by silica gel chromatography using 0 to 10% diethyl ether in hexane to furnish tert-butyl 3-(trimethylsilylmethoxy)pyrazole-1-carboxylate (2.146 g, 72%) as a clear oil. $^1$H NMR (250 MHz, Chloroform-d) δ 7.82 (d, J=2.9 Hz, 1H), 5.86 (d, J=2.9 Hz, Into a solution of trimethyl(1H-pyrazol-3-yloxymethyl) silane (3.03 g, 12.99 mmol) and tert-butyl 2,6-dichloropyridine-3-carboxylate (3.22 g, 12.97 mmol) in anhydrous DMF (20 mL) were added potassium carbonate (7.22 g, 52.24 mmol) and DABCO (311 mg, 2.77 mmol). The reaction was stirred at rt overnight. The reaction was quenched with water (50 mL), and extracted with diethyl ether (3×50 mL). The combined ether layers were washed with brine (3×50 mL), dried over anhydrous sodium sulfate and concentrated under vacuum. The residue was purified by silica gel chromatography using 0 to 2% diethyl ether in hexane (120 g column, loaded with toluene) to furnish tert-butyl 2-chloro-6-[3-(trimethylsilylmethoxy)pyrazol-1-yl]pyridine-3-carboxylate (2.645 g, 53%) as a clear oil. ESI-MS m/z calc. 381.1275, found 382.2 (M+1)⁺, Retention time: 8.39 minutes (LC method C).

Step 4: 2-Chloro-6-[3-(trimethylsilylmethoxy)pyrazol-1-yl]pyridine-3-carboxylic acid

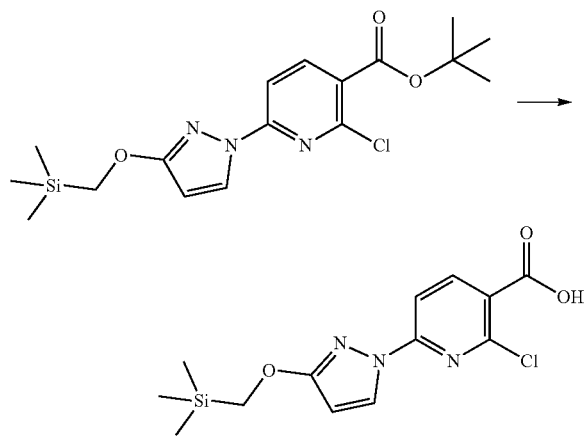

Into a solution of tert-butyl 2-chloro-6-[3-(trimethylsilylmethoxy)pyrazol-1-yl]pyridine-3-carboxylate (2.64 g, 6.92 mmol) in DCM (10 mL) was added TFA (10 mL, 129.80 mmol). The reaction was stirred at rt for 16 hours. The reaction was diluted with water (50 mL) and diethyl ether (50 mL). The two layers were separated, and the aqueous layer was extracted with diethyl ether (2×50 mL). The combined organic layers were washed with brine (50 mL), dried over anhydrous magnesium sulfate and concentrated under vacuum. The white solid residue was triturated with hexane (25 mL) to furnish 2-chloro-6-[3-(trimethylsilylmethoxy) pyrazol-1-yl]pyridine-3-carboxylic acid (2.023 g, 86%) as a white solid. ¹H NMR (500 MHz, DMSO-d₆) δ 8.43-8.37 (m, 2H), 7.74 (d, J=8.4 Hz, 1H), 6.20 (d, J=2.9 Hz, 1H), 3.99 (s, 2H), 0.12 (s, 9H). ESI-MS m/z calc. 325.0649, found 326.1 (M+1)⁺; Retention time: 2.81 minutes (LC method H).

Step 5: 2-Chloro-N-(1,3-dimethylpyrazol-4-yl)sulfonyl-6-[3-(trimethylsilylmethoxy) pyrazol-1-yl]pyridine-3-carboxamide

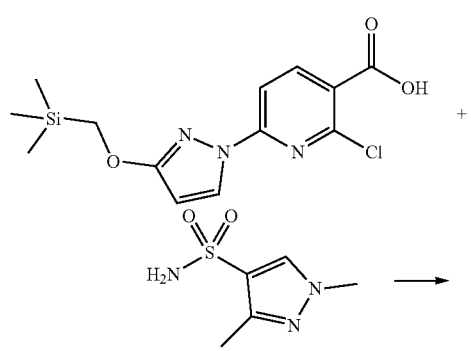

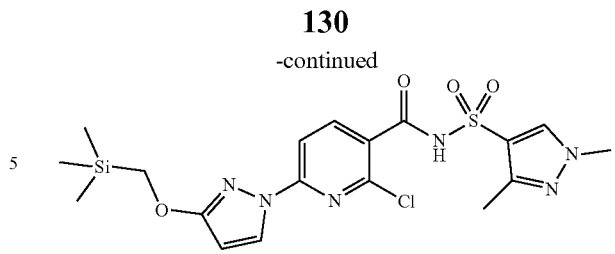

To a stirring suspension of 2-chloro-6-[3-(trimethylsilylmethoxy)pyrazol-1-yl]pyridine-3-carboxylic acid (606 mg, 1.86 mmol) and 1,3-dimethylpyrazole-4-sulfonamide (485 mg, 2.77 mmol) in anhydrous DCM (20 mL) at room temperature under nitrogen was added DMAP (684 mg, 5.60 mmol), followed by EDC (1.052 g, 5.49 mmol). Within 5 minutes, the reaction mixture became a homogeneous solution. The reaction mixture was stirred at this temperature for 24 hours. The reaction was quenched with 10% aqueous citric acid (35 mL), and two layers were separated. The aqueous layer was extracted with DCM (2×25 mL). Combined organic layers were washed with brine (20 mL), dried over anhydrous sodium sulfate and concentrated. The crude was purified by silica gel chromatography using 0-5% methanol gradient in dichloromethane to afford 2-chloro-N-(1,3-dimethylpyrazol-4-yl)sulfonyl-6-[3-(trimethylsilylmethoxy)pyrazol-1-yl]pyridine-3-carboxamide (639 mg, 68%) as white solid. ESI-MS m/z calc. 482.0959, found 483.4 (M+1)⁺; Retention time: 6.37 minutes (LC method C).

Step 6: N-(1,3-Dimethylpyrazol-4-yl)sulfonyl-2-[(4S)-2,2,4-trimethylpyrrolidin-1-yl]-6-[3-(trimethylsilylmethoxy)pyrazol-1-yl]pyridine-3-carboxamide (Compound (2-3))

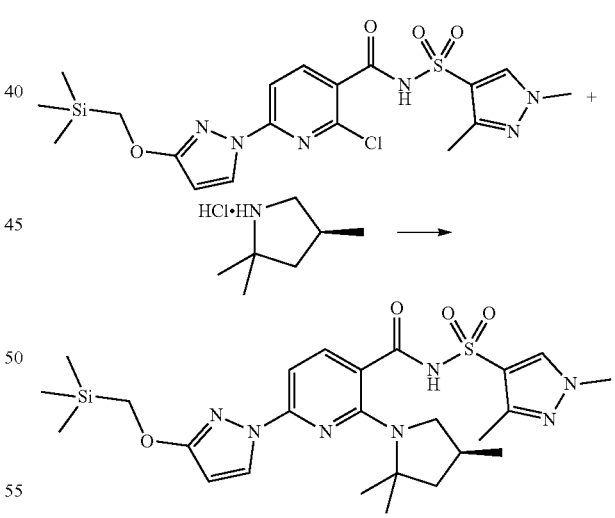

To a stirring solution of 2-chloro-N-(1,3-dimethylpyrazol-4-yl)sulfonyl-6-[3-(trimethylsilylmethoxy)pyrazol-1-yl]pyridine-3-carboxamide (610 mg, 1.26 mmol) and (4S)-2,2,4-trimethylpyrrolidine (hydrochloride salt) (574 mg, 3.84 mmol) in anhydrous DMSO (8 mL) at room temperature under nitrogen was added sodium carbonate (1.12 g, 10.57 mmol). The reaction mixture was heated to 160° C. for 7 hours. After cooling to room temperature, the reaction mixture was poured into a stirring mixture of 10% aqueous citric acid (50 mL) and ethyl acetate (40 mL). Two layers were separated, and the aqueous layer was extracted with ethyl acetate (2×30 mL). Combined organic layers were washed with brine (25 mL), dried over anhydrous sodium sulfate and concentrated. The crude was purified by silica gel chromatography using 0-20% acetone gradient in hexanes to afford N-(1,3-dimethylpyrazol-4-yl)sulfonyl-2-[(4S)-2,2,4-trimethylpyrrolidin-1-yl]-6-[3-(trimethylsilylmethoxy)pyrazol-1-yl]pyridine-3-carboxamide (549 mg, 75%) as white solid. $^1$H NMR (500 MHz, DMSO-$d_6$) δ 12.33 (s, 1H), 8.38 (s, 1H), 8.19 (d, J=2.7 Hz, 1H), 7.74 (d, J=8.2 Hz, 1H), 6.93 (d, J=8.2 Hz, 1H), 6.12 (d, J=2.8 Hz, 1H), 3.95 (s, 2H), 3.81 (s, 3H), 2.59-2.53 (m, 1H), 2.46-2.39 (m, 1H), 2.33 (s, 3H), 2.25-2.14 (m, 1H), 1.92-1.84 (m, 1H), 1.57 (s, 3H), 1.54 (s, 3H), 1.42 (t, J=12.1 Hz, 1H), 0.82 (d, J=6.3 Hz, 3H), 0.12 (s, 9H). ESI-MS m/z calc. 559.2397, found 560.2 (M+1)$^+$; Retention time: 3.31 minutes (LC method B).

Example 14: Preparation of N-(1,3-dimethylpyrazol-4-yl)sulfonyl-2-[(4S)-2,2,4-trimethylpyrrolidin-1-yl]-6-[3-(2-trimethylsilylethoxy)pyrazol-1-yl]pyridine-3-carboxamide (Compound (2-4))

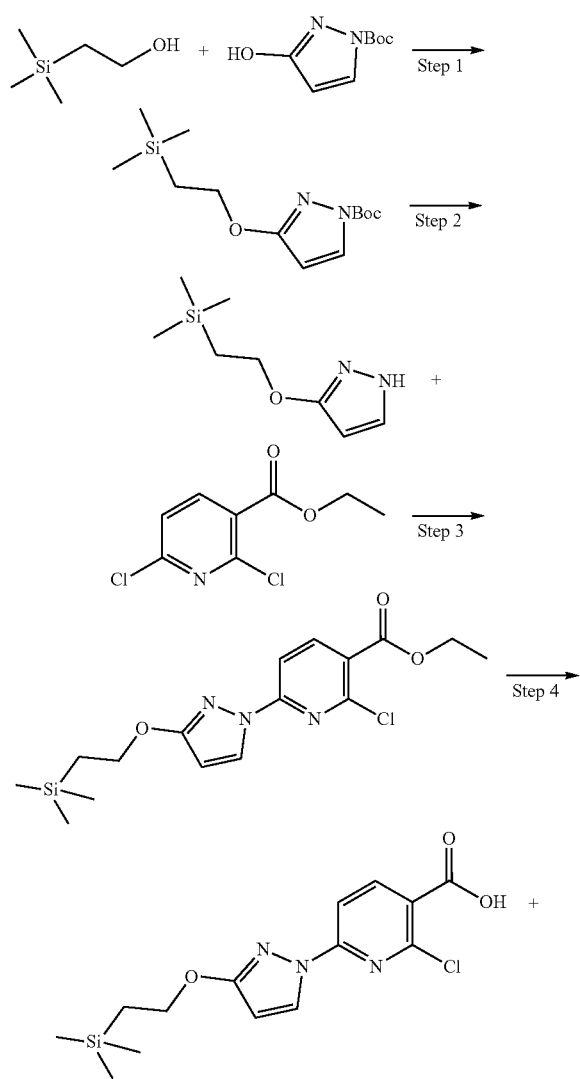

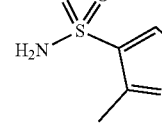

Step 1: Tert-Butyl 3-(2-trimethylsilylethoxy)pyrazole-1-carboxylate

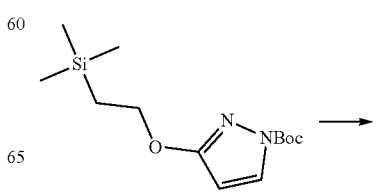

Into a solution of tert-butyl 3-hydroxypyrazole-1-carboxylate (5.01 g, 27.20 mmol) and triphenylphosphine (14.3 g, 54.52 mmol) in anhydrous THF (50 mL) was added DIAD (10.5 mL, 54.21 mmol) at 0° C. The reaction was stirred at rt overnight. The reaction was concentrated under vacuum to remove most of THF. The residue was diluted with ethyl acetate (300 mL), and washed with brine (100 mL). The organic layer was dried over anhydrous sodium sulfate and concentrated under vacuum. The residue was suspended in a 20% diethyl ether in hexane solution (400 mL). The solid was filtered off. The filtrate was concentrated under vacuum and purified by silica gel chromatography using 0 to 10% ethyl acetate in hexane to furnish tert-butyl 3-(2-trimethylsilylethoxy)pyrazole-1-carboxylate (4.559 g, 59%) as a clear oil. ESI-MS m/z calc. 284.1556, found 285.1 (M+1)$^+$; Retention time: 6.7 minutes (LC method C).

Step 2: Trimethyl-[2-(1H-pyrazol-3-yloxy)ethyl]silane

-continued

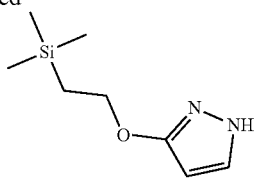

Into a solution of tert-butyl 3-(2-trimethylsilylethoxy) pyrazole-1-carboxylate (4.076 g, 14.33f mmol) in a solvent mixture of THF (29 mL) and EtOH (58 mL) was added an aqueous solution of NaOH (14.5 mL of 2 M, 29.00 mmol). The reaction was stirred at rt for 3 hours. The reaction was diluted with water (100 mL), and extracted with ethyl acetate (3×100 mL). The combined organic layers were washed with brine (100 mL), dried over anhydrous sodium sulfate and concentrated under vacuum to furnish trimethyl-[2-(1H-pyrazol-3-yloxy)ethyl]silane (2.919 g, 99%) as a clear oil. The product was used in the next step without purification. $^1$H NMR (250 MHz, Chloroform-d) δ 7.36 (d, J=1.7 Hz, 1H), 5.72 (d, J=1.8 Hz, 1H), 4.35-4.14 (m, 2H), 1.21-1.03 (m, 2H), 0.06 (s, 9H). ESI-MS m/z calc. 184.1032, found 185.4 (M+1)$^+$; Retention time: 4.44 minutes (LC method C).

Step 3: Ethyl 2-chloro-6-[3-(2-trimethylsilylethoxy) pyrazol-1-yl]pyridine-3-carboxylate

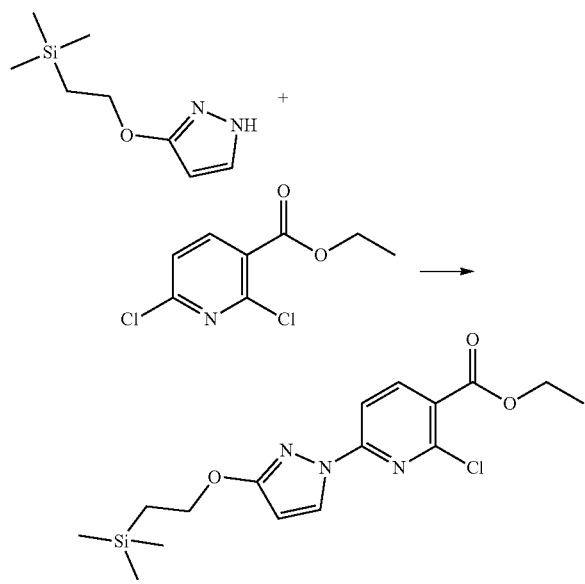

Into a solution of trimethyl-[2-(1H-pyrazol-3-yloxy) ethyl]silane (2.919 g, 14.25 mmol) in anhydrous DMF (30 mL) were added ethyl 2,6-dichloropyridine-3-carboxylate (3.147 g, 14.30 mmol) and potassium carbonate (5.909 g, 42.75 mmol). A catalytic amount of DABCO (321 mg, 2.86 mmol) was added to the reaction mixture. The reaction was stirred at rt for 16 hours. The reaction was diluted with water (100 mL) and diethyl ether (50 mL). The aqueous layer was extracted with diethyl ether (3×50 mL). The combined organic layers were washed with brine (3×50 mL), dried over anhydrous sodium sulfate and concentrated under vacuum. The residue was purified by silica gel chromatography using 0 to 5% diethyl ether. The desired fractions were combined and concentrated to form a white solid. The crude product was then triturated with ethanol (20 mL) to furnish ethyl 2-chloro-6-[3-(2-trimethylsilylethoxy)pyrazol-1-yl] pyridine-3-carboxylate (3.783 g, 72%) as a white solid. ESI-MS m/z calc. 367.1119, found 368.1 (M+1)$^+$; Retention time: 8.04 minutes (LC method C).

Step 4: 2-Chloro-6-[3-(2-trimethylsilylethoxy)pyrazol-1-yl]pyridine-3-carboxylic Acid

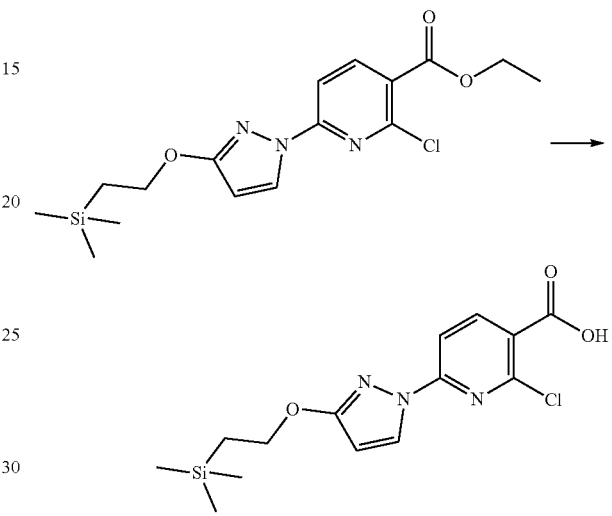

Into a solution of ethyl 2-chloro-6-[3-(2-trimethylsilylethoxy)pyrazol-1-yl]pyridine-3-carboxylate (3.783 g, 10.28 mmol) in methanol (15 mL) and THF (30 mL), was added an aqueous solution of NaOH (15 mL of 2 M, 30.00 mmol). The reaction was stirred at rt overnight. The pH of the reaction was adjusted to 3 with 1 N HCl (aq.). The reaction was diluted with ethyl acetate (50 mL). Two layers were separated, and the aqueous layer was extracted with ethyl acetate (2×50 mL). The combined organic layers were washed with brine (2×50 mL), dried over anhydrous sodium sulfate and concentrated under vacuum. The crude product was triturated with hexane to furnish 2-chloro-6-[3-(2-trimethylsilylethoxy)pyrazol-1-yl]pyridine-3-carboxylic acid (3.301 g, 94%) as a white solid. $^1$H NMR (250 MHz, dimethylsulfoxide-d$_6$) δ 8.38 (d, J=2.9 Hz, 1H), 8.26 (d, J=8.4 Hz, 1H), 7.67 (d, J=8.3 Hz, 1H), 6.14 (d, J=2.8 Hz, 1H), 4.42-4.21 (m, 2H), 1.23-1.01 (m, 2H), 0.07 (s, 9H). ESI-MS m/z calc. 339.0806, found 340.3 (M+1)$^+$; Retention time: 6.52 minutes (LC method C).

Step 5: 2-Chloro-N-(1,3-dimethylpyrazol-4-yl)sulfonyl-6-[3-(2-trimethylsilylethoxy) pyrazol-1-yl]pyridine-3-carboxamide

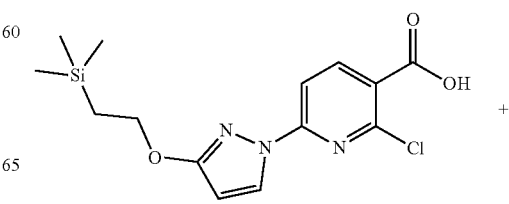

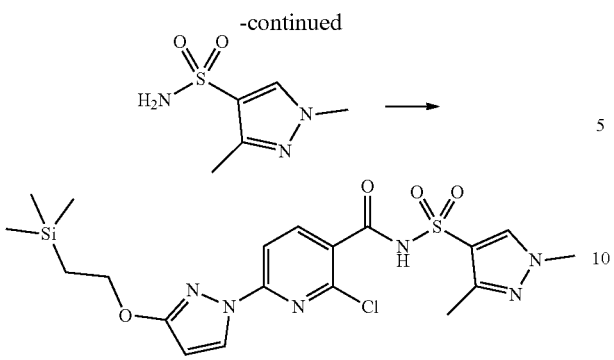

To a stirring suspension of 2-chloro-6-[3-(2-trimethylsilylethoxy)pyrazol-1-yl]pyridine-3-carboxylic acid (350 mg, 1.03 mmol) and 1,3-dimethylpyrazole-4-sulfonamide (271 mg, 1.55 mmol) in anhydrous DCM (10 mL) at room temperature under nitrogen was added DMAP (380 mg, 3.11 mmol), followed by EDC (570 mg, 2.97 mmol). Within 5 minutes, the reaction mixture became a homogeneous solution. The reaction mixture was stirred at this temperature for 18 hours. The reaction was quenched with 10% aqueous citric acid (25 mL), and two layers were separated. The aqueous layer was extracted with DCM (2×30 mL). The combined organic layers were washed with brine (20 mL), dried over anhydrous sodium sulfate and concentrated. The crude was purified by silica gel chromatography using 0-5% methanol gradient in dichloromethane to afford 2-chloro-N-(1,3-dimethylpyrazol-4-yl)sulfonyl-6-[3-(2-trimethylsilylethoxy)pyrazol-1-yl]pyridine-3-carboxamide (292 mg, 54%) as a white solid. ESI-MS m/z calc. 496.1116, found 497.4 (M+1)$^+$; Retention time: 6.7 minutes (LC method C).

Step 6: N-(1,3-dimethylpyrazol-4-yl)sulfonyl-2-[(4S)-2,2,4-trimethylpyrrolidin-1-yl]-6-[3-(2-trimethylsilylethoxy)pyrazol-1-yl]pyridine-3-carboxamide (Compound (2-4))

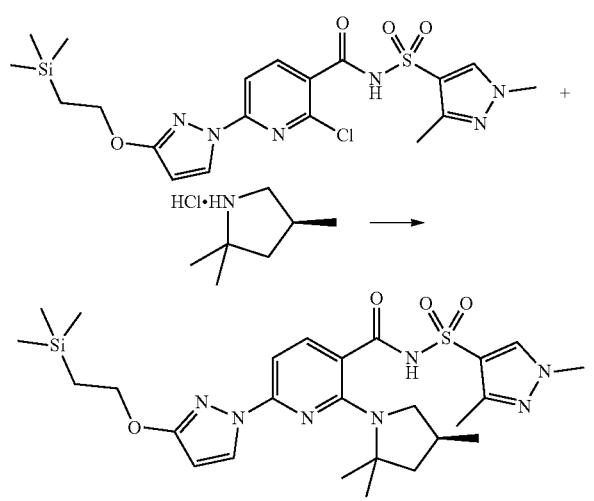

To a stirring solution of 2-chloro-N-(1,3-dimethylpyrazol-4-yl)sulfonyl-6-[3-(2-trimethylsilylethoxy)pyrazol-1-yl]pyridine-3-carboxamide (261 mg, 0.53 mmol) and (4S)-2,2,4-trimethylpyrrolidine (hydrochloride salt) (242 mg, 1.62 mmol) in anhydrous DMSO (4 mL) at room temperature under nitrogen was added sodium carbonate (461 mg, 4.35 mmol). The reaction mixture was heated to 160° C. for 14 hours. After cooling to room temperature, the reaction mixture was poured into a stirring mixture of 10% aqueous citric acid (35 mL) and ethyl acetate (25 mL). Two layers were separated, and the aqueous layer was extracted with ethyl acetate (2×25 mL). The combined organic layers were washed with brine (20 mL), dried over anhydrous sodium sulfate and concentrated. The crude was purified by silica gel chromatography using 0-25% acetone gradient in hexanes to afford N-(1,3-dimethylpyrazol-4-yl)sulfonyl-2-[(4S)-2,2,4-trimethylpyrrolidin-1-yl]-6-[3-(2-trimethylsilylethoxy)pyrazol-1-yl]pyridine-3-carboxamide (212 mg, 68%) as a white solid. $^1$H NMR (500 MHz, DMSO-d$_6$) δ 12.34 (s, 1H), 8.38 (s, 1H), 8.20 (d, J=2.8 Hz, 1H), 7.74 (d, J=8.2 Hz, 1H), 6.91 (d, J=8.2 Hz, 1H), 6.08 (d, J=2.7 Hz, 1H), 4.35-4.24 (m, 2H), 3.81 (s, 3H), 2.60-2.53 (m, 1H), 2.46-2.38 (m, 1H), 2.33 (s, 3H), 2.25-2.13 (m, 1H), 1.92-1.83 (m, 1H), 1.57 (s, 3H), 1.54 (s, 3H), 1.42 (t, J=12.1 Hz, 1H), 1.15-1.10 (m, 2H), 0.82 (d, J=6.3 Hz, 3H), 0.07 (s, 9H). ESI-MS m/z calc. 573.2553, found 574.6 (M+1)$^+$; Retention time: 3.41 minutes (LC method B).

Example 15: Preparation of N-(1,3-dimethylpyrazol-4-yl)sulfonyl-2-[(4S)-2,2,4-trimethylpyrrolidin-1-yl]-6-[3-(3-trimethylsilylpropoxy)pyrazol-1-yl]pyridine-3-carboxamide (Compound (2-6))

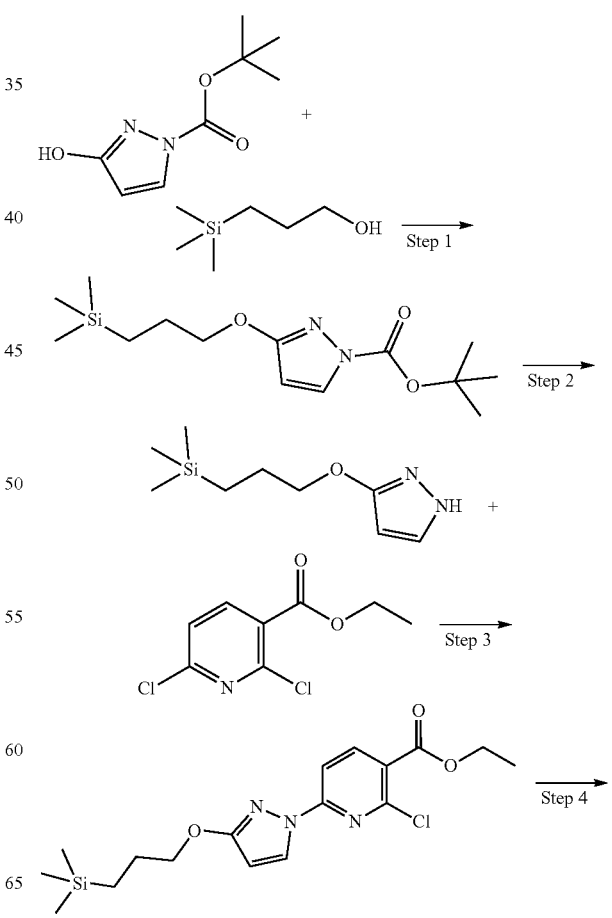

-continued

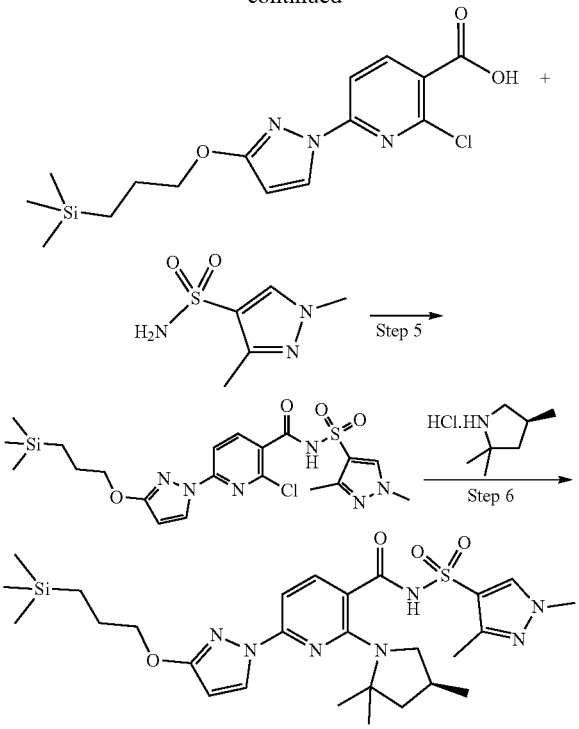

Step 1: Tert-Butyl 3-(3-trimethylsilylpropoxy)pyrazole-1-carboxylate

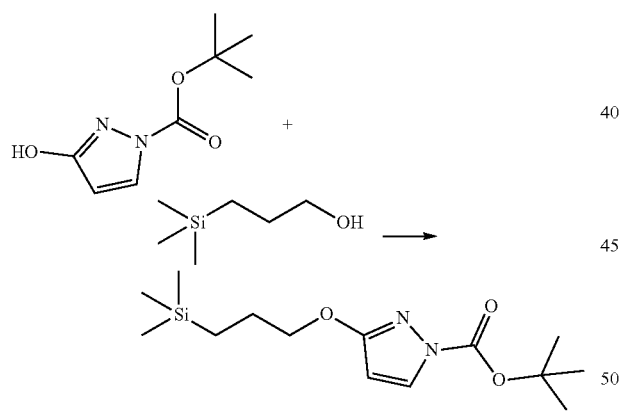

To a solution of tert-butyl 3-hydroxypyrazole-1-carboxylate (2 g, 10.86 mmol), 3-trimethylsilylpropan-1-ol (1.9 mL, 11.24 mmol), and triphenylphosphine (5.7 g, 21.73 mmol) in THF (20 mL) was added DIAD (3.2 mL, 15.87 mmol) at 0° C. After 4 h at room temperature, the solvent was removed under reduced pressure, and the reaction diluted into EtOAc (100 mL). The organic layer was washed with brine (50 mL), dried over Na$_2$SO$_4$, and concentrated under reduced pressure. The crude was then suspended in 10:1 hexanes:Et$_2$O (v:v) (150 mL) and filtered. The solvent was removed from the supernatant under reduced pressure. Column chromatography (silica, 120 g) eluting with 0-10% EtOAc in hexanes yielded tert-butyl 3-(3-trimethylsilyl propoxy)pyrazole-1-carboxylate (3.3 g, 53%) as a clear oil. $^1$H NMR (250 MHz, CDCl$_3$) δ 7.83 (d, J=3.0 Hz, 1H), 5.86 (d, J=3.0 Hz, 1H), 4.24 (t, J=6.9 Hz, 2H), 1.84-1.67 (m, 2H), 1.62 (s, 9H), 0.71-0.46 (m, 2H), 0.01 (s, 9H). ESI-MS m/z calc. 298.1713, found 299.3 (M+1)$^+$; Retention time: 4.02 minutes (LC method B).

Step 2: Trimethyl-[3-(1H-pyrazol-3-yloxy)propyl]silane

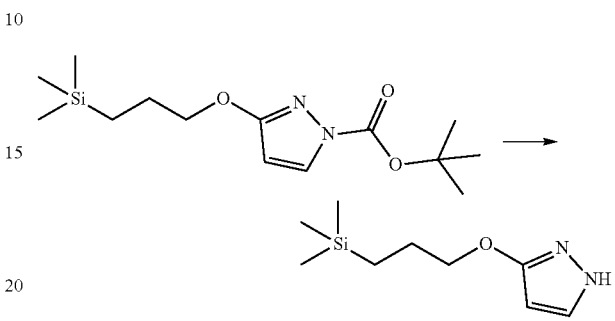

To a solution of tert-butyl 3-(3-trimethylsilylpropoxy)pyrazole-1-carboxylate (3.1 g, 5.67 mmol) in THF (25 mL) and EtOH (50 mL) was added aqueous NaOH (10.5 mL of 2 M, 21.00 mmol) at room temperature. The reaction was stirred at room temperature for 4 h, then diluted into water (100 mL), and extracted with EtOAc (3×100 mL). The organic portions were washed with brine (100 mL), dried over Na$_2$SO$_4$, filtered and concentrated under reduced pressure. Column chromatography (silica, 120 g) eluting with 10-50% EtOAc in hexanes yielded trimethyl-[3-(1H-pyrazol-3-yloxy)propyl]silane (877 mg, 77%) as a clear liquid. $^1$H NMR (250 MHz, CDCl$_3$) δ 7.36 (d, J=2.4 Hz, 1H), 5.91-5.52 (m, 1H), 4.24-3.92 (m, 2H), 1.76 (m, 2H), 0.71-0.44 (m, 2H), 0.18--0.19 (m, 9H). ESI-MS m/z calc. 198.1188, found 199.3 (M+1)$^+$; Retention time: 2.94 minutes (LC method B).

Step 3: Ethyl 2-chloro-6-[3-(3-trimethylsilylpropoxy)pyrazol-1-yl]pyridine-3-carboxylate

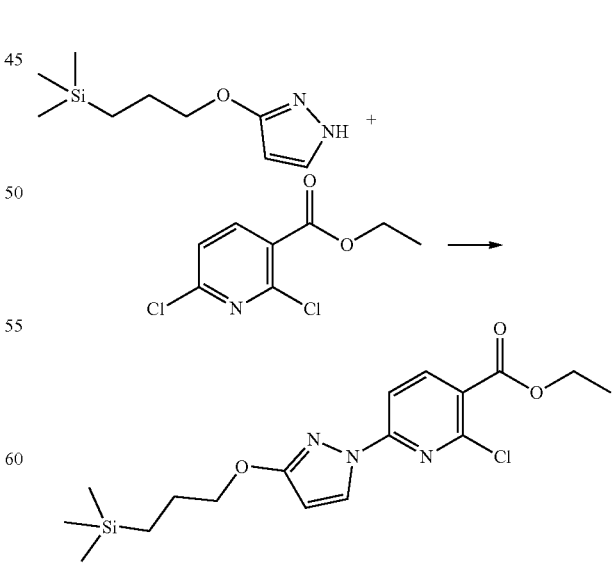

To a solution of trimethyl-[3-(1H-pyrazol-3-yloxy)propyl]silane (590 mg, 2.98 mmol), ethyl 2,6-dichloropyridine- 3-carboxylate (660 mg, 2.94 mmol) and K$_2$CO$_3$ (1.24 g, 8.97 mmol) in DMF (10 mL) was added DABCO (70 mg, 0.62 mmol) at room temperature. The reaction was stirred overnight then diluted into water (100 mL) and Et$_2$O (50 mL), and extracted with Et$_2$O (3×50 mL). The combined organics were washed with brine (2×50 mL), dried over Na$_2$SO$_4$, and concentrated under reduced pressure. Column chromatography (silica, 120 g) eluting with 0-10% Et$_2$O in hexanes yielded ethyl 2-chloro-6-[3-(3-trimethylsilylpropoxy)pyrazol-1-yl]pyridine-3-carboxylate (935 mg, 82%) as a white solid. $^1$H NMR (250 MHz, CDCl$_3$) δ 8.35 (d, J=2.9 Hz, 1H), 8.26 (d, J=8.5 Hz, 1H), 7.70 (d, J=8.5, 1H), 5.98-5.92 (d, J=2.9 Hz, 1H), 4.45-4.34 (m, 2H), 4.20 (t, J=6.9 Hz, 2H), 1.87-1.71 (m, 2H), 1.41 (t, J=7.2 Hz, 3H), 0.67-0.55 (m, 2H), 0.02 (s, 9H). ESI-MS m/z calc. 381.1275, found 382.2 (M+1)$^+$; Retention time: 4.56 minutes (LC method B).

Step 4: 2-Chloro-6-[3-(3-trimethylsilylpropoxy) pyrazol-1-yl]pyridine-3-carboxylic acid

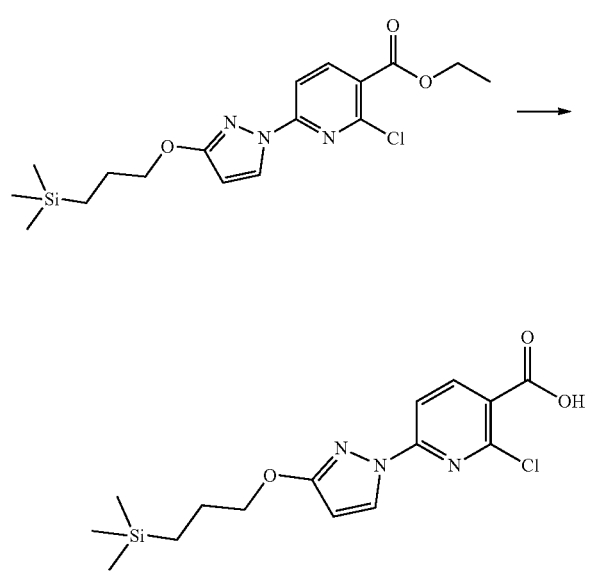

To a solution of ethyl 2-chloro-6-[3-(3-trimethylsilylpropoxy)pyrazol-1-yl]pyridine-3-carboxylate (835 mg, 2.19 mmol) in THF (20 mL) and MeOH (10 mL) was added aqueous NaOH (2.5 mL of 3 M, 7.50 mmol) at room temperature. After 3 h, the reaction was acidified to pH 6 with aqueous HCl (2M), then diluted with 50 mL EtOAc. Two layers were separated, and the aqueous layer was extracted with EtOAc (3×50 mL). The combined organic layers were washed with brine (50 mL), dried over Na$_2$SO$_4$ and concentrated under reduced pressure to yield 2-chloro-6-[3-(3-trimethylsilylpropoxy)pyrazol-1-yl]pyridine-3-carboxylic acid (766 mg, 99%) as a white solid. $^1$H NMR (250 MHz, DMSO) δ 8.59-8.23 (m, 2H), 7.71 (d, J=8.5 Hz, 1H), 6.19 (d, J=2.7 Hz, 1H), 4.17 (m, 2H), 1.73 (m, 2H), 0.75-0.44 (m, 2H), 0.01 (m, 9H). ESI-MS m/z calc. 353.0962, found 354.2 (M+1)$^+$; Retention time: 3.89 minutes (LC method B).

Step 5: 2-Chloro-N-(1,3-dimethylpyrazol-4-yl)sulfonyl-6-[3-(3-trimethylsilylpropoxy)pyrazol-1-yl]pyridine-3-carboxamide

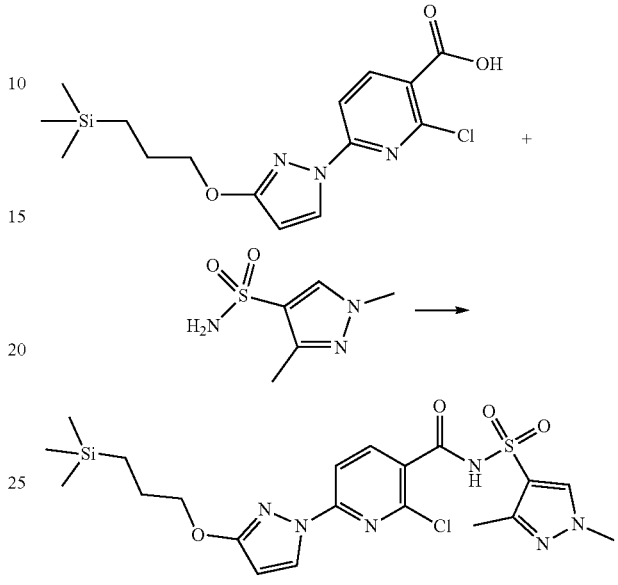

A solution of 2-chloro-6-[3-(3-trimethylsilylpropoxy) pyrazol-1-yl]pyridine-3-carboxylic acid (300 mg, 0.85 mmol) and CDI (210 mg, 1.30 mmol) in THF (10 mL) was stirred overnight at room temperature. 1,3-Dimethylpyrazole-4-sulfonamide (180 mg, 1.03 mmol) then DBU (0.4 mL, 2.67 mmol) was added. After 2 h, 1,3-dimethylpyrazole-4-sulfonamide (20 mg, 0.11 mmol) was added and the reaction was stirred for an additional 4 h. The reaction was quenched with a 1:1 mixture of saturated ammonium chloride and brine solutions (100 mL), then extracted with EtOAc (3×50 mL). The combined organic layers were washed with brine (1×50 mL), dried over Na$_2$SO$_4$, filtered and evaporated. The product was suspended in hexanes and filtered to yield 2-chloro-N-(1,3-dimethylpyrazol-4-yl) sulfonyl-6-[3-(3-trimethylsilyl propoxy)pyrazol-1-yl]pyridine-3-carboxamide (397 mg, 92%) as a white solid. $^1$H NMR (250 MHz, DMSO) δ 8.35 (d, J=3.0 Hz, 1H), 8.06 (d, J=8.3 Hz, 1H), 7.90 (s, 1H), 7.59 (d, J=8.3 Hz, 1H), 7.17 (s, 1H), 6.11 (d, J=2.9 Hz, 1H), 4.16 (m, 2H), 3.74 (s, 3H), 2.25 (s, 3H), 1.72 (m, 2H), 0.58 (m, 2H), 0.02 (m, 9H). ESI-MS m/z calc. 510.1272, found 511.4 (M+1)$^+$; Retention time: 3.73 minutes (LC method B).

Step 6: N-(1,3-Dimethylpyrazol-4-yl)sulfonyl-2-[(4S)-2,2,4-trimethylpyrrolidin-1-yl]-6-[3-(3-trimethylsilylpropoxy)pyrazol-1-yl]pyridine-3-carboxamide (Compound (2-6))

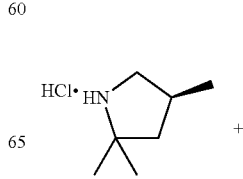

-continued

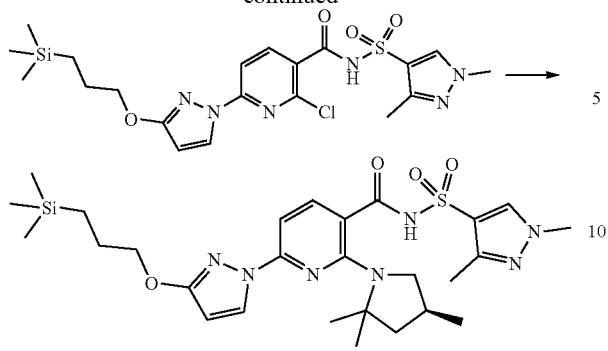

A solution of (4S)-2,2,4-trimethylpyrrolidine (hydrochloride salt) (100 mg, 0.67 mmol), 2-chloro-N-(1,3-dimethylpyrazol-4-yl)sulfonyl-6-[3-(3-trimethylsilylpropoxy)pyrazol-1-yl]pyridine-3-carboxamide (140 mg, 0.27 mmol), and $K_2CO_3$ (180 mg, 1.30 mmol) in DMSO (2 mL) was prepared in a 5 mL microwave vial. The solution was cycled with vacuum and nitrogen 3 times, then sealed and heated with microwave to 170° C. for 5 h. The reaction was diluted into water (50 mL) and extracted with DCM (3×50 mL). The organic portions were washed with brine (1×50 mL), dried over $Na_2SO_4$, and concentrated under reduced pressure. Column chromatography (silica, 12 g) eluting with 10-40% acetone in hexane followed by reverse phase HPLC using 0-100% acetonitrile in water (buffered with 0.1% TFA) yielded N-(1,3-dimethylpyrazol-4-yl)sulfonyl-2-[(4S)-2,2,4-trimethylpyrrolidin-1-yl]-6-[3-(3-trimethyl silyl propoxy) pyrazol-1-yl]pyridine-3-carboxamide (42.2 mg, 26%) as a white solid. 41 NMR (500 MHz, DMSO-$d_6$) δ 12.35 (s, 1H), 8.38 (s, 1H), 8.20 (d, J=2.8 Hz, 1H), 7.74 (d, J=8.2 Hz, 1H), 6.91 (d, J=8.2 Hz, 1H), 6.10 (d, J=2.7 Hz, 1H), 4.16 (t, J=6.8 Hz, 2H), 3.81 (s, 3H), 2.55 (t, J=10.4 Hz, 1H), 2.47-2.39 (m, 1H), 2.33 (s, 3H), 2.24-2.14 (m, 1H), 1.92-1.85 (m, 1H), 1.78-1.69 (m, 2H), 1.57 (s, 3H), 1.54 (s, 3H), 1.42 (t, J=12.2 Hz, 1H), 0.82 (d, J=6.2 Hz, 3H), 0.63-0.54 (m, 2H), 0.02 (s, 9H). ESI-MS m/z calc. 587.271, found 588.5 (M+1)$^+$; Retention time: 3.57 minutes (LC method H).

Example 16: Preparation of N-(1,3-dimethylpyrazol-4-yl)sulfonyl-2-[(4S)-2,2,4-trimethylpyrrolidin-1-yl]-6-[3-[2-(1-trimethylsilylcyclopropyl)ethoxy]pyrazol-1-yl]pyridine-3-carboxamide (Compound (2-2))

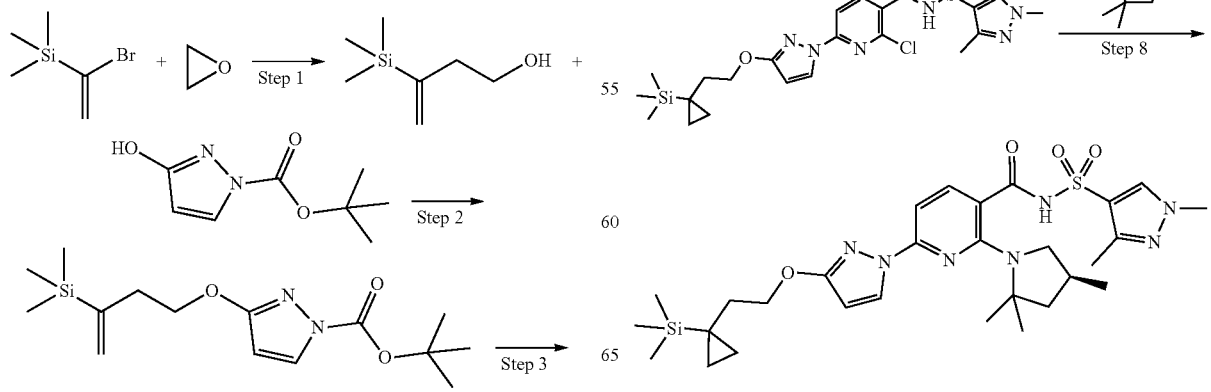

-continued

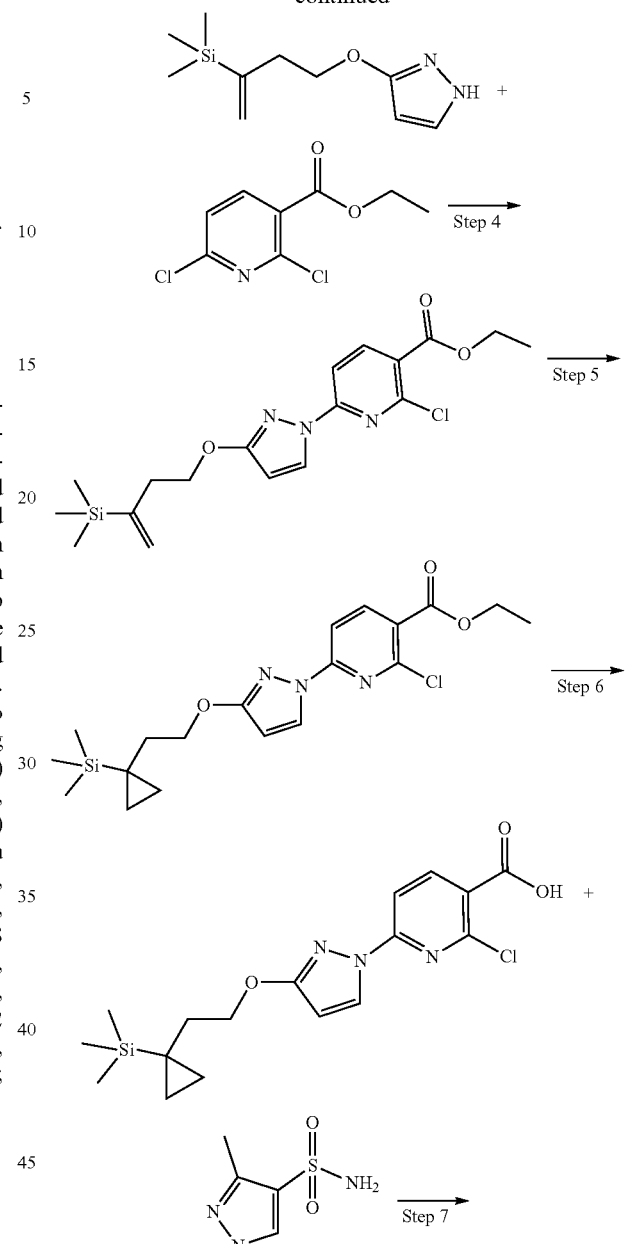

Step 1: 3-Trimethylsilylbut-3-en-1-ol

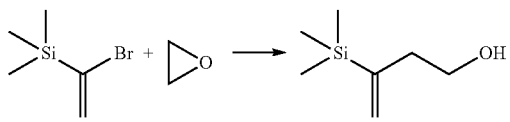

1-Bromovinyl(trimethyl)silane (14.7 mL, 87.42 mmol) was added dropwise to magnesium (3.35 g, 137.14 mmol) in tetrahydrofuran (45 mL) at 40° C. under nitrogen. Simultaneously, 1,2-dibromoethane (0.3 mL) was added to initiate the reaction. On completion of the addition, the mixture was stirred for 1 h at 40° C. before it was allowed to cool to room temperature and more tetrahydrofuran (150 mL) was added. The mixture was then added slowly to a suspension of copper iodide (17.45 g, 91.17 mmol) in tetrahydrofuran (100 mL) at −78° C. After the mixture had been allowed to warm to −30° C., it was stirred for 30 min and then a solution of oxirane (22 mL, 436.08 mmol) in tetrahydrofuran (35 mL), cooled to −78° C., was added. The temperature of the reaction mixture was maintained at −30° C. for 2 hours, before being allowed to rise to room temperature at which temperature it was stirred for 1 hour. The reaction was quenched with saturated aqueous ammonium chloride (150 mL) and water (150 mL), the latter then being extracted with MTBE (3×150 mL). The combined organic extracts were dried over sodium sulfate and evaporated. The residue was purified by silica-gel column chromatography on a 330 g column, eluting from 0% to 15% of MTBE in heptane to provide 3-trimethylsilylbut-3-en-1-ol (8.62 g, 68%) as a yellowish oil. $^1$H NMR (400 MHz, CDCl$_3$) δ 5.69-5.65 (m, 1H), 5.48 (d, J=2.9 Hz, 1H), 3.69 (q, J=6.4 Hz, 2H), 2.44 (t, J=6.6 Hz, 2H), 1.44 (br. s., 1H), 0.15-0.08 (m, 9H). ESI-MS m/z calc. 144.097, found 145.2 (M+1)$^+$; Retention time: 1.723 minutes (LC method E).

Step 2: tert-Butyl 3-(3-trimethylsilylbut-3-enoxy)pyrazole-1-carboxylate

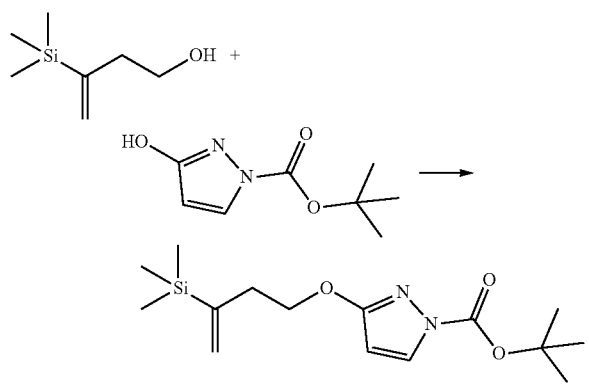

Into a solution of 3-trimethylsilylbut-3-en-1-ol (2 g, 13.86 mmol), tert-butyl 3-hydroxypyrazole-1-carboxylate (2.564 g, 13.92 mmol) and triphenylphosphine (7.284 g, 27.77 mmol) in anhydrous THF (20 mL) was added DIAD (4.0 mL, 20.65 mmol) dropwise at 0° C. The reaction was stirred at rt overnight. The volatiles were removed under vacuum. The residue was purified by silica gel column chromatography using 0 to 10% diethyl ether in hexane to furnish tert-butyl 3-(3-trimethylsilylbut-3-enoxy)pyrazole-1-carboxylate (2.221 g, 52%) as a clear liquid. ESI-MS m/z calc. 310.1713, found 311.0 (M+1)$^+$; Retention time: 7.15 minutes (LC method C).

Step 3: Trimethyl-[1-methylene-3-(1H-pyrazol-3-yloxy)propyl]silane

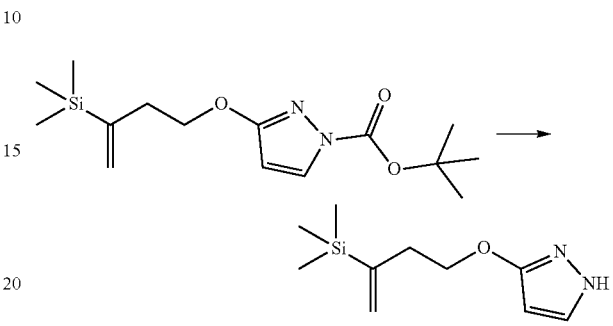

Into a solution of tert-butyl 3-(3-trimethylsilylbut-3-enoxy)pyrazole-1-carboxylate (2.221 g, 7.15 mmol) in DCM (28 mL) was added TFA (14 mL). The reaction was stirred at rt for 1 hour, then it was quenched with saturated sodium bicarbonate (300 mL). The solution was extracted with DCM (3×100 mL). The combined organic layers were washed with brine (100 mL), dried over anhydrous sodium sulfate and concentrated under vacuum to furnish trimethyl-[1-methylene-3-(1H-pyrazol-3-yloxy)propyl]silane (1.367 g, 91%) as a clear oil. ESI-MS m/z calc. 210.1188, found 211.0 (M+1)$^+$; Retention time: 3.0 minutes (LC method B).

Step 4: Ethyl 2-chloro-6-[3-(3-trimethylsilylbut-3-enoxy)pyrazol-1-yl]pyridine-3-carboxylate

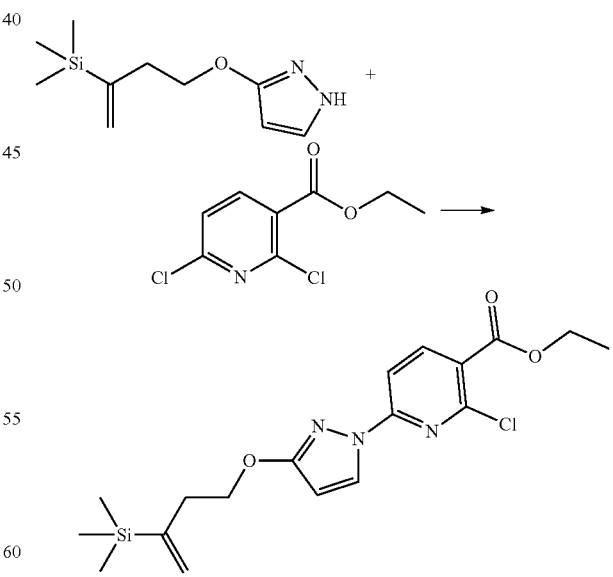

Into a solution of trimethyl-[1-methylene-3-(1H-pyrazol-3-yloxy)propyl]silane (1.367 g, 6.50 mmol) in anhydrous DMF (14 mL) was added ethyl 2,6-dichloropyridine-3-carboxylate (1.719 g, 7.81 mmol) and potassium carbonate (2.708 g, 19.59 mmol). A catalytic amount of DABCO (159 mg, 1.42 mmol) was added to the reaction mixture. The reaction was stirred for 24 hours. The reaction was diluted with brine (50 mL) and diethyl ether (50 mL). Two layers were separated and the aqueous layer was extracted with diethyl ether (2×50 mL). The combined organic layers were washed with brine (2×50 mL), dried over anhydrous sodium sulfate and concentrated under vacuum. The residue was purified by silica gel chromatography using 0 to 15% diethyl ether in hexane to furnish ethyl 2-chloro-6-[3-(3-trimethylsilylbut-3-enoxy)pyrazol-1-yl]pyridine-3-carboxylate (2.066 g, 81%) as a clear oil. ESI-MS m/z calc. 393.1275, found 394.1 (M+1)⁺; Retention time: 8.32 minutes (LC method C).

Step 5: Ethyl 2-chloro-6-[3-[2-(1-trimethylsilylcyclopropyl)ethoxy]pyrazol-1-yl]pyridine-3-carboxylate

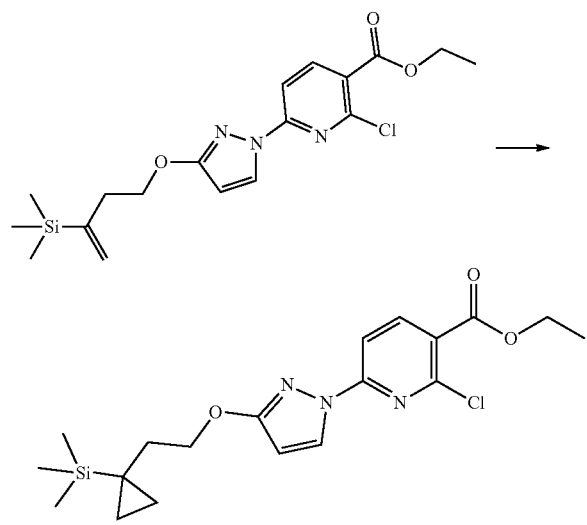

Diethyl zinc (26.2 mL of 1 M, 26.20 mmol) in hexane was added to anhydrous DCM (30 mL), and TFA (2.0 mL, 26.135 mmol) was added at 0° C. The reaction was stirred for 20 minutes at 0° C. diiodomethane (2.1 mL, 26.031 mmol) was then added to the reaction mixture, and the reaction was stirred for another 20 minutes. A solution of ethyl 2-chloro-6-[3-(3-trimethylsilylbut-3-enoxy)pyrazol-1-yl]pyridine-3-carboxylate (2.066 g, 5.24 mmol) in anhydrous DCM (20 mL) was added to the reaction mixture at 0° C. The reaction mixture was stirred at rt for 5 hours. The reaction was quenched with saturated ammonium chloride (50 mL). Two layers were separated. The aqueous layer was extracted with DCM (2×50 mL). The combined organic layers were washed with brine (50 mL), dried over anhydrous magnesium sulfate and concentrated under vacuum. The residue was purified by silica gel chromatography using 0 to 15% diethyl ether in hexane to furnish ethyl 2-chloro-6-[3-[2-(1-trimethylsilylcyclo propyl)ethoxy]pyrazol-1-yl]pyridine-3-carboxylate (2.026 g, 95%) as a clear oil. ¹H NMR (250 MHz, Chloroform-d) δ 8.36 (d, J=2.9 Hz, 1H), 8.28 (d, J=8.4 Hz, 1H), 7.70 (d, J=8.5 Hz, 1H), 5.94 (d, J=2.9 Hz, 1H), 4.41 (q, J=7.1 Hz, 2H), 4.27 (t, J=7.6 Hz, 2H), 1.74 (t, J=7.6 Hz, 2H), 1.42 (t, J=7.1 Hz, 3H), 0.55-0.40 (m, 2H), 0.40-0.27 (m, 2H), 0.01 (s, 9H). ESI-MS m/z calc. 407.1432, found 408.2 (M+1)⁺; Retention time: 8.6 minutes (LC method C).

Step 6: 2-Chloro-6-[3-[2-(1-trimethylsilylcyclopropyl)ethoxy]pyrazol-1-yl]pyridine-3-carboxylic Acid

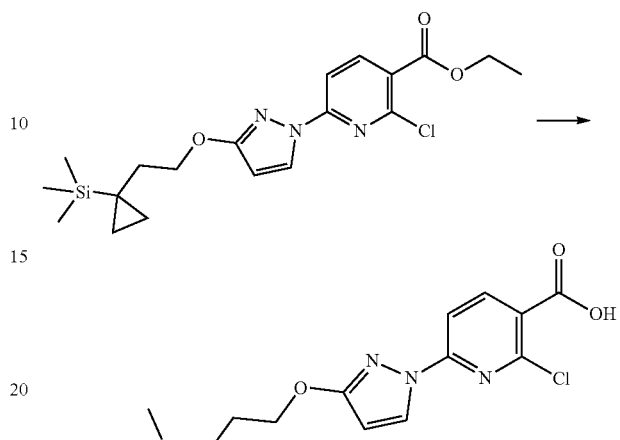

Into a solution of ethyl 2-chloro-6-[3-[2-(1-trimethylsilylcyclopropyl)ethoxy]pyrazol-1-yl]pyridine-3-carboxylate (2.026 g, 4.97 mmol) in a solvent mixture of methanol (8 mL) and THF (16 mL) was added an aqueous solution of NaOH (7.5 mL of 2 M, 15.00 mmol). The reaction mixture was stirred at rt overnight. The reaction was acidified with 1 N HCl (aq.) to pH 2, and then it was diluted with ethyl acetate (50 mL). Two layers were separated and the aqueous layer was extracted with ethyl acetate (2×50 mL). The combined organic layers were washed with brine (2×50 mL), dried over anhydrous magnesium sulfate and concentrated under vacuum to furnish 2-chloro-6-[3-[2-(1-trimethylsilylcyclopropyl)ethoxy]pyrazol-1-yl]pyridine-3-carboxylic acid (1.78 g, 94%) as a white solid. ESI-MS m/z calc. 379.1119, found 380.2 (M+1)⁺; Retention time: 7.2 minutes (LC method C).

Step 7: 2-Chloro-N-(1,3-dimethylpyrazol-4-yl)sulfonyl-6-[3-[2-(1-trimethylsilylcyclopropyl)ethoxy]pyrazol-1-yl]pyridine-3-carboxamide

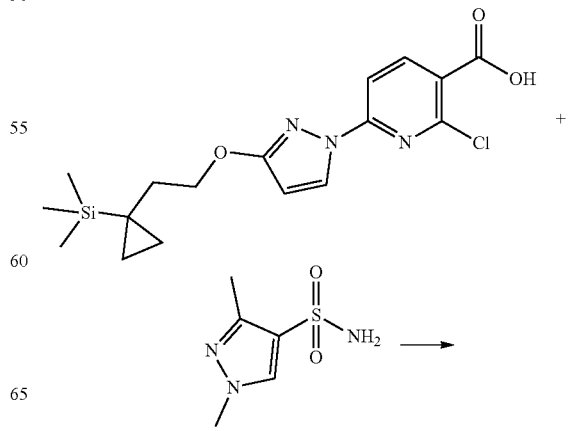

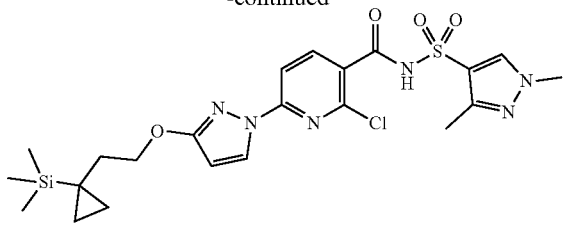

A solution of 2-chloro-6-[3-[2-(1-trimethylsilylcyclopropyl)ethoxy]pyrazol-1-yl]pyridine-3-carboxylic acid (317 mg, 0.83 mmol) and CDI (208 mg, 1.28 mmol) in anhydrous THF (10 mL) was stirred at rt for 16 hours. 1,3-Dimethylpyrazole-4-sulfonamide (177 mg, 1.01 mmol) and DBU (0.38 mL, 2.5410 mmol) were added. The reaction was stirred at rt for another 2 hours. The reaction was quenched with 10% citric acid (20 mL), and extracted with ethyl acetate (3×20 mL). The combined organic layers were washed with brine (20 mL), dried over anhydrous sodium sulfate and concentrated under vacuum. The residue was triturated with hexane to furnish 2-chloro-N-(1,3-dimethylpyrazol-4-yl)sulfonyl-6-[3-[2-(1-trimethylsilyl cyclopropyl)ethoxy]pyrazol-1-yl]pyridine-3-carboxamide (396 mg, 82%) as a white solid. ESI-MS m/z calc. 536.1429, found 537.0 (M+1)$^+$; Retention time: 6.91 minutes (LC method C).

Step 8: N-(1,3-dimethylpyrazol-4-yl)sulfonyl-2-[(4S)-2,2,4-trimethylpyrrolidin-1-yl]-6-[3-[2-(1-trimethylsilylcyclopropyl)ethoxy]pyrazol-1-yl]pyridine-3-carboxamide (Compound (2-2))

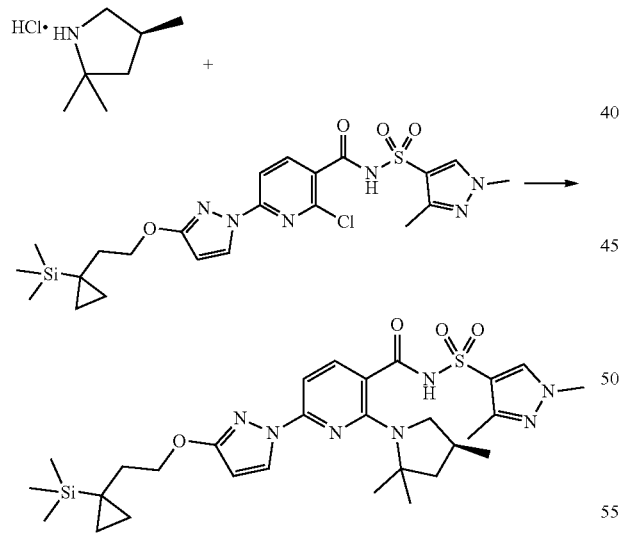

Into a reaction vial was charged with (4S)-2,2,4-trimethylpyrrolidine (hydrochloride salt) (61 mg, 0.41 mmol), 2-chloro-N-(1,3-dimethylpyrazol-4-yl)sulfonyl-6-[3-[2-(1-trimethylsilylcyclopropyl)ethoxy]pyrazol-1-yl]pyridine-3-carboxamide (156 mg, 0.27 mmol) in DMSO (3 mL). The reaction was stirred at 150° C. for 20 hours. After being cooled to rt, the reaction was diluted with 10% citric acid (aq.) (15 mL) and ethyl acetate (15 mL). Two layers were separated, and the aqueous layer was extracted with ethyl acetate (2×15 mL). The combined organic layers were washed with brine (15 mL), dried over anhydrous sodium sulfate and concentrated under vacuum. The residue was purified by preparative HPLC using 0 to 100% acetonitrile in water (buffered with 0.1% TFA) to furnish N-(1,3-dimethylpyrazol-4-yl)sulfonyl-2-[(4S)-2,2,4-trimethylpyrrolidin-1-yl]-6-[3-[2-(1-trimethylsilylcyclopropyl)ethoxy]pyrazol-1-yl]pyridine-3-carboxamide (69.6 mg, 41%) as a white powder. $^1$H NMR (500 MHz, DMSO-d$_6$) δ 12.34 (s, 1H), 8.38 (s, 1H), 8.20 (d, J=2.8 Hz, 1H), 7.75 (d, J=8.3 Hz, 1H), 6.90 (d, J=8.2 Hz, 1H), 6.07 (d, J=2.7 Hz, 1H), 4.21 (t, J=7.2 Hz, 2H), 3.81 (s, 3H), 2.59-2.53 (m, 1H), 2.46-2.39 (m, 1H), 2.33 (s, 3H), 2.24-2.14 (m, 1H), 1.92-1.84 (m, 1H), 1.74-1.64 (m, 2H), 1.57 (s, 3H), 1.54 (s, 3H), 1.47-1.38 (m, 1H), 0.82 (d, J=6.3 Hz, 3H), 0.45-0.38 (m, 2H), 0.38-0.33 (m, 2H), −0.00 (s, 9H). ESI-MS m/z calc. 613.2867, found 614.3 (M+1)$^+$; Retention time: 3.72 minutes (LC method H).

Example 17: Preparation of N-(1,3-dimethylpyrazol-4-yl)sulfonyl-6-(3-trimethylgermylpyrazol-1-yl)-2-[(4S)-2,2,4-trimethylpyrrolidin-1-yl]pyridine-3-carboxamide (Compound (3-3))

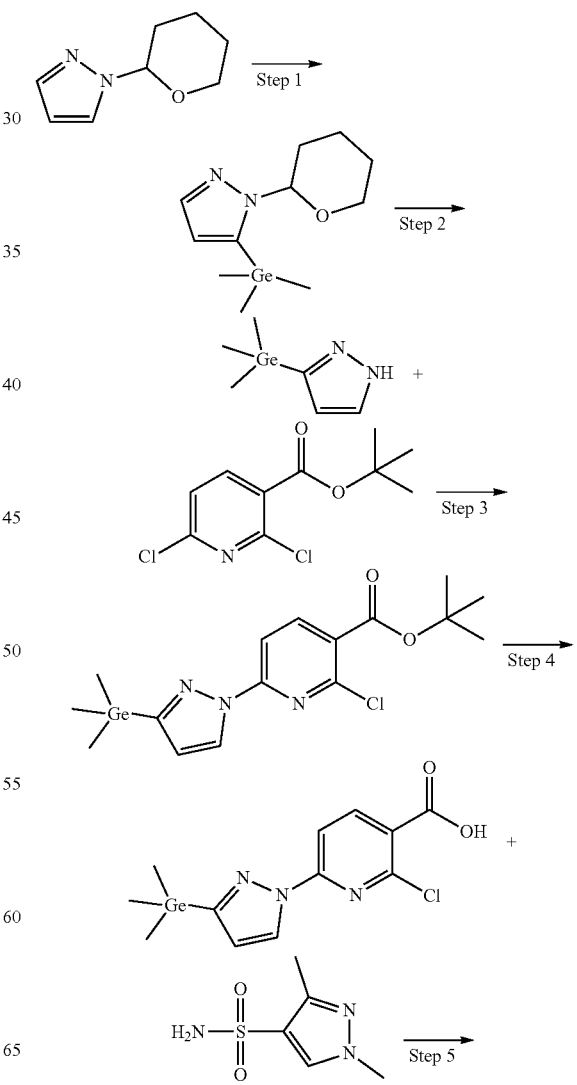

Step 1: Trimethyl-(2-tetrahydropyran-2-ylpyrazol-3-yl)germane

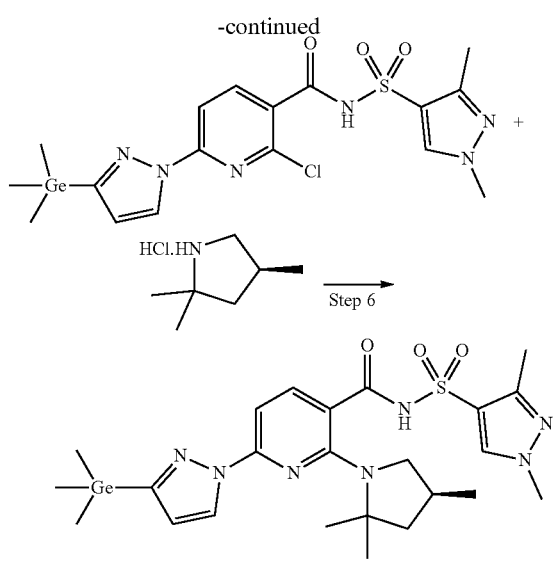

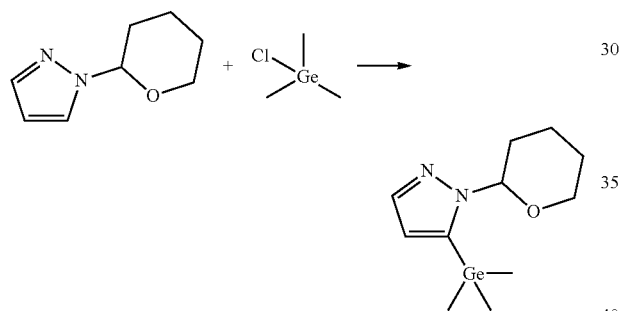

A stirred solution of 1-tetrahydropyran-2-ylpyrazole (2 g, 13.14 mmol) in anhydrous tetrahydrofuran (15 mL) was cooled to −35° C. Then n-butyllithium in hexanes (5.8 mL of 2.5 M, 14.50 mmol) was added dropwise from a dropping funnel over 5 min and after the addition was complete, the resulting solution was stirred for an additional 1 h at −35° C. A solution of chloro(trimethyl)germane (2.42 g, 15.80 mmol) in anhydrous tetrahydrofuran (1.0 mL) was added dropwise from the dropping funnel over 3 min. After the end of the addition, the reaction was stirred for an additional 10 min at that temperature, and then the bath was removed and allowed to warm to room temperature. Then after stirring for another 3 h, a saturated ammonium chloride solution (30 mL) was added and the mixture was extracted with ether (3×30 mL). The combined organics were washed with brine (20 mL), dried over sodium sulfate, filtered and concentrated under reduced pressure. The crude material (pale yellow light oil) was used in the subsequent step without further purification. Trimethyl-(2-tetrahydropyran-2-ylpyrazol-3-yl)germane (3.47 g, 98%). $^1$H NMR (400 MHz, Chloroform-d) δ 7.57 (d, J=1.7 Hz, 1H), 6.34 (d, J=1.7 Hz, 1H), 5.27 (dd, J=9.6, 2.6 Hz, 1H), 4.02 (dp, J=11.6, 2.5 Hz, 1H), 3.62 (td, J=11.2, 2.6 Hz, 1H), 2.52-2.38 (m, 1H), 2.14-2.07 (m, 1H), 2.07-1.99 (m, 1H), 1.76-1.63 (m, 2H), 1.63-1.56 (m, 1H), 0.46 (s, 9H). ESI-MS m/z calc. 270.07874, found 271.0 (M+1)$^+$; Retention time: 1.59 minutes (LC method A).

Step 2: Trimethyl(1H-pyrazol-3-yl)germane

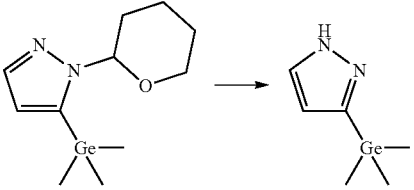

To a stirred solution of trimethyl-(2-tetrahydropyran-2-ylpyrazol-3-yl)germane (3.25 g, 12.08 mmol) in ethanol (5 mL) was added aqueous hydrochloric acid (6 mL of 5.0 M, 30.00 mmol) and heated at 50° C. for 4 h. The reaction was allowed to cool to ambient temperature and a saturated aqueous NaHCO$_3$ solution was added slowly (vigorous CO$_2$ gas evolution) to quench the acid and the resulting solution was extracted with ethyl acetate (2×30 mL). The combined organics were washed with brine (20 mL), dried over sodium sulfate, filtered and concentrated under reduced pressure. The crude material (yellow oil) was used in the subsequent reaction without further purification. Trimethyl (1H-pyrazol-3-yl)germane (1.56 g, 70%). $^1$H NMR (400 MHz, DMSO-d$_6$) δ 12.73 (s, 1H), 7.49 (s, 1H), 6.31 (d, J=1.6 Hz, 1H), 0.39 (s, 9H). ESI-MS m/z calc. 186.02122, found 187.1 (M+1)$^+$; Retention time: 0.87 minutes (LC method A).

Step 3: tert-Butyl 2-chloro-6-(3-trimethylgermylpyrazol-1-yl)pyridine-3-carboxylate

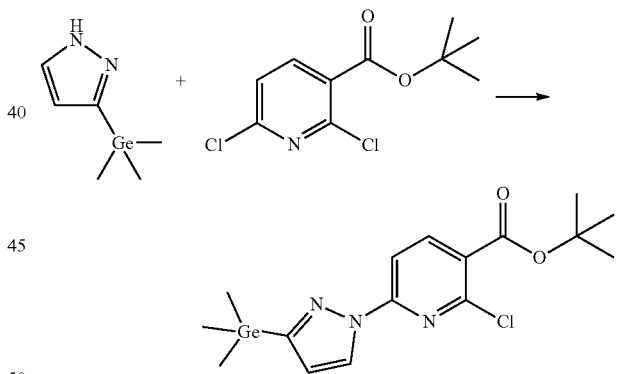

To a stirred solution of tert-butyl 2,6-dichloropyridine-3-carboxylate (1.35 g, 5.441 mmol) in anhydrous dimethyl sulfoxide (15 mL) were added trimethyl(1H-pyrazol-3-yl)germane (1.0 g, 5.41 mmol), potassium carbonate (975 mg, 7.05 mmol) and DABCO (125 mg, 1.11 mmol), in that order, under nitrogen and stirred at ambient temperature for 20 h. The reaction was diluted with cold water (60 mL) and stirred for 30 min. The resulting white solid was collected via filtration and washed with water (3×30 mL). The solid was further dried to furnish the desired tert-butyl 2-chloro-6-(3-trimethylgermylpyrazol-1-yl)pyridine-3-carboxylate (1.91 g, 89%) as a white solid. $^1$H NMR (400 MHz, Chloroform-d) δ 8.55 (d, J=2.6 Hz, 1H), 8.21 (d, J=8.4 Hz, 1H), 8.00 (d, J=8.4 Hz, 1H), 6.53 (d, J=2.6 Hz, 1H), 1.62 (s, 9H), 0.47 (s, 9H). ESI-MS m/z calc. 397.06122, found 398.1 (M+1)$^+$; Retention time: 2.4 minutes (LC method A).

Step 4: 2-Chloro-6-(3-trimethylgermylpyrazol-1-yl)pyridine-3-carboxylic Acid

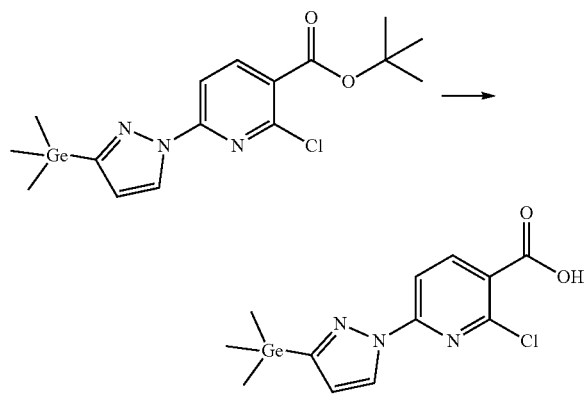

In a 100 mL flask, to a solution of tert-butyl 2-chloro-6-(3-trimethylgermylpyrazol-1-yl)pyridine-3-carboxylate (1.8 g, 4.54 mmol) in anhydrous dichloromethane (20 mL) was added trifluoroacetic acid (5.5 mL, 71.39 mmol) at ambient temperature under nitrogen. The reaction was allowed to stir for 4 h and the volatiles were removed under reduced pressure. The crude residue was subjected to three cycles of addition and evaporation with dichloromethane-hexanes (1:1, 20 mL) until a solid was obtained. After further drying under vacuum, the desired 2-chloro-6-(3-trimethylgermylpyrazol-1-yl)pyridine-3-carboxylic acid (1.55 g, 100%) was obtained as a white solid. It was used in the subsequent reaction without further purification. $^1$H NMR (400 MHz, DMSO-$d_6$) δ 8.59 (d, J=2.6 Hz, 1H), 8.43 (d, J=8.4 Hz, 1H), 7.99 (d, J=8.4 Hz, 1H), 6.73 (d, J=2.6 Hz, 1H), 0.44 (s, 9H). ESI-MS m/z calc. 340.99863, found 342.0 (M+1)$^+$; Retention time: 1.78 minutes (LC method A).

Step 5: 2-Chloro-N-(1,3-dimethylpyrazol-4-yl)sulfonyl-6-(3-trimethylgermylpyrazol-1-yl)pyridine-3-carboxamide

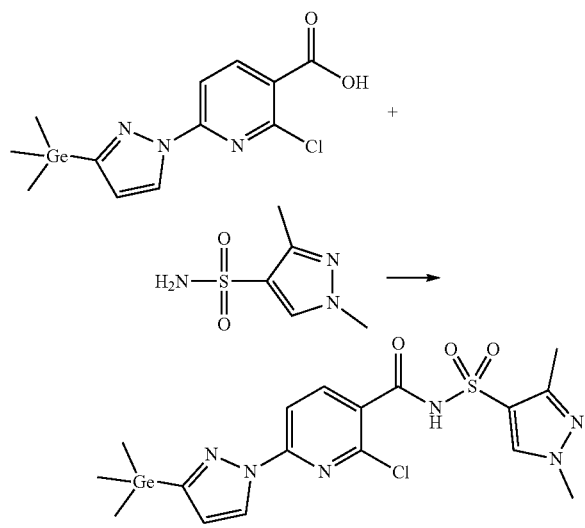

In a 50 mL flask, to a stirred solution of 2-chloro-6-(3-trimethylgermylpyrazol-1-yl)pyridine-3-carboxylic acid (300 mg, 0.88 mmol) in anhydrous tetrahydrofuran (3 mL) was added CDI (258 mg, 1.59 mmol) under nitrogen and stirred at room temperature for 4 h. Then 1,3-dimethylpyrazole-4-sulfonamide (156 mg, 0.89 mmol) and DBU (700 μL, 4.68 mmol) were added in that order and the solution was stirred at room temperature for 14 h. Then aqueous 10% citric acid (20 mL) was added carefully (to mitigate carbon dioxide gas evolution). The suspension was extracted with ethyl acetate (2×25 mL). The combined organics were further washed with 10% citric acid (20 mL), followed by brine (20 mL). The organics were dried over anhydrous sodium sulfate, filtered and concentrated under reduced pressure. The crude material 2-chloro-N-(1,3-dimethylpyrazol-4-yl)sulfonyl-6-(3-trimethylgermylpyrazol-1-yl)pyridine-3-carboxamide (429 mg, 98%) was obtained as yellowish solid and used in the subsequent step without further purification. 1H NMR (400 MHz, Chloroform-d) δ 9.37 (s, 1H), 8.51 (d, J=2.7 Hz, 1H), 8.31 (d, J=8.5 Hz, 1H), 8.11-8.06 (m, 2H), 6.55 (d, J=2.7 Hz, 1H), 3.89 (s, 3H), 2.50 (s, 3H), 0.46 (s, 9H). ESI-MS m/z calc. 498.0296, found 498.9 (M+1)$^+$; Retention time: 1.74 minutes (LC method A).

Step 6: N-(1,3-dimethylpyrazol-4-yl)sulfonyl-6-(3-trimethylgermylpyrazol-1-yl)-2-[(4S)-2,2,4-trimethylpyrrolidin-1-yl]pyridine-3-carboxamide (Compound (3-3))

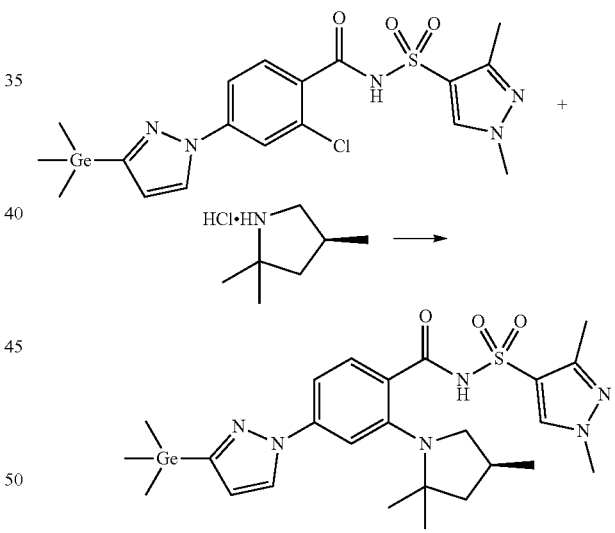

In a 20 mL microwave tube, to a stirred solution of 2-chloro-N-(1,3-dimethylpyrazol-4-yl)sulfonyl-6-(3-trimethylgermylpyrazol-1-yl)pyridine-3-carboxamide (300 mg, 0.60 mmol) in anhydrous dimethylsulfoxide (3.5 mL) were added potassium carbonate (420 mg, 3.04 mmol) and (4S)-2,2,4-trimethylpyrrolidine (hydrochloride salt) (272 mg, 1.82 mmol), in that order, under nitrogen at ambient temperature. The tube was capped under nitrogen and the heterogeneous mixture was stirred at 130° C. for 16 h in an oil-bath. The reaction was allowed to cool to ambient temperature and partitioned between ethyl acetate (30 mL) and cold 10% citric acid solution (20 mL). The organics were separated and the aqueous was re-extracted with ethyl acetate (20 mL). The combined organics were further washed with 10% citric acid (20 mL), followed by brine (20 mL). The organics were dried over anhydrous sodium sulfate, filtered and concentrated under reduced pressure. The crude material was purified from silica gel chromatography (80 g silica gel column, eluting with 5-70% ethyl acetate in hexanes over 30 min; compound came at 40% ethyl acetate). The residue was taken up in DMSO (3 mL) and the solution was micro-filtered through a Whatman 0.45 µM PTFE syringe filter disc and purified from preparative reverse phase HPLC ($C_{18}$) (5-99% acetonitrile in water over 30 min, HCl as a modifier, column 50×100 mm, one injection). The desired fractions were combined and extracted with ethyl acetate (3×30 mL). The combined organics were washed with brine (25 mL), dried over sodium sulfate, filtered and concentrated under reduced pressure. The solid was further purified from silica gel chromatography (40 g silica gel column, eluting with 5-70% ethyl acetate in hexanes over 30 min; compound eluted at 40% ethyl acetate). The desired fractions were combined and concentrated under reduced pressure and further dried under reduced pressure to furnish N-(1,3-dimethylpyrazol-4-yl)sulfonyl-6-(3-trimethylgermylpyrazol-1-yl)-2-[(4S)-2,2,4-trimethylpyrrolidin-1-yl]pyridine-3-carboxamide (120 mg, 34%) as white solid. $^1$H NMR (400 MHz, DMSO-$d_6$) δ 12.39 (s, 1H), 8.45-8.29 (m, 2H), 7.77 (d, J=8.2 Hz, 1H), 7.14 (d, J=8.2 Hz, 1H), 6.66 (d, J=2.5 Hz, 1H), 3.81 (s, 3H), 2.56 (t, J=10.4 Hz, 1H), 2.45 (t, J=8.5 Hz, 1H), 2.33 (s, 3H), 2.19 (dd, J=11.7, 6.3 Hz, 1H), 1.88 (dd, J=12.1, 5.6 Hz, 1H), 1.58 (s, 3H), 1.55 (s, 3H), 1.43 (t, J=12.2 Hz, 1H), 0.82 (d, J=6.2 Hz, 3H), 0.42 (s, 9H). ESI-MS m/z calc. 575.1734, found 576.1 (M+1)$^+$; Retention time: 2.11 minutes (LC method A).

Example 18: Preparation of N-(1,3-dimethylpyrazol-4-yl)sulfonyl-6-[13-(trimethylgermylmethoxy)pyrazol-1-yl]-2-[(4S)-2,2,4-trimethylpyrrolidin-1-yl]pyridine-3-carboxamide (Compound (3-1))

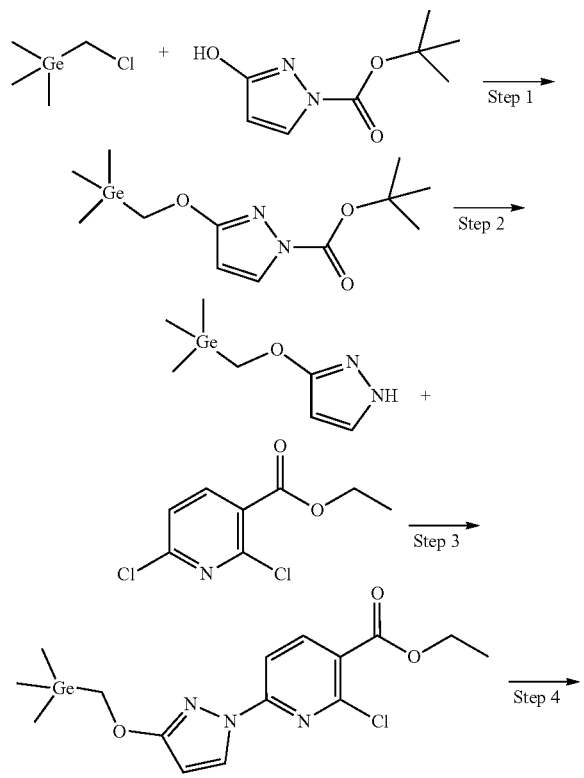

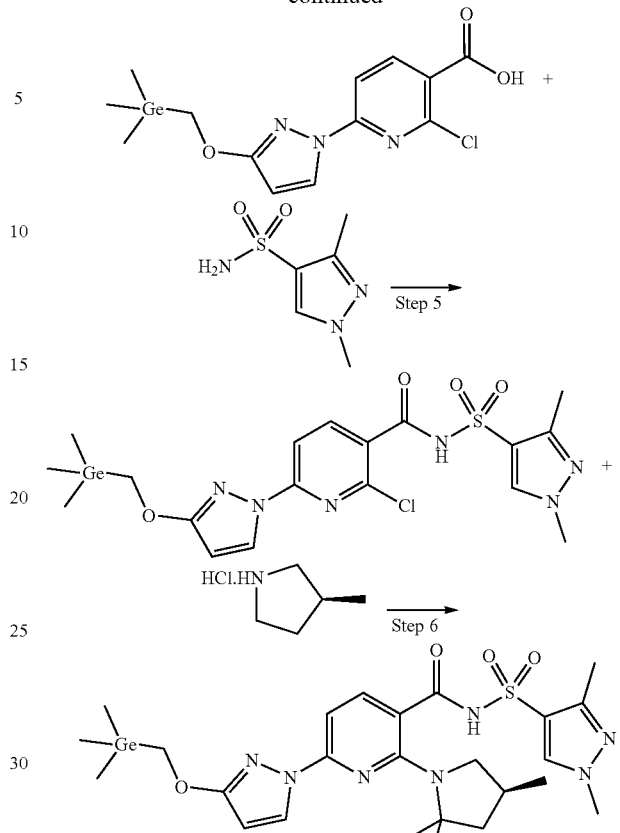

Step 1: tert-Butyl 3-(trimethylgermylmethoxy)pyrazole-1-carboxylate

A 75 mL thick flask was charged with tert-butyl 3-hydroxypyrazole-1-carboxylate (2.38 g, 12.92 mmol), chloromethyl(trimethyl)germane (2.27 g, 13.57 mmol), potassium carbonate (3.4 g, 24.60 mmol) and DMA (25 mL). The reaction was heated at 70° C. in an oil bath for 26 hours. The reaction mixture was diluted with NaHCO$_3$, and ethyl acetate. Two layers were separated. The organic layer was washed with water, brine, dried over anhydrous sodium sulfate and concentrated to give a crude material which was purified by chromatography to afford tert-butyl 3-(trimethylgermylmethoxy)pyrazole-1-carboxylate (2.57 g, 62%) as a clear oil. $^1$H NMR (250 MHz, CDCl$_3$) δ 7.83 (d, J=3.0 Hz, 1H), 5.85 (d, J=3.1 Hz, 1H), 4.20 (s, 2H), 1.61 (s, 9H), 0.23 (s, 9H). ESI-MS m/z calc. 316.0842, found 317.0 (M+1)$^+$; Retention time: 3.33 minutes (LC method B).

Step 2: Trimethyl(1H-pyrazol-3-yloxymethyl)germane

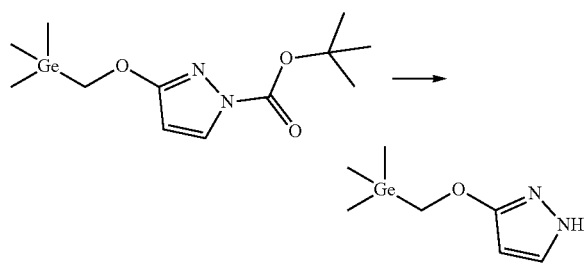

Into a solution of tert-butyl 3-(trimethylgermylmethoxy)pyrazole-1-carboxylate (2.56 g, 7.97 mmol) in DCM (25 mL) was added TFA (12.5 mL). The reaction was stirred at rt for 1 hour. All the volatiles were removed and EtOAc was added. The resulting mixture was then washed once with saturated aqueous NaHCO$_3$, dried over sodium sulfate, filtered and concentrated to afford crude trimethyl(1H-pyrazol-3-yloxymethyl)germane (1.7 g, 94%) as a yellow oil which was used directly in the next step. $^1$H NMR (250 MHz, CDCl$_3$) δ 7.35 (d, J=2.4 Hz, 1H), 5.73 (d, J=2.5 Hz, 1H), 4.06 (s, 2H), 0.25 (s, 9H).

Step 3: Ethyl 2-chloro-6-[3-(trimethylgermylmethoxy)pyrazol-1-yl]pyridine-3-carboxylate

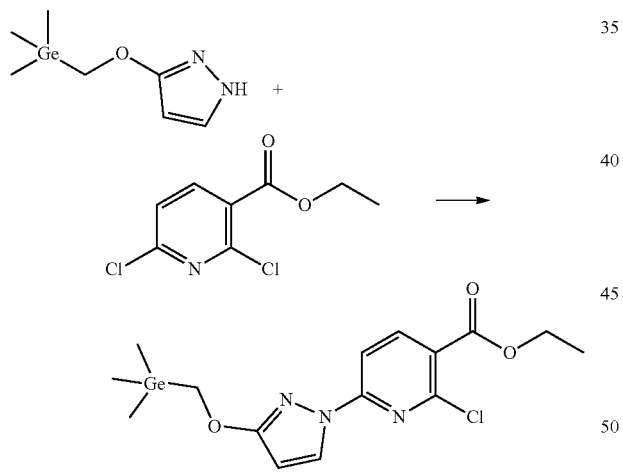

Into a solution of trimethyl(1H-pyrazol-3-yloxymethyl)germane (1.7 g, 7.12 mmol) and ethyl 2,6-dichloropyridine-3-carboxylate (1.9 g, 8.63 mmol) in anhydrous DMF (70 mL) was added potassium carbonate (1.2 g, 8.68 mmol) and DABCO (190 mg, 1.69 mmol). The reaction was stirred at rt overnight. The reaction was quenched with water (50 mL), and extracted with EtOAc (3×50 mL). The combined organic layers were washed with brine (3×50 mL), dried over anhydrous sodium sulfate and concentrated under vacuum. The residue was purified by silica gel chromatography using 0 to 5% EtOAc in hexane (120 g column) to furnish ethyl 2-chloro-6-[3-(trimethylgermylmethoxy)pyrazol-1-yl]pyridine-3-carboxylate (2.73 g, 94%) as a white solid. $^1$H NMR (250 MHz, DMSO) δ 8.52-8.32 (m, 2H), 7.74 (d, J=8.5 Hz, 1H), 6.21 (d, J=2.9 Hz, 1H), 4.34 (q, J=7.1 Hz, 2H), 4.22 (s, 2H), 1.34 (t, J=7.1 Hz, 3H), 0.24 (s, 9H).

Step 4: 2-Chloro-6-[3-(trimethylgermylmethoxy)pyrazol-1-yl]pyridine-3-carboxylic Acid

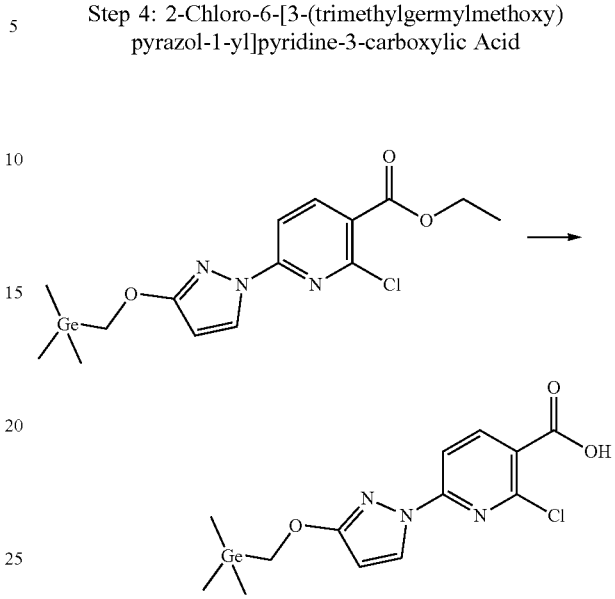

Into a solution of ethyl 2-chloro-6-[3-(trimethylgermylmethoxy)pyrazol-1-yl]pyridine-3-carboxylate (2.71 g, 6.66 mmol) in methanol (10 mL) and THF (20 mL), was added an aqueous solution of NaOH (10 mL of 2 M, 20.00 mmol). The reaction was stirred at rt for 1h. The pH of the reaction was adjusted to 3 with 1 N HCl (aqueous). The reaction was diluted with ethyl acetate (50 mL). Two layers were separated, and the aqueous layer was extracted with ethyl acetate (2×50 mL). The combined organic layers were washed with brine (2×50 mL), dried over anhydrous sodium sulfate and concentrated under vacuum. The crude product was triturated with hexane to furnish 2-chloro-6-[3-(trimethylgermylmethoxy)pyrazol-1-yl]pyridine-3-carboxylic acid (2.4 g, 92%) as a white solid. $^1$H NMR (250 MHz, DMSO) δ 8.51-8.30 (m, 2H), 7.73 (d, J=8.4 Hz, 1H), 6.19 (d, J=2.9 Hz, 1H), 4.22 (s, 2H), 0.23 (s, 9H).

Step 5: 2-Chloro-N-(1,3-dimethylpyrazol-4-yl)sulfonyl-6-[3-(trimethylgermyl methoxy)pyrazol-1-yl]pyridine-3-carboxamide

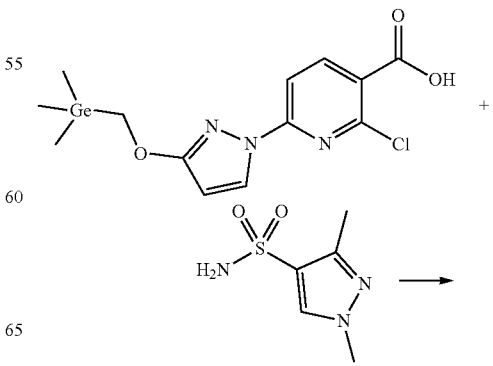

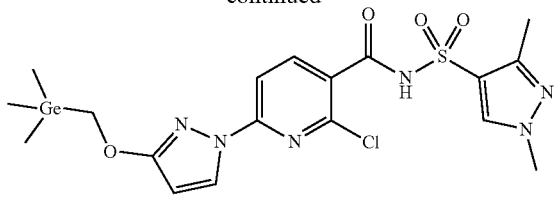

To a stirring suspension of 2-chloro-6-[3-(trimethylgermylmethoxy)pyrazol-1-yl]pyridine-3-carboxylic acid (621 mg, 1.64 mmol) and 1,3-dimethylpyrazole-4-sulfonamide (347 mg, 1.98 mmol) in anhydrous DCM (12 mL) at room temperature under nitrogen was added DMAP (612 mg, 5.01 mmol). EDC (960 mg, 5.01 mmol) was added, and the reaction mixture was stirred at this temperature for 18 hours. The reaction was quenched with 10% aqueous citric acid (30 mL), and two layers were separated. The aqueous layer was extracted with DCM (2×30 mL). The combined organic layers were washed with brine (30 mL), dried over anhydrous sodium sulfate and concentrated. The crude product (combined with a crude product from another similar 50 mg scale reaction) was purified by silica gel chromatography (80 g column) using 0-5% DCM in MeOH to afford 2-chloro-N-(1,3-dimethylpyrazol-4-yl)sulfonyl-6-[3-(trimethylgermylmethoxy)pyrazol-1-yl]pyridine-3-carboxamide (850 mg, 93%) as a white wax. ESI-MS m/z calc. 528.0402, found 529.0 (M+1)$^+$; Retention time: 3.07 minutes (LC method B).

Step 6: N-(1,3-Dimethylpyrazol-4-yl)sulfonyl-6-[3-(trimethylgermylmethoxy)pyrazol-1-yl]-2-[(4S)-2,2,4-trimethylpyrrolidin-1-yl]pyridine-3-carboxamide (Compound (3-1))

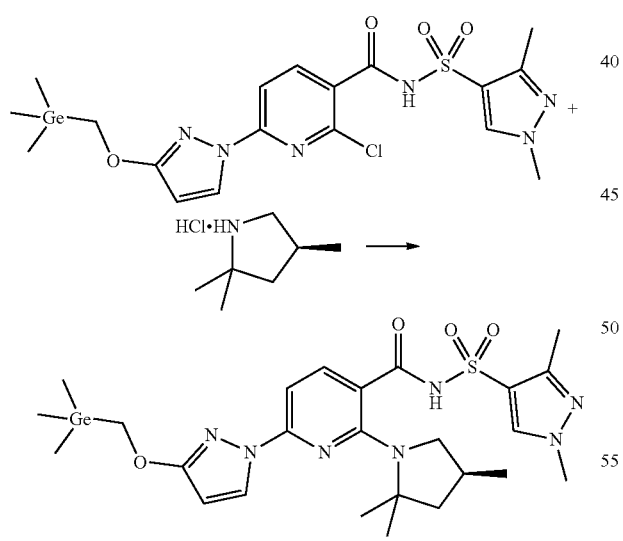

To a stirring solution of 2-chloro-N-(1,3-dimethylpyrazol-4-yl)sulfonyl-6-[3-(trimethylgermylmethoxy)pyrazol-1-yl]pyridine-3-carboxamide (820 mg, 1.48 mmol) and (4S)-2,2,4-trimethylpyrrolidine (hydrochloride salt) (714 mg, 4.77 mmol) in anhydrous DMSO (10 mL) at room temperature under nitrogen was added potassium carbonate (1.35 g, 9.77 mmol). The reaction mixture was heated to 160° C. for 7 hours. After cooling to room temperature, the reaction was slowly quenched with 10% aqueous citric acid (50 mL). The product was extracted with ethyl acetate (3×40 mL)). The combined organic layers were washed with brine (25 mL), dried over anhydrous sodium sulfate and concentrated. The crude material was purified by silica gel chromatography using 0-20% EtOAc in hexanes to afford N-(1,3-dimethylpyrazol-4-yl)sulfonyl-6-[3-(trimethylgermylmethoxy)pyrazol-1-yl]-2-[(4S)-2,2,4-trimethylpyrrolidin-1-yl]pyridine-3-carboxamide (547.4 mg, 61%) as a white solid. $^1$H NMR (500 MHz, DMSO-d$_6$) δ 12.34 (s, 1H), 8.38 (s, 1H), 8.19 (d, J=2.8 Hz, 1H), 7.75 (d, J=8.2 Hz, 1H), 6.92 (d, J=8.2 Hz, 1H), 6.11 (d, J=2.7 Hz, 1H), 4.19 (s, 2H), 3.81 (s, 3H), 2.56 (t, J=10.4 Hz, 1H), 2.42 (t, J=8.7 Hz, 1H), 2.33 (s, 3H), 2.25-2.14 (m, 1H), 1.91-1.84 (m, 1H), 1.57 (s, 3H), 1.54 (s, 3H), 1.42 (t, J=12.1 Hz, 1H), 0.82 (d, J=6.3 Hz, 3H), 0.23 (s, 9H). ESI-MS m/z calc. 605.184, found 606.0 (M+1)$^+$; Retention time: 3.26 minutes (LC method B).

Example 19: Preparation of N-(1,3-dimethylpyrazol-4-yl)sulfonyl-6-[3-(3,3,3-trifluoro-2,2-dimethylpropoxy)pyrazol-1-yl]-2-[(4S)-2,2,4-trimethylpyrrolidin-1-yl]-5-trimethylsilyl-pyridine-3-carboxamide

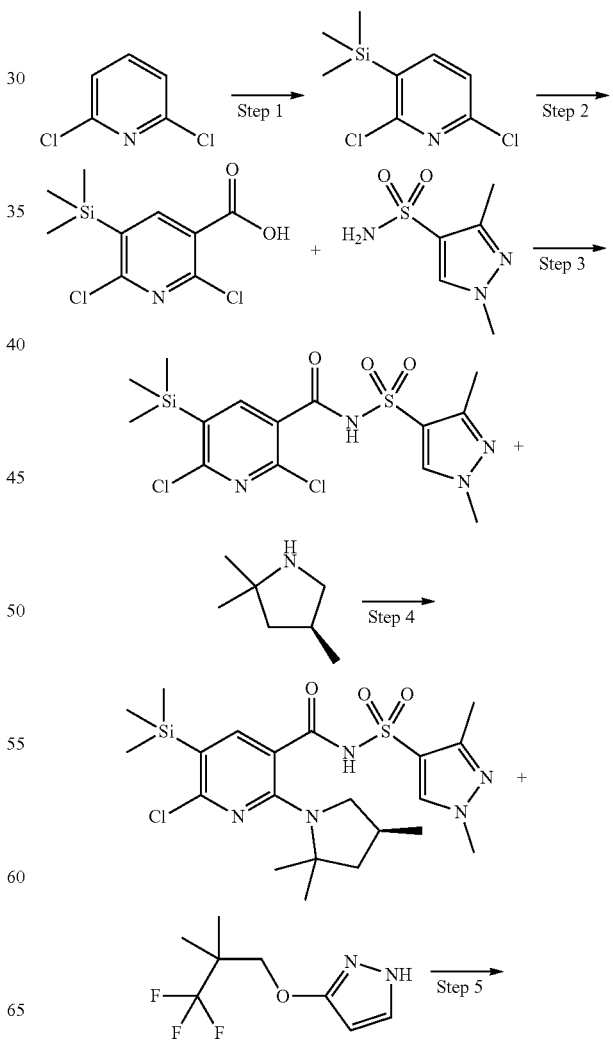

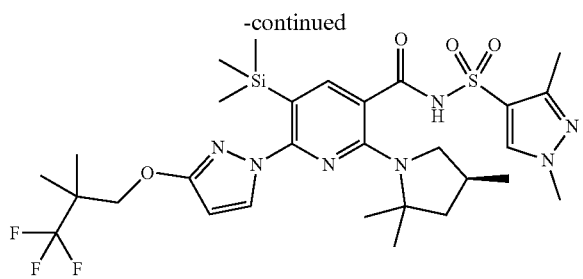

Step 1: (2,6-Dichloro-3-pyridyl)-trimethyl-silane

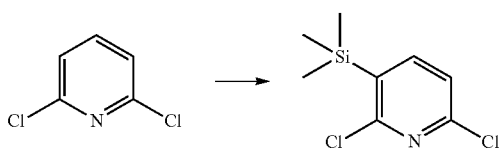

2,6-Dichloropyridine (4.01 g, 27.10 mmol) was dissolved in THF (80 mL) and cooled in a dry ice/acetone bath. LDA in THF/heptane/ethylbenzene (15 mL of 2 M, 30.00 mmol) was added slowly and the reaction was stirred at −75° C. for 1 h. At this point, TMS-Cl (3.5 mL, 27.58 mmol) was added and the reaction mixture was stirred at −75° C. for an additional 1 h. The reaction was quenched with aq HCl (50 mL of 1 M, 50.00 mmol) and allowed to warm to room temperature. The layers were separated, and the aqueous layer was further extracted with diethyl ether. The organics were combined, washed with brine, dried over sodium sulfate and evaporated. The crude liquid was purified by silica gel chromatography eluting with 0-10% ethyl acetate in hexanes to yield (2,6-dichloro-3-pyridyl)-trimethyl-silane (3.933 g, 66%) as a clear liquid. $^1$H NMR (400 MHz, DMSO-$d_6$) δ 7.93 (d, J=7.7 Hz, 1H), 7.56 (d, J=7.7 Hz, 1H), 0.36 (s, 9H). ESI-MS m/z calc. 219.00378, found 220.1 (M+1)$^+$; Retention time: 0.76 minutes (LC method D).

Step 2: 2,6-Dichloro-5-trimethylsilyl-pyridine-3-carboxylic Acid

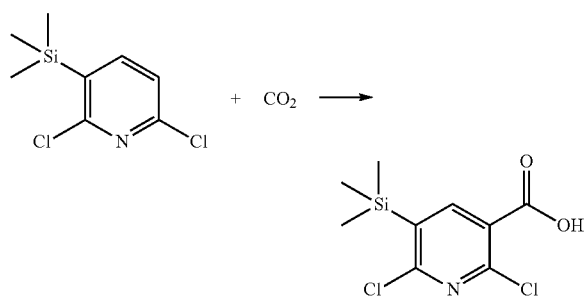

(2,6-Dichloro-3-pyridyl)-trimethyl-silane (531 mg, 2.41 mmol) was dissolved in THF (10 mL) and cooled to −75° C. in a dry ice:acetone bath. LDA in THF/heptane/ethylbenzene (1.25 mL of 2 M, 2.50 mmol) was added slowly and the reaction mixture was stirred an additional 1 h. CO$_2$ gas was bubbled through the reaction mixture for 1 min. The reaction was allowed to warm to room temperature and stir for 15 min. The reaction mixture was diluted with ethyl acetate and washed with 1M aq HCl. The organics were separated, washed with brine, dried over sodium sulfate and evaporated. The crude material was triturated with hexanes and the resulting solid was collected by vacuum filtration. The solid was further dried to give 2,6-dichloro-5-trimethylsilyl-pyridine-3-carboxylic acid (353 mg, 55%) as a white solid. $^1$H NMR (400 MHz, DMSO-$d_6$) δ 13.96 (s, 1H), 8.21 (s, 1H), 0.38 (s, 9H). ESI-MS m/z calc. 262.99362, found 264.1 (M+1)$^+$; Retention time: 0.65 minutes (LC method D).

Step 3: 2,6-Dichloro-N-(1,3-dimethylpyrazol-4-yl)sulfonyl-5-trimethylsilyl-pyridine-3-carboxamide

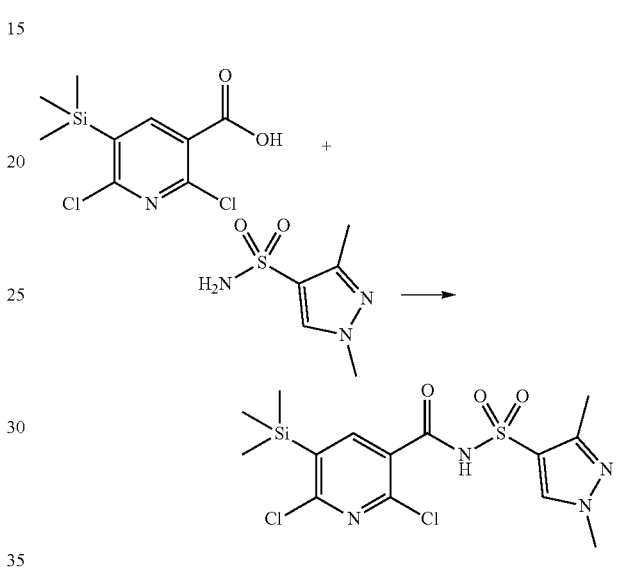

2,6-Dichloro-5-trimethylsilyl-pyridine-3-carboxylic acid (100 mg, 0.378 mmol) was dissolved in THF (1 mL), and carbonyl diimidazole (76 mg, 0.469 mmol) was added. After stirring at room temperature for 1 hour, 1,3-dimethylpyrazole-4-sulfonamide (73.2 mg, 0.418 mmol) was added followed by DBU (70 µL, 0.468 mmol). The reaction mixture was allowed to stir overnight at room temperature. The reaction mixture was then diluted with EtOAc and washed with 1M aqueous citric acid solution, then brine. The organic layer was dried over sodium sulfate, filtered and concentrated under reduced pressure. The crude material was purified by silica gel chromatography eluting with 0-100% ethyl acetate in hexanes to give 2,6-dichloro-N-(1,3-dimethylpyrazol-4-yl)sulfonyl-5-trimethylsilyl-pyridine-3-carboxamide (151 mg, 95%) as a white solid. ESI-MS m/z calc. 420.0246, found 421.1 (M+1)$^+$; Retention time: 0.63 minutes (LC method D).

Step 4: 6-Chloro-N-(1,3-dimethylpyrazol-4-yl)sulfonyl-2-[(4S)-2,2,4-trimethylpyrrolidin-1-yl]-5-trimethylsilyl-pyridine-3-carboxamide

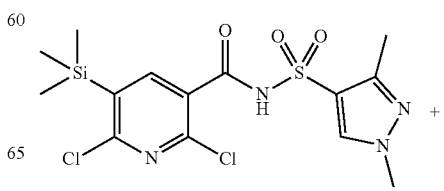

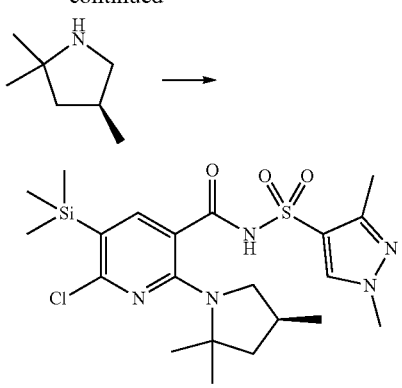

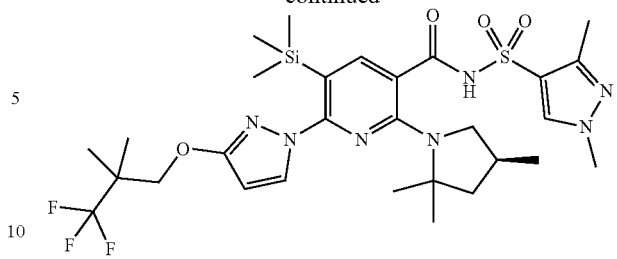

2,6-Dichloro-N-(1,3-dimethylpyrazol-4-yl)sulfonyl-5-trimethylsilyl-pyridine-3-carboxamide (151 mg, 0.358 mmol), (4S)-2,2,4-trimethylpyrrolidine (hydrochloride salt) (131 mg, 0.875 mmol), and potassium carbonate (314 mg, 2.272 mmol) were combined in DMSO (0.6 mL) and heated at 130° C. for 16 h. The reaction mixture was cooled and partitioned between ethyl acetate and a 10% citric acid solution. The organics were separated, washed with brine, dried over sodium sulfate and evaporated. The crude material was purified by silica gel chromatography eluting with 0-100% ethyl acetate in hexanes to give 6-chloro-N-(1,3-dimethylpyrazol-4-yl)sulfonyl-2-[(4S)-2,2,4-trimethylpyrrolidin-1-yl]-5-trimethylsilyl-pyridine-3-carboxamide (35.8 mg, 20%) as an off white solid. $^1$H NMR (400 MHz, DMSO-$d_6$) δ 12.44 (s, 1H), 8.38 (s, 1H), 7.51 (s, 1H), 3.80 (s, 3H), 2.48-2.45 (m, 1H), 2.38 (t, J=9.0 Hz, 1H), 2.31 (s, 3H), 2.24-2.09 (m, 1H), 1.85 (dd, J=12.0, 5.6 Hz, 1H), 1.49 (s, 3H), 1.48 (s, 3H), 1.40 (t, J=12.2 Hz, 1H), 0.81 (d, J=6.3 Hz, 3H), 0.31 (s, 9H). ESI-MS m/z calc. 497.16837, found 498.6 (M+1)+; Retention time: 0.84 minutes (LC method D).

Step 5: N-(1,3-Dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]-5-trimethylsilyl-pyridine-3-carboxamide

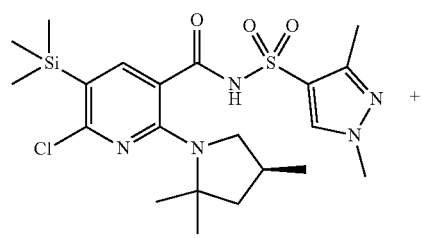

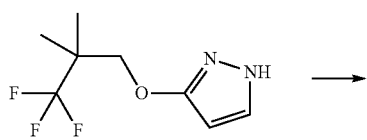

6-Chloro-N-(1,3-dimethylpyrazol-4-yl)sulfonyl-2-[(4S)-2,2,4-trimethylpyrrolidin-1-yl]-5-trimethylsilyl-pyridine-3-carboxamide (35.8 mg, 0.072 mmol), 3-(3,3,3-trifluoro-2,2-dimethyl-propoxy)-1H-pyrazole (16 mg, 0.077 mmol), potassium carbonate (23 mg, 0.166 mmol) and (1R,2R)—N1,N2-dimethylcyclohexane-1,2-diamine (11.2 mg, 0.0787 mmol) were combined in DMF (150 Copper (I) iodide (3 mg, 0.0157 mmol) was added and the reaction mixture was stirred under nitrogen at 115° C. for 16 h. More 3-(3,3,3-trifluoro-2,2-dimethyl-propoxy)-1H-pyrazole (16.4 mg, 0.0788 mmol), copper (I) iodide (4 mg, 0.0210 mmol), potassium carbonate (24 mg, 0.174 mmol), and (1R,2R)—N1,N2-dimethylcyclohexane-1,2-diamine (14 mg, 0.0984 mmol) was added and the reaction was stirred at 125° C. for an additional 24 h. The reaction mixture was cooled, diluted with DMSO and purified by reverse phase preparative HPLC utilizing a gradient of 1-99% acetonitrile in 5 mM aq HCl to yield N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]-5-trimethylsilyl-pyridine-3-carboxamide (17.4 mg, 35%) as an off white solid. $^1$H NMR (400 MHz, DMSO-$d_6$) δ 12.43 (s, 1H), 8.38 (s, 1H), 8.20 (d, J=2.8 Hz, 1H), 7.73 (s, 1H), 6.17 (d, J=2.8 Hz, 1H), 4.24-4.17 (m, 2H), 3.81 (s, 3H), 2.56 (t, J=10.3 Hz, 1H), 2.45 (t, J=8.4 Hz, 1H), 2.33 (s, 3H), 2.26-2.10 (m, 1H), 1.88 (dd, J=12.0, 5.6 Hz, 1H), 1.55 (s, 3H), 1.52 (s, 3H), 1.42 (t, J=12.2 Hz, 1H), 1.23 (s, 6H), 0.83 (d, J=6.2 Hz, 3H), 0.27 (s, 9H). ESI-MS m/z calc. 669.27405, found 670.5 (M+1)+; Retention time: 2.41 minutes (LC method A).

Bioactivity Assays

Solutions

Base medium (ADF+++) consists of Advanced DMEM/Ham's F12, 2 mM Glutamax, 10 mM HEPES, 1 µg/mL penicillin/streptomycin.

Intestinal enteroid maintenance medium (IEMM) consists of ADF+++, 1× B27 supplement, 1× N2 supplement, 1.25 mM N-acetyl cysteine, 10 mM Nicotinamide, 50 ng/mL hEGF, 10 nM Gastrin, 1 µg/mL hR-spondin-1, 100 ng/mL hNoggin, TGF-b type 1 inhibitor A-83-01, 100 µg/mL Primocin, 10 µM P38 MAPK inhibitor SB202190.

Bath 1 Buffer consists of 1 mM MgCl2, 160 mM NaCl, 4.5 mM KCl, 10 mM HEPES, 10 mM Glucose, 2 mM CaCl$_2$).

Chloride Free Buffer consists of 1 mM Magnesium Gluconate, 2 mM Calcium Gluconate, 4.5 mM Potassium Gluconate, 160 mM Sodium Gluconate, 10 mM HEPES, 10 mM Glucose.

Bath 1 Dye Solution consists of Bath 1 Buffer, 0.04% Pluronic F127, 20 Methyl Oxonol, 30 µM CaCCinh-A01, 30 µM Chicago Sky Blue.

Chloride Free Dye Solution consists of Chloride Free Buffer, 0.04% Pluronic F127, 20 µM Methyl Oxonol, 30 µM CaCCinh-A01, 30 µM Chicago Sky Blue.

Chloride Free Dye Stimulation Solution consists of Chloride Free Dye Solution, 10 μM forskolin, 100 μM IBMX, and 300 nM Compound III.

Cell Culture

Human intestinal epithelial enteroid cells may be obtained from the Hubrecht Institute for Developmental Biology and Stem Cell Research, Utrecht, The Netherlands and expanded in T-Flasks as previously described (Dekkers J F, Wiegerinck C L, de Jonge H R, Bronsveld I, Janssens H M, de Winter-de Groot K M, Brandsma A M, de Jong N W M, Bijvelds M J C, Scholte B J, Nieuwenhuis E E S, van den Brink S, Clevers H, van der Ent C K, Middendorp S and M Beekman J M. A functional CFTR assay using primary cystic fibrosis intestinal organoids. Nat Med. 2013 July; 19(7):939-45).

Enteroid Cell Harvesting and Seeding

Cells may be recovered in cell recovery solution, collected by centrifugation at 650 rpm for 5 min at 4° C., resuspended in TryPLE and incubated for 5 min at 37° C. Cells can then be collected by centrifugation at 650 rpm for 5 min at 4° C. and resuspended in IEMM containing 10 μM ROCK inhibitor (RI). The cell suspension is then passed through a 40 μm cell strainer and resuspended at 1×106 cells/mL in IEMM containing 10 μM RI. Cells may be seeded at 5000 cells/well into multi-well plates and incubated for overnight at 37° C., 95% humidity and 5% $CO_2$ prior to assay.

Membrane Potential Dye Assay

Enteroid cells may be incubated with test compound in IEMM for 18-24 hours at 37° C., 95% humidity and 5% $CO_2$. Following compound incubations, a membrane potential dye assay can be employed using a FLIPR Tetra to directly measure the potency and efficacy of the test compound on CFTR-mediated chloride transport following acute addition of 10 μM forskolin and 300 nM N-[2,4-bis(1,1-dimethylethyl)-5-hydroxyphenyl]-1,4-dihydro-4-oxoquinoline-3-carboxamide. Briefly, cells are washed 5 times in Bath 1 Buffer. Bath 1 Dye Solution is added and the cells are incubated for 25 min at room temperature. Following dye incubation, cells are washed 3 times in Chloride Free Dye Solution. Chloride transport is initiated by addition of Chloride Free Dye Stimulation Solution and the fluorescence signal is read for 15 min. The CFTR-mediated chloride transport for each condition may be determined from the AUC of the fluorescence response to acute forskolin and 300 nM N-[2,4-bis(1,1-dimethylethyl)-5-hydroxyphenyl]-1,4-dihydro-4-oxoquinoline-3-carboxamide stimulation.

Chloride transport may be expressed as a percentage of the chloride transport following treatment with one or more reference standards or positive controls. Suitable reference standards/controls include one or more of Compound II, Compound III, Compound IV, and Compound A. Compound A is:

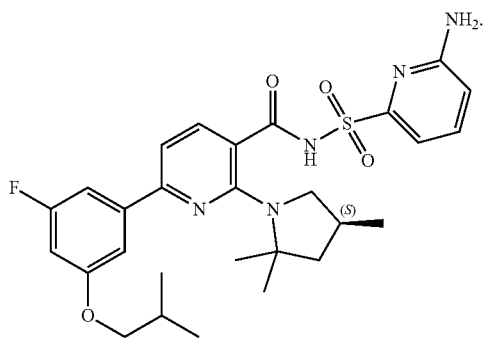

Other assays may also be used to determine CFTR-modulating activity in the compounds of the invention.

A. Membrane Potential Optical Methods for Assaying Properties of F508del-CFTR Modulators Assay utilizing fluorescent voltage sensing dyes to measure changes in membrane potential using a fluorescent plate reader (e.g., FLIPR III, Molecular Devices, Inc.) as a read-out for increase in functional F508del in NIH 3T3 cells can be used. The driving force for the response is the creation of a chloride ion gradient in conjunction with channel activation and concurrent with compound treatment by a single liquid addition step after the cells have previously been loaded with a voltage sensing dye.

A1. Identification of F508del-CFTR Modulators

To identify modulators of F508del, a fluorescence based HTS assay format may be used. The HTS assay utilizes fluorescent voltage sensing dyes to measure changes in membrane potential on the FLIPR III as a measurement for increase in gating (conductance) of F508del NIH 3T3 cells. The driving force for the response is the creation of a chloride ion gradient in conjunction with channel activation and concurrent with compound treatment by a single liquid addition step after the cells have previously been loaded with a voltage sensing dye.

Exemplary Solutions

Bath Solution #1: (in mM) NaCl 160, KCl 4.5, $CaCl_2$ 2, $MgCl_2$ 1, HEPES 10, pH 7.4 with NaOH, Glucose 10.

Chloride-free bath solution: Chloride salts in Bath Solution #1 (above) are substituted with gluconate salts.

Exemplary Cell Culture

NIH3T3 mouse fibroblasts stably expressing F508del may be used for optical measurements of membrane potential. The cells can be maintained at 37° C. in 5% $CO_2$ and 90% humidity in Dulbecco's modified Eagle's medium supplemented with 2 mM glutamine, 10% fetal bovine serum, 1×NEAA, β-ME, 1×pen/strep, and 25 mM HEPES in 175 $cm^2$ culture flasks. For all optical assays, the cells can be seeded at 12,000 cells/well in 384-well matrigel-coated plates and cultured for 18-24 hrs at 37° C. for the potentiator assay. For the correction assays, the cells can be cultured at 37° C. with and without compounds for 18-24 hours.

Electrophysiological Assays for Assaying F508del Modulation Properties of Compounds.

Ussing Chamber Assay

Ussing chamber experiments can be performed on polarized airway epithelial cells expressing F508del to further characterize the F508del modulators identified in the optical assays. Non-CF and CF airway epithelia can be isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that can be precoated with NIH3T3-conditioned media. After four days the apical media can be removed and the cells can be grown at an air liquid interface for >14 days prior to use. A monolayer of fully differentiated columnar cells that are ciliated, features that are characteristic of airway epithelia, may result. Non-CF HBE may be isolated from non-smokers without known lung disease. CF-HBE may be isolated from patients homozygous for F508del or compound heterozygous for F508del with an different disease causing mutation on the other allele.

HBE grown on Costar® Snapwell™ cell culture inserts can be mounted in an Ussing chamber (Physiologic Instruments, Inc., San Diego, Calif.), and the transepithelial resistance and short-circuit current in the presence of a basolateral to apical Cl⁻ gradient ($I_{SC}$) can be measured using a voltage-clamp system (Department of Bioengineering, University of Iowa, Iowa). Briefly, HBE can be examined under voltage-clamp recording conditions ($V_{hold}$=0 mV) at 37° C. The basolateral solution may contain (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution may contain (in mM) 145 NaGluconate, 1.2 $MgCl_2$, 1.2 $CaCl_2$, 10 glucose, 10 HEPES (pH adjusted to 7.35 with NaOH).

A2. Identification of F508del-CFTR Modulators

A basolateral to apical membrane Cl⁻ concentration gradient may be used. To set up this gradient, normal ringers can be used on the basolateral membrane, whereas apical NaCl can be replaced by equimolar sodium gluconate (titrated to pH 7.4 with NaOH) to give a large Cl⁻ concentration gradient across the epithelium. Modulators can be added either to the basolateral side 18-24 prior to assay or to the apical side during the assay. Forskolin (10 μM) can be added to the apical side during the assay to stimulate CFTR-mediated transport.

Patch-Clamp Recordings

Total Cl⁻ current in F508del-NIH3T3 cells can be monitored using the perforated-patch recording configuration as previously described (Rae, J., Cooper, K., Gates, P., & Watsky, M. (1991) *J. Neurosci. Methods* 37, 15-26). Voltage-clamp recordings can be performed at 22° C. using an Axopatch 200B patch-clamp amplifier (Axon Instruments Inc., Foster City, Calif.). The pipette solution may contain (in mM) 150 N-methyl-D-glucamine (NMDG)-Cl, 2 $MgCl_2$, 2 $CaCl_2$, 10 EGTA, 10 HEPES, and 240 μg/mL amphotericin-B (pH adjusted to 7.35 with HCl). The extracellular medium contained (in mM) 150 NMDG-Cl, 2 $MgCl_2$, 2 $CaCl_2$, 10 HEPES (pH adjusted to 7.35 with HCl). Pulse generation, data acquisition, and analysis can be performed using a PC equipped with a Digidata 1320 A/D interface in conjunction with Clampex 8 (Axon Instruments Inc.). To activate F508del, 10 μM forskolin and 20 □M genistein can be added to the bath and the current-voltage relation can be monitored every 30 sec.

A3. Identification of F508del-CFTR Modulators

The ability of F508del-CFTR modulators to increase the macroscopic F508del Cl⁻ current ($I_{F508del}$) in NIH3T3 cells stably expressing F508del can be investigated using perforated-patch-recording techniques. Modulators identified from the optical assays may evoke a dose-dependent increase in $I\Delta_{F508}$ with similar potency and efficacy may be observed in the optical assays.

Cell Culture

NIH3T3 mouse fibroblasts stably expressing F508del can be used for whole-cell recordings. The cells can be maintained at 37° C. in 5% $CO_2$ and 90% humidity in Dulbecco's modified Eagle's medium supplemented with 2 mM glutamine, 10% fetal bovine serum, 1×NEAA, □-ME, 1×pen/strep, and 25 mM HEPES in 175 cm² culture flasks. For whole-cell recordings, 2,500-5,000 cells can be seeded on poly-L-lysine-coated glass coverslips and cultured for 18-24 hrs in the presence or absence of modulators 37° C.

Single-Channel Recordings

Gating activity of F508del-CFTR expressed in NIH3T3 cells following modulator treatment may observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette may contain (in mM): 150 NMDG, 150 aspartic acid, 5 $CaCl_2$, 2 $MgCl_2$, and 10 HEPES (pH adjusted to 7.35 with Tris base). The bath may contain (mM): 150 NMDG-Cl, 2 $MgCl_2$, 5 EGTA, 10 TES, and 14 Tris base (pH adjusted to 7.35 with HCl). After excision, both wt- and F508del can be activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which may prevent current rundown. The pipette potential can be maintained at 80 mV. Channel activity can be analyzed from membrane patches containing 2 active channels. The maximum number of simultaneous openings may determine the number of active channels during the course of an experiment. To determine the single-channel current amplitude, the data recorded from 120 sec of F508del activity can be filtered "off-line" at 100 Hz and then can be used to construct all-point amplitude histograms that can be fitted with multigaussian functions using Bio-Patch Analysis software (Bio-Logic Comp. France). The total microscopic current and open probability ($P_o$) can be determined from 120 sec of channel activity. The $P_o$ can be determined using the Bio-Patch software or from the relationship $P_o$=I/i(N), where I=mean current, i=single-channel current amplitude, and N=number of active channels in patch.

Cell Culture

NIH3T3 mouse fibroblasts stably expressing F508del can be used for excised-membrane patch-clamp recordings. The cells can be maintained at 37° C. in 5% $CO_2$ and 90% humidity in Dulbecco's modified Eagle's medium supplemented with 2 mM glutamine, 10% fetal bovine serum, 1×NEAA, □-ME, 1×pen/strep, and 25 mM HEPES in 175 cm² culture flasks. For single channel recordings, 2,500-5,000 cells can be seeded on poly-L-lysine-coated glass coverslips and cultured for 18-24 hrs in the presence or absence of modulators at 37° C.

B. Chromatographic Determination of Human Serum Albumin (HSA) Assay

Chromatographic determination of Human Serum Albumin (HSA) values can be performed on a UPLC-MS system using a ChiralPak® HSA column (p/n: 58469AST) from Sigma Aldrich. Mobile phase A may consist of 50 mM ammonium acetate buffer in water adjusted to pH=7.4, and mobile phase B can be 2-propanol. The column compartment can be kept at constant temperature of 30° C. Determination of retention time on the HSA column can be performed by injecting 3 mL of 0.5 mM of compound (in DMSO) using a linear gradient from 0%-30% B in 2.5 minutes, followed by a hold at 30% B for 2 minutes, and the final equilibration step from 30%-0% B in 1.5 minutes, for a total run time of 6 minutes. Flow rate can be kept constant throughout the gradient and set to 1.8 mL/min. Compound retention time on the HSA column can be converted to % HSA values according to a previously published protocol (Valko, K., Nunhuck, S., Bevan, C., Abraham, M. H., Reynolds, D. P. Fast Gradient HPLC Method to Determine Compounds Binding to Human Serum Albumin. Relationships with Octanol/Water and Immobilized Artificial Membrane Lipophilicity. J. of Pharm. Sci. 2003, 92, 2236-2248).

C. Protocol for Rat IV and PO PK studies

The tested compound can be administered to male Sprague-Dawley rats as a single nominal intravenous dose of 3.0 mg/kg as a solution in 10% NMP, 10% solutol, 15% EtOH, 35% PEG400 and 30% D5W. The tested compound can be also administered to male Sprague-Dawley rats at single nominal oral dose of 3 mg/kg as a solution in 5% NMP, 30% PEG400, 10% TPGS, 5% PVP-K30 at 5 mL/kg dose volume. Analyses of plasma and dose preparations can be performed using LC/MS/MS.

Plasma concentration-time profiles of the tested compound in Sprague-Dawley rats at scheduled (nominal) sampling times can be analyzed by noncompartmental pharmacokinetic methods using PK function within Watson LIMS software, Version 7.4.2 (Thermo Scientific Inc, Waltham, Mass.). AUC values can be calculated using the linear trapezoidal rule.

D. Protocol for PXR assay

The propensity for PXR mediated CYP3A4 induction can be assessed using the DPX-2 cell line in vitro. This cell line, which has been licensed from Puracyp Inc. can be derived from HepG2 cells and can be been stably transfected with genes encoding human PXR as well as a modified luciferase reporter linked to the CYP3A4 promoter region and related distal and proximal enhancers.

The assay can be run in 384 well format and each test article can be administered in 11 doses ranging from 0.1 to 60 μM. On day 1, DPX-2 cells which have previously been expanded in-house and cryopreserved can be thawed and seeded in tissue culture plates. The following day, media can be changed and cells can be cultured in media containing test article, vehicle control or the positive control compound, the clinically validated CYP3A4 inducer rifampicin. Cells can be cultured in the presence of test article for 48 hours and then cell viability can be assessed using fluorescence based assay (Cell Titer-Fluor, Promega) with an EnVision Plate Reader (PerkinElmer). Subsequently, CYP3A4 transactivation, which is proportional to luciferase activity, can be measured by reading luminescense using the Promega One-Glo reagent system using the same plate reader.

Data processing within the Genedata software package may allow reporting of max fold induction compared to vehicle control, an $EC_{50}$ value for CYP3A4 inducers and an 11 point-dose response curve. Wells with cell viability less than 70% are not used for the analysis and plates where the rifampicin positive control response falls outside of the expected range, either in potency or max fold induction, are not reported.

Table 6 confirms CFTR modulating activity for representative compounds of the invention generated using one or more of the assays disclosed herein.

TABLE 6

| Compound | Structure | Bioactivity CFTR Modulating Activity |
|---|---|---|
| (3-1) | 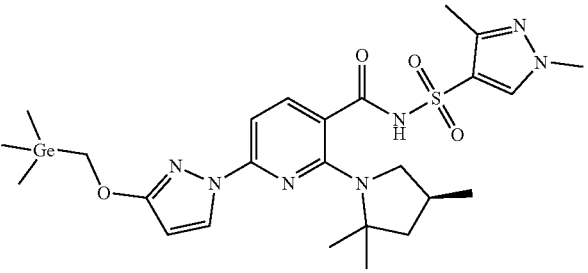 | Active |
| (2-1) | 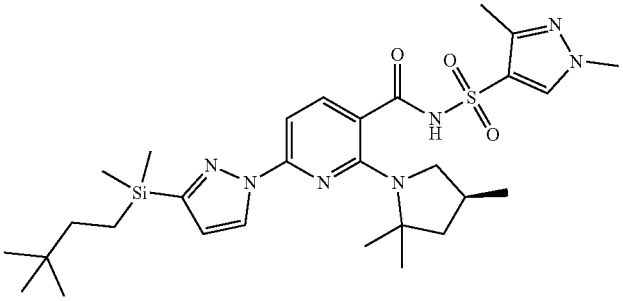 [SMILES: Cc1nn(C)cc1S(=O)(=O)NC(=O)c1ccc(-n2ccc([Si](C)(C)CCC(C)(C)C)n2)nc1N1C[C@@H](C)CC1(C)C] | Active |
| (3-2) Enantiomer 1 | 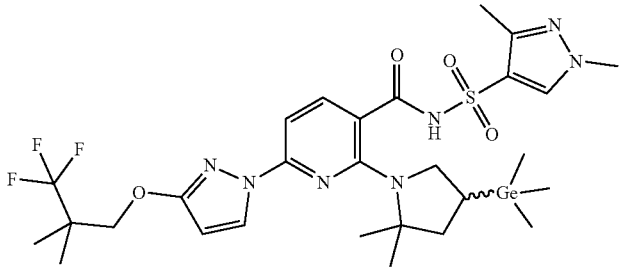 | ND |

TABLE 6-continued
| Compound | Structure | CFTR Modulating Activity |
|---|---|---|
| (3-2) Enantiomer 2 | 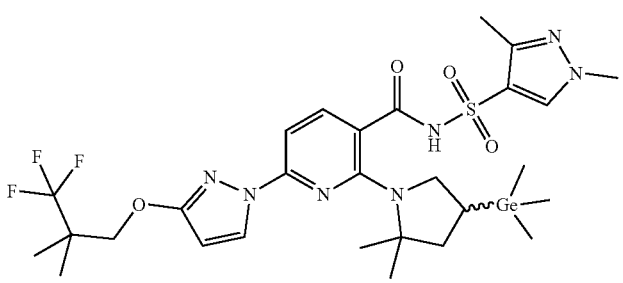 | Active |
| (2-2) | 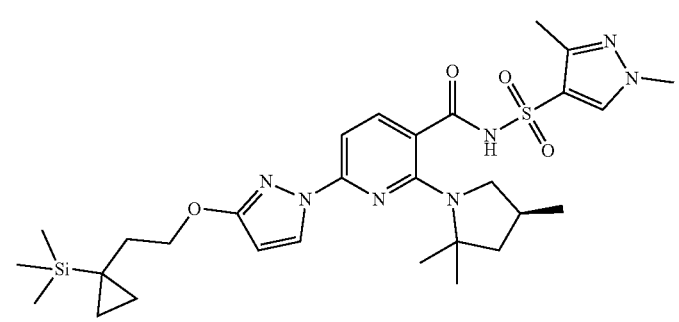 | Active |
| (2-3) | 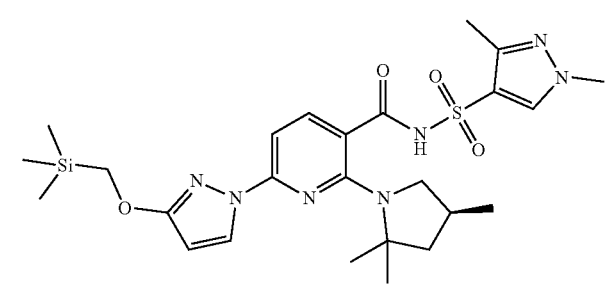 | Active |
| (2-4) | 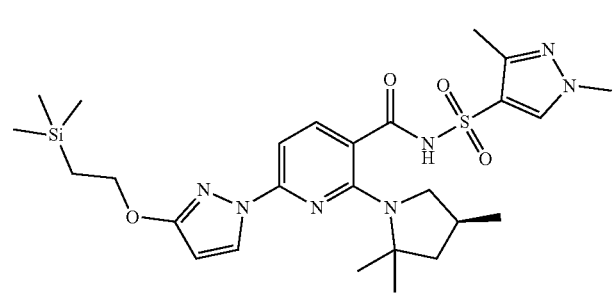 | Active |
| (2-5) | 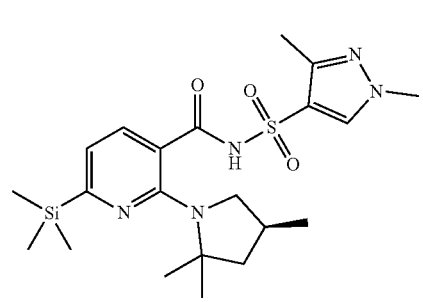 | Active |

TABLE 6-continued

| Compound | Structure | CFTR Modulating Activity |
|---|---|---|
| (3-3) | 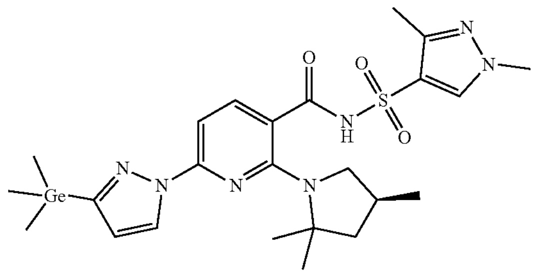 | Active |
| (2-6) | 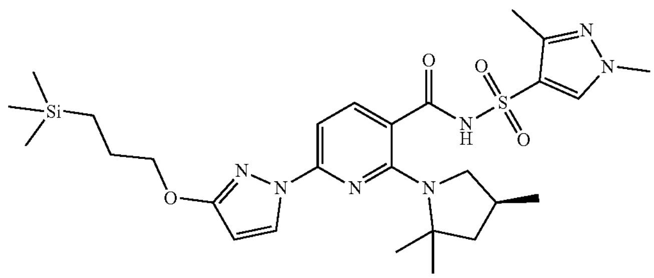 | Active |
| (2-7) | 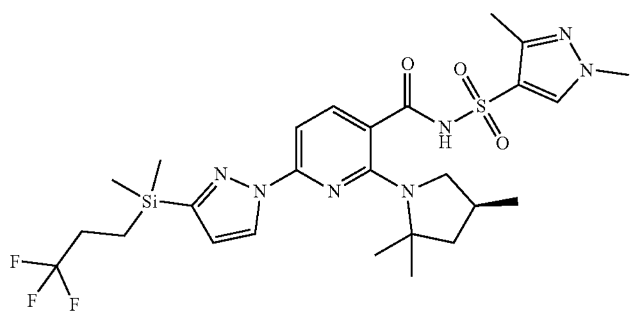 [SMILES: Cc1nn(C)cc1S(=O)(=O)NC(=O)c1ccc(-n2ccc([Si](C)(C)CCC(F)(F)F)n2)nc1N1C[C@@H](C)CC1(C)C] | Active |
| (2-8) Enantiomer 1 | 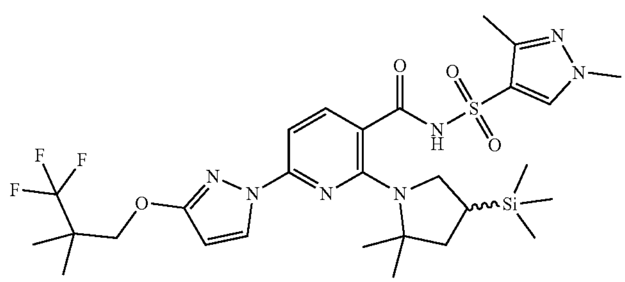 [SMILES: Cc1nn(C)cc1S(=O)(=O)NC(=O)c1ccc(-n2ccc(OCC(C)(C)C(F)(F)F)n2)nc1N1CC([Si](C)(C)C)CC1(C)C] | ND |
| (2-8) Enantiomer 2 | 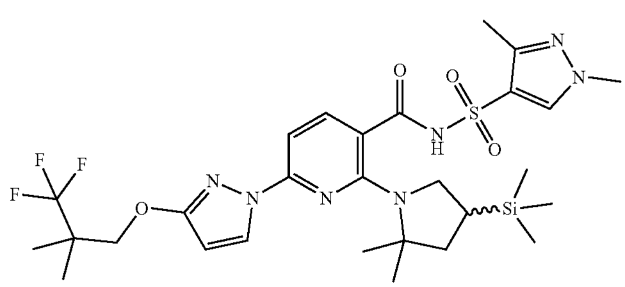 [SMILES: Cc1nn(C)cc1S(=O)(=O)NC(=O)c1ccc(-n2ccc(OCC(C)(C)C(F)(F)F)n2)nc1N1CC([Si](C)(C)C)CC1(C)C] | Active |

TABLE 6-continued

| Compound | Structure | CFTR Modulating Activity |
|---|---|---|
| (2-9) Stereoisomer 1 | 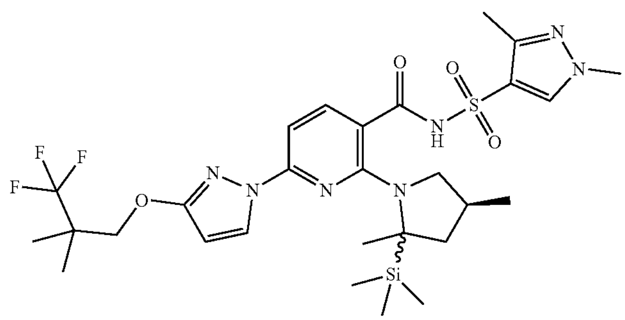 [SMILES: Cc1nn(C)cc1S(=O)(=O)NC(=O)c1ccc(-n2ccc(OCC(C)(C)C(F)(F)F)n2)nc1N1C[C@@H](C)CC1(C)[Si](C)(C)C] | Active |
| (2-9) Stereoisomer 2 | 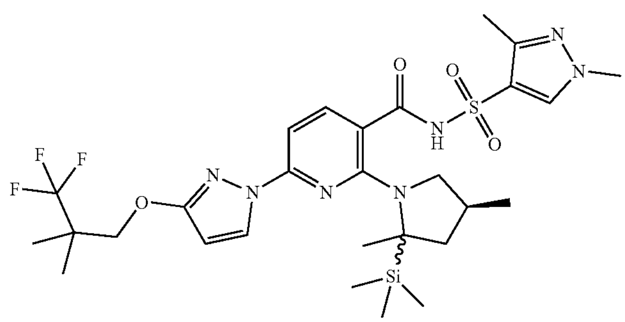 [SMILES: Cc1nn(C)cc1S(=O)(=O)NC(=O)c1ccc(-n2ccc(OCC(C)(C)C(F)(F)F)n2)nc1N1C[C@@H](C)CC1(C)[Si](C)(C)C] | ND |
| (2-10) | 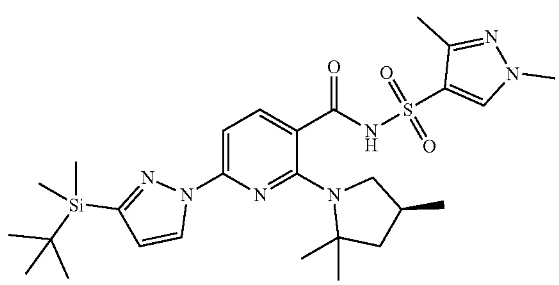 [SMILES: Cc1nn(C)cc1S(=O)(=O)NC(=O)c1ccc(-n2ccc([Si](C)(C)C(C)(C)C)n2)nc1N1C[C@@H](C)CC1(C)C] | Active |
| (2-11) | 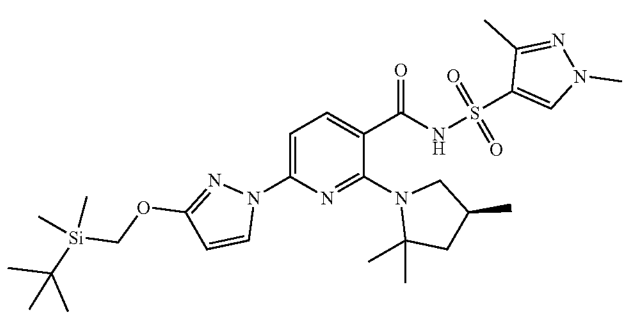 [SMILES: Cc1nn(C)cc1S(=O)(=O)NC(=O)c1ccc(-n2ccc(OC[Si](C)(C)C(C)(C)C)n2)nc1N1C[C@@H](C)CC1(C)C] | Active |

TABLE 6-continued

Bioactivity

| Compound | Structure | CFTR Modulating Activity |
|---|---|---|
| (2-12) | 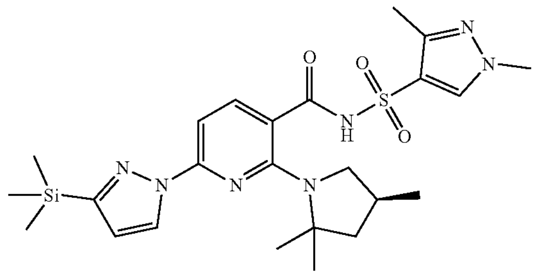 | Active |

ND-not detected

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A compound of Formula (1):

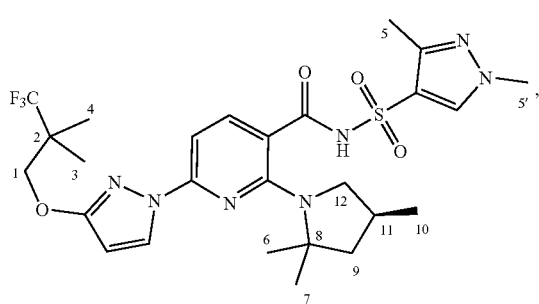

(1)

a pharmaceutically acceptable salt thereof, or a deuterated derivative of any of the foregoing, wherein:
  at least one of the carbon atoms at positions 2 and 8 of Formula (1) is replaced by a silicon atom;
  at least one of the methyl groups at positions 3, 4, 5, 5', 6, 7, and 10 of Formula (1) is replaced by a group chosen from —Si(R)₃ groups, —Si(R)2(OR) groups, and —Si(R)(OR)₂ groups;
  at least one of the methylene groups at positions 1, 9, and 12 of Formula (1) is replaced by a group chosen from >Si(R)₂ groups and >Si(R)(OR) groups; and/or
  the methine group at position 11 of Formula (1) is replaced by a group chosen from ≡Si(R) groups and ≡Si(OR) groups; and
wherein each R, which may be identical or different, is independently chosen from hydrogen, hydroxyl, and C₁-C₄ alkyl groups.

2. A compound according to claim 1, a pharmaceutically acceptable salt thereof, or a deuterated derivative of any of the foregoing, wherein at least one of the carbon atoms at positions 2 and 8 of Formula (1) is replaced by a silicon atom.

3. A compound according to claim 1, a pharmaceutically acceptable salt thereof, or a deuterated derivative of any of the foregoing, wherein at least one of the methyl groups at positions 3, 4, 5, 5', 6, 7, and 10 of Formula (1) is replaced by a group chosen from —Si(R)₃ groups, —Si(R)₂(OR) groups, and —Si(R)(OR)2 groups.

4. A compound according to claim 1, a pharmaceutically acceptable salt thereof, or a deuterated derivative of any of the foregoing, wherein at least one of the methylene groups at positions 1, 9, and 12 of Formula (1) is replaced by a group chosen from >Si(R)₂ groups and >Si(R)(OR) groups.

5. A compound according to claim 1, a pharmaceutically acceptable salt thereof, or a deuterated derivative of any of the foregoing, wherein the methine group at position 11 of Formula (1) is replaced by a group chosen from ≡Si(R) groups and ≡Si(OR) groups.

6. A compound according to claim 1 chosen from Compound (1-1):

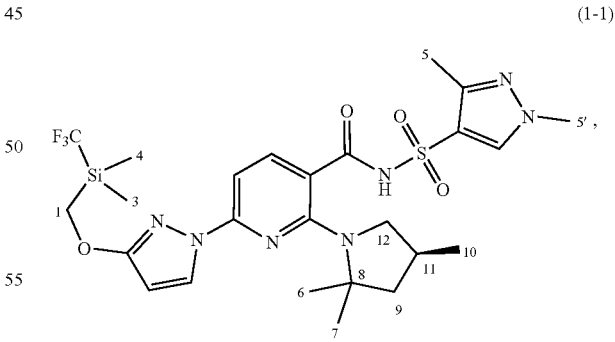

(1-1)

and pharmaceutically acceptable salts and deuterated derivatives thereof.

7. A compound according to claim 1 chosen from Compound (1-2):

(1-2)
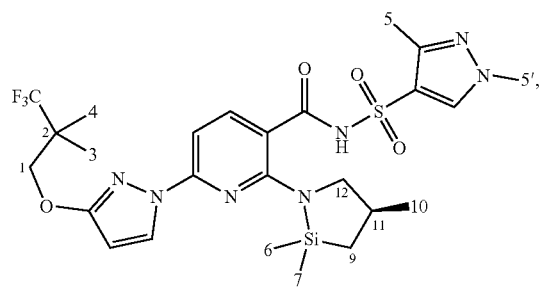
and pharmaceutically acceptable salts and deuterated derivatives thereof.
8. A compound according to claim 1 chosen from compounds of Formula (1-3), compounds of Formula (1-4), compounds of Formula (1-5), compounds of Formula (1-6), compounds of Formula (1-7), compounds of Formula (1-8), compounds of Formula (1-9), compounds of Formula (1-10), and compounds of Formula (1-11):
(1-3)
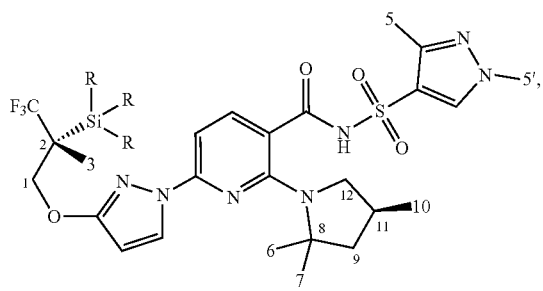
(1-4)
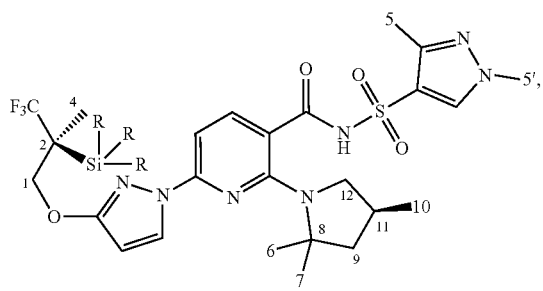
(1-5)
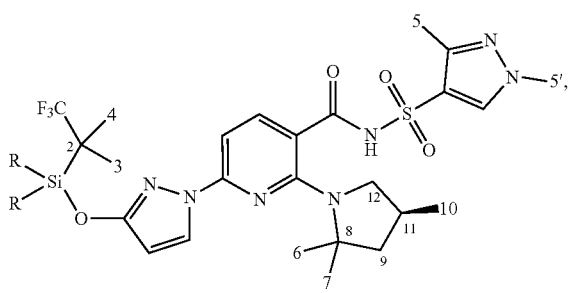
-continued
(1-6)
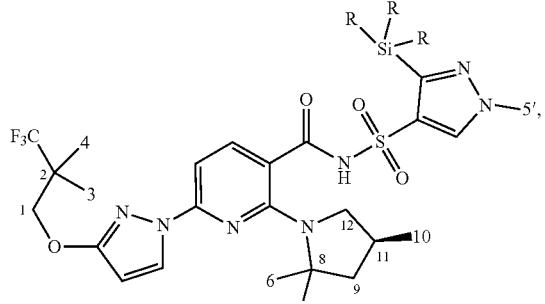
(1-7)
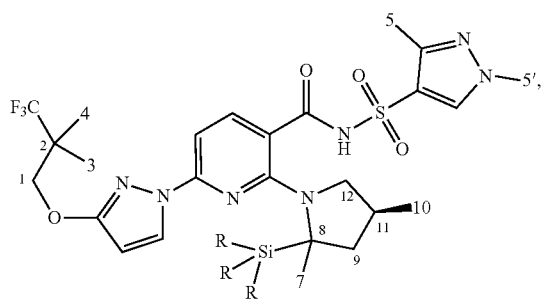
(1-8)
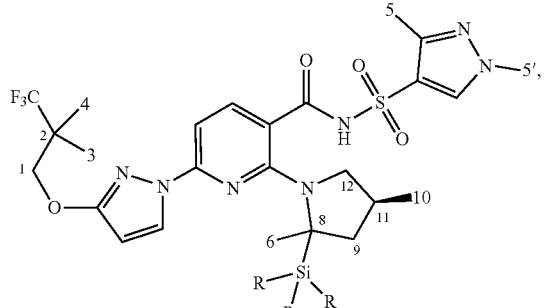
(1-9)
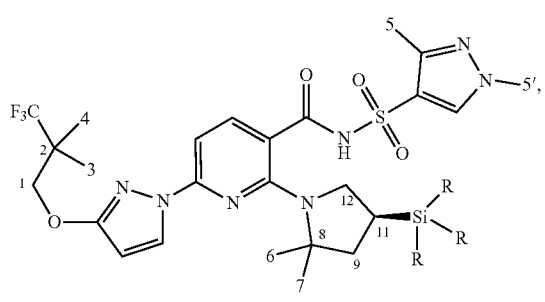
(1-10)
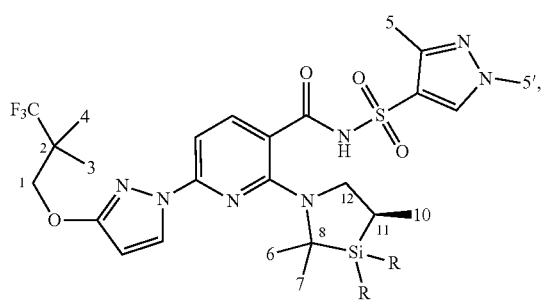

-continued (1-11)

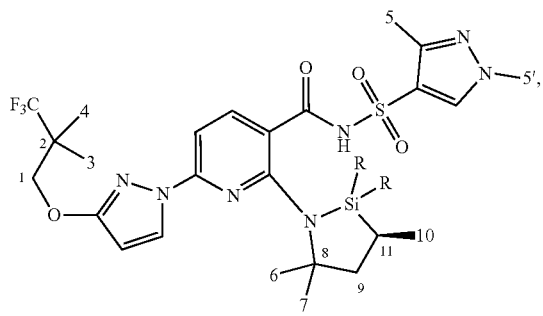

wherein each R is independently selected from H, —OH, —O(C$_1$-C$_4$ alkyl), and C$_{1-4}$ alkyl groups, and pharmaceutically acceptable salts and deuterated derivatives thereof.

9. A compound according to claim 1, a pharmaceutically acceptable salt thereof, or a deuterated derivative of any of the foregoing, wherein at least one hydrogen atom of at least one R group is replaced by a deuterium atom.

10. A compound according to claim 1, a pharmaceutically acceptable salt thereof, or a deuterated derivative of any of the foregoing, wherein each R is independently chosen from C$_1$ alkyl groups and C2 alkyl groups.

11. A compound according to claim 1, a pharmaceutically acceptable salt thereof, or a deuterated derivative of any of the foregoing, wherein each R is independently —CH$_3$ or —CD$_3$.

12. A compound according to claim 1, a pharmaceutically acceptable salt thereof, or a deuterated derivative of any of the foregoing, wherein each R is independently —CH$_3$.

13. A compound according to claim 1 chosen from compounds of Formulae (1-12) and (1-13):

(1-12)

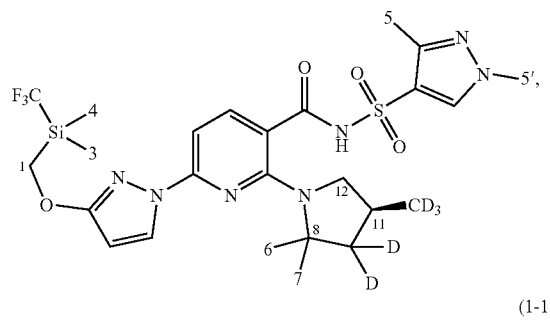

(1-13)

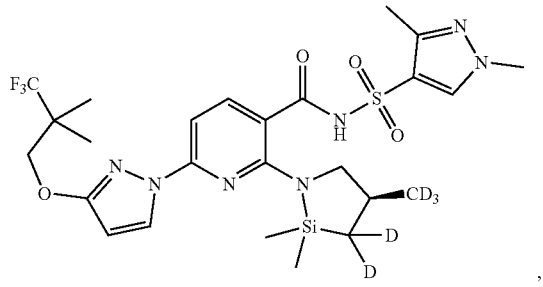

and pharmaceutically acceptable salts and deuterated derivatives thereof.

14. A compound of Formula (1-14):

(1-14)

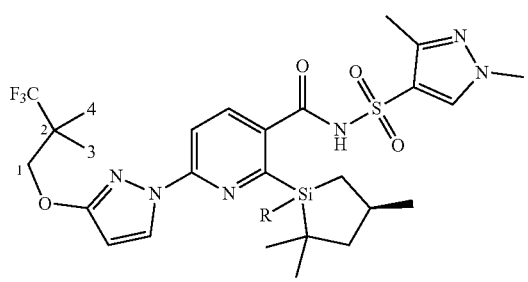

or a pharmaceutically acceptable salt or deuterated derivative thereof, wherein R is H, —OH, —O(C$_1$-C$_4$ alkyl), or C$_1$-C$_4$ alkyl groups.

15. A compound according to claim 14, wherein R is a C$_1$-C$_4$ alkyl group.

16. A pharmaceutical composition comprising:
(a) at least one compound chosen from compounds according to claim 1, pharmaceutically acceptable salts thereof, and deuterated derivatives of any of the foregoing;
(b) at least one pharmaceutically acceptable carrier; and
optionally one or more of:
(c) Compound (II):

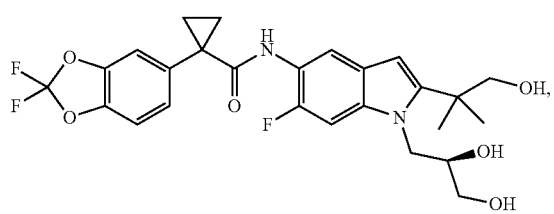 [SMILES: CC(C)(CO)c1cc2cc(NC(=O)C3(c4ccc5c(c4)OC(F)(F)O5)CC3)c(F)cc2n1C[C@@H](O)CO]

a pharmaceutically acceptable salt thereof, or a deuterated derivative of any of the foregoing; and
(d) Compound (III):

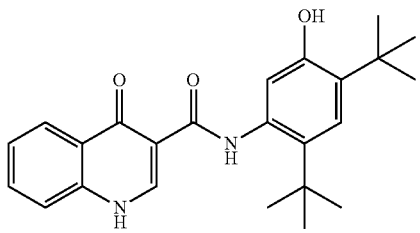

a pharmaceutically acceptable salt thereof, or a deuterated derivative of any of the foregoing.

17. A method of treating cystic fibrosis comprising administering to a patient in need thereof a pharmaceutical composition according to claim 16, pharmaceutically acceptable salts thereof, and deuterated derivatives of any of the foregoing.

18. A compound of Formula (2):
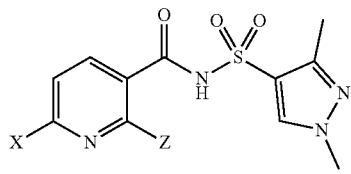
(2)
or a pharmaceutically acceptable salt or deuterated derivative thereof, wherein:
X is selected from —Si(CH$_3$)$_3$,
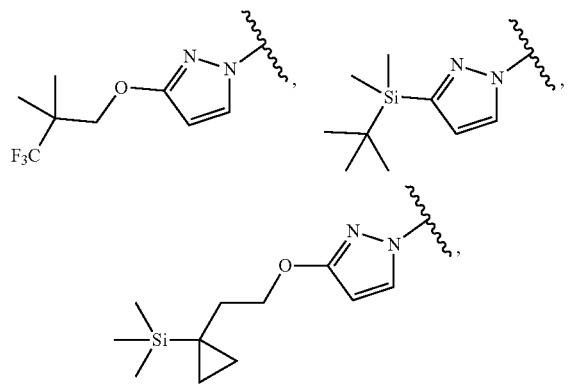
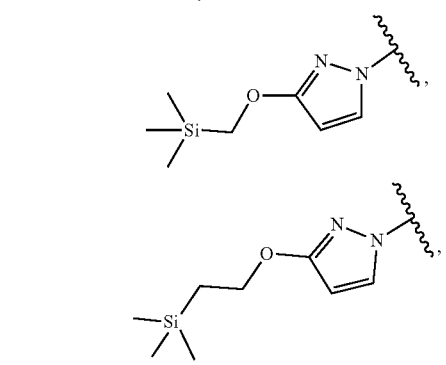
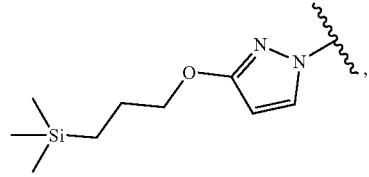
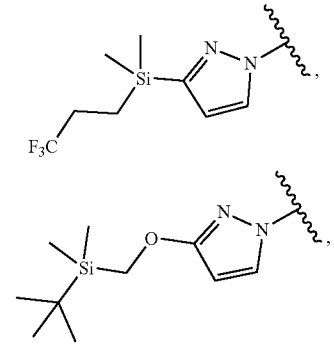
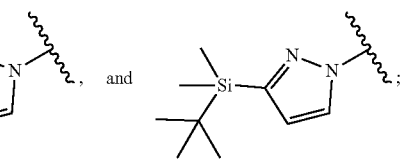
Z is selected from
and
wherein each compound of Formula (2) contains at least one Si atom.
19. The compound of claim 18, wherein the compound is chosen from:
Compound (2-1)
Compound (2-2)

Compound (2-3)
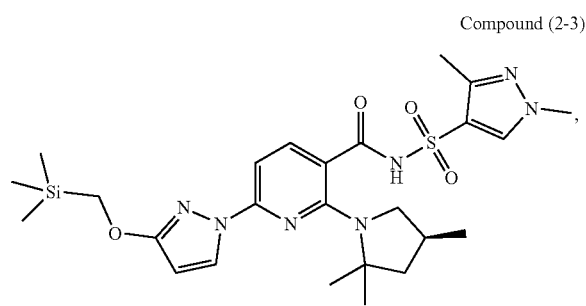
Compound (2-4)
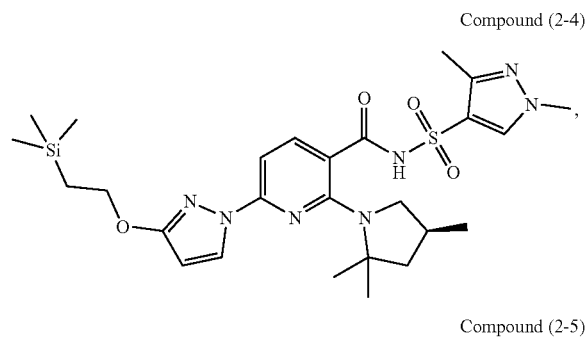
Compound (2-5)
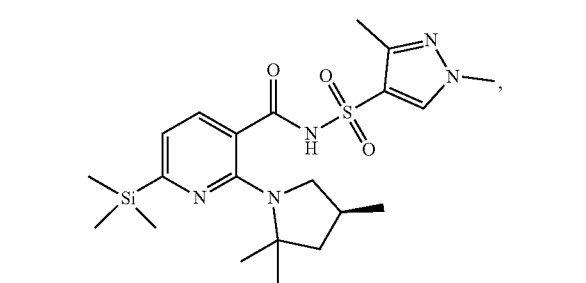
Compound (2-6)
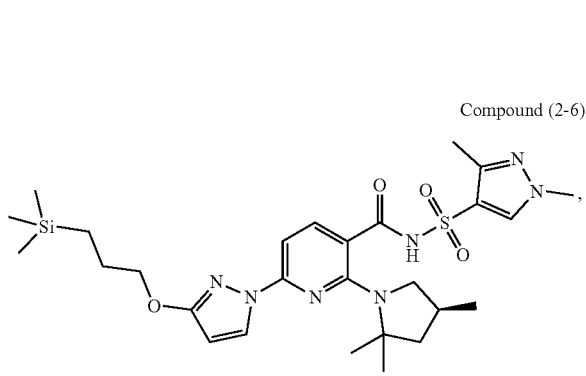
Compound (2-7)
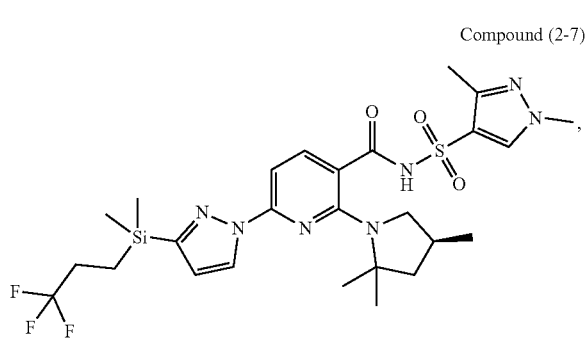
Compound (2-8)
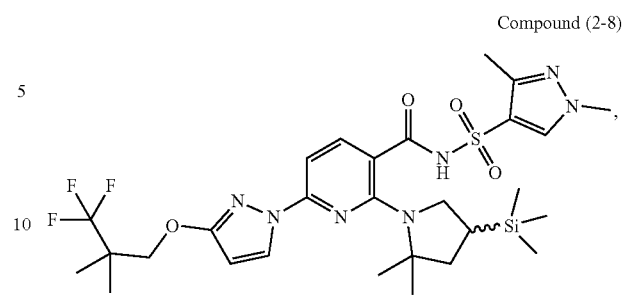
Compound (2-9)
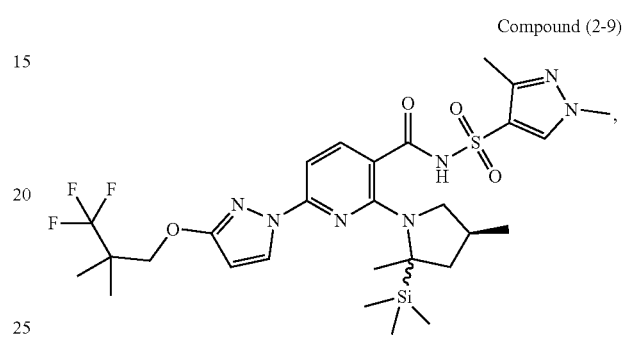
Compound (2-10)
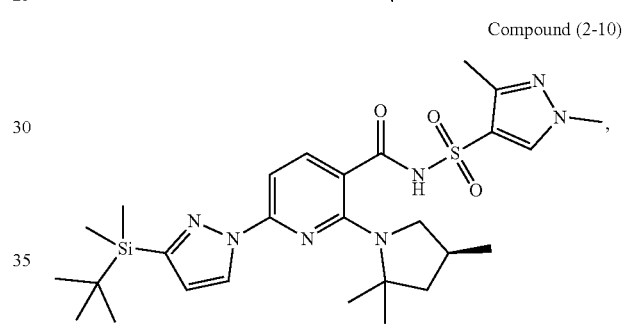
Compound (2-11)
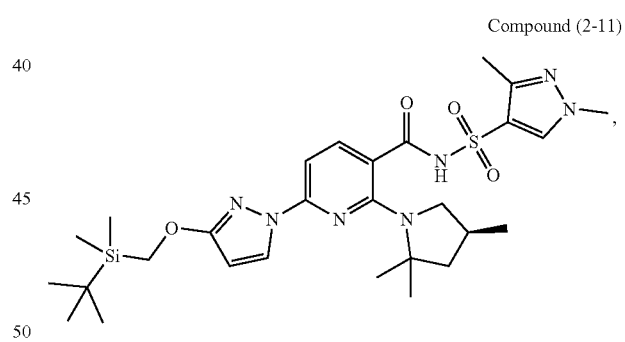
Compound (2-12)
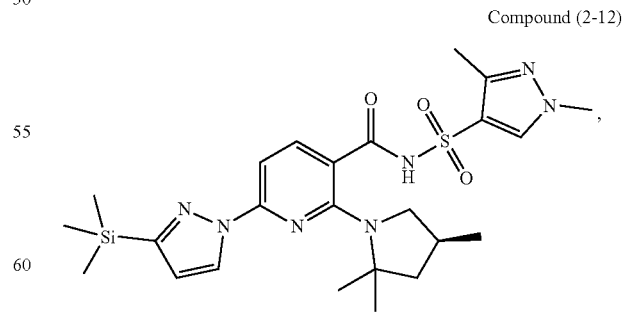
and pharmaceutically acceptable salts and deuterated derivatives thereof.

20. A compound of Formula (3):

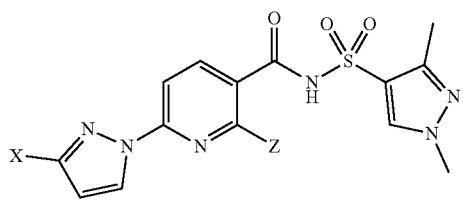

or a pharmaceutically acceptable salts or deuterated derivative thereof, wherein:

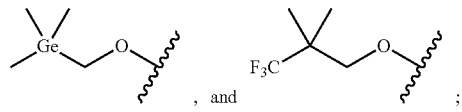

X is selected from —Ge(CH$_3$)$_3$,

Z is selected from

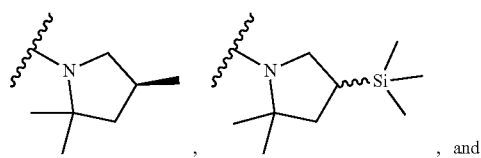

and wherein each compound of Formula (3) contains at least one Ge atom.

21. The compound of claim 20, wherein the compound is chosen from:

Compound (3-1)

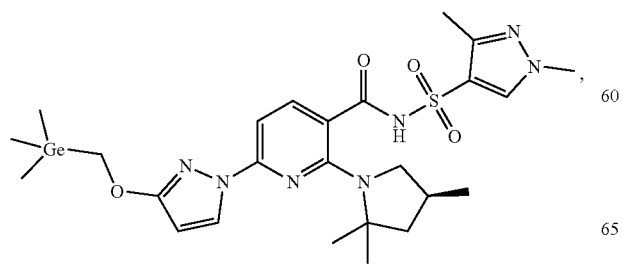

Compound (3-2)

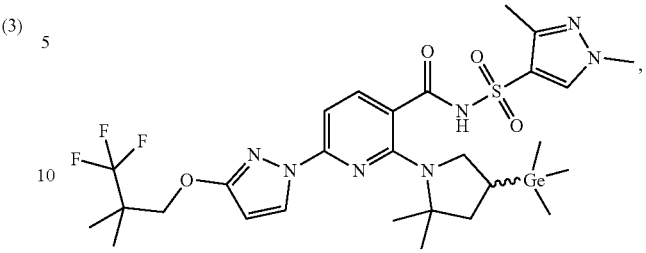

Compound (3-3)

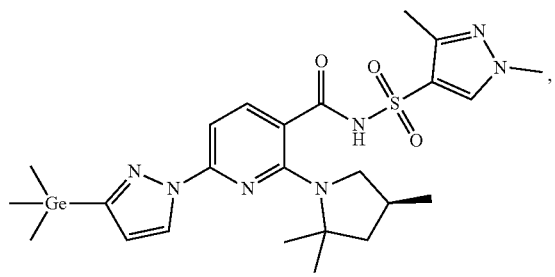

and pharmaceutically acceptable salts and deuterated derivatives thereof.

22. A pharmaceutical composition comprising:
(a) at least one compound chosen from compounds of claim 18;
(b) at least one pharmaceutically acceptable carrier; and
optionally one or more of:
(c) (i) a compound chosen from Compound (II):

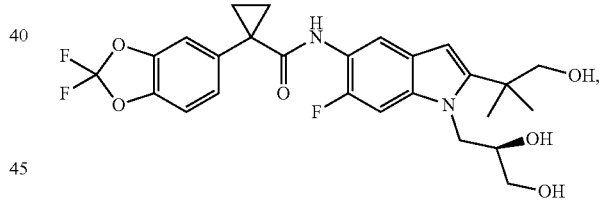

and pharmaceutically acceptable salts and deuterated derivatives thereof; and
(ii) a compound chosen from Compound (III), Compound (III-d):

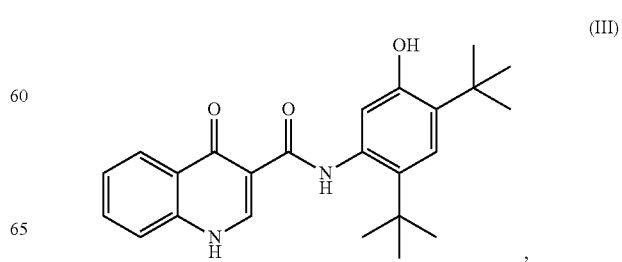

(III)

,

-continued

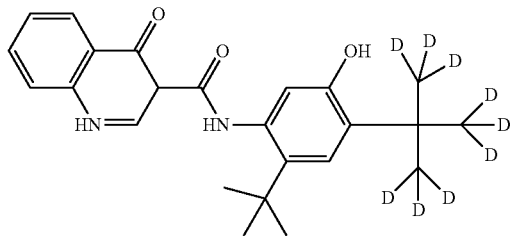
(III-d)

and pharmaceutically acceptable salts and deuterated derivatives thereof.

23. A pharmaceutical composition comprising a compound of claim 19 and a pharmaceutically acceptable carrier.

24. The pharmaceutical composition of claim 23, further comprising at least one compound selected from Compound (II):

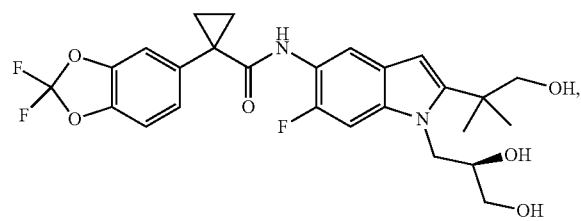 [SMILES: CC(C)(CO)c1cc2cc(NC(=O)C3(c4ccc5c(c4)OC(F)(F)O5)CC3)c(F)cc2n1C[C@@H](O)CO]
Compound (III)

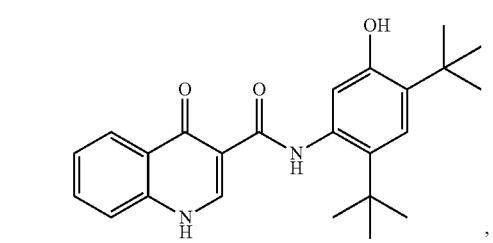
Compound (III-d)

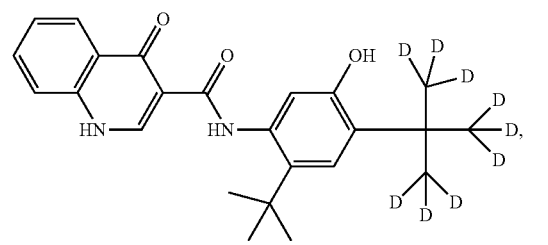
(III-d)

pharmaceutically acceptable salts thereof.

25. The pharmaceutical composition of claim 24, wherein the pharmaceutical composition comprises Compound (II) and Compound (III).

26. The pharmaceutical composition of claim 24, wherein the pharmaceutical composition comprises Compound (II) and Compound (III-d).

27. A pharmaceutical composition comprising a compound of claim 21 and a pharmaceutically acceptable carrier.

28. The pharmaceutical composition of claim 27, further comprising at least one compound selected from Compound (II):

Compound (III)

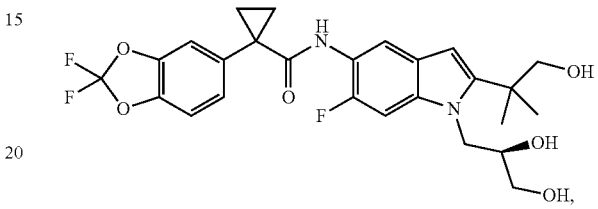

Compound (III-D)

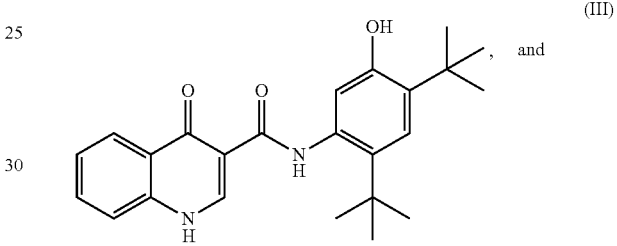
(III)

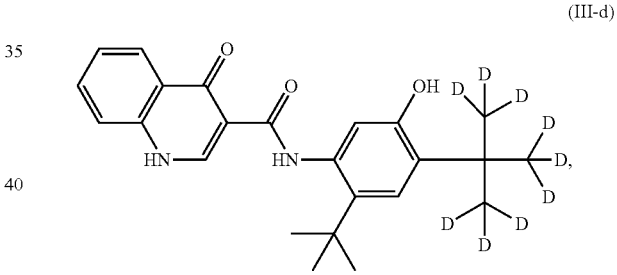
(III-d)

pharmaceutically acceptable salts thereof.

29. The pharmaceutical composition of claim 28, wherein the pharmaceutical composition comprises Compound (II) and Compound (III).

30. The pharmaceutical composition of claim 28, wherein the composition comprises Compound (II) and Compound (III-d).

31. A method of treating cystic fibrosis comprising administering to a patient in need thereof, a pharmaceutical composition according to claim 22.

* * * * *